US012351565B2

(12) United States Patent
Xue et al.

(10) Patent No.: US 12,351,565 B2
(45) Date of Patent: Jul. 8, 2025

(54) AROMATIC COMPOUND AND PREPARATION METHOD THEREFOR AND USE THEREOF

(71) Applicant: SHANGHAI JIANHE PHARMACEUTICAL & TECHNOLOGY CO. LTD., Shanghai (CN)

(72) Inventors: Tao Xue, Shanghai (CN); Jing Huang, Shanghai (CN); Wenke Wang, Shanghai (CN); Yilang Chen, Shanghai (CN)

(73) Assignee: Shanghai Zhigen Pharmaceutical & Technology Co., Ltd., Shanghai (CN)

( * ) Notice: Subject to any disclaimer, the term of this patent is extended or adjusted under 35 U.S.C. 154(b) by 1221 days.

(21) Appl. No.: 17/045,004

(22) PCT Filed: Apr. 4, 2019

(86) PCT No.: PCT/CN2019/081533
§ 371 (c)(1),
(2) Date: Feb. 19, 2021

(87) PCT Pub. No.: WO2019/192602
PCT Pub. Date: Oct. 10, 2019

(65) Prior Publication Data
US 2021/0171487 A1    Jun. 10, 2021

(30) Foreign Application Priority Data

Apr. 4, 2018    (CN) .......................... 201810301241.8

(51) Int. Cl.
| | |
|---|---|
| *C07D 309/30* | (2006.01) |
| *A61P 25/24* | (2006.01) |
| *C07C 225/20* | (2006.01) |
| *C07C 237/02* | (2006.01) |

(52) U.S. Cl.
CPC ............ *C07D 309/30* (2013.01); *A61P 25/24* (2018.01); *C07C 225/20* (2013.01); *C07C 237/02* (2013.01)

(58) Field of Classification Search
None
See application file for complete search history.

(56) References Cited

U.S. PATENT DOCUMENTS

| 11,110,070 B2 * | 9/2021 | Brachman ................ A61P 25/22 |
| 11,613,514 B2 * | 3/2023 | Thomas ................ C07C 269/06 564/393 |
| 2018/0057470 A1 | 3/2018 | Gomez et al. |

FOREIGN PATENT DOCUMENTS

| CN | 104395283 A | 3/2015 |
| JP | 2009531277 A | 9/2009 |
| JP | 2011517668 A | 6/2011 |
| JP | 2012514655 A | 6/2012 |
| JP | 2017-514871 A | 6/2017 |
| WO | 2013056229 A1 | 4/2013 |
| WO | 2017087388 A1 | 5/2017 |
| WO | 2017208031 A1 | 12/2017 |
| WO | 2018104729 A1 | 6/2018 |
| WO | 2019025792 A1 | 2/2019 |
| WO | 2019077332 A1 | 4/2019 |

OTHER PUBLICATIONS

Yale, Journal of Medicinal and Pharmaceutical Chemistry 1959 1 (2), 121-133 (Year: 1959).*
Isidro-Llobet et al., Chemical Reviews 2009 109 (6), 2455-2504 (Year: 2009).*
Simple Enantioselective Syntheses of (2R,6R)-Hydroxynorketamine and Related Potential Rapid-Onset Antidepressants Yixin Han, Karla Mahender Reddy, and E. J. Corey Organic Letters 2017 19 (19), 5224-5227 DOI: 10.1021/acs.orglett.7b02498 (Year: 2017).*
Han, Yixin, et al., "Simple Enantioselective Syntheses of (2R,6R)-Hydroxynorketamine and Related Potential Rapid-Onset Antigepressants," Organic Letters, ACS Publications, Aug. 11, 2017.
Morris, Patrick J., et al, "Synthesis and N-Methyl-D-aspartate (NMDA) Receptor Activity of Ketamine Metabolites," American Chemical Society, Aug. 22, 2017, pp. 4572-4575.
Highland, Jaclyn N., et al, "Mouse, rat, and dog bioavailability and mouse oral antidepressant efficacy of (2R,6R)-hydroxynorketamine," Journal of Psychopharmacology, (2018), pp. 1-13.
Toki, Hidetoh, et al, "A rapid and sensitive chiral LC-MS/MS method for the determination of ketamine and norketamine in mouse plasma, brain and cerbrospinal fluid applicable to the steroselective pharmacokinetic study of ketamine," Journal of Pharmaceutical and Biomedical Analysis, vol. 148 (2018), pp. 288-297.
Zanos, P. et al, "Effects of a ketamine metabolite on synaptic NMDAR function," Nature, 2017, vol. 546, pp. E1-E3.
Zanos, P., et al, "NMDAR inhibition-independent antidepressant actions of ketamine metabolites," Nature, 2016, vol. 533, pp. 481-486.
International Search Report issued Jul. 3, 2019 in PCT/CN2019/081533.
Written Opinion issued Jul. 3, 2019 in PCT/CN2019/081533.
Supplementary European Search Report issued Jun. 15, 2021 in corresponding European Patent Application No. 19781996.4.
Theurillat, Regula, et al., "Development of a method for analysis of ketamine and norketamine enantiomers in equine brain and cerebrospinal fluid by capillary electrophoresis," Electrophoresis, vol. 35, No. 19, pp. 2863-2869, Jul. 10, 2014.

* cited by examiner

*Primary Examiner* — Jeffrey S Lundgren
*Assistant Examiner* — Anthony Joseph Seitz
(74) *Attorney, Agent, or Firm* — Ice Miller LLP

(57) ABSTRACT

The present invention relates to an aromatic compound and a preparation method therefor and the use thereof. Specifically, disclosed are a compound as shown in the following general formula (I), or a tautomer, an enantiomer, a diastereomer or a racemate thereof or a mixture thereof, or a pharmaceutically acceptable salt thereof. Also disclosed are a method for preparing the above compound and the use of same in the treatment of nervous system diseases.

14 Claims, No Drawings

AROMATIC COMPOUND AND PREPARATION METHOD THEREFOR AND USE THEREOF

CROSS-REFERENCE TO RELATED APPLICATION

This application is a Section 371 of International Application No. PCT/CN2019/081533 filed Apr. 4, 2029, which was published in the Chinese language Oct. 10, 2019, under International Publication No. WO 2019/192602 A1, which claims priority under 35 U.S.C. § 119 (b) to Chinese Patent Application No. 201810301241.8 filed Apr. 4, 2018, the disclosures of which are incorporated herein by reference in their entireties.

TECHNICAL FIELD

The present invention relates to the field of medicine, and specifically, to a new type of aromatic compound and its preparation method and its use as a biologically active substance in medicine in the treatment and/or prevention of depression-related diseases.

BACKGROUND ART

Depression usually refers to mood disorders. It is a kind of affective psychosis characterized by being down in spirits, sadness, despair and depression, accompanied by symptoms such as sleep disorders, anxiety, and physical discomfort. It is a common and serious mental illness, which seriously affects the patient's ability to work, quality of life, and is even life-threatening. With the intensification of multiple stress factors, depression has become a common disease and high incidence in modern society, and its incidence is rising rapidly year by year. According to the World Health Organization's forecast, there are approximately 300 million people suffering from depression worldwide, and by 2020, it may become the second largest disease after cardiovascular and cerebrovascular diseases.

The pathogenesis of depression is complex and is related to multiple factors such as genetics, environment and society. The pathogenesis is not clear, and there is no clear mechanism that has been widely recognized. The traditional monoamine transmitter hypothesis indicates that too low content of neurotransmitters such as central norepinephrine (NE) or 5-hydroxytryptamine (5-HT), dopamine (DA) or its poor receptor function are believed to be the main causes of depression.

Currently, the main treatment for depression is still medication. Antidepressants have been on the market for more than 60 years. According to the mechanism of action, they can be divided into two generations of antidepressants. The first-generation antidepressants are mainly tricyclic antidepressants (TCAs, imipramine, clomipramine, amitriptyline, etc.) and monoamine oxidase inhibitors (MAOIs, moclobemide, etc.). Although the first-generation antidepressants have made major breakthroughs and are effective in the treatment of depression, their numerous adverse reactions have severely restricted their clinical use. Most of the second-generation antidepressants mainly act on central neurotransmitters, such as selective 5-hydroxytryptamine (5-HT) reuptake inhibitors (SSRIs, fluoxetine, paroxetine, citalopram, sertraline, fluvoxamine, etc.), selective norepinephrine (NE) reuptake inhibitors (NaRIs, reboxetine), 5-HT and NE reuptake inhibitors (SNRIs, venlafaxine, duloxetine, etc.), NE and specific 5-HT reuptake inhibitors (NaSSAs, mirtazapine) etc. Compared with the first-generation antidepressants, they have better pharmacokinetics and pharmacodynamic properties, good curative effect, high safety, and convenient taking, so that they are favored by doctors and patients and have become first-line medication in the current treatment for depression. But these drugs also have serious shortcomings. (1) Onset is slow, and it usually takes 2-4 weeks, or even longer to exhibit a relatively obvious effect. (2) Treatment response rate is low. Only about ⅓ of the patients respond to the first treatment medication, while about 2/3 of the patients only respond after trying several antidepressants. In particular, for patients with major depressive disorder (MDD) who have suicidal tendencies, all existing antidepressants have the disadvantage of slow onset of action (Medication should be taken for 2-4 weeks to have significant effects), which is extremely unfavorable for patients with high risk of suicide.

Ketamine has been used clinically as a traditional anesthetic for more than 50 years. But in a later study (Arch Gen Psychiatry, 2006; 63(8): 856-864), it has been found that the sub-anesthetic dose of ketamine has a rapid (a few hours), significant and relative long-lasting (approximately one week) antidepressant effect on patients with treatment resistant depression (TRD), and it then gradually became clinically concerned. At present, esketamine developed by Johnson & Johnson is in Phase III clinical studies, and has achieved FDA-approved breakthrough therapy designation (BTD) for drug treatment resistant depression and major depression disorder with immediate suicide risk.

Although ketamine exhibits rapid and sustained antidepressant effects, it also has some problems that may affect its clinical use. (1). Side effects exist, including psychosis-like, dissociative side effects and respiratory depression side effects; long-term application may cause urinary tract dysfunction and even renal failure. (2). Oral bioavailability is low, and oral administration is difficult; (3). It causes euphoria, hallucinations, and is addictive. These side effects of ketamine are unacceptable when it is generally used in clinic.

In May 2016, Zanos et al. published research results (Nature, 2016, 533, 481-486) which showed that the rapid and sustained antidepressant effect of ketamine was mainly derived from its metabolites (2R, 6R)-HNK instead of ketamine itself. At present, the rapid antidepressant mechanism of this compound is still not very clear. It may be due to the activation of the AMPAR receptor to exert an antidepressant effect.

(2R,6R)-HNK has the very desirable feature of being able to treat depression quickly. However, it still has many shortcomings. For example, the druggability of the compound is not good, the metabolic properties in mice are not ideal, $T_{1/2}$<1 h, the clearance is fast, the plasma exposure is not high, the antidepressant activity is relatively weak, and the amount of the drug distributed to the central nervous system is not high. Therefore, it is difficult to directly develop it into a drug.

Therefore, there is an urgent clinical need to develop new antidepressant drugs with fast onset, definite efficacy and high safety.

SUMMARY OF THE INVENTION

The purpose of the present invention is to provide a kind of compounds with novel structure, rapid and long-lasting antidepressant activity and good druggability.

In the first aspect of the present invention, it provides a compound represented by the following general formula (I), or a tautomer, an enantiomer, a diastereomer, a racemate, or a mixture thereof, or a pharmaceutically acceptable salt thereof;

general formula (I)

wherein,
A is $CH_2$ or O;
$N_1$ and $N_2$ are each independently 0, 1, 2, 3 or 4;
$R^1$ and $R^2$ are each independently hydrogen, $C_1$-$C_6$ alkyl or $C_1$-$C_6$ alkylcarbonyl, and the above-mentioned alkyl can be independently substituted by 1 to 2 substituents selected from the group consisting of halogen, hydroxyl, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;
$R^3$ is hydrogen, $C_1$-$C_6$ alkyl, $C_1$-$C_6$ haloalkyl, $C_1$-$C_6$ alkoxy, $C_1$-$C_6$ haloalkoxy or halogen; and when A is $CH_2$ and $N_1$ is 1, $R^3$ is not chlorine;
$R^4$ is hydrogen, $C_1$-$C_6$ alkyl, $C_1$-$C_6$ haloalkyl, $C_1$-$C_6$ alkoxy, $C_1$-$C_6$ haloalkoxy, halogen, nitro, $C_1$-$C_4$ amide or cyano; and $R^3$ and $R^4$ are not hydrogen at the same time; or when $R^3$ is fluorine, not all of the substituents at other positions of the benzene ring are hydrogen or position 5 of the benzene ring is not fluorine; and
the stereo configuration of α- or β-position carbon atom is each independently R, S or (R, S).

In another preferred embodiment, the compound is a compound represented by general formula (I-A), (I-B) or (I-C):

general formula (I-A) compound wherein, in formula (I-A), A, $N_1$, $N_2$, $R^3$ and $R^4$ are as defined above;

general formula (I-B) compound wherein, in formula (I-B), A, $N_1$, $N_2$, $R^3$ and $R^4$ are as defined above, $R^1$ and $R^2$ are each independently hydrogen or $C_1$-$C_6$ alkyl, and the above alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;

general formula (I-C) compound wherein, in formula (I-C), A, $N_1$, $N_2$, $R^3$ and $R^4$ are as defined above, $R^1$ is $C_1$-$C_6$ alkylcarbonyl, and the above-mentioned alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide.

In another preferred embodiment, A is $CH_2$.
In another preferred embodiment, $N_1$ is 1.
In another preferred embodiment, $N_2$ can be 0, 1, or 2.
In another preferred embodiment, each of $R^1$ and $R^2$ is independently hydrogen, methyl, ethyl or acetyl.
In another preferred embodiment, $N_2$ is 1;
$R^3$ is hydrogen;
$R^4$ is $C_1$-$C_6$ haloalkyl;
$R^4$ is located at the 4-position of the benzene ring.
In another preferred embodiment, $N_2$ is 1;
$R^3$ is halogen;
$R^4$ is $C_1$-$C_6$ haloalkoxy;
$R^4$ is located at the 3-position of the benzene ring.
In another preferred embodiment, $R^3$ is hydrogen, fluorine, methyl, trifluoromethyl or trifluoromethoxy.
In another preferred embodiment, $R^4$ is hydrogen, fluorine, chlorine, methyl, methoxy, trifluoromethyl, trifluoromethoxy or cyano.
In another preferred embodiment, the compound or its tautomer, enantiomer, diastereomer, racemate or mixture, or its pharmaceutically acceptable salt is selected from the group consisting of:

TABLE 1

Compound 1

Compound 2

TABLE 1-continued
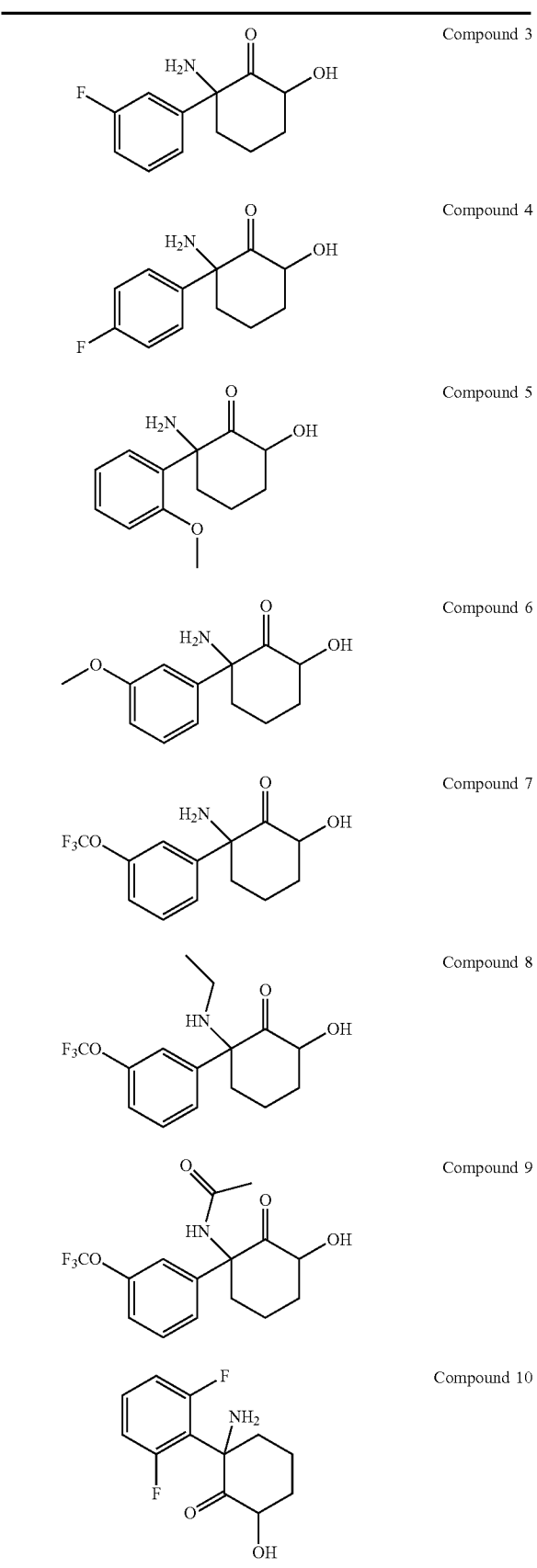
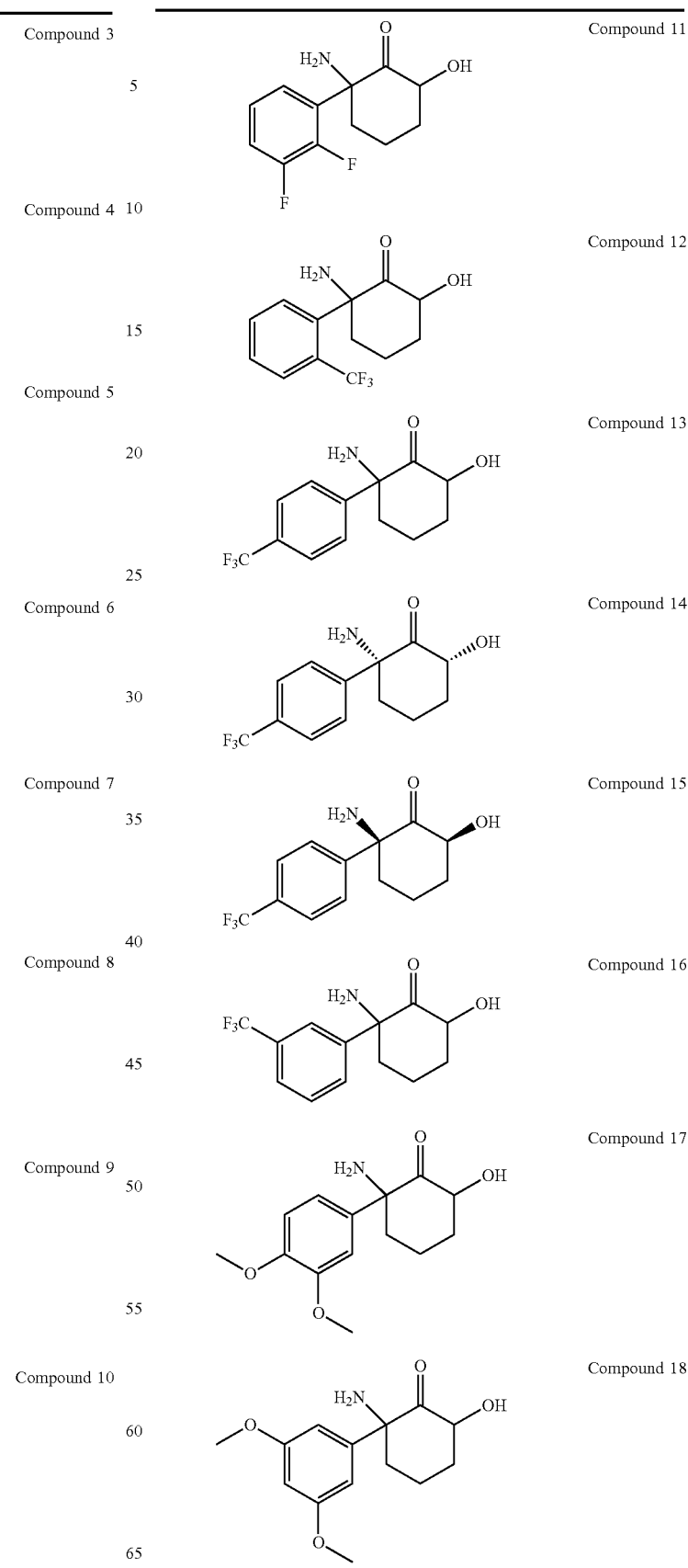

TABLE 1-continued
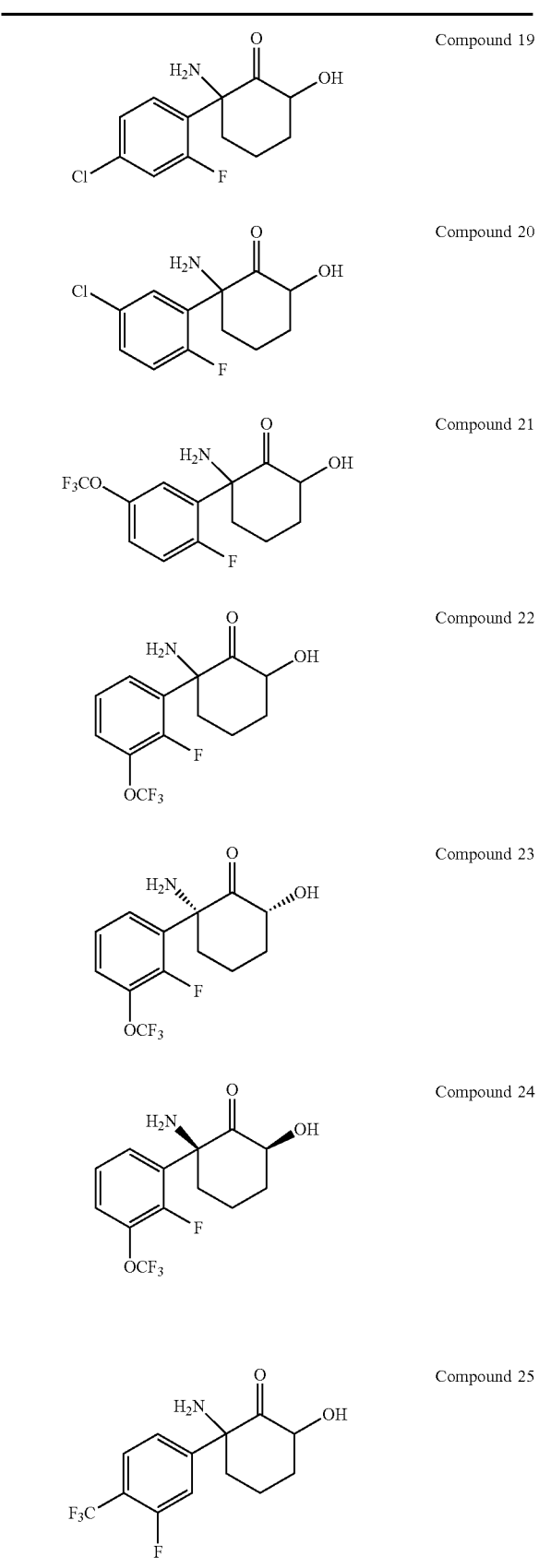
Compound 19
Compound 20
Compound 21
Compound 22
Compound 23
Compound 24
Compound 25
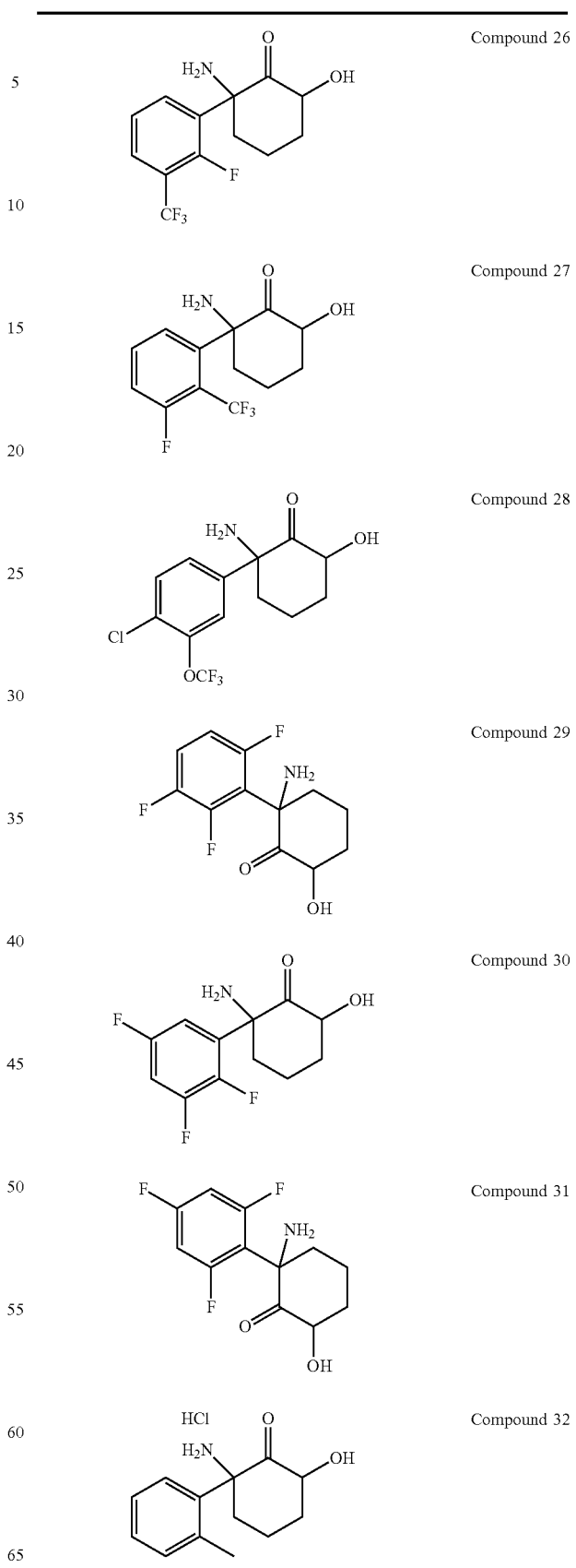
Compound 26
Compound 27
Compound 28
Compound 29
Compound 30
Compound 31
Compound 32

TABLE 1-continued

Compound 33: HCl, H2N, 2-(3-methylphenyl)-6-hydroxycyclohexanone

Compound 34: HCl, H2N, 2-(3-fluorophenyl)-6-hydroxycyclohexanone

Compound 35: HCl, H2N, 2-(4-fluorophenyl)-6-hydroxycyclohexanone

Compound 36: HCl, H2N, 2-(2-methoxyphenyl)-6-hydroxycyclohexanone

Compound 37: HCl, H2N, 2-(3-methoxyphenyl)-6-hydroxycyclohexanone

Compound 38: HCl, H2N, 2-(3-trifluoromethoxyphenyl)-6-hydroxycyclohexanone

Compound 39: HCl, HN(CH3), 2-(3-trifluoromethoxyphenyl)-6-hydroxycyclohexanone

Compound 40: HCl, N(CH3)2, 2-(3-trifluoromethoxyphenyl)-6-hydroxycyclohexanone

Compound 41: HCl, HN(Et), 2-(3-trifluoromethoxyphenyl)-6-hydroxycyclohexanone

Compound 42: HCl, H2N, 2-(3-chloro-2-fluorophenyl)-6-hydroxycyclohexanone

Compound 43: HCl, NH2, 2-(2,6-difluorophenyl)-6-hydroxycyclohexanone

Compound 44: HCl, H2N, 2-(2,3-difluorophenyl)-6-hydroxycyclohexanone

Compound 45: HCl, H2N, 2-(2-trifluoromethylphenyl)-6-hydroxycyclohexanone

Compound 46: HCl, H2N, 2-(4-trifluoromethylphenyl)-6-hydroxycyclohexanone

Compound 47: CH3SO3H, H2N, 2-(4-trifluoromethylphenyl)-6-hydroxycyclohexanone

Compound 48: H2SO4, H2N, 2-(4-trifluoromethylphenyl)-6-hydroxycyclohexanone

TABLE 1-continued
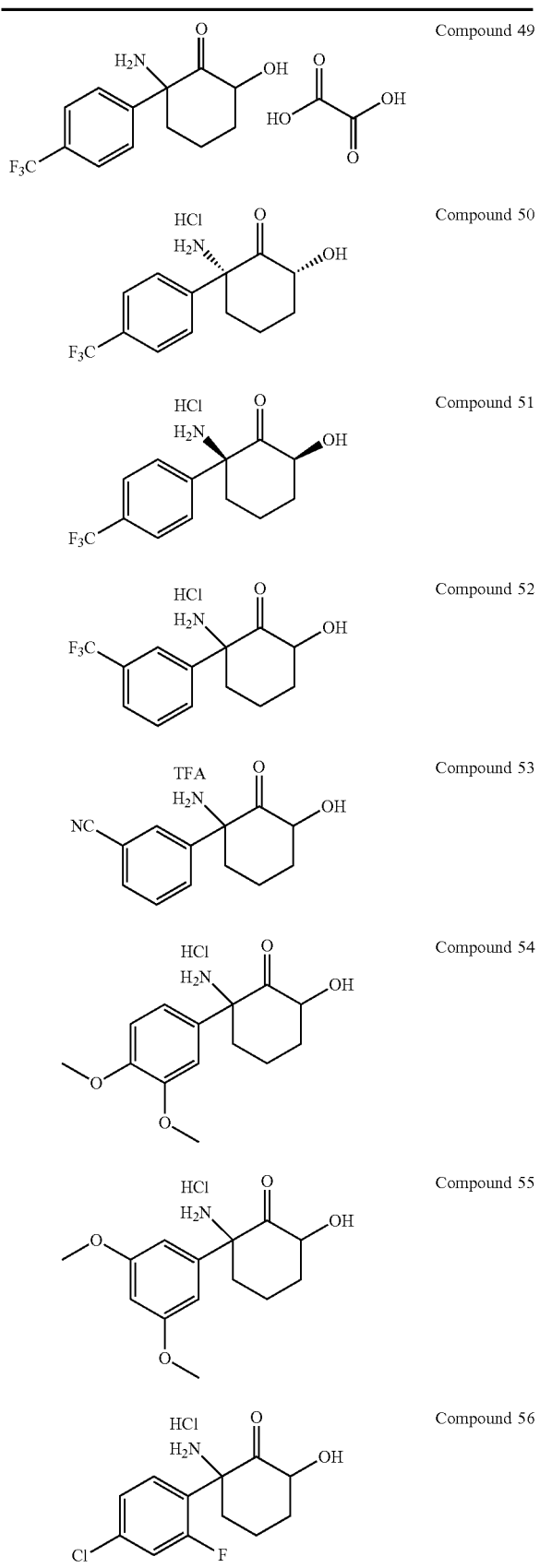
Compound 49
Compound 50
Compound 51
Compound 52
Compound 53
Compound 54
Compound 55
Compound 56
TABLE 1-continued
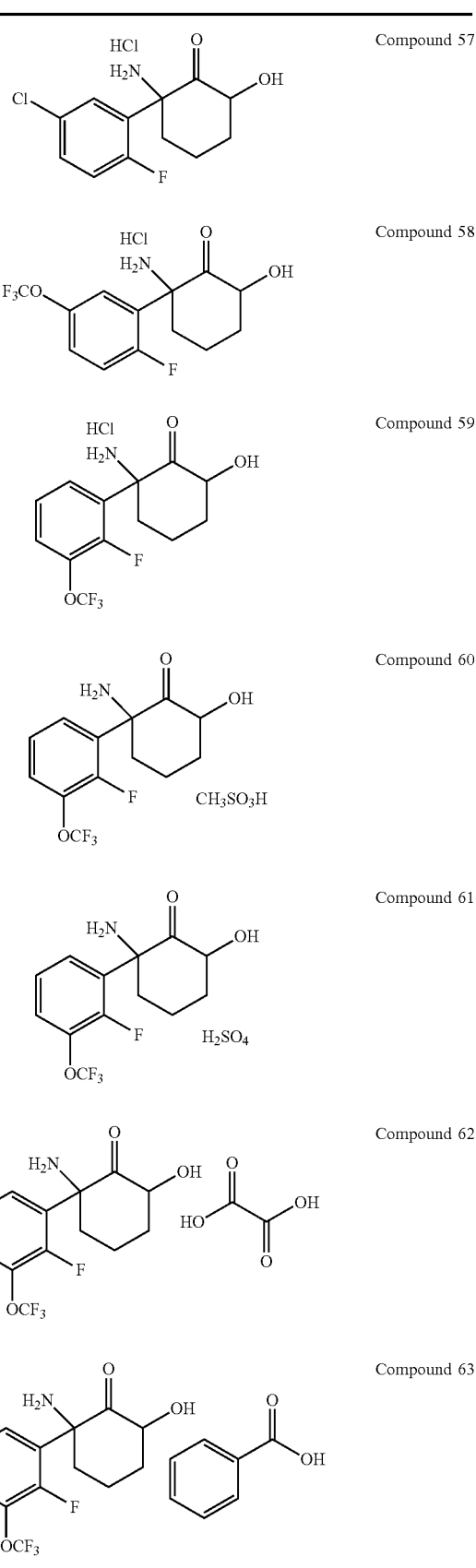
Compound 57
Compound 58
Compound 59
Compound 60
Compound 61
Compound 62
Compound 63

TABLE 1-continued
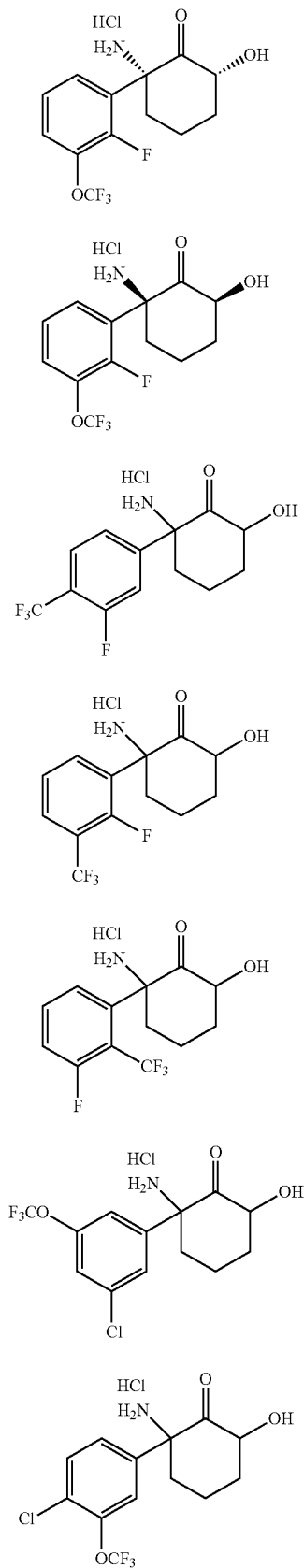
Compound 64
Compound 65
Compound 66
Compound 67
Compound 68
Compound 69
Compound 70
TABLE 1-continued
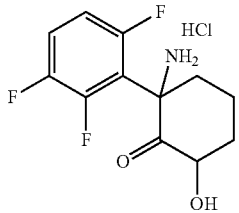 [SMILES: NC1(c2c(F)ccc(F)c2F)CCCC(O)C1=O ; Cl]
Compound 71
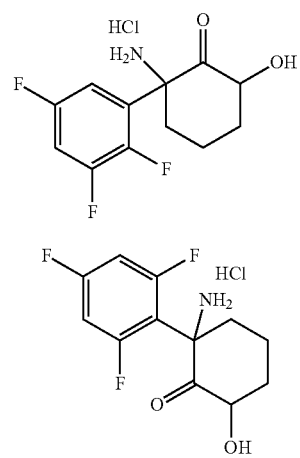
Compound 72
Compound 73
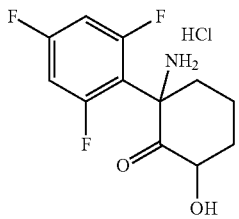 [SMILES: NC1(c2c(F)cc(F)cc2F)CCCC(O)C1=O ; Cl]
Compound 74
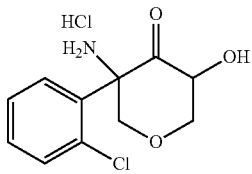 [SMILES: NC1(c2ccccc2Cl)COCC(O)C1=O ; Cl]
Compound 75
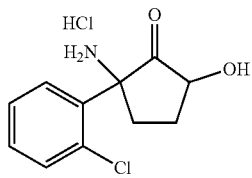 [SMILES: NC1(c2ccccc2Cl)CCC(O)C1=O ; Cl]
Compound 76
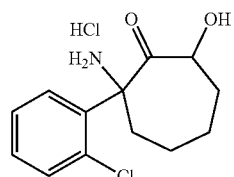
Compound 77
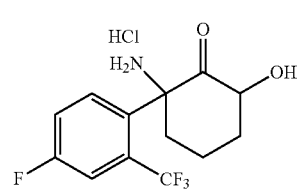 [SMILES: NC1(c2ccc(F)cc2C(F)(F)F)CCCC(O)C1=O ; Cl]
Compound 78
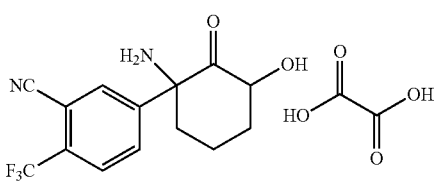

TABLE 1-continued

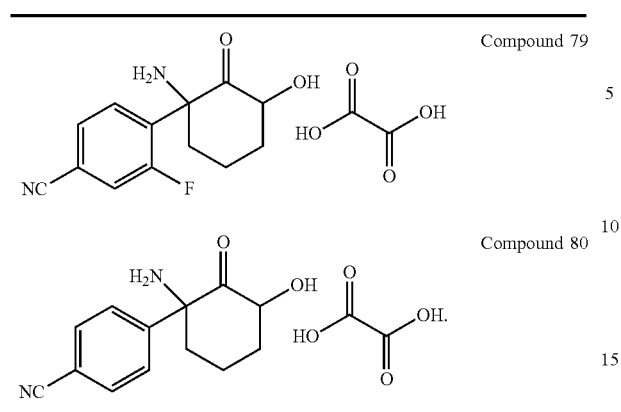

Compound 79

Compound 80

In the second aspect of the present invention, it provides a pharmaceutical composition comprising the compound, or its tautomers, enantiomers, diastereomers, racemates or mixtures, or its pharmaceutically acceptable salt of the first aspect of the present invention; and a pharmaceutically acceptable carrier or excipient.

In the third aspect of the present invention, it provides a use of the compound, or its tautomers, enantiomers, diastereomers, racemates or mixtures, or its pharmaceutically acceptable salt of the first aspect of the present invention or the pharmaceutical composition of the second aspect in the preparation of a medicament for the treatment of a disease related to the nervous system.

In another preferred embodiment, the disease related to the nervous system is depression.

In the fourth aspect of the present invention, it provides a method for preparing the compound, or its tautomers, enantiomers, diastereomers, racemates or mixtures, or its pharmaceutically acceptable salt of the first aspect of the present invention, wherein (1) the method comprises the steps:

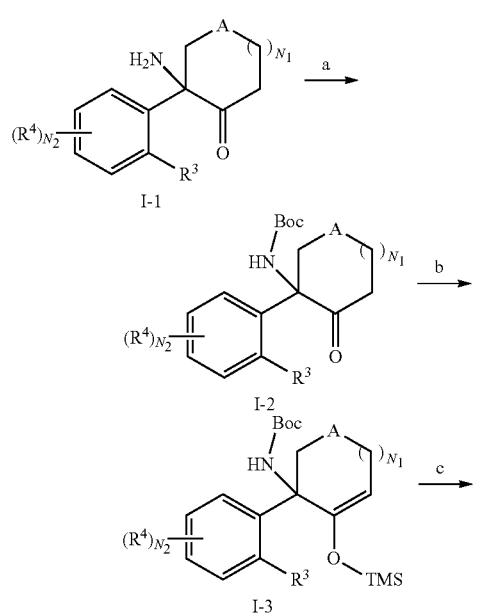

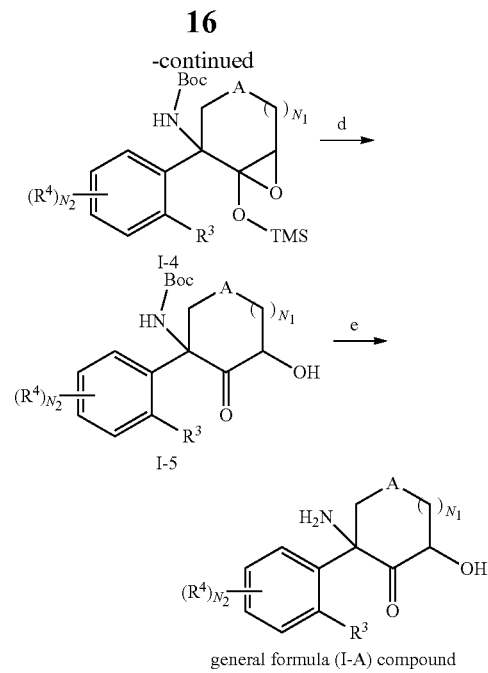

general formula (I-A) compound wherein, A, $N_1$, $N_2$, $R^3$ and $R^4$ are as defined above;
a. compound I-1 is reacted with di-tert-butyl dicarbonate in a protic solvent or an aprotic solvent or a mixed solvent thereof to form compound I-2;
b. in an aprotic solvent, compound I-2 is reacted with trimethylchlorosilane to form compound I-3;
c. in an aprotic solvent, compound I-3 is oxidized by an oxidizing agent to form compound I-4;
d. in an aprotic solvent, a trimethylsilyl protecting group is removed from compound I-4 to form compound I-5;
e. in a polar aprotic solvent, a tert-butoxycarbonyl protecting group is removed from compound I-5 to form compound I-A;

or (2) the method comprises the steps:

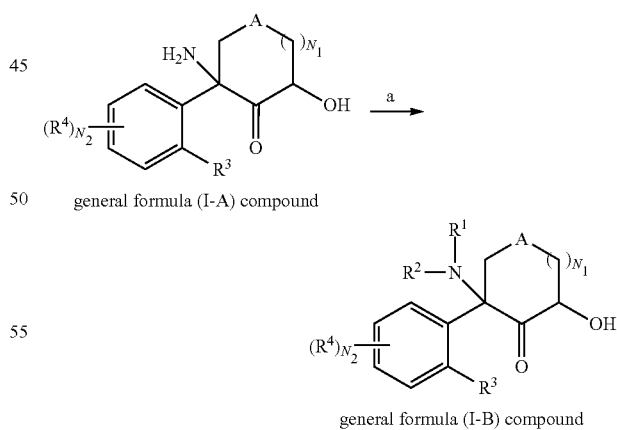

general formula (I-A) compound general formula (I-B) compound wherein, A, $N_1$, $N_2$, $R^3$ and $R^4$ are as defined above, $R^1$ and $R^2$ are each independently hydrogen or $C_1$-$C_6$ alkyl, and the above-mentioned alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;

a. in a protic or an aprotic solvent or a mixed solvent thereof and in the presence of a catalyst and a hydrogen source, compound I-A is reacted with an aldehyde to form compound I-B;

or (3) the method comprises the steps:

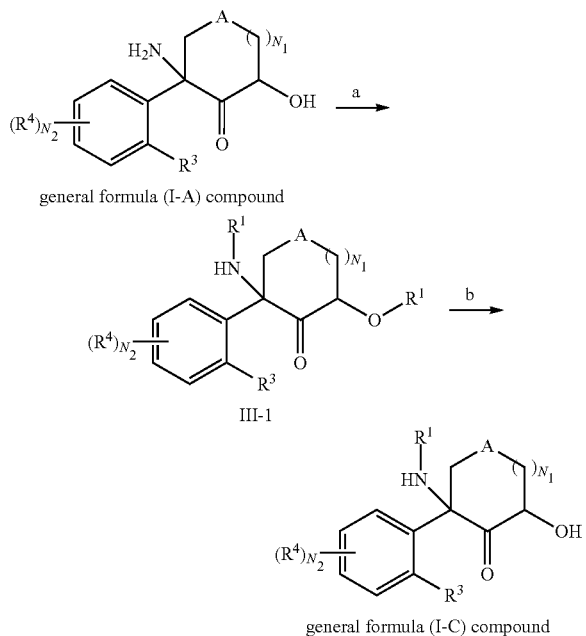

general formula (I-A) compound

III-1 general formula (I-C) compound wherein, A, $N_1$, $N_2$, $R^3$ and $R^4$ are as defined above, $R^1$ is $C_1$-$C_6$ alkylcarbonyl, and the above-mentioned alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;

a. in an aprotic solvent, compound I-A is reacted with acyl chloride or acid anhydride to form compound III-1;

b. in a protic or an aprotic solvent or a mixed solvent thereof, compound III-1 is deprotected to form compound I-C.

In another preferred embodiment, the method for preparing compound I-1 comprises the steps:

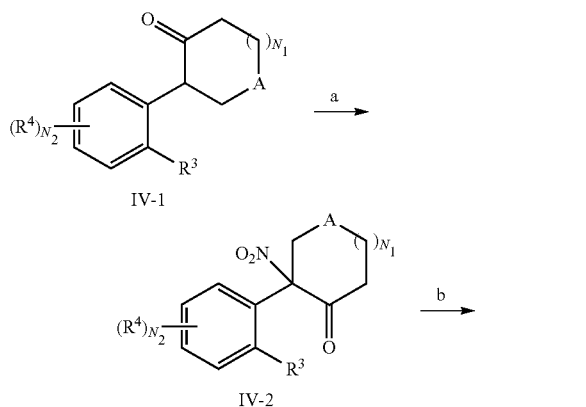

IV-1

IV-2

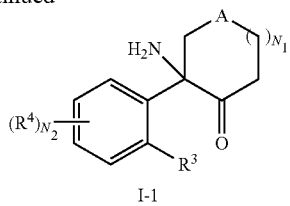

I-1 wherein, in each formula, A, $N_1$, $N_2$, $R^3$ and $R^4$ are as defined above;

a. in an aprotic solvent, compound IV-1 is reacted with a nitrating reagent under the action of a catalyst to form compound IV-2;

b. in a protic or an aprotic solvent or a mixed solvent thereof, compound IV-2 is reduced by a metal reducing agent under the action of an organic or inorganic acid to form compound I-1;

or the method for preparing compound I-1 comprises the steps:

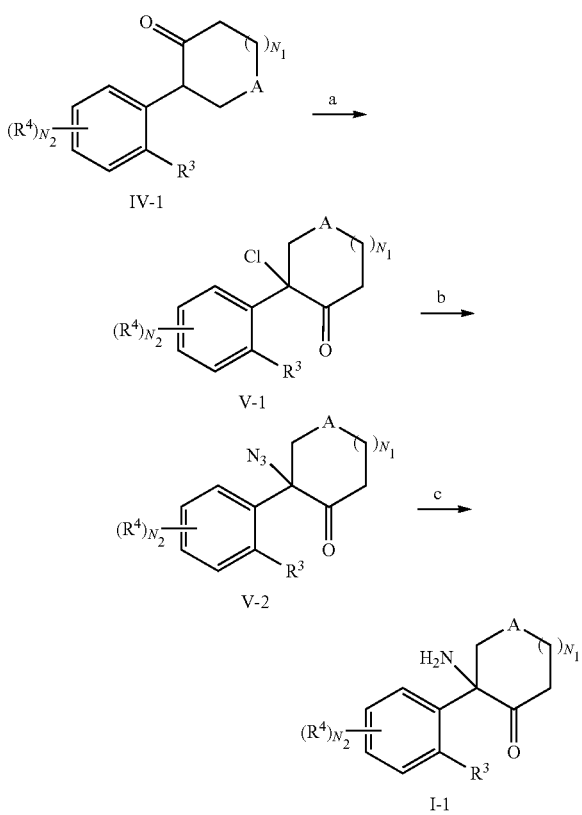

IV-1

V-1

V-2

I-1 wherein, in each formula, A, $N_1$, $N_2$, $R^3$ and $R^4$ are as defined above;

a. in an aprotic solvent, compound IV-1 is reacted with a halogenated reagent to form compound V-1;

b. in an aprotic solvent, compound V-1 is reacted with an azide reagent to form compound V-2;

c. in a protic or an aprotic solvent or a mixed solvent thereof, compound V-2 is reacted in the presence of a catalyst and a hydrogen source to form compound I-1.

In another preferred embodiment, the method for preparing compound IV-1 comprises the steps:

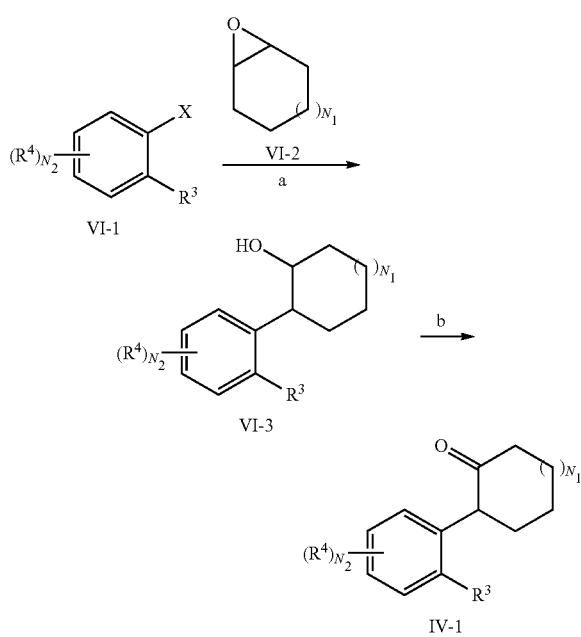

wherein, in each formula, X can be H, Br or I; $N_1$, $N_2$, $R^3$ and $R^4$ are as defined above;

a. in an aprotic solvent, compound VI-1 is reacted with epoxy compound VI-2 to form compound VI-3;

b. in an aprotic solvent, the compound VI-3 is oxidized by an oxidizing agent to form the compound IV-1;

or the method for preparing compound IV-1 comprises the steps:

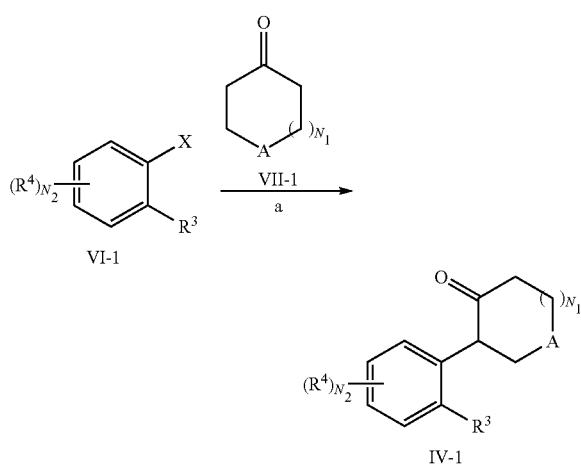

wherein, in each formula, X can be Br or I; A, $N_1$, $N_2$, $R^3$ and $R^4$ are as defined above;

a. in an aprotic solvent, compound VI-1 is reacted with cyclic ketone compound VII-1 under catalysis of a metal-containing catalyst and a phosphine-containing ligand to form compound IV-1.

It should be understood that in the present invention, any of the technical features specifically described above and below (such as in the Examples) can be combined with each other, which will not redundantly be described one by one herein.

DETAILED DESCRIPTION OF THE INVENTION

After extensive experiments and researches on drug design, chemical synthesis and structural testing, the inventors of the present application have synthesized a series of compounds having a structural general formula as shown in (I) with novel structures, which have passed the most classic antidepressant pharmacological experiment—mouse forced swimming experiment, metabolic research and other scientific experiments. It is found for the first time that the compounds represented by the following general formula (I) have fast onset, strong and long-lasting antidepressant activity, and excellent druggability, so that they are particularly suitable as antidepressants useful to treat depression and nervous system related diseases. The inventors have completed the present invention on this basis.

Terms

As used herein, $C_1$-$C_6$ alkyl refers to a straight or branched alkyl having 1 to 6 carbon atoms. Similarly, $C_1$-$C_4$ alkyl refers to a straight or branched alkyl having 1 to 4 carbon atoms, for example, methyl, ethyl, n-propyl, isopropyl, n-butyl, isobutyl, tert-butyl and similar groups.

As used herein, $C_1$-$C_6$ alkoxy refers to a straight or branched alkoxy having 1 to 6 carbon atoms, for example, methoxy, ethoxy, n-propoxy, isopropoxy, n-butoxy, isobutoxy, tert-butoxy and similar groups.

As used herein, $C_1$-$C_4$ ester refers to —$C_1$-$C_4$ alkyl-(C═O)—O— or —(C═O)—O—$C_1$-$C_4$ alkyl-.

As used herein, $C_1$-$C_4$ amide refers to —$C_1$-$C_4$ alkyl-(C═O)—NH— or —(C═O)—NH—$C_1$-$C_4$ alkyl-.

As used herein, "halo" refers to substituted with one or more halogen (fluorine, chlorine, bromine, or iodine) atoms.

Compound of the Invention

The compound of the present invention is a compound represented by the general formula (I), and also includes its tautomers, enantiomers, diastereomers, racemates or mixtures, or its pharmaceutically acceptable salt.

It should be understood that in the present invention, the configuration of the compound can be selected from the group consisting of: R, S and (R, S).

The compound of the present invention can be prepared by the following method, but the conditions of the method, such as reactants, solvent, acid, base, amount of compound used, reaction temperature, reaction time, etc., are not limited to the following description. Various synthetic methods described in this specification or known to those skilled in the art can also be optionally combined to conveniently prepare the compound of the present invention.

The compound of the general formula (I) of the present invention can be prepared according to the method of the preferred reaction formula (1), reaction formula (2) or reaction formula (3).

Reaction formula (1)

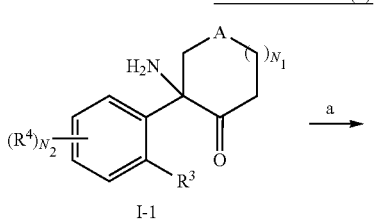

-continued

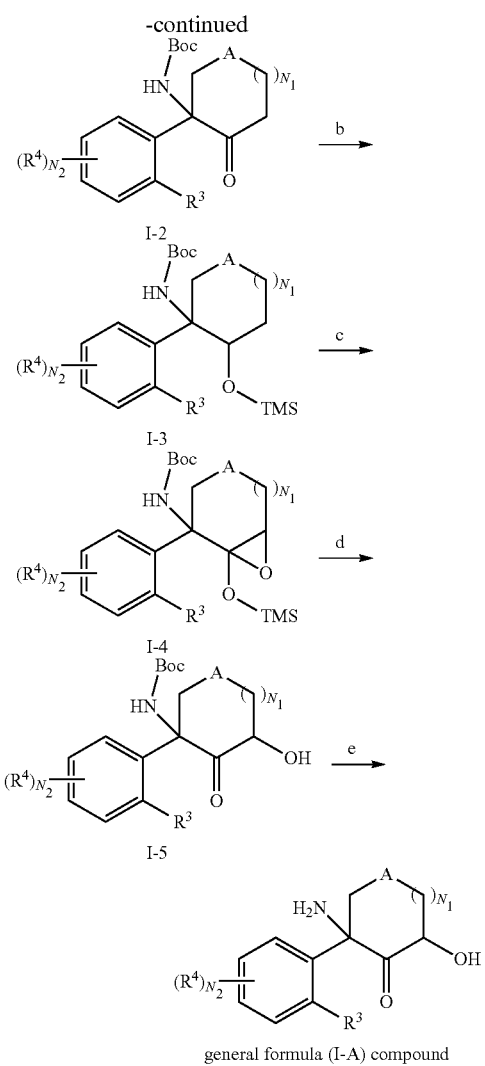

wherein, A, $N_1$, $N_2$, $R^3$ and $R^4$ are as defined above.

a. compound I-1 is reacted with di-tert-butyl dicarbonate in the presence of an inorganic or organic base in a protic solvent or an aprotic solvent or a mixed solvent thereof at room temperature to 100° C. to obtain the compound I-2. The inorganic base can be sodium carbonate, potassium carbonate, cesium carbonate, sodium hydroxide, potassium hydroxide; the organic base can be triethylamine, imidazole, 4-dimethylaminopyridine, 1,8-diazabicyclo[5.4.0]undec-7-ene; and the protic solvent or aprotic solvent can be methanol, ethanol, water, toluene, tetrahydrofuran, ethyl acetate, dichloromethane, 1,4-dioxane, N,N-dimethylformamide.

b. the compound I-2 is reacted with trimethylchlorosilane under the protection of inert gas in an aprotic solvent at −80° C. to room temperature and in the presence of an organic base to obtain compound I-3. The aprotic solvent can be tetrahydrofuran, 2-methyltetrahydrofuran; the organic base can be lithium diisopropylamide, lithium hexamethyldisilazide, potassium hexamethyldisilazide, butyl lithium; and the inert gas can be nitrogen or argon.

c. compound I-3 is oxidized with an oxidant in an aprotic solvent under the condition of −40° C. to room temperature to obtain compound I-4. The aprotic solvent can be tetrahydrofuran, 2-methyltetrahydrofuran, dichloromethane, chloroform; and the oxidant can be m-chloroperoxybenzoic acid, hydrogen peroxide.

d. a trimethylsilyl protecting group of compound I-4 is removed by a fluorine-containing reagent in an aprotic solvent at 0° C. to room temperature to obtain compound I-5. The aprotic solvent can be tetrahydrofuran, 2-methyltetrahydrofuran, dichloromethane, chloroform; and the fluorine-containing reagent can be tetrabutylammonium fluoride.

e. a tert-butoxycarbonyl protective group of compound I-5 is removed under the action of an organic acid or inorganic acid in polar aprotic solvent at 0° C. to room temperature to obtain compound I-A. The organic acid or inorganic acid may be hydrochloric acid, sulfuric acid, hydrobromic acid, trifluoroacetic acid; and the polar aprotic solvent may be tetrahydrofuran or dichloromethane.

Reaction formula (2)

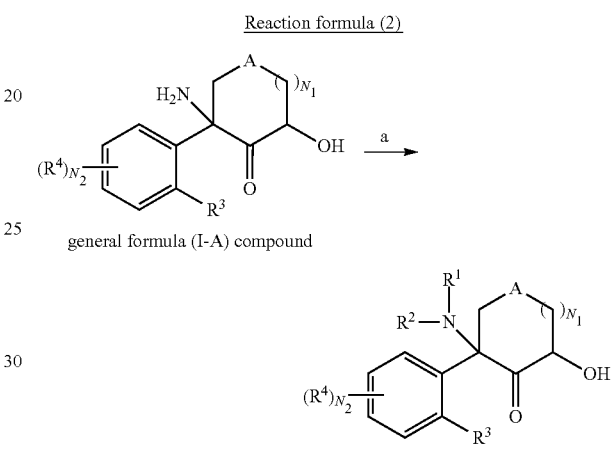

wherein, A, $N_1$, $N_2$, $R^3$ and $R^4$ are as defined above, $R^1$ and $R^2$ are each independently hydrogen or $C_1$-$C_6$ alkyl, and the above-mentioned alkyl can be independently substituted by 1 to 2 substituents selected from the group consisting of halogen, hydroxyl, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide.

a. Compound I-A is reacted with aldehyde in a protic or an aprotic solvent or a mixed solvent thereof in the presence of a catalyst and a hydrogen source to obtain compound I-B with substituents on the amino. The aldehyde can be $C_1$-$C_6$ alkylaldehyde, benzaldehyde, or p-methoxybenzaldehyde; the protic or aprotic solvent can be methanol, ethanol, water, tetrahydrofuran, ethyl acetate, dichloromethane, 1,4-dioxane; and the catalyst can be Pd/C, Pd(OH)$_2$/C; the hydrogen source can be hydrogen.

Reaction formula (3)

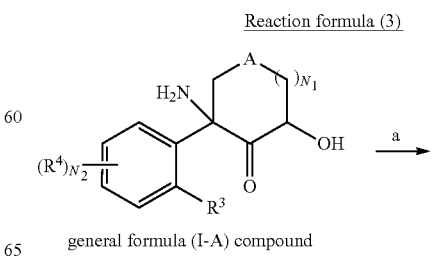

-continued

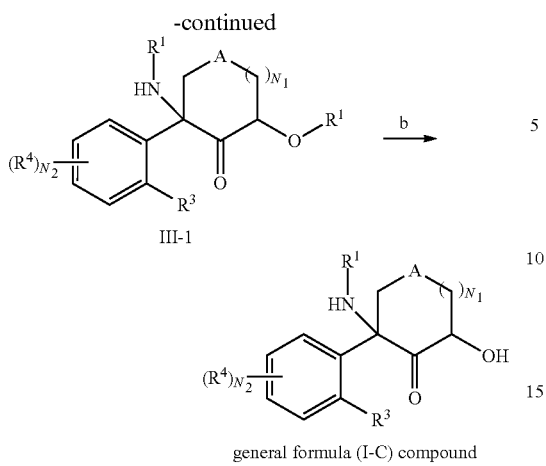

III-1

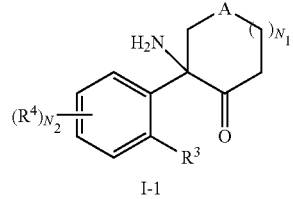

general formula (I-C) compound wherein, A, $N_1$, $N_2$, $R^3$ and $R^4$ are as defined above, $R^1$ is $C_1$-$C_6$ alkylcarbonyl, and the above-mentioned alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;

a. the compound I-A is reacted with acid chloride or acid anhydride in an aprotic solvent at 0° C. to room temperature under organic base conditions to obtain compound III-1. The aprotic solvent can be tetrahydrofuran, 2-methyltetrahydrofuran, dichloromethane, chloroform, ethyl acetate; the organic base can be triethylamine, imidazole, 4-dimethylaminopyridine, 1,8-diazabicyclo[5.4.0]undec-7-ene, pyridine; the acid chloride can be $C_2$-$C_6$ alkyl acid chloride; and the acid anhydride can be $C_4$-$C_{12}$ alkyl anhydride.

b. compound I-C is obtained from compound III-1 in a protic or an aprotic solvent or its mixed solvent under the action of an organic or inorganic base. The protic or aprotic solvent can be methanol, ethanol, water, tetrahydrofuran, dioxane; and the organic or inorganic base can be sodium hydroxide, potassium hydroxide, sodium carbonate, potassium carbonate, sodium bicarbonate, ammonia, ammonia methanol solution.

The intermediate I-1 can be prepared according to the method of reaction formula (4) or reaction formula (5).

Reaction formula (4)

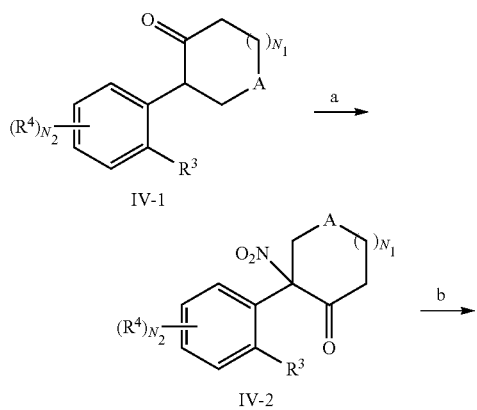

I-1 wherein, A, $N_1$, $N_2$, $R^3$ and $R^4$ are as defined above.

a. the compound IV-1 is reacted with the nitrating reagent in an aprotic solvent under the protection of an inert gas and under the conditions of 50° C. to 130° C. under the action of a catalyst to obtain compound IV-2. The nitrating reagent can be cerium ammonium nitrate or nitric acid; the catalyst can be copper acetate; the aprotic solvent can be 1,2-dichloroethane, toluene, acetonitrile; and the inert gas can be nitrogen or argon.

b. compound IV-2 is reduced by a metal reducing agent in a protic or an aprotic solvent or its mixed solvent under the action of an organic or inorganic acid to obtain compound I-1. The protic or aprotic solvent can be methanol, ethanol, tetrahydrofuran, ethyl acetate, dioxane. The organic acid or inorganic acid may be acetic acid, hydrochloric acid, or trifluoroacetic acid; and the metal reducing agent may be zinc powder or iron powder.

Reaction formula (5)

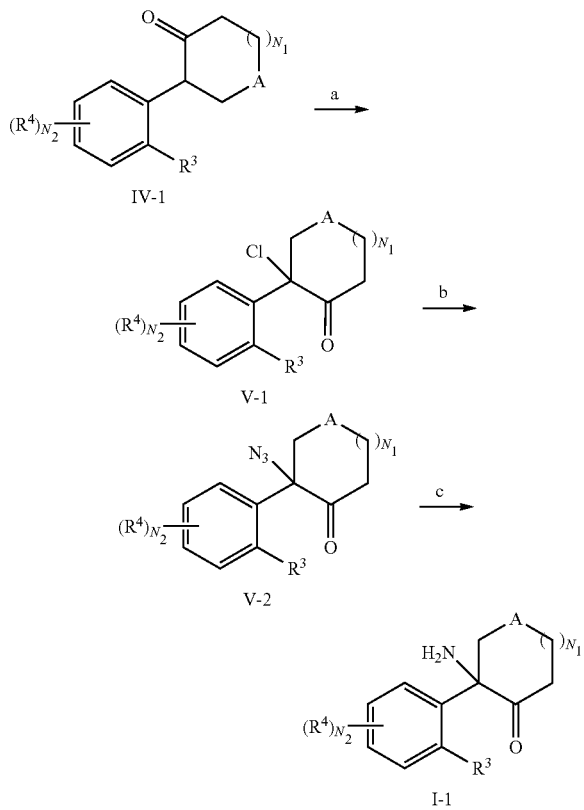

wherein, A, $N_1$, $N_2$, $R^3$ and $R^4$ are as defined above.

a. compound IV-1 is reacted with a halogenated reagent under the action of a free radical initiator with an acid or without an acid in an aprotic solvent at 50° C. to 120° C. to obtain compound V-1. The halogenated reagent can be N-bromosuccinimide, N-chlorosuccinimide, liquid bromine; the free radical initiator can be azobisisobutyronitrile, benzoyl peroxide; the aprotic solvent can be carbon tetrachloride; when the reaction system has an added acid, the acid can be trifluoroacetic acid, hydrochloric acid, acetic acid.

b. compound V-1 is reacted with an azide reagent in an aprotic solvent at room temperature to 80° C. to obtain compound V-2. The aprotic solvent can be N,N-dimethylformamide, acetonitrile, or tetrahydrofuran; and the azide reagent can be sodium azide or trimethylsilyl azide.

c. compound V-2 is reacted in a protic or an aprotic solvent or a mixed solvent thereof in the presence of a catalyst and a hydrogen source to obtain compound I-1. The protic or aprotic solvent can be methanol, ethanol, water, tetrahydrofuran, ethyl acetate, dichloromethane, 1,4-dioxane; the catalyst can be Pd/C, Pd(OH)$_2$/C; and the hydrogen source can be hydrogen.

The intermediate IV-1 can be prepared according to the method of reaction formula (6) or reaction formula (7).

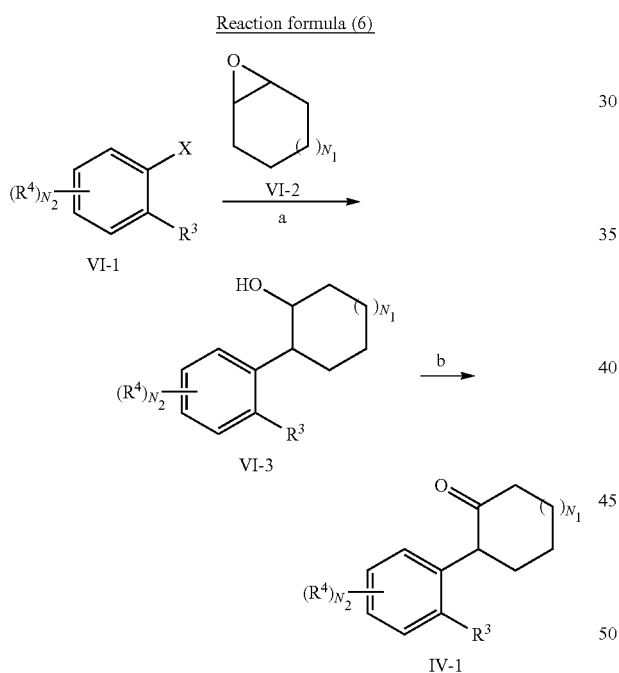

wherein X can be H, Br or I; and $N_1$, $N_2$, $R^3$ and $R^4$ are as defined above.

a. compound VI-1 is reacted with an epoxy compound VI-2 under the action of an organic base and a Lewis acid, under the protection of an inert gas at −100° C. to room temperature in an aprotic solvent to obtain compound VI-3. The aprotic solvent can be tetrahydrofuran, 2-methyltetrahydrofuran; the organic base can be butyl lithium; the Lewis acid can be boron trifluoride ether, titanium tetrachloride; and the inert gas can be nitrogen or argon.

b. compound VI-3 is oxidized by an oxidizing agent in an aprotic solvent to obtain compound IV-1. The aprotic solvent can be dichloromethane, chloroform, tetrahydrofuran, ethyl acetate; and the oxidizing agent can be Dess-Martin oxidant, pyridine chlorochromate.

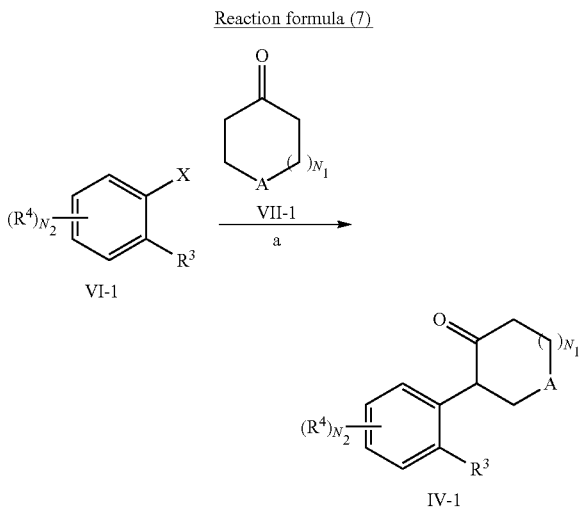

wherein X can be Br or I; A, $N_1$, $N_2$, $R^3$ and $R^4$ are as defined above.

a. Compound VI-1 is reacted with a cyclic ketone compound VII-1 under the catalysis of a metal-containing palladium catalyst and a phosphine-containing ligand in basic condition and in an aprotic solvent under the protection of an inert gas at room temperature to 140° C. for 2-48 hours to obtain compound IV-1. The metal-containing palladium catalyst can be palladium acetate [Pd(OAc)$_2$], tris(dibenzylideneacetone)dipalladium [Pd$_2$(dba)$_3$], bis(dibenzylideneacetone)palladium [Pd(dba)$_2$]; the phosphine-containing ligand can be 4,5-bis(diphenylphosphine)-9,9-dimethylxanthene [Xantphos], (±)-2,2'-bis-(diphenylphosphino)-1,1'-binaphthalene [BINAP] or 1,1'-bis(diphenylphosphino)ferrocene [dppf]; the base used in the basic condition can be cesium carbonate, sodium tert-butoxide, potassium phosphate, potassium carbonate; the aprotic solvent can be 1,4-dioxane, toluene, dimethylformamide; and the inert gas can be nitrogen or argon.

The single configuration of compound I-1 can be resolved by the following methods:

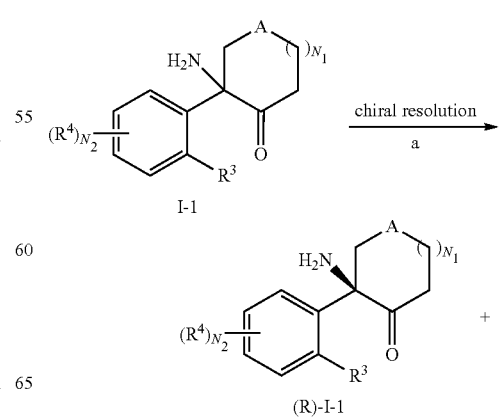

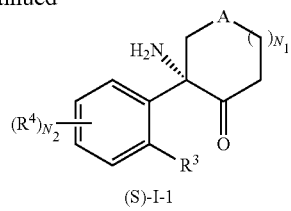

(S)-I-1 wherein, $A$, $N_1$, $N_2$, $R^3$ and $R^4$ are as defined above.

a. Compound I-1 and a chiral acid of a single configuration form a salt in a protic or an aprotic solvent or a mixed solvent thereof, and the resulted salt is recrystallized multiple times in a protic or an aprotic solvent or a mixed solvent thereof to obtain a chiral acid salt of the compound I-1 having a single configuration. The obtained chiral acid salt of the compound I-1 having a single configuration is freed with a base to obtain compound I-1 having a single configuration. The single-configuration chiral acid may be a single-configuration tartaric acid, dibenzoyl tartaric acid, camphorsulfonic acid, ibuprofen, or mandelic acid; and the protic or aprotic solvent may be ethyl acetate, dichloromethane, chloroform, tetrahydrofuran, n-hexane, n-heptane, cyclohexane, petroleum ether, 1,4-dioxane, acetone, 2-butanone, toluene, N,N-dimethylformamide, dimethyl sulfoxide, water, methanol, ethanol, isopropanol.

The corresponding other compound I-1 having a single configuration can be obtained in a similar way by using the corresponding other single-configuration chiral acid.

The pharmaceutically acceptable salt is a pharmaceutically acceptable salt of a compound of the formula (I) (for example, a compound of the formula (I-A) or a compound of the formula (I-B)) with an inorganic acid or an organic acid or the like. Preferably, the inorganic acid suitable for salt formation is hydrochloric acid, hydrobromic acid, hydrofluoric acid, sulfuric acid, trifluoroacetic acid, nitric acid, or phosphoric acid; the organic acid suitable for salt formation is formic acid, acetic acid, propionic acid, oxalic acid, benzoic acid, malonic acid, succinic acid, fumaric acid, maleic acid, lactic acid, malic acid, tartaric acid, citric acid, picric acid, methanesulfonic acid, ethanesulfonic acid, benzenesulfonic acid, glutamic acid, aspartic acid.

The pharmaceutically acceptable salt of the compound I can be prepared by the following method: a compound of formula I (such as compound I-A or I-B) or general formula I-5 is reacted with various organic or inorganic acids in an aprotic solvent or a protic solvent or a mixed solvent thereof to obtain the corresponding organic acid salt or inorganic acid salt of the compound I.

The aprotic solvent or protic solvent can be methanol, ethanol, water, dichloromethane, tetrahydrofuran, ethyl acetate, dioxane; the organic acid or inorganic acid can be hydrochloric acid, hydrobromic acid, hydrofluoric acid, sulfuric acid, trifluoroacetic acid, nitric acid, phosphoric acid, formic acid, acetic acid, propionic acid, oxalic acid, benzoic acid, malonic acid, succinic acid, fumaric acid, maleic acid, lactic acid, malic acid, tartaric acid, citric acid, picric acid, methanesulfonic acid, ethanesulfonic acid, benzenesulfonic acid, aspartic acid, or glutamic acid.

The Main Advantages of the Invention are as Follows

The present invention provides a class of compounds with novel structure, rapid and long-lasting antidepressant activity and good druggability.

The compounds of the present invention have better metabolic properties, greatly prolonged half-life, reduced clearance rate, significantly increased plasma exposure and brain distribution, and are expected to be developed as a new antidepressant drug with fast onset and long-lasting efficacy.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless otherwise stated, percentages and parts are percentages by weight and parts by weight.

In all the examples, $^1$H-NMR was recorded with a Varian Mercury 300 or Varian Mercury 400 nuclear magnetic resonance instrument, and the chemical shift was expressed as δ (ppm); silica gel was used for separation, and it was 200-300 mesh if not specified. The ratio of the eluent was volume ratio.

PREPARATION EXAMPLES

Example 1: Preparation of 2-amino-6-hydroxy-2-o-tolylcyclohexane-1-one (Compound 1)

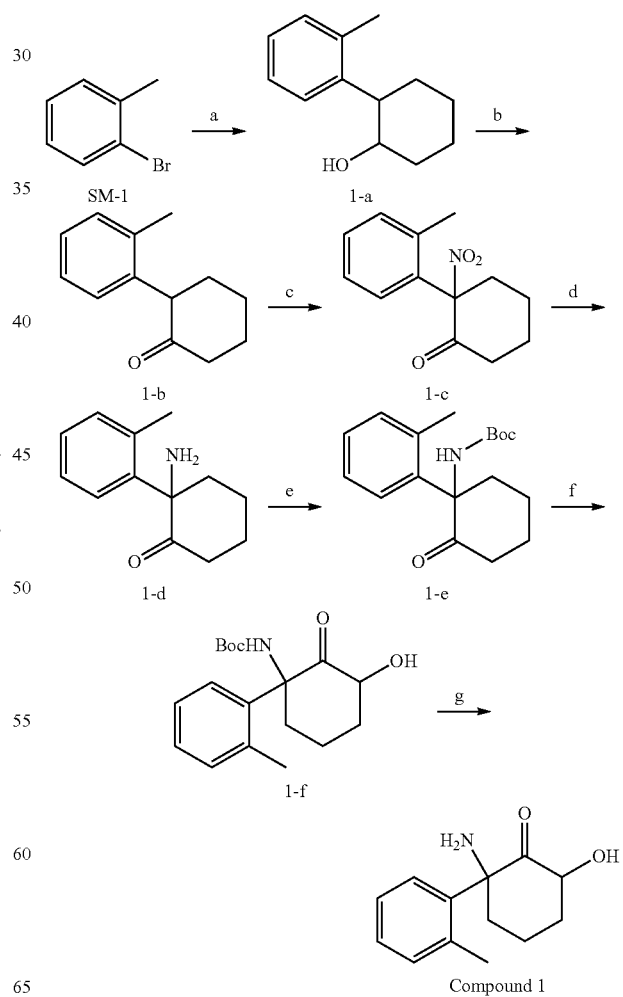

Step a: Preparation of 1-a

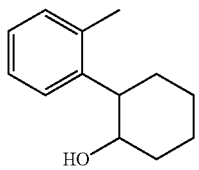

2-bromotoluene (13 g, 76 mmol) was dissolved in dry THF (120 mL) under Ar protection, cooled down to −90° C. with liquid nitrogen and ethanol, and n-BuLi (31.92 mL, 79.8 mmol) was added dropwise in 30 minutes. The mixture was stirred at −90° C. for 30 min and then epoxycyclohexane (8.49 mL, 83.6 mmol) and boron trifluoride ether solution (10.55 mL, 83.6 mmol) were added dropwise, and it was continued to stir in liquid nitrogen and ethanol for 1.5 hours. The reaction was monitored by TLC (EA:PE=1:5). After the reaction was completed, the reaction was quenched with saturated NH$_4$Cl solution (100 mL), diluted with H$_2$O (150 ml), and extracted with ethyl acetate (150 mL×3), the organic phases were combined, washed with saturated NaCl solution, dried with anhydrous sodium sulfate, filtered and the filtrate was distilled to remove the solvent of low boiling point, and separated by column chromatography (EA:PE=1:30-1:5), to obtain 8.25 g of yellow oil, yield: 57.1%. $^1$H NMR (400 MHz, CDCl$_3$) δ 7.27 (s, 1H), 7.22 (d, J=7.6 Hz, 1H), 7.18 (d, J=8.2 Hz, 1H), 7.12 (dd, J=10.3, 4.2 Hz, 1H), 3.80 (td, J=9.8, 4.4 Hz, 1H), 2.77 (td, J=11.5, 3.4 Hz, 1H), 2.37 (s, 3H), 2.14 (dd, J=8.4, 3.9 Hz, 1H), 1.87 (dd, J=6.0, 3.1 Hz, 1H), 1.82-1.72 (m, 2H), 1.61 (d, J=7.4 Hz, 1H), 1.49-1.40 (m, 3H), 1.40-1.34 (m, 1H). MS (M+Na)$^+$: 213.

Step b: Preparation of 1-b

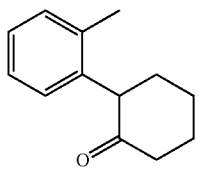

Compound 1-a (5.6 g, 29.45 mmol) was dissolved in DCM (30 mL), cooled in an ice bath, Dess-Martin oxidant (16.24 g, 38.29 mmol) was added in batches. After the addition, the mixture was heated to room temperature and stirred for 3 hours. After the reaction was completed, saturated sodium sulfite solution (100 mL) was added to quench the reaction, then saturated NaHCO$_3$ solution (100 mL) was added to neutralize, and the mixture was extracted with dichloromethane (100 mL×3). The organic phases were combined, washed with saturated NaCl solution, dried with anhydrous sodium sulfate, and filtered. The filtrate was rotary evaporated to remove the solvent of low boiling point, and separated by column chromatography (EA:PE=10:90). 4.49 g of yellow oily was obtained, yield: 81.1%. $^1$H NMR (400 MHz, CDCl$_3$) δ 7.24-7.10 (m, 4H), 3.79 (dd, J=12.9, 5.3 Hz, 1H), 2.54 (ddd, J=18.8, 13.2, 8.5 Hz, 2H), 2.31-2.16 (m, 5H), 2.06 (d, J=8.6 Hz, 2H), 1.92-1.79 (m, 2H). MS (M+Na)$^+$: 211.

Step c: Preparation of 1-c

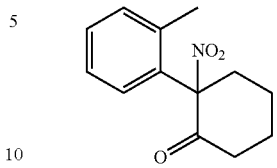

Compound 1-b (2.17 g, 11.52 mmol) was dissolved in 1,2-dichloroethane (30 mL), cerium ammonium nitrate (12.65 g, 23.0, 7 mmol) and copper acetate (419 mg, 2.30, 7 mmol) were added under Ar protection, and the mixture was stirred in oil bath at 80° C. for 7 hours. After the reaction was completed, the mixture was filtered, and the filtrate was subjected to column chromatography (EA:PE=1:10) to obtain 1.375 g of yellow oil, yield: 51.1%. $^1$H NMR (400 MHz, CDCl$_3$) δ 7.38-7.33 (m, 2H), 7.29 (t, J=7.0 Hz, 2H), 3.15-3.06 (m, 1H), 2.89 (ddd, J=14.7, 11.5, 3.5 Hz, 1H), 2.79-2.70 (m, 1H), 2.59 (ddd, J=13.0, 10.8, 6.1 Hz, 1H), 2.29 (s, 3H), 2.02-1.86 (m, 3H), 1.75 (ddt, J=14.7, 11.1, 5.5 Hz, 1H). MS (M+Na)$^+$: 256.

Step d: Preparation of 1-d

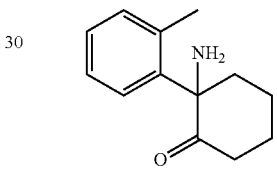

Compound 1-c (1.37 g, 5.87 mmol) was dissolved in acetic acid (6 mL) and zinc powder (3.08 g, 47.04 mmol) was added under Ar protection, and the mixture was stirred overnight at room temperature. The reaction mixture was filtered, the low boiling solvent was evaporated off under reduced pressure, and the residue was dissolved in ethyl acetate (10 mL). Saturated sodium bicarbonate solution was used to adjust PH to be >7, and the mixture was extracted with ethyl acetate (10 mL×3). The organic phases were combined, washed with saturated NaCl solution, dried with anhydrous sodium sulfate, and filtered. The filtrate was rotary evaporated to remove the low-boiling solvent and then was subjected to column chromatography (EA:PE=30:70) to obtain 708 mg of yellow oil, yield: 58.0%. $^1$H NMR (400 MHz, CDCl$_3$) δ 7.55 (d, J=7.5 Hz, 1H), 7.24 (dd, J=5.3, 1.4 Hz, 1H), 7.21 (dd, J=7.2, 1.2 Hz, 1H), 7.16 (d, J=7.3 Hz, 1H), 2.94-2.86 (m, 1H), 2.49-2.34 (m, 2H), 2.17 (s, 3H), 2.00 (s, 3H), 1.79 (dddd, J=17.0, 13.1, 6.5, 2.8 Hz, 3H), 1.67-1.59 (m, 1H). MS (M+H)$^+$: 204.

Step e: Preparation of 1-e

The compound 1-d (700 mg, 3.44 mmol) was dissolved in toluene (5 mL), and K$_2$CO$_3$ (1.43 g, 10.35 mmol) and Boc anhydride (1.13 g, 5.175 mmol) were added, and the mixture was stirred at 90° C. for 3 hour. H$_2$O (20 mL) was added. The mixture was extracted with ethyl acetate (15 mL×3), the organic phases were combined, washed with saturated NaCl solution, dried with anhydrous sodium sulfate, and filtered. The filtrate was rotary evaporated to remove low boiling solvents and then was subjected to column chromatography (EA:PE=10:90) to obtain 935 mg of colorless oil, yield: 89.5%. $^1$H NMR (400 MHz, CDCl$_3$) δ 7.75 (s, 1H), 7.30 (d, J=11.0 Hz, 1H), 7.21 (t, J=7.2 Hz, 1H), 7.11 (d, J=7.6 Hz, 1H), 6.54 (s, 1H), 3.84 (s, 1H), 2.37-2.26 (m, 2H), 2.10-2.02 (m, 4H), 1.96 (dd, J=25.3, 11.6 Hz, 1H), 1.80-1.72 (m, 2H), 1.68 (d, J=16.4 Hz, 1H), 1.31 (s, 9H). MS (M+Na)$^+$: 326.

Step f: Preparation of 1-f

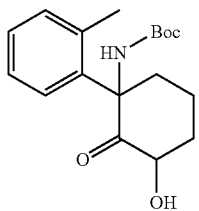 [SMILES: Cc1ccccc1C1(NC(=O)OC(C)(C)C)CCCC(O)C1=O]

Step 1: Under Ar gas protection, Compound 1-e (930 mg, 3.07 mmol) was dissolved in dry THF (6 mL), cooled down to −78° C., and LDA (4.6 mL, 9.21 mmol) was added dropwise. After the addition, the mixture was stirred at −78° C. for 30 min, then TMSCl (1.17 mL, 9.21 mmol) was added. The mixture was continuously stirred for 30 min and then warmed to room temperature to react for 1 hour. Saturated NH$_4$Cl solution (20 mL) was added to quench the reaction. The mixture was extracted with ethyl acetate (15 mL×3), and the organic phases were combined, washed with saturated NaCl solution, dried with anhydrous sodium sulfate, and filtered. the solvent was evaporated off under reduced pressure to obtain a crude product.

Step 2: Under Ar protection, the obtained crude product was dissolved in DCM (5 mL), cool to −20° C., and m-CPBA (1.25 g, 6.14 mmol) was added. The mixture was stirred and reacted at −20° C. for 30 min and then warmed to room temperature and stirred for 1 hour. After the reaction was completed, saturated Na$_2$SO$_3$ solution (20 mL) and saturated NaHCO$_3$ solution (20 mL) were added, the mixture was extracted with DCM (20 mL×3), the organic phases were combined, and the solvent was removed via rotary evaporation to obtain a crude product.

Step 3: The crude product was dissolved in THF (3 mL), cooled in an ice bath, and a solution of TBAF (1.16 g, 3.684 mmol) dissolved in THF (2 mL) was added dropwise. After the reaction was completed, saturated NaHCO$_3$ solution (15 mL) was added to quench the reaction, and the mixture was extracted with ethyl acetate (10 mL×3). The organic phases were combined, washed with saturated NaCl solution, dried with anhydrous sodium sulfate, filtered, and the filtrate was subjected to column chromatography (EA:PE=20:80) to obtain 634 mg of yellow oil, yield: 64.7%. $^1$H NMR (400 MHz, CDCl$_3$) δ 7.68 (s, 1H), 7.29 (d, J=7.3 Hz, 1H), 7.22 (td, J=7.3, 1.1 Hz, 1H), 7.12 (d, J=7.7 Hz, 1H), 6.47 (s, 1H), 4.08 (dd, J=11.9, 6.7 Hz, 1H), 3.85 (s, 1H), 3.32 (s, 1H), 2.41-2.34 (m, 1H), 2.06 (s, 3H), 1.92 (dd, J=24.9, 9.9 Hz, 1H), 1.72 (ddd, J=24.5, 14.3, 8.6 Hz, 2H), 1.51 (ddd, J=25.6, 12.4, 4.7 Hz, 1H), 1.31 (s, 9H). MS (M+Na)$^+$: 342.

Step g: Preparation of Compound 1

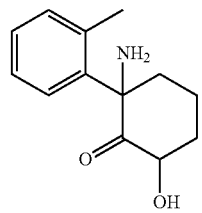 [SMILES: Cc1ccccc1C1(N)CCCC(O)C1=O]

Compound 1-f (140 mg, 0.44 mmol) was dissolved in DCM (3 mL), 4M HCl in 1,4-dioxane (1 mL) was added. The mixture was stirred at room temperature for 1.5 hours, the solvent was rotary evaporated off, the residue was neutralized with saturated NaHCO$_3$ (10 ml), and ethyl acetate (10 mL×3) was added for extraction. The organic phases were combined, washed with saturated NaCl solution, and dried with anhydrous sodium sulfate, filtrated. The filtrate was subjected to column chromatography (DCM/MeOH=20:1) to obtain 82 mg of colorless oil, yield: 85.4%. $^1$H NMR (400 MHz, CDCl$_3$) δ 7.50 (d, J=7.5 Hz, 1H), 7.30-7.21 (m, 2H), 7.16 (d, J=7.1 Hz, 1H), 4.16 (dd, J=11.7, 6.9 Hz, 1H), 3.00-2.92 (m, 1H), 2.34 (dtd, J=9.6, 6.6, 3.3 Hz, 1H), 1.73 (tdd, J=9.7, 6.6, 3.7 Hz, 2H), 1.64-1.53 (m, 1H), 1.45 (ddd, J=24.9, 12.4, 5.1 Hz, 1H). MS(M+H)$^+$: 220.1

Example 2: Preparation of 2-amino-6-hydroxy-2-m-tolylcyclohexane-1-one (Compound 2)

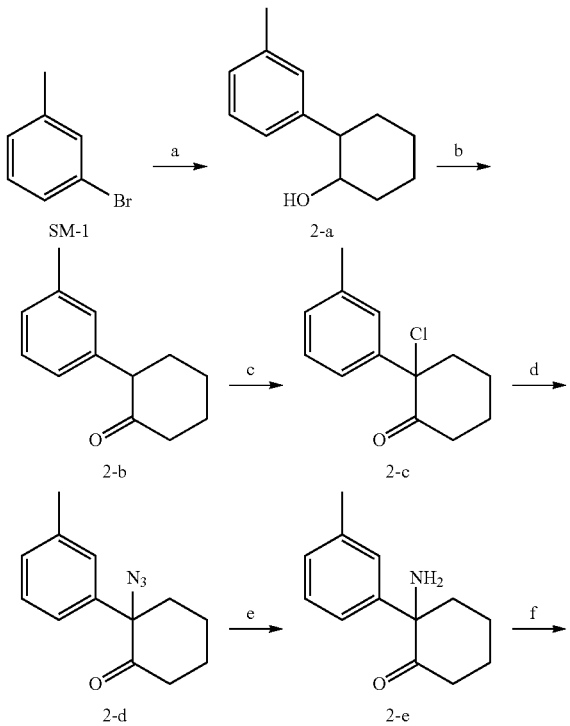

-continued

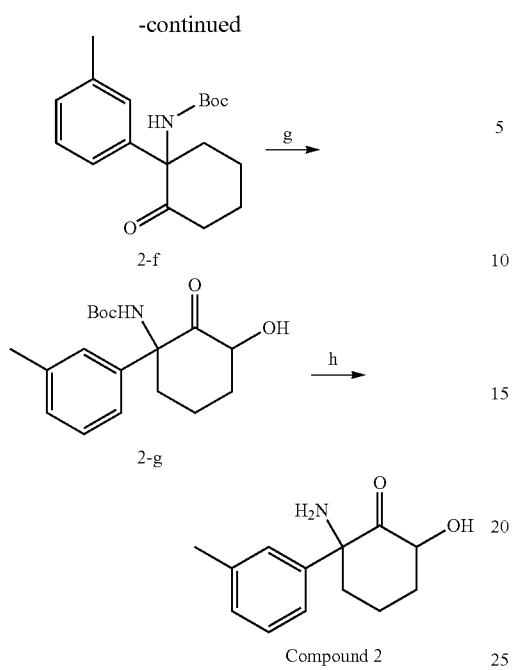

(dd, J=12.1, 5.4 Hz, 1H), 2.56-2.43 (m, 2H), 2.35 (s, 3H), 2.30-2.22 (m, 1H), 2.19-2.12 (m, 1H), 2.09-1.95 (m, 2H)), 1.84 (dd, J=18.4, 7.2 Hz, 2H). MS(M+Na)$^+$: 211.1

Step c: Preparation of 2-c

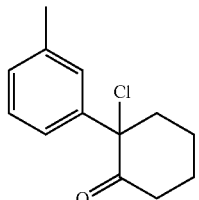

Under Ar protection, Compound 2-b (1.33 g, 7.06 mmol) was dissolved in CCl$_4$ (15 mL), NCS (1.23 g, 9.21 mmol), AIBN (116 mg, 0.71 mmol) and TFA (3 drops) were added, and the mixture was stirred at 60° C. for 16 h. After the reaction was completed, the mixture was filtered, and the filtrate was subjected to column chromatography (PE:EA=10:1) to obtain 1.2 g of pale yellow oily liquid, yield: 76.3%. $^1$H NMR (400 MHz, CDCl$_3$) δ 7.30-7.24 (m, 2H), 7.19 (t, J=9.3 Hz, 2H), 2.98 (ddd, J=14.5, 6.5, 3.1 Hz, 1H), 2.86-2.78 (m, 1H), 2.47-2.39 (m, 2H), 2.37 (s, 3H), 2.00 (ddd, J=10.9, 9.4, 5.9 Hz, 2H), 1.93-1.86 (m, 2H). MS(M+Na)$^+$: 245.1

Step a: Preparation of 2-a

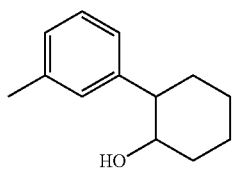

Using m-bromotoluene (13.2 g, 77.17 mmol) and epoxy-cyclohexane (8.3 g, 84.56 mmol) as raw materials, the method described in step a in Example 1 was conducted accordingly to obtain 10.95 g of yellow oily liquid, yield: 74.6%. $^1$H NMR (400 MHz, CDCl$_3$) δ 7.23 (t, J=7.4 Hz, 1H), 7.06 (d, J=7.9 Hz, 3H), 3.71-3.60 (m, 1H), 2.41 (dd, J=12.3, 3.3 Hz, 1H), 2.36 (d, J=5.3 Hz, 3H), 2.12 (dd, J=8.1, 3.6 Hz, 1H), 1.90-1.81 (m, 2H), 1.80-1.72 (m, 1H), 1.47-1.30 (m, 4H). MS(M+Na)$^+$: 213.1

Step d: Preparation of 2-d

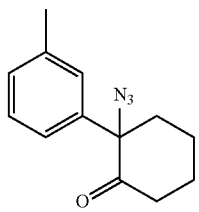

Step b: Preparation of 2-b

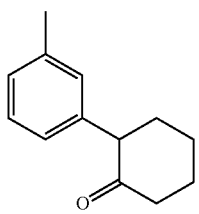

Using the compound 2-a (1.53 g, 8.04 mmol) as a raw material, the method described in step b in Example 1 was conducted accordingly to obtain 1.33 g of yellow oily liquid, yield: 88.1%. $^1$H NMR (400 MHz, CDCl$_3$) δ 7.24 (t, J=7.5 Hz, 1H), 7.08 (d, J=7.4 Hz, 1H), 6.95 (d, J=7.7 Hz, 2H), 3.58

Compound 2-c (955 mg, 4.29 mmol) was dissolved in DMSO (10 mL), NaN$_3$ (559 mg, 8.6 mmol) was added, and the mixture was stirred at room temperature for 3 hours. Water (50 mL) was added, the mixture was extracted with ethyl acetate (30 mL×3), the organic phases were combined, washed with saturated NaCl solution, dried with anhydrous sodium sulfate, and filtered. The filtrate was subjected to column chromatography (PE:EA=20:1) to obtain 707 mg of pale yellow oil, yield: 71.9%. $^1$H NMR (400 MHz, CDCl$_3$) δ 7.34 (t, J=7.6 Hz, 1H), 7.21 (d, J=7.5 Hz, 1H), 7.10 (d, J=9.4 Hz, 2H), 2.85-2.76 (m, 1H), 2.58-2.48 (m, 1H), 2.45-2.40 (m, 1H), 2.39 (s, 3H), 2.00-1.89 (m, 2H), 1.88-1.81 (m, 1H), 1.78-1.64 (m, 2H). MS (M+Na)$^+$: 252.1

Step e: Preparation of 2-e

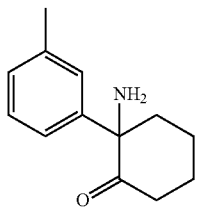

Compound 2-d (707 mg, 3.08 mmol) was dissolved in methanol (8 mL), Pd(OH)$_2$ (70 mg) was added. The atmosphere was replaced with H$_2$. The mixture was stirred at room temperature for 2 hours and filtrated. The filtrate was evaporated under reduced pressure to remove the low boiling solvent to obtain 588 mg of yellow oily liquid, which was directly used in the next step of the reaction without purification. MS (M+H)$^+$: 204.1

Step f: Preparation of 2-f

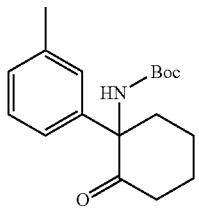 [SMILES: Cc1cccc(C2(NC(=O)OC(C)(C)C)CCCCC2=O)c1]

Using the crude compound 2-e (588 mg crude product) as a raw material, the method described in step e in Example 1 was conducted accordingly to obtain 773 mg of yellow oily liquid, yield: 82.6% (two steps together). $^1$H NMR (400 MHz, CDCl$_3$) δ 7.23 (d, J=7.7 Hz, 1H), 7.17 (d, J=5.6 Hz, 1H), 7.08 (d, J=6.8 Hz, 2H), 6.25 (s, 1H)), 3.56 (d, J=11.9 Hz, 1H), 2.38 (d, J=13.5 Hz, 1H), 2.33 (s, 3H), 2.27 (s, 1H), 1.97 (s, 2H), 1.84 (s, 2H), 1.74 (dd, J=10.3, 6.1 Hz, 1H), 1.32 (s, 9H). MS (M+Na)$^+$: 326.1

Step g: Preparation of 2-g

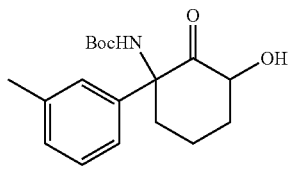 [SMILES: Cc1cccc(C2(NC(=O)OC(C)(C)C)CCCC(O)C2=O)c1]

Using the compound 2-f (773 mg, 2.55 mmol) as a raw material, the method described in step f in Example 1 was conducted accordingly to obtain 591 mg of yellow oily liquid, yield: 72.6%. $^1$H NMR (400 MHz, CDCl$_3$) δ 7.28-7.23 (m, 1H), 7.12 (t, J=8.6 Hz, 2H), 7.06 (s, 1H), 6.09 (s, 1H), 4.12-3.99 (m, 1H), 3.51 (s, 1H), 3.42 (s, 1H), 2.34 (s, 4H), 2.11 (s, 1H), 1.85 (s, 2H), 1.66-1.57 (m, 1H), 1.33 (s, 9H). MS (M+Na)$^+$: 342.1

Step h: Preparation of Compound 2

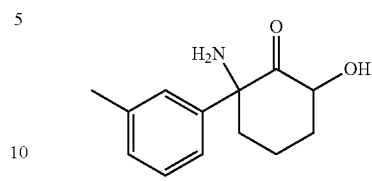

Using the compound 2-g (168 mg, 0.52 mmol) as a raw material, the method described in step g in Example 1 was conducted accordingly to obtain 101 mg of colorless oil, yield: 87.8%. $^1$H NMR (400 MHz, CDCl$_3$) δ 7.30-7.25 (m, 1H), 7.12 (d, J=7.6 Hz, 1H), 7.01 (d, J=8.0 Hz, 2H), 4.23 (dd, J=12.2, 7.0 Hz, 1H), 2.88 (dd, J=8.5, 2.8 Hz, 1H), 1.81-1.66 (m, 4H), 1.52 (qd, J=12.2, 5.0 Hz, 1H). MS (M+H)$^+$: 220.1

Example 3: Preparation of 2-amino-6-hydroxy-2-m-fluorophenylcyclohexane-1-one (Compound 3)

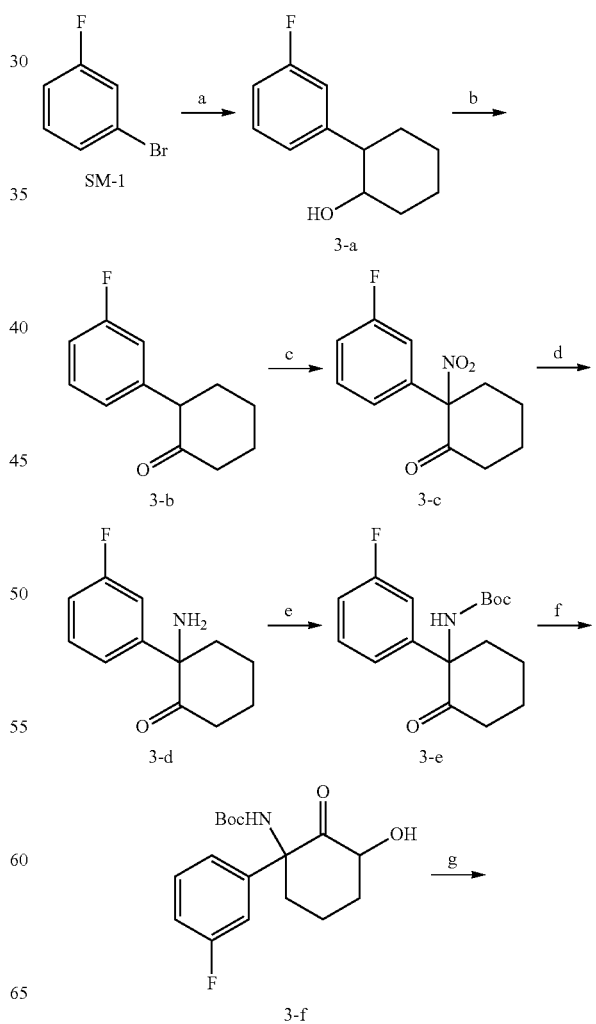

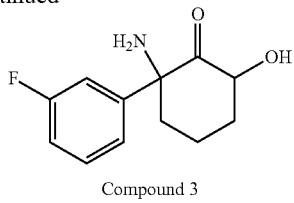

Compound 3

Step a: Preparation of 3-a

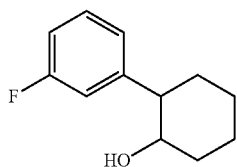 [SMILES: OC1CCCCC1c1cccc(F)c1]

Using m-fluorobromobenzene (9.63 g, 55.03 mmol) and epoxycyclohexane (5.94 g, 60.52 mmol) as raw materials, the method described in step a in Example 1 was conducted accordingly to obtain 8.21 g of yellow oily liquid, yield: 76.8%. $^1$H NMR (400 MHz, CDCl$_3$) δ 7.32-7.27 (m, 1H), 7.03 (d, J=7.5 Hz, 1H), 6.94 (dd, J=16.8, 9.1 Hz, 2H), 3.64 (td, J=9.9, 4.2 Hz, 1H), 2.49-2.38 (m, 1H), 2.12 (d, J=8.0 Hz, 1H), 1.86 (d, J=10.2 Hz, 2H), 1.77 (d, J=12.2 Hz, 1H), 1.48-1.32 (m, 4H). MS(M+Na)$^+$: 217

Step b: Preparation of 3-b

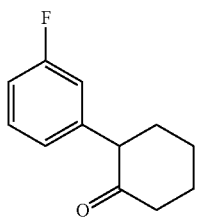 [SMILES: O=C1CCCCC1c1cccc(F)c1]

Using the compound 3-a (1.829 g, 9.42 mmol) as a raw material, the method described in step b in Example 1 was conducted accordingly to obtain 1.303 g of yellow oily liquid, yield: 72.0%. $^1$H NMR (400 MHz, CDCl$_3$) δ 7.32-7.27 (m, 1H), 6.94 (ddd, J=18.4, 7.3, 4.8 Hz, 2H), 6.88-6.83 (m, 1H), 3.61 (dd, J=12.1, 5.4 Hz, 1H), 2.57-2.50 (m, 1H), 2.49-2.41 (m, 1H), 2.31-2.24 (m, 1H), 2.19-2.12 (m, 1H), 2.03-1.96 (m, 2H), 1.86-1.78 (m, 2H). MS (M+Na)$^+$: 215.

Step c: Preparation of 3-c

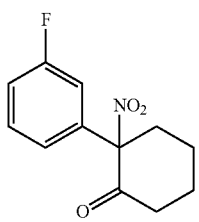 [SMILES: O=C1CCCCC1(c1cccc(F)c1)[N+](=O)[O-]]

Using the compound 3-b (1.275 g, 6.63 mmol) as a raw material, the method described in step c in Example 1 was conducted accordingly to obtain 565 mg of yellow oily liquid, yield: 35.9%. $^1$H NMR (400 MHz, CDCl$_3$) δ 7.44 (td, J=8.1, 6.1 Hz, 1H), 7.19-7.10 (m, 2H), 7.09-7.04 (m, 1H), 3.09 (ddd, J=13.4, 9.6, 3.5 Hz, 1H), 2.82-2.73 (m, 1H), 2.69 (dd, J=13.4, 6.8 Hz, 1H), 2.60-2.51 (m, 1H), 1.93 (tdd, J=9.6, 7.4, 3.6 Hz, 3H), 1.79 (ddd, J=13.1, 9.1, 4.5 Hz, 1H). MS(M+Na)$^+$: 260

Step d: Preparation of 3-d

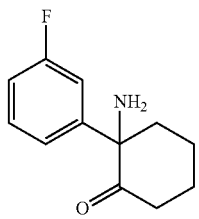 [SMILES: NC1(c2cccc(F)c2)CCCCC1=O]

Using the compound 3-c (540 mg, 2.28 mmol) as a raw material, the method described in step d in Example 1 was conducted accordingly to obtain 394 mg of yellow oily liquid, which was directly cast into the reaction in next step without purification.

Step e: Preparation of 3-e

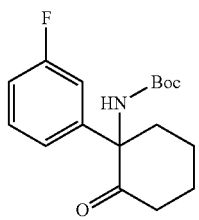 [SMILES: CC(C)(C)OC(=O)NC1(c2cccc(F)c2)CCCCC1=O]

Using the crude compound 3-d (394 mg crude product) as a raw material, the method described in step e in Example 1 was conducted accordingly to obtain 456 mg of yellow oily liquid, yield: 65.1% (two steps together). $^1$H NMR (400 MHz, CDCl$_3$) δ 7.33 (dd, J=11.0, 4.9 Hz, 1H), 7.07 (d, J=10.3 Hz, 2H), 7.02-6.94 (m, 1H), 6.34 (s, 1H), 3.57 (d, J=10.8 Hz, 1H), 2.46-2.38 (m, 1H), 2.26 (d, J=5.2 Hz, 1H), 2.01 (d, J=5.7 Hz, 1H), 1.88 (s, 3H), 1.80-1.68 (m, 1H), 1.32 (s, 9H). MS (M+Na)$^+$: 330.

Step f: Preparation of 3-f

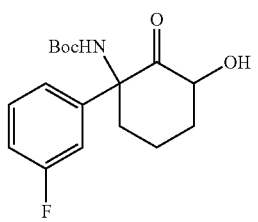 [SMILES: CC(C)(C)OC(=O)NC1(c2cccc(F)c2)CCCC(O)C1=O]

Using the compound 3-e (300 mg, 0.98 mmol) as a raw material, the method described in step f in Example 1 was conducted accordingly to obtain 150 mg of yellow oily liquid, yield: 47.5%. $^1$H NMR (400 MHz, CDCl$_3$) δ 7.34 (tt, J=10.3, 5.3 Hz, 1H), 7.03 (ddd, J=20.1, 13.4, 5.3 Hz, 3H), 6.28 (s, 1H), 4.06 (dd, J=12.1, 6.6 Hz, 1H), 3.60 (s, 1H), 3.37 (s, 1H), 2.37 (ddd, J=12.5, 6.6, 3.1 Hz, 1H), 1.99 (dd, J=12.0, 8.8 Hz, 1H), 1.87 (s, 2H), 1.64-1.59 (m, 1H), 1.32 (s, 9H). MS (M+Na)$^+$: 346.

Step g: Preparation of Compound 3

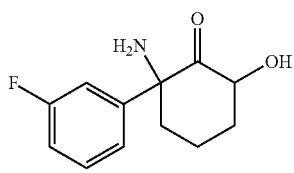

Using the compound 3-f (140 mg, 0.43 mmol) as a raw material, the method described in step g in Example 1 was conducted accordingly to obtain 88 mg of pale yellow oily substance, yield: 90.7%. $^1$H NMR (400 MHz, CDCl$_3$) δ 7.40-7.33 (m, 1H), 7.05-6.92 (m, 3H), 4.19 (dd, J=12.1, 7.0 Hz, 1H), 2.87-2.79 (m, 1H)), 2.39-2.33 (m, 1H), 1.77 (ddd, J=27.8, 12.8, 8.2 Hz, 3H), 1.60-1.50 (m, 1H). MS (M+H)$^+$: 224.

Example 4: Preparation of 2-amino-6-hydroxy-2-p-fluorophenylcyclohexane-1-one (Compound 4)

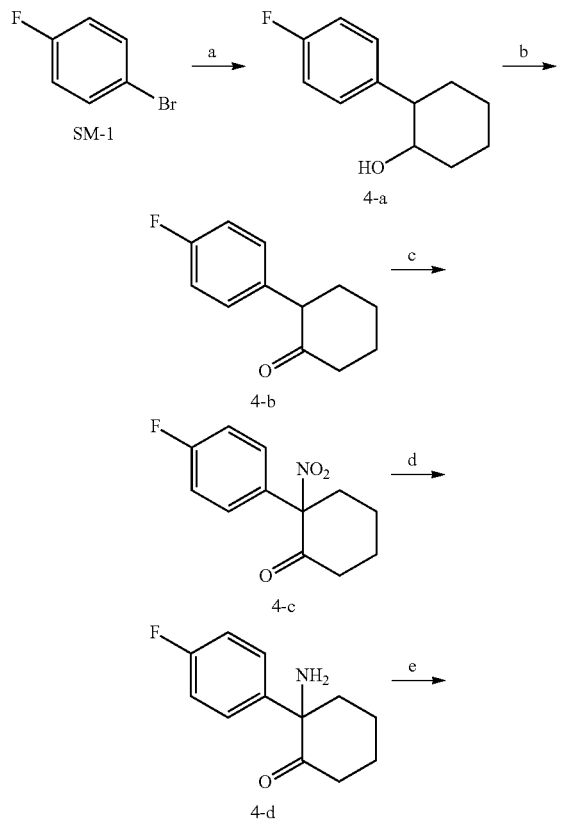

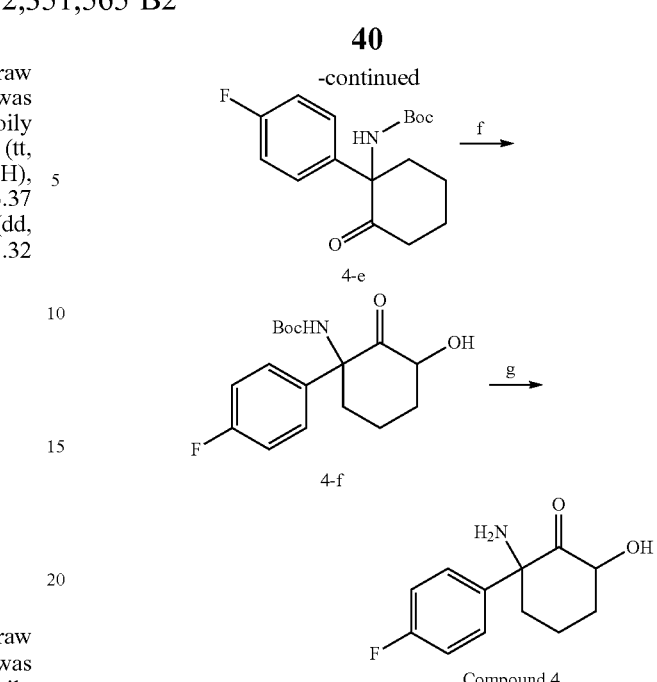

Step a: Preparation of 4-a

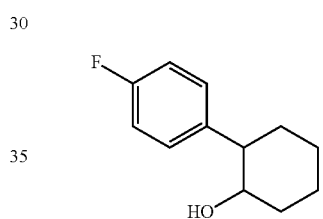

Using p-fluorobromobenzene (5 g, 28.57 mmol) and epoxycyclohexane (3.08 g, 31.38 mmol) as raw materials, the method described in step a in Example 1 was conducted accordingly to obtain 3.91 g of yellow oily liquid, yield: 70.4%. $^1$H NMR (400 MHz, CDCl$_3$) δ 7.25-7.17 (m, 2H), 7.02 (t, J=8.6 Hz, 2H), 3.70-3.55 (m, 1H), 2.50-2.35 (m, 1H), 2.11 (d, J=8.8 Hz, 1H), 1.84 (dd, J=9.7, 2.2 Hz, 2H), 1.75 (s, 1H), 1.42-1.29 (m, 4H). MS(M+Na)$^+$: 217

Step b: Preparation of 4-b

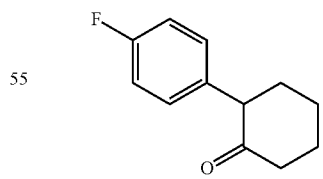

Using the compound 4-a (3.91 g, 20.13 mmol) as a raw material, the method described in step b in Example 1 was conducted accordingly to obtain 3.01 g of yellow oily liquid, yield: 77.8%. $^1$H NMR (400 MHz, CDCl$_3$) δ 7.09 (tt, J=4.9, 2.4 Hz, 2H), 7.05-6.98 (m, 2H), 3.82-3.37 (m, 1H), 2.58-2.39 (m, 2H), 2.31-2.22 (m, 1H), 2.20-2.12 (m, 1H), 2.04-1.93 (m, 2H), 1.87-1.76 (m, 2H). MS (M+H)$^+$: 193.1

Step c: Preparation of 4-c

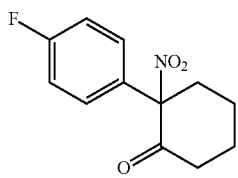 [SMILES: O=C1CCCCC1(c1ccc(F)cc1)[N+](=O)[O-]]

Using the compound 4-b (500 mg, 2.6 mmol) as a raw material, the method described in step c in Example 1 was conducted accordingly to obtain 200 mg of white solid, yield: 32.4%. $^1$H NMR (400 MHz, CDCl$_3$) δ 7.38-7.32 (m, 2H), 7.18-7.12 (m, 2H), 3.11 (ddd, J=13.5, 9.8, 3.4 Hz, 1H), 2.83-2.75 (m, 1H)), 2.72-2.64 (m, 1H), 2.58-2.49 (m, 1H), 2.42-2.12 (m, 1H), 1.93 (ddd, J=17.1, 8.9, 5.5 Hz, 3H), 1.84-1.72 (m, 1H). MS(M+Na)$^+$: 260

Step d: Preparation of 4-d

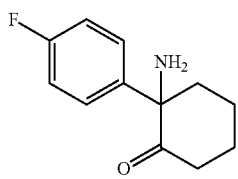 [SMILES: NC1(c2ccc(F)cc2)CCCCC1=O]

Using the compound 4-c (200 mg, 2.28 mmol) as a raw material, the method described in step d in Example 1 was conducted accordingly to obtain 142 mg of yellow oily liquid, which was directly cast into the reaction in next step without purification.

Step e: Preparation of 4-e

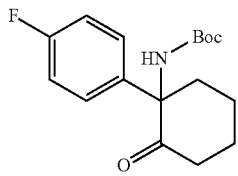 [SMILES: CC(C)(C)OC(=O)NC1(c2ccc(F)cc2)CCCCC1=O]

Using the crude compound 4-d (142 mg crude product) as a raw material, the method described in step e in Example 1 was conducted accordingly to obtain 198 mg of yellow oily liquid, yield: 76.4% (two steps together). $^1$H NMR (400 MHz, CDCl$_3$) δ 7.30 (dd, J=15.6, 10.2 Hz, 2H), 7.11-6.98 (m, 2H), 6.34 (s, 1H), 3.59 (d, J=12.2 Hz, 1H), 2.40 (d, J=13.5 Hz, 1H), 2.33-2.21 (m, 1H), 2.01 (d, J=6.1 Hz, 1H), 1.94-1.82 (m, 2H), 1.75 (dd, J=14.3, 10.0 Hz, 2H), 1.39-1.27 (m, 9H). MS (M+Na)$^+$: 330.1.

Step f: Preparation of 4-f

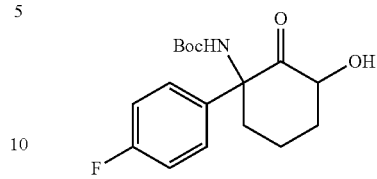

Using the compound 4-e (198 mg, 0.64 mmol) as a raw material, the method described in step f in Example 1 was conducted accordingly to obtain 63 mg of white solid powder, yield: 30.3%. $^1$H NMR (400 MHz, CDCl$_3$) δ 7.31-7.27 (m, 2H), 7.07 (t, J=8.6 Hz, 2H), 6.26 (s, 1H), 4.11-4.02 (m, 1H), 3.63 (d, J=17.0 Hz, 1H), 3.37 (d, J=4.3 Hz, 1H), 2.36 (ddd, J=12.5, 6.6, 3.1 Hz, 1H), 2.01-1.94 (m, 1H), 1.87 (d, J=11.7 Hz, 2H), 1.61 (d, J=4.8 Hz, 1H), 1.32 (s, 9H). MS (M+Na)$^+$: 346.

Step g: Preparation of Compound 4

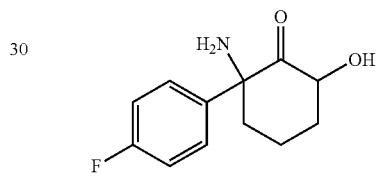

Using the compound 4-f (61 mg, 0.19 mmol) as a raw material, the method described in step g in Example 1 was conducted accordingly to obtain 36 mg of colorless oily liquid, yield: 85.7%. $^1$H NMR (400 MHz, CDCl$_3$) δ 7.23-7.18 (m, 2H), 7.11-7.06 (m, 2H), 4.20 (dd, J=12.0, 7.0 Hz, 1H), 2.84 (dt, J=5.0, 2.7 Hz, 1H), 2.40-2.32 (m, 1H), 1.78-1.65 (m, 3H), 1.54 (dd, J=12.4, 4.0 Hz, 1H). MS (M+H)$^+$: 224.

Example 5: Preparation of 2-amino-6-hydroxy-2-(2-methoxyphenyl)cyclohexane-1-one (Compound 5)

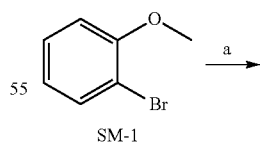

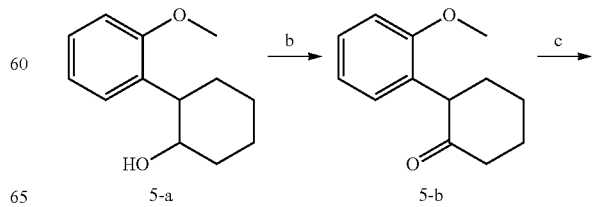

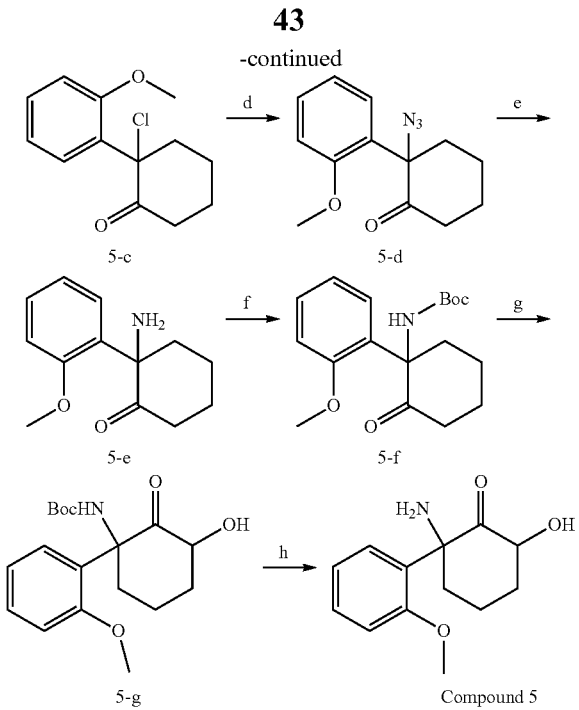

6.88 (d, J=8.1 Hz, 1H), 3.95 (dd, J=12.7, 5.5 Hz, 1H), 3.78 (s, 3H), 2.56-2.48 (m, 2H), 2.25-2.12 (m, 2H), 2.07-1.97 (m, 2H), 1.82 (ddd, J=17.0, 9.4, 5.6 Hz, 2H). MS(M+H)$^+$: 205.1

Step c: Preparation of 5-c

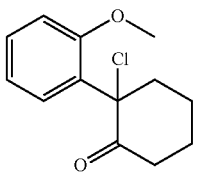 [SMILES: COc1ccccc1C1(Cl)CCCCC1=O]

Using the compound 5-b (4 g, 19.6 mmol) as a raw material, the method described in step c in Example 2 was conducted accordingly to obtain 2.08 g of light yellow oily liquid, yield: 44.5%. $^1$H NMR (400 MHz, CDCl$_3$) δ 7.68 (dd, J=7.8, 1.5 Hz, 1H), 7.35 (td, J=8.2, 1.5 Hz, 1H), 7.06 (t, J=7.3 Hz, 1H), 6.91 (t, J=7.1 Hz, 1H), 3.77 (s, 3H), 2.97-2.86 (m, 1H), 2.74 (dt, J=14.5, 7.3 Hz, 1H), 2.54-2.45 (m, 1H), 2.29-2.18 (m, 1H), 1.96-1.85 (m, 3H), 1.78 (ddd, J=20.3, 12.4, 3.7 Hz, 1H). MS (M+H)$^+$: 239.0

Step a: Preparation of 5-a

Step d: Preparation of 5-d

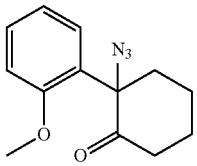 [SMILES: COc1ccccc1C1(N=[N+]=[N-])CCCCC1=O]

Using o-methoxy bromobenzene (12 g, 64.16 mmol) and epoxycyclohexane (6.98 g, 71.12 mmol) as raw materials, the method described in step a in Example 1 was conducted accordingly to obtain 9.6 g of colorless oily liquid, yield: 72.5%. $^1$H NMR (400 MHz, CDCl$_3$) δ 7.26-7.15 (m, 2H), 6.97 (t, J=7.4 Hz, 1H), 6.89 (d, J=8.2 Hz, 1H), 3.83 (s, 3H), 3.76 (d, J=15.1 Hz, 1H), 3.05-2.97 (m, 1H), 2.17-2.10 (m, 1H), 1.89-1.78 (m, 3H), 1.77-1.71 (m, 1H), 1.48-1.36 (m, 3H). MS (M+H)$^+$: 229.1

Using the compound 5-c (2 g, 8.4 mmol) as a raw material, the method described in step d in Example 2 was conducted accordingly to obtain 1.78 g of pale yellow oily liquid, yield: 86.6%. $^1$H NMR (400 MHz, CDCl$_3$) δ 7.45 (dd, J=7.8, 1.5 Hz, 1H), 7.40-7.36 (m, 1H), 7.11-7.07 (m, 1H), 6.96 (d, J=8.1 Hz, 1H), 3.75 (s, 3H), 2.65 (dddd, J=14.0, 5.4, 3.3, 2.0 Hz, 1H), 2.49-2.43 (m, 2H), 1.93-1.89 (m, 2H), 1.86-1.82 (m, 1H), 1.79-1.73 (m, 2H). MS (M+Na)$^+$: 268

Step b: Preparation of 5-b

Step e: Preparation of 5-e

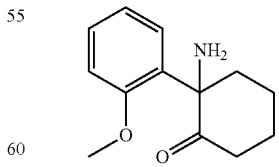

Using the compound 5-a (2.7 g, 13.1 mmol) as a raw material, the method described in step b in Example 1 was conducted accordingly to obtain 2.18 g of white solid, yield: 81.5%. $^1$H NMR (400 MHz, CDCl$_3$) δ 7.25 (td, J=8.2, 1.7 Hz, 1H), 7.12 (dd, J=7.5, 1.4 Hz, 1H), 6.96 (t, J=7.5 Hz, 1H), Using the compound 5-d (1.78 g, 7.26 mmol) as a raw material, the method described in step e in Example 2 was conducted accordingly to obtain 1.02 g of light yellow oily liquid, which was directly cast into the reaction in next step without purification. MS (M+H)$^+$: 220.1

Step f: Preparation of 5-f

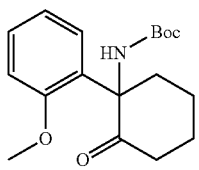 [SMILES: COc1ccccc1C1(NC(=O)OC(C)(C)C)CCCCC1=O]

Using the crude compound 5-e (1.02 g of crude product) as a raw material, the method described in step e in Example 1 was conducted accordingly to obtain 1.34 g of yellow oily liquid, yield: 57.8% (two steps together). $^1$H NMR (400 MHz, CDCl$_3$) δ 7.75 (s, 1H), 7.32-7.27 (m, 1H), 7.04 (t, J=6.9 Hz, 1H), 6.85 (d, J=8.1 Hz, 1H), 6.50 (s, 1H), 3.87-3.78 (m, 1H), 3.68 (s, 3H), 2.29 (d, J=7.7 Hz, 2H), 1.98 (s, 1H), 1.77-1.58 (m, 4H), 1.30 (s, 9H). MS (M+Na)$^+$: 342.1

Step g: Preparation of 5-g

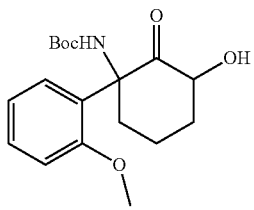 [SMILES: COc1ccccc1C1(NC(=O)OC(C)(C)C)CCCC(O)C1=O]

Using the compound 5-f (600 mg, 1.88 mmol) as a raw material, the method described in step f in Example 1 was conducted accordingly to obtain 409 mg of white solid, yield: 64.9%. $^1$H NMR (400 MHz, CDCl$_3$) δ 7.71 (s, 1H), 7.34-7.28 (m, 1H), 7.04 (t, J=7.5 Hz, 1H), 6.86 (d, J=8.1 Hz, 1H), 6.43 (s, 1H), 4.11-4.01 (m, 1H), 3.83 (s, 1H), 3.69 (s, 3H), 3.41 (d, J=6.4 Hz, 1H), 2.35-2.24 (m, 1H), 1.73-1.55 (m, 3H), 1.43 (dd, J=11.7, 5.8 Hz, 1H), 1.32 (s, 9H). MS (M+Na)$^+$: 358.1

Step h: Preparation of Compound 5

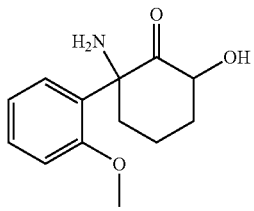 [SMILES: COc1ccccc1C1(N)CCCC(O)C1=O]

Using the compound 5-g (202 mg, 0.6 mmol) as a raw material, the method described in step g in Example 1 was conducted accordingly to obtain 132 mg of pale yellow oily liquid, yield: 93.0%. $^1$H NMR (400 MHz, CDCl$_3$) δ 7.48 (d, J=7.8 Hz, 1H), 7.35-7.30 (m, 1H), 7.05 (t, J=7.6 Hz, 1H), 6.89 (d, J=8.2 Hz, 1H), 4.11 (dd, J=11.8, 6.8 Hz, 1H), 2.82 (ddd, J=13.8, 5.5, 2.7 Hz, 1H), 2.31-2.25 (m, 1H), 1.65 (ddd, J=10.2, 6.6, 3.6 Hz, 2H), 1.56-1.48 (m, 1H), 1.36 (ddd, J=19.8, 12.0, 6.2 Hz, 1H). MS (M+H)$^+$: 236.1

Example 6: Preparation of 2-amino-6-hydroxy-2-(3-methoxyphenyl)cyclohexane-1-one (Compound 6)

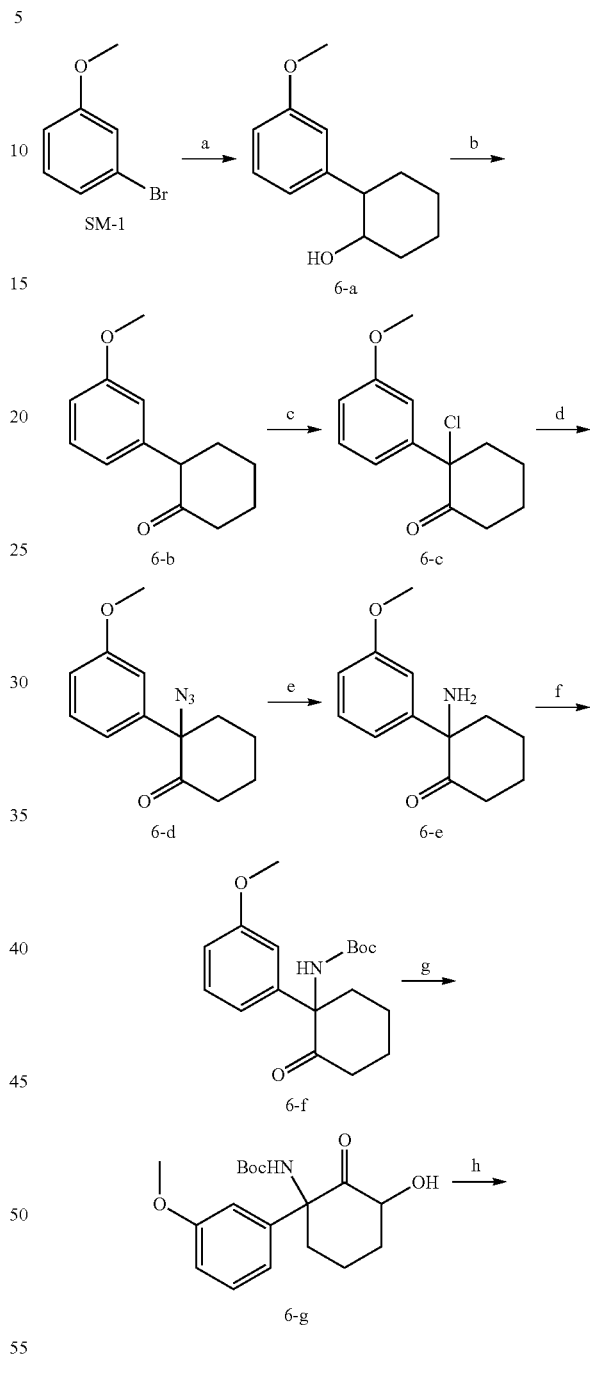

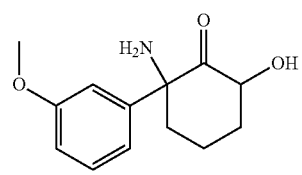

Compound 6

Step a: Preparation of 6-a

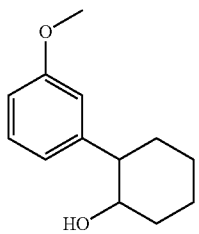

Using m-methoxy bromobenzene (15 g, 80.2 mmol) and epoxycyclohexane (8.66 g, 88.23 mmol) as raw materials, the method described in step a in Example 1 was conducted accordingly to obtain 14.99 g of light yellow oily liquid, yield: 90.6%. $^1$H NMR (400 MHz, CDCl$_3$) δ 7.25 (t, J=7.7 Hz, 1H), 6.85 (d, J=7.6 Hz, 1H), 6.82-6.77 (m, 2H), 3.81 (s, 3H), 3.69-3.62 (m, 1H), 2.41 (ddd, J=13.1, 10.0, 3.4 Hz, 1H), 2.11 (dd, J=8.0, 3.6 Hz, 1H), 1.90-1.83 (m, 2H), 1.80-1.73 (m, 1H), 1.60 (d, J=4.5 Hz, 1H), 1.51 (dd, J=12.9, 3.1 Hz, 1H), 1.43-1.36 (m, 2H). MS(M+H)$^+$: 229.1

Step b: Preparation of 6-b

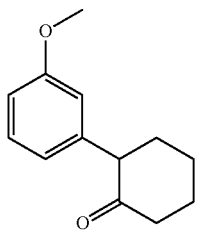

Using the compound 6-a (10 g, 48.48 mmol) as a raw material, the method described in step b in Example 1 was conducted accordingly to obtain 8.53 g of yellow oily liquid, yield: 86.2%. $^1$H NMR (400 MHz, CDCl$_3$) δ 7.29-7.24 (m, 1H), 6.80 (dd, J=8.2, 2.5 Hz, 1H), 6.76-6.68 (m, 2H), 3.80 (s, 3H), 3.59 (dd, J=12.0, 5.3 Hz, 1H), 2.57-2.39 (m, 2H), 2.32-2.22 (m, 1H), 2.14 (dd, J=5.9, 3.8 Hz, 1H), 2.07-1.95 (m, 2H), 1.89-1.75 (m, 2H). MS (M+Na)$^+$: 227.

Step c: Preparation of 6-c

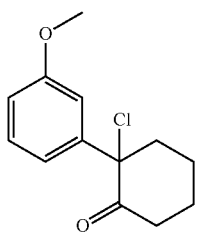 [SMILES: COc1cccc(C2(Cl)CCCCC2=O)c1]

Using the compound 6-b (5 g, 24.48 mmol) as a raw material, the method described in step c in Example 2 was conducted accordingly to obtain 3.5 g of colorless oily liquid, yield: 59.9%. $^1$H NMR (400 MHz, CDCl$_3$) δ 7.31 (dd, J=13.0, 5.0 Hz, 1H), 6.99-6.92 (m, 2H), 6.90-6.85 (m, 1H), 3.81 (s, 3H), 3.00-2.91 (m, 1H), 2.86-2.78 (m, 1H), 2.44 (d, J=6.0 Hz, 2H), 2.04-1.95 (m, 1H), 1.93-1.79 (m, 3H). MS (M+Na)$^+$: 261.

Step d: Preparation of 6-d

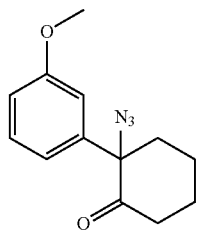 [SMILES: COc1cccc(C2(N=[N+]=[N-])CCCCC2=O)c1]

Using the compound 6-c (235 mg, 0.98 mmol) as a raw material, the method described in step d in Example 2 was conducted accordingly to obtain 145 mg of colorless oily liquid, yield: 60.2%. $^1$H NMR (400 MHz, CDCl$_3$) δ 7.26 (t, J=7.9 Hz, 1H), 6.81 (dd, J=8.2, 2.2 Hz, 1H), 6.72 (dd, J=14.9, 4.8 Hz, 2H), 3.80 (s, 3H), 3.60 (dd, J=12.0, 5.4 Hz, 1H), 2.57-2.50 (m, 1H), 2.46 (dd, J=9.0, 3.1 Hz, 1H), 2.32-2.22 (m, 1H), 2.14 (s, 1H), 2.03-1.97 (m, 1H), 1.89-1.78 (m, 2H). MS (M+Na)$^+$: 268.

Step e: Preparation of 6-e

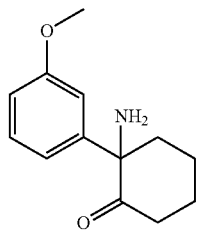 [SMILES: COc1cccc(C2(N)CCCCC2=O)c1]

Using the compound 6-d (145 mg, 0.59 mmol) as a raw material, the method described in step e in Example 2 was conducted accordingly to obtain 140 mg of pale yellow oily liquid, which was directly cast into the reaction in next step without purification. MS (M+H)$^+$: 220.1

Step f: Preparation of 6-f

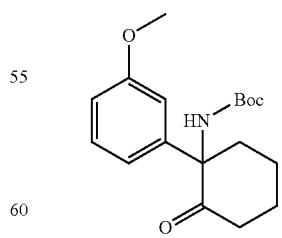

Using the crude compound 6-e (140 mg crude product) as a raw material, the method described in step e in Example 1 was conducted accordingly to obtain 169 mg of yellow oily liquid, yield: 89.4% (two steps together). $^1$H NMR (400 MHz, CDCl$_3$) δ 7.31-7.25 (m, 1H), 6.95 (s, 1H), 6.88-6.84

(m, 1H), 6.82 (dd, J=8.1, 2.3 Hz, 1H), 6.27 (s, 1H), 3.79 (s, 3H), 3.55 (d, J=10.6 Hz, 1H), 2.39 (d, J=13.2 Hz, 1H), 2.30 (d, J=12.8 Hz, 1H), 1.98 (s, 2H), 1.86 (s, 2H), 1.77-1.67 (m, 1H), 1.33 (s, 9H). MS (M+Na)+: 342.

Step g: Preparation of 6-g

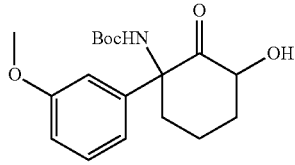

Using the compound 6-f (1.2 g, 3.76 mmol) as a raw material, the method described in step f in Example 1 was conducted accordingly to obtain 428 mg of yellow oil, yield: 33.97%. $^1$H NMR (400 MHz, CDCl$_3$) δ 7.29 (t, J=8.3 Hz, 1H), 6.90 (d, J=7.1 Hz, 1H), 6.86-6.81 (m, 2H), 6.12 (s, 1H), 4.07 (s, 1H), 3.79 (s, 3H), 3.51 (s, 1H), 3.41 (s, 1H), 2.34 (ddd, J=12.3, 6.4, 3.0 Hz, 1H), 1.87 (s, 2H), 1.60 (s, 2H), 1.34 (s, 9H). MS (M+Na)+: 358.

Step h: Preparation of Compound 6

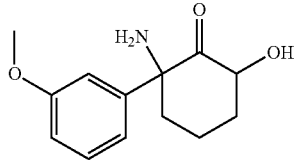

Using the compound 6-g (243 mg, 0.72 mmol) as a raw material, the method described in step g in Example 1 was conducted accordingly to obtain 155 mg of pale yellow oily liquid, yield: 91.2%. $^1$H NMR (400 MHz, CDCl$_3$) δ 7.31 (t, J=8.2 Hz, 1H), 6.87-6.82 (m, 1H), 6.79-6.75 (m, 2H), 4.22 (dd, J=12.2, 7.0 Hz, 1H), 2.85 (d, J=10.8 Hz, 1H), 2.35 (ddd, J=12.3, 6.6, 3.1 Hz, 1H), 1.81-1.68 (m, 3H), 1.53 (ddd, J=18.7, 12.2, 6.5 Hz, 1H). MS (M+H)+: 236.

Example 7: Preparation of 2-amino-6-hydroxy-2-(3-trifluoromethoxyphenyl)cyclohexane-1-one (Compound 7)

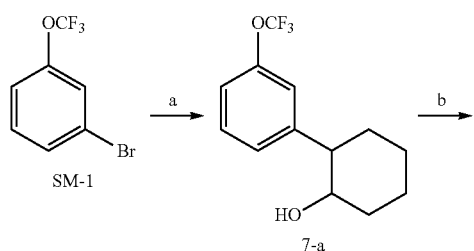

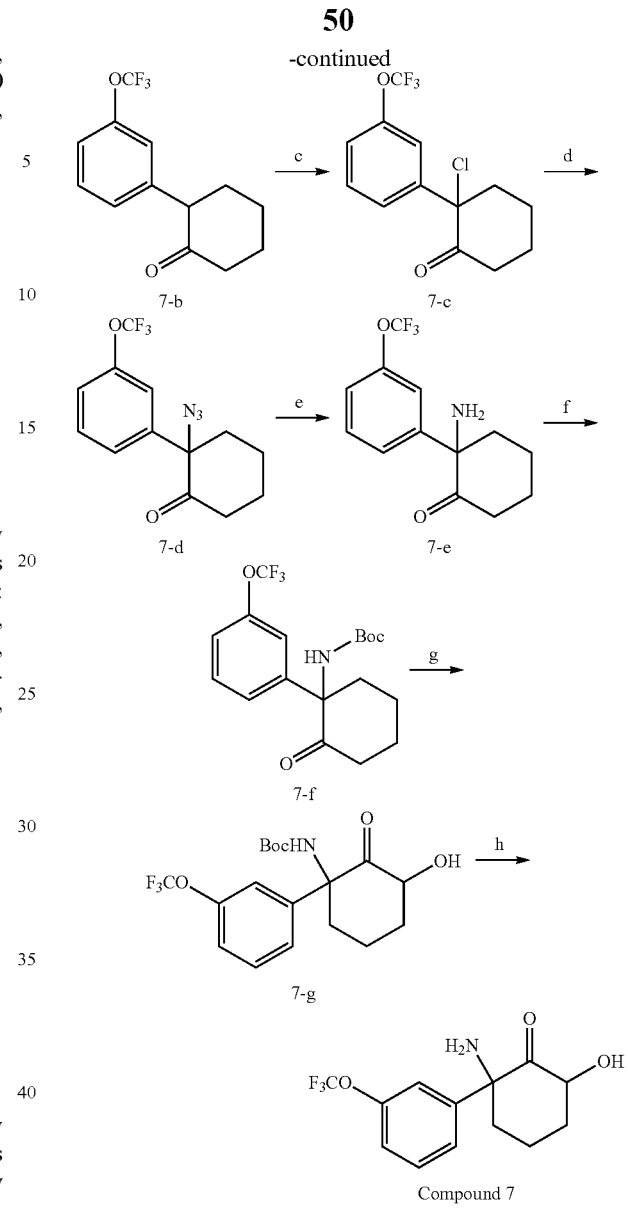

Step a: Preparation of 7-a

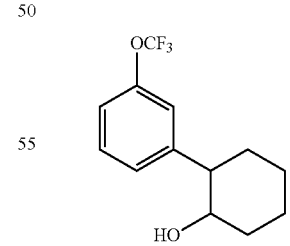

Using 1-bromo-3-trifluoromethoxybenzene (5 g, 20.75 mmol) and epoxycyclohexane (2.24 g, 22.82 mmol) as raw materials, the method described in step a in Example 1 was conducted accordingly to obtain 4.1 g of light yellow oily liquid, yield: 75.9%. $^1$H NMR (400 MHz, CDCl$_3$) δ 7.38-7.32 (m, 1H), 7.19 (d, J=7.7 Hz, 1H), 7.10 (d, J=7.5 Hz, 2H), 3.70-3.61 (m, 1H), 2.51-2.43 (m, 1H), 2.12 (d, J=8.6 Hz, 1H), 1.90-1.83 (m, 2H), 1.81-1.74 (m, 1H), 1.50 (d, J=5.3 Hz, 1H), 1.40 (dd, J=14.0, 5.6 Hz, 2H), 1.35-1.29 (m, 1H). MS(M+H)⁺: 229.1

Step b: Preparation of 7-b

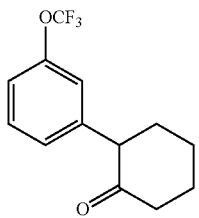

Using the compound 7-a (4.1 g, 15.75 mmol) as a raw material, the method described in step b in Example 1 was conducted accordingly to obtain 2.47 g of yellow oily liquid, yield: 60.72%. ¹H NMR (400 MHz, CDCl₃) δ 7.38-7.31 (m, 1H), 7.11 (dd, J=7.2, 1.0 Hz, 1H), 7.07 (d, J=7.7 Hz, 1H), 7.00 (s, 1H), 3.63 (dd, J=12.1, 5.3 Hz, 1H), 2.50 (tdd, J=13.7, 9.7, 4.5 Hz, 2H), 2.29 (ddd, J=8.7, 5.4, 2.8 Hz, 1H), 2.22-2.14 (m, 1H), 2.04-1.94 (m, 2H), 1.87-1.78 (m, 2H). MS (M+Na)⁺: 281.0

Step c: Preparation of 7-c

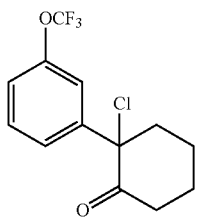 [SMILES: O=C1CCCCC1(Cl)c1cccc(OC(F)(F)F)c1]

Using the compound 7-b (2.26 g, 8.75 mmol) as a raw material, the method described in step c in Example 2 was conducted accordingly to obtain 1.53 g of colorless oily liquid, yield: 59.7%. ¹H NMR (400 MHz, CDCl₃) δ 7.37 (ddd, J=28.9, 17.1, 9.1 Hz, 3H), 7.20 (d, J=8.1 Hz, 1H), 2.99 (ddd, J=14.5, 9.2, 5.6 Hz, 1H), 2.74 (ddd, J=15.6, 9.6, 5.2 Hz, 1H), 2.53-2.44 (m, 1H), 2.32-2.24 (m, 1H), 2.16-2.06 (m, 1H), 2.00 (ddd, J=18.3, 8.4, 3.6 Hz, 1H), 1.93-1.82 (m, 2H). MS (M+H)⁺: 293.

Step d: Preparation of 7-d

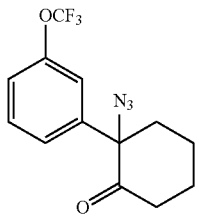 [SMILES: [N-]=[N+]=NC1(c2cccc(OC(F)(F)F)c2)CCCCC1=O]

Using the compound 7-c (1.53 g, 5.23 mmol) as a raw material, the method described in step d in Example 2 was conducted accordingly to obtain 900 mg of colorless oily liquid, yield: 57.5%. ¹H NMR (400 MHz, CDCl₃) δ 7.50 (t, J=8.0 Hz, 1H), 7.27 (d, J=9.2 Hz, 1H), 7.24-7.16 (m, 2H), 2.73-2.65 (m, 1H), 2.60 (dt, J=13.8, 3.7 Hz, 1H), 2.36 (ddd, J=14.0, 12.1, 6.0 Hz, 1H), 2.07-1.95 (m, 2H), 1.94-1.86 (m, 1H), 1.86-1.74 (m, 1H), 1.73-1.63 (m, 1H). MS (M+Na)⁺: 268.

Step e: Preparation of 7-e

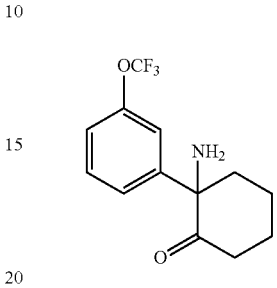

Using the compound 7-d (900 mg, 3.01 mmol) as a raw material, the method described in step e in Example 2 was conducted accordingly to obtain 677 mg of pale yellow oily liquid, which was directly cast into the reaction in next step without purification. MS (M+H)⁺: 274.1

Step f: Preparation of 7-f

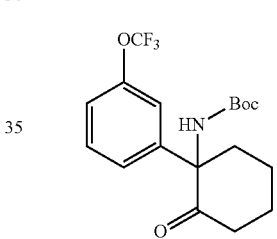

Using the crude compound 7-e (677 mg crude product) as a raw material, the method described in step e in Example 1 was conducted accordingly to obtain 700 mg of colorless oily liquid, yield: 62.3% (two steps together). ¹H NMR (400 MHz, CDCl₃) δ 7.39 (t, J=8.0 Hz, 1H), 7.31 (d, J=3.5 Hz, 1H), 7.22-7.11 (m, 2H), 6.36 (d, J=19.9 Hz, 1H), 3.55 (d, J=12.1 Hz, 1H), 2.43 (dt, J=23.8, 12.0 Hz, 1H), 2.22 (dd, J=17.1, 9.8 Hz, 1H), 2.06-1.98 (m, 1H), 1.96-1.72 (m, 4H), 1.28 (d, J=21.8 Hz, 9H). MS (M+Na)⁺: 396.

Step g: Preparation of 7-g

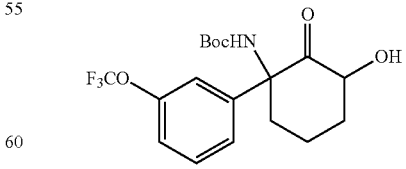

Using the compound 7-f (700 mg, 1.87 mmol) as a raw material, the method described in step f in Example 1 was conducted accordingly to obtain 220 mg of yellow oil, yield: 30.1%. ¹H NMR (400 MHz, CDCl₃) δ 7.43-7.38 (m, 1H), 7.22 (d, J=12.5 Hz, 1H), 7.18 (s, 2H), 6.32 (s, 1H), 4.05 (dd, J=11.7, 6.5 Hz, 1H), 3.62 (s, 1H), 3.41 (s, 1H), 2.37 (ddd, J=12.4, 6.5, 3.0 Hz, 1H), 2.06-1.94 (m, 1H), 1.92-1.78 (m, 2H), 1.60 (ddd, J=25.1, 12.5, 4.6 Hz, 1H), 1.29 (d, J=10.6 Hz, 9H). MS (M+H)$^+$: 390.1

Step h: Preparation of Compound 7

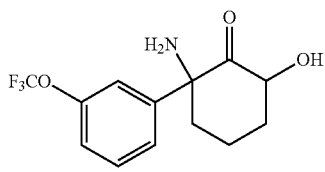 [SMILES: NC1(c2cccc(OC(F)(F)F)c2)CCCC(O)C1=O]

Using the compound 7-g (220 mg, 0.56 mmol) as a raw material, the method described in step g in Example 1 was conducted accordingly to obtain 151 mg of colorless oily substance, yield: 92.6%. $^1$H NMR (400 MHz, CDCl$_3$) δ 7.22 (t, J=8.2 Hz, 1H), 7.05 (d, J=8.6 Hz, 1H), 6.92 (d, J=6.9 Hz, 2H), 4.02 (dd, J=11.8, 6.8 Hz, 1H), 2.21 (m, 1H), 2.14-2.03 (m, 1H), 1.79 (m, 2H), 1.61 (dd, J=9.9, 6.9 Hz, 1H), 1.58-1.50 (m, 1H). MS (M+H)$^+$: 290.1

Example 8: Preparation of 2-ethylamino-6-hydroxyl-2-(3-trifluoromethoxyphenyl)cyclohexane-1-one (Compound 8)

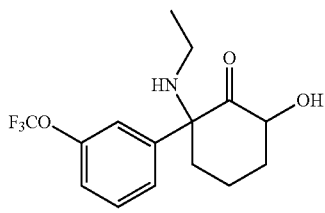 [SMILES: CCNC1(c2cccc(OC(F)(F)F)c2)CCCC(O)C1=O]

Under Ar protection, compound 7 (200 mg, 0.614 mmol) was dissolved in a mixed solvent of EA (3 mL) and MeOH (3 ml), Pd/C (60 mg) and CH$_3$CHO (2.2 ml) were added. After hydrogen replacement, the reaction was conducted at room temperature for 6 h. After the raw materials were completely reacted, the mixture was filtered, and the filtrate was subjected to column chromatography to obtain 191 mg of colorless oily liquid, yield: 87.2%. $^1$H NMR (400 MHz, CDCl$_3$) δ 7.32 (t, J=8.2 Hz, 1H), 7.08 (d, J=8.6 Hz, 1H), 6.99 (d, J=6.9 Hz, 2H), 3.98 (dd, J=12.0, 6.9 Hz, 1H), 2.81 (dd, J=14.0, 2.6 Hz, 1H), 2.25 (ddd, J=12.2, 6.8, 3.2 Hz, 1H), 2.18 (ddd, J=14.3, 8.8, 5.2 Hz, 1H), 2.04-1.98 (m, 1H), 1.75 (ddd, J=9.5, 8.2, 4.2 Hz, 2H), 1.58 (dd, J=9.9, 6.9 Hz, 1H), 1.52-1.44 (m, 1H), 0.90 (t, J=7.1 Hz, 3H). MS (M+H)$^+$: 318.

Example 9: Preparation of N-(3-hydroxyl-2-oxo-1-(3-trifluoromethoxyphenyl)cyclohexyl)acetamide (Compound 9)

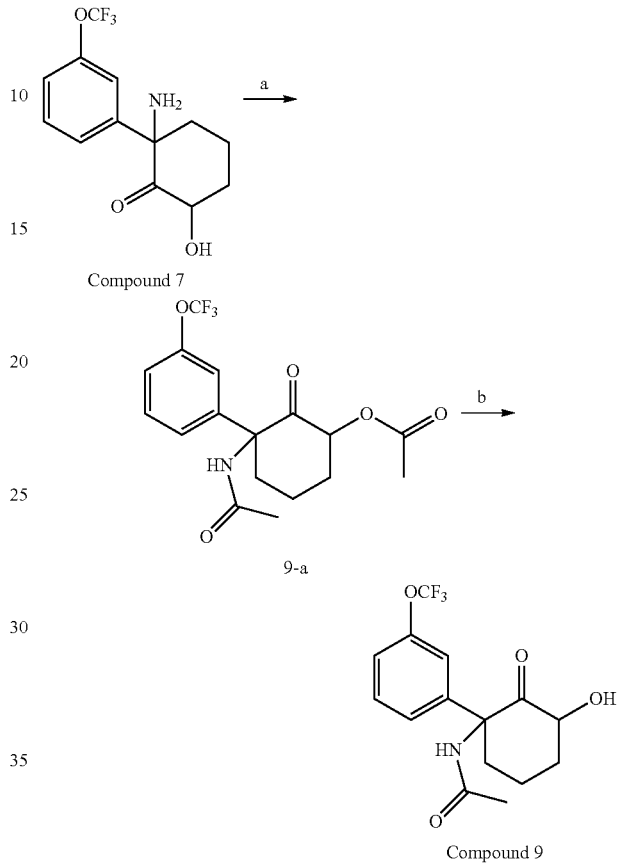

Step a: Preparation of 9-a

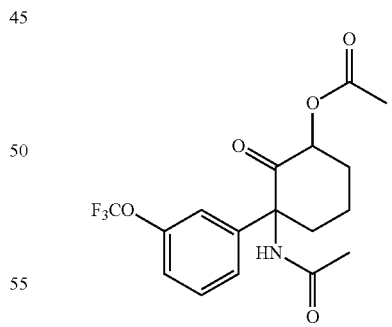

The compound 7 (360 mg, 1.24 mmol) was dissolved in DMF (5 mL). TEA (450 mg, 4.45 mmol) and catalytic amount of DMAP were added under stirring, and Ac$_2$O (320 mg, 3.13 mmol) was slowly added under ice water cooling. After the addition, the mixture was slowly warmed to room temperature and reacted for 30 min, detected by TLC (PE/EA=1/1). After the reaction was completed, ice water (20 ml) was added into the reaction solution to quench the reaction, and the mixture was extracted with EA (15 ml×3).

The organic phases were combined, washed with saturated sodium chloride solution, dried with anhydrous sodium sulfate, filtered with suction and concentrated, and subject to column chromatography (PE/EA=2/1) to obtain 421 mg of colorless oily liquid, yield: 90.5%. $^1$H NMR (400 MHz, CDCl$_3$) δ 7.43 (t, J=8.0 Hz, 1H), 7.36-7.29 (m, 2H), 7.22-7.16 (m, 2H), 5.05-4.95 (m, 1H), 3.92 (dd, J=11.5, 2.5 Hz, 1H), 2.24 (dt, J=11.2, 5.7 Hz, 1H), 2.16 (s, 3H), 1.97-1.93 (m, 1H), 1.88 (s, 3H), 1.81 (dd, J=15.3, 5.8 Hz, 3H). MS (M+H)$^+$: 374

Step b: Preparation of Compound 9

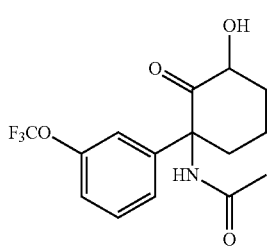 [SMILES: CC(=O)NC1(c2cccc(OC(F)(F)F)c2)CCCC(O)C1=O]

The compound 9-a (100 mg, 0.268 mmol) was dissolved in DCM (2 mL), 7N ammonia methanol solution (2 ml) was added with stirring, and mixture was reacted at room temperature overnight. After the reaction was completed, the mixture was directly subjected to column chromatography (pure ethyl acetate) to obtain 26 mg of product, which was then beat with PE/EA=3/1 to obtain 8 mg of white solid, yield: 8.9%. $^1$H NMR (400 MHz, CDCl$_3$) δ 7.41 (t, J=7.9 Hz, 1H), 7.24 (d, J=7.8 Hz, 2H), 7.17 (d, J=8.2 Hz, 2H), 3.88 (ddd, J=11.2, 7.1, 4.3 Hz, 1H), 2.39 (ddd, J=12.5, 6.6, 2.9 Hz, 1H), 2.03-1.97 (m, 1H), 1.91 (s, 3H), 1.88-1.82 (m, 2H), 1.60 (dd, J=12.4, 4.8 Hz, 2H). MS (M+H)$^+$: 332

Example 10: Preparation of 2-amino-2-(2,6-difluorophenyl)-6-hydroxycyclohexane-1-one (Compound 10)

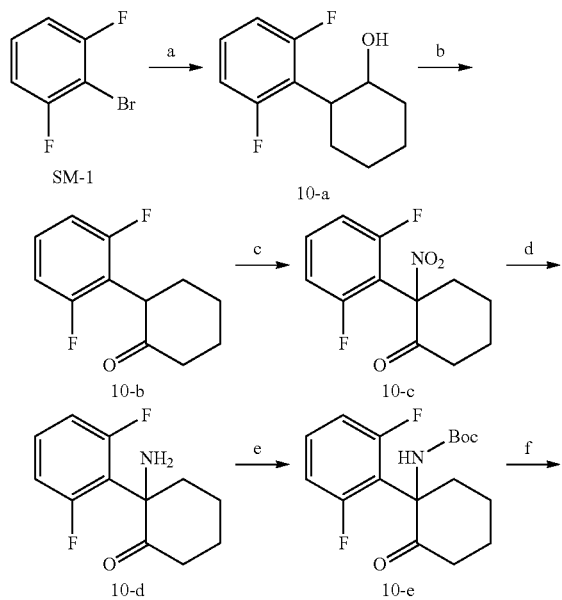

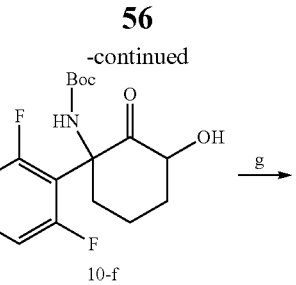

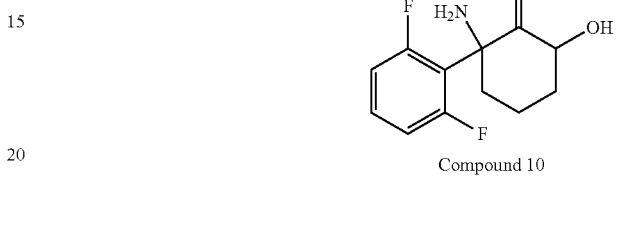

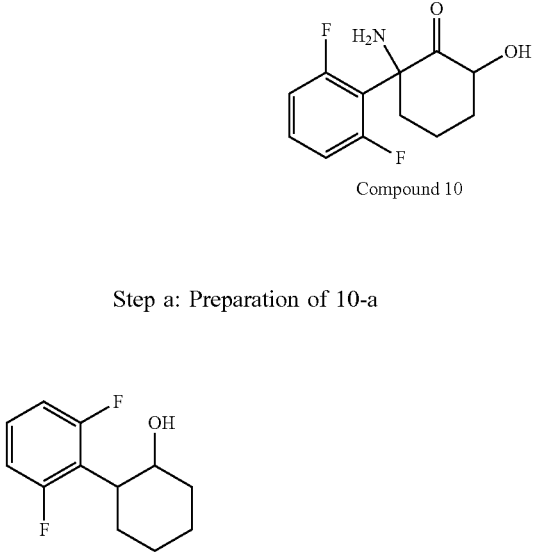

Step a: Preparation of 10-a

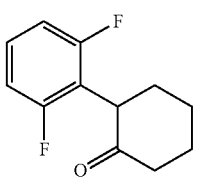 [SMILES: O=C1CCCCC1c1c(F)cccc1F]

Using 2,6-difluorobromobenzene (5 g, 25.91 mmoL) and epoxycyclohexane (2.8 g, 28.5 mmol) as raw materials, the method described in step a in Example 1 was conducted accordingly to obtain 3.5 g of colorless oily liquid, yield: 63.6%. $^1$H NMR (400 MHz, CDCl$_3$) δ 7.14 (tt, J=8.3, 6.3 Hz, 1H), 6.85 (t, J=8.8 Hz, 2H), 4.01 (ddd, J=10.4, 6.3, 4.3 Hz, 1H), 3.01-2.89 (m, 1H), 2.17-2.07 (m, 1H), 1.82 (dddd, J=18.7, 16.4, 8.4, 6.8 Hz, 4H), 1.44-1.28 (m, 3H). MS (M+H)$^+$: 213.1

Step b: Preparation of 10-b

Using the compound 10-a (3.5 g, 16.49 mmol) as a raw material, the method described in step b in Example 1 was conducted accordingly to obtain 2.2 g of yellow oily liquid, yield: 63.6%. $^1$H NMR (400 MHz, CDCl$_3$) δ 7.24-7.16 (m, 1H), 6.87 (t, J=8.4 Hz, 2H), 3.92 (dd, J=11.5, 7.3 Hz, 1H), 2.66-2.57 (m, 1H), 2.47-2.35 (m, 1H), 2.18 (dd, J=14.2, 8.6 Hz, 3H), 2.00 (dd, J=7.0, 4.8 Hz, 1H), 1.83 (ddd, J=12.1, 8.3, 3.5 Hz, 2H). MS (M+H)$^+$: 211

Step c: Preparation of 10-c

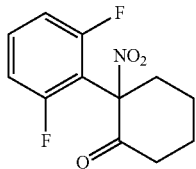 [SMILES: O=C1CCCCC1(c1c(F)cccc1F)[N+](=O)[O-]]

Using the compound 10-b (2.17 g, 10.32 mmol) as a raw material, the method described in step c in Example 1 was conducted accordingly to obtain 1.1 g of white solid, yield: 41.8%. $^1$H NMR (400 MHz, CDCl$_3$) δ 7.48 (tt, J=8.4, 6.2 Hz, 1H), 7.02 (dd, J=10.2, 8.5 Hz, 2H), 3.38-3.28 (m, 1H), 2.82-2.56 (m, 3H), 2.04-1.95 (m, 2H), 1.88 (ddd, J=20.6, 13.1, 7.0 Hz, 1H), 1.66-1.54 (m, 1H). MS (M+Na)$^+$: 278.0

Step d: Preparation of 10-d

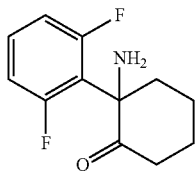 [SMILES: NC1(c2c(F)cccc2F)CCCCC1=O]

Using the compound 10-c (780 mg, 3.06 mmol) as a raw material, the method described in step d in Example 1 was conducted accordingly to obtain 690 mg of crude yellow oily liquid, which was directly cast into the reaction in next step without purification. MS (M+H)$^+$: 226.0

Step e: Preparation of 10-e

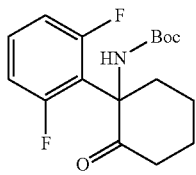 [SMILES: CC(C)(C)OC(=O)NC1(c2c(F)cccc2F)CCCCC1=O]

Using crude compound 10-d (690 mg crude product) as a raw material, the method described in step e in Example 1 was conducted accordingly to obtain 632 mg of yellow oily liquid, yield: 63.5% (two steps together). $^1$H NMR (400 MHz, CDCl$_3$) δ 7.26 (dq, J=8.3, 6.1 Hz, 1H), 6.88 (dd, J=9.9, 8.5 Hz, 2H), 6.47 (s, 1H), 3.82 (s, 1H), 2.47-2.34 (m, 2H), 2.07-2.01 (m, 1H), 1.76 (dt, J=20.7, 9.0 Hz, 3H), 1.50 (s, 1H), 1.31 (s, 9H). MS (M+Na)$^+$: 348.1

Step f: Preparation of 10-f

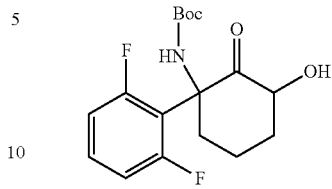

Using compound 10-e (478 mg, 1.47 mmol) as a raw material, the method described in step f in Example 1 was conducted accordingly to obtain 290 mg of white foamy solid, yield: 57.8%. $^1$H NMR (400 MHz, CDCl$_3$) δ 7.31 (ddd, J=14.5, 8.3, 6.1 Hz, 1H), 6.91 (dd, J=10.1, 8.5 Hz, 2H), 6.46 (s, 1H), 4.24 (dd, J=11.2, 5.6 Hz, 1H), 3.89 (s, 1H), 3.32 (d, J=5.6 Hz, 1H), 2.42 (dtd, J=9.7, 6.6, 3.3 Hz, 1H), 1.81 (ddd, J=33.9, 18.7, 8.5 Hz, 2H), 1.55-1.45 (m, 2H), 1.33 (s, 9H). MS (M+Na)$^+$: 364.0

Step g: Preparation of Compound 10

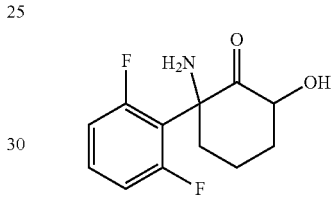

Using compound 10-f (220 mg, 0.64 mmol) as a raw material, the method described in step g in Example 1 was conducted accordingly to obtain 138 mg of white solid, yield: 89.0%. $^1$H NMR (400 MHz, CDCl$_3$) δ 7.36-7.27 (m, 1H), 6.93 (dd, J=10.0, 8.5 Hz, 2H), 4.32 (dd, J=11.5, 7.2 Hz, 1H), 3.23 (dd, J=14.0, 2.6 Hz, 1H), 2.39 (ddd, J=12.4, 6.7, 3.0 Hz, 1H), 1.84-1.75 (m, 1H), 1.60 (dd, J=27.3, 13.6 Hz, 1H), 1.47 (dt, J=21.6, 8.6 Hz, 2H). MS (M+H)$^+$: 278.0

Example 11: Preparation of 2-amino-2-(2,3-difluorophenyl)-6-hydroxycyclohexane-1-one (Compound 11)

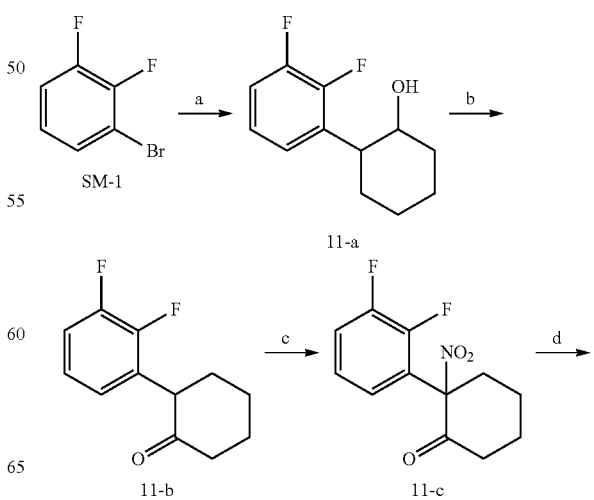

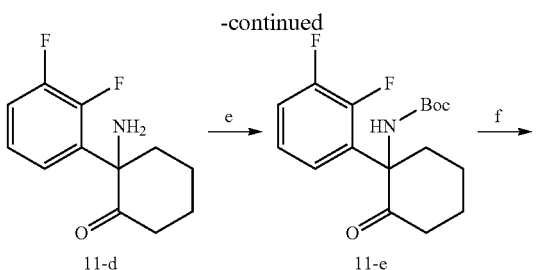

11-d → 11-e →

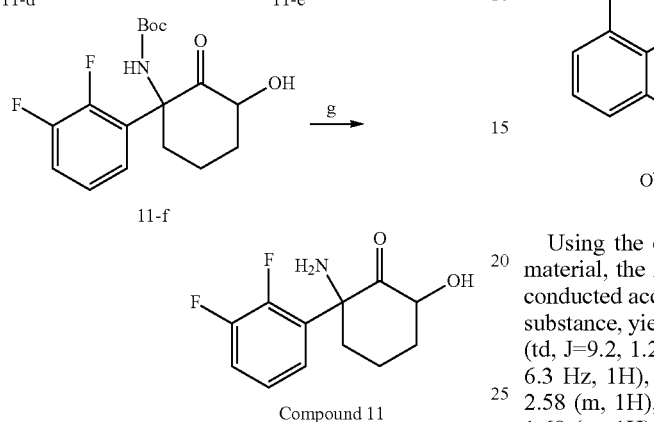

11-f

Compound 11

Step a: Preparation of 11-a

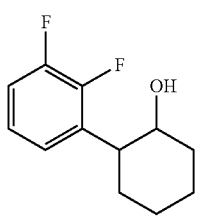 [SMILES: OC1CCCCC1c1cccc(F)c1F]

Using 2,3-difluorobromobenzene (9.5 g, 49.2 mmoL) and epoxycyclohexane (5.3 g, 54 mmol) as raw materials, the method described in step a in Example 1 was conducted accordingly to obtain 8.5 g of colorless oily liquid, yield: 81.4%. $^1$H NMR (400 MHz, CDCl$_3$) δ 7.09-6.97 (m, 3H), 3.76 (s, 1H), 2.90-2.77 (m, 1H), 2.18-2.10 (m, 1H), 1.91-1.82 (m, 2H)), 1.80-1.72 (m, 1H), 1.49-1.31 (m, 4H). MS (M+Na)$^+$: 235.0

Step b: Preparation of 11-b

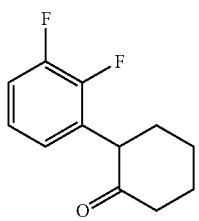

Using the compound 11-a (2.1 g, 9.9 mmol) as a raw material, the method described in step b in Example 1 was conducted accordingly to obtain 1.0 g of white solid, yield: 48.1%. $^1$H NMR (400 MHz, CDCl$_3$) δ 7.09-7.02 (m, 2H), 6.91 (ddd, J=6.1, 4.9, 1.5 Hz, 1H), 3.86 (dd, J=12.9, 5.6 Hz, 1H), 2.61-2.45 (m, 2H), 2.31-2.16 (m, 2H), 2.08-1.97 (m, 2H), 1.89-1.76 (m, 2H). MS (M+Na)$^+$: 233.1

Step c: Preparation of 11-c

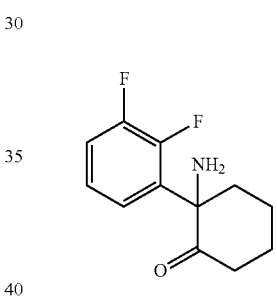

Using the compound 11-b (1.0 g, 4.76 mmol) as a raw material, the method described in step c in Example 1 was conducted accordingly to obtain 450 mg of pale yellow oily substance, yield: 37.1%. $^1$H NMR (400 MHz, CDCl$_3$) δ 7.30 (td, J=9.2, 1.2 Hz, 1H), 7.22-7.15 (m, 1H), 6.98 (dd, J=7.8, 6.3 Hz, 1H), 3.02-2.86 (m, 2H), 2.79-2.71 (m, 1H), 2.67-2.58 (m, 1H), 2.02-1.95 (m, 2H), 1.93-1.84 (m, 1H), 1.77-1.68 (m, 1H). MS (M+Na)$^+$: 278.0

Step d: Preparation of 11-d

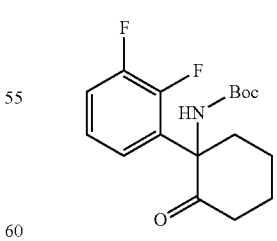

Using the compound 11-c (450 mg, 1.76 mmol) as a raw material, the method described in step d in Example 1 was conducted accordingly to obtain 312 mg of pale yellow oily liquid crude product, which was directly cast into the reaction in next step without purification. MS (M+H)$^+$: 226.1

Step e: Preparation of 11-e

Using the crude compound 11-d (312 mg crude product) as a raw material, the method described in step e in Example 1 was conducted accordingly to obtain 320 mg of colorless oily liquid, yield: 55.7% (two steps together). $^1$H NMR (400 MHz, CDCl$_3$) δ 7.45 (s, 1H), 7.18-7.09 (m, 2H), 6.46 (s, 1H), 3.72 (d, J=7.7 Hz, 1H), 2.48 (d, J=11.6 Hz, 1H), 2.42-2.32 (m, 1H), 2.10-1.99 (m, 1H), 1.86-1.66 (m, 4H), 1.33 (s, 9H). MS (M+Na)⁺: 348.1

Step f: Preparation of 11-f

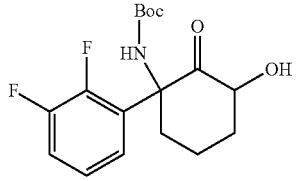 [SMILES: CC(C)(C)OC(=O)NC1(c2cccc(F)c2F)CCCC(O)C1=O]

Using the compound 11-e (300 mg, 0.92 mmol) as a raw material, the method described in step f in Example 1 was conducted accordingly to obtain 137 mg of white solid, yield: 43.5%. ¹H NMR (400 MHz, CDCl₃) δ 7.45 (s, 1H), 7.16 (dd, J=8.8, 4.1 Hz, 2H), 6.51 (s, 1H), 4.18 (dd, J=11.9, 6.9 Hz, 1H), 3.82 (s, 1H), 3.37 (s, 1H), 2.40 (ddd, J=12.4, 6.6, 3.0 Hz, 1H), 1.82-1.68 (m, 3H), 1.59-1.51 (m, 1H), 1.32 (s, 9H). MS (M+Na)⁺: 364.1

Step g: Preparation of Compound 11

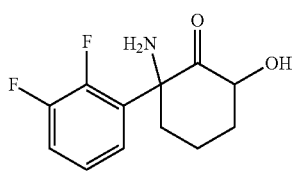 [SMILES: NC1(c2cccc(F)c2F)CCCC(O)C1=O]

Using the compound 11-f (134 mg, 0.39 mmol) as a raw material, the method described in step g in Example 1 was conducted accordingly to obtain 92 mg of light yellow oily liquid, yield: 96.8%. ¹H NMR (400 MHz, CDCl₃) δ 7.23-7.12 (m, 3H), 4.25 (dd, J=11.8, 7.0 Hz, 1H), 2.89 (dt, J=5.8, 2.7 Hz, 1H), 2.38 (ddd, J=12.4, 6.8, 3.3 Hz, 1H), 1.77 (td, J=5.6, 2.9 Hz, 1H), 1.70-1.63 (m, 2H), 1.52 (td, J=12.1, 4.4 Hz, 1H). MS (M+H)⁺: 242.1.

Example 12: Preparation of 2-amino-6-hydroxy-2-(2-(trifluoromethyl)phenyl)cyclohexane-1-one (Compound 12)

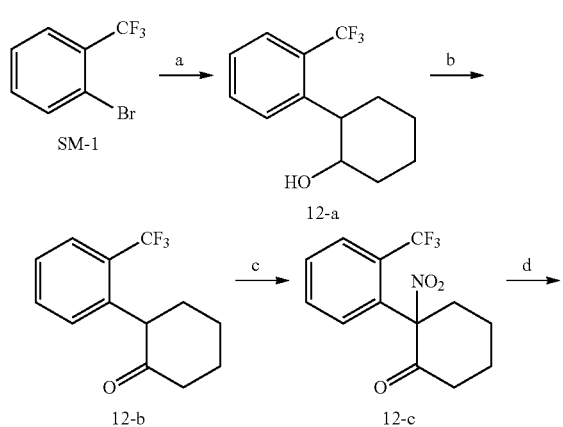

-continued

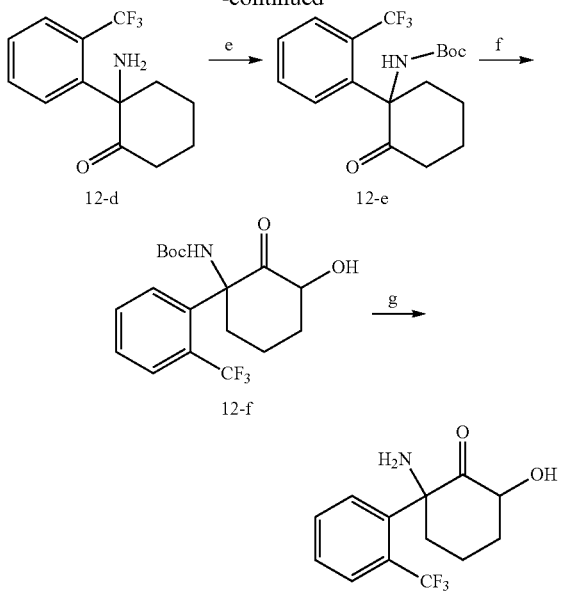

Step a: Preparation of 12-a

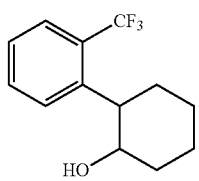 [SMILES: OC1CCCCC1c1ccccc1C(F)(F)F]

Using 2-trifluoromethyl bromobenzene (10 g, 44.44 mmoL) and epoxycyclohexane (4.8 g, 48.9 mmol) as raw materials, the method described in step a in Example 1 was conducted accordingly to obtain 5.08 g of colorless oily liquid, yield: 46.8%. ¹H NMR (400 MHz, CDCl₃) δ 7.65 (d, J=7.9 Hz, 1H), 7.57-7.49 (m, 2H), 7.31 (t, J=7.4 Hz, 1H), 3.85 (dd, J=11.4, 7.9 Hz, 1H), 2.92 (dd, J=15.4, 5.7 Hz, 1H), 2.22-2.12 (m, 1H), 1.88 (dd, J=9.7, 3.1 Hz, 2H), 1.74 (dd, J=8.1, 5.1 Hz, 1H), 1.40 (ddd, J=16.1, 12.1, 5.9 Hz, 4H). MS (M+Na)⁺: 267.1

Step b: Preparation of 12-b

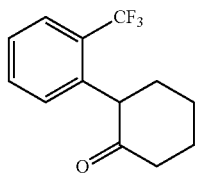 [SMILES: O=C1CCCCC1c1ccccc1C(F)(F)F]

Using the compound 12-a (4.9 g, 20.06 mmol) as a raw material, the method described in step b in Example 1 was conducted accordingly to obtain 3.58 g of light yellow oil, yield: 73.7%. ¹H NMR (400 MHz, CDCl₃) δ 7.64 (d, J=7.9 Hz, 1H), 7.54 (t, J=7.6 Hz, 1H), 7.35 (t, J=8.1 Hz, 2H), 4.06

(dd, J=12.4, 5.1 Hz, 1H), 2.56-2.50 (m, 2H), 2.32-2.26 (m, 1H), 2.25-2.18 (m, 1H), 2.00 (dd, J=13.9, 2.0 Hz, 2H), 1.90-1.81 (m, 2H). MS (M+Na)+: 243.1

Step c: Preparation of 12-c

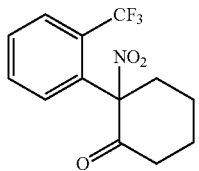 [SMILES: O=C1CCCCC1(c1ccccc1C(F)(F)F)[N+](=O)[O-]]

Using the compound 12-b (1.58 g, 6.52 mmol) as a raw material, the method described in step c in Example 1 was conducted accordingly to obtain 507 mg of pale yellow oily substance, yield: 27%. ¹H NMR (400 MHz, CDCl₃) δ 7.81 (dd, J=7.2, 2.1 Hz, 1H), 7.64-7.53 (m, 2H), 7.15 (dd, J=8.3, 6.3 Hz, 1H), 3.05-2.89 (m, 2H), 2.79-2.70 (m, 2H), 2.02-1.91 (m, 2H), 1.89-1.77 (m, 1H), 1.74-1.63 (m, 1H). MS (M+Na)+: 310.1

Step d: Preparation of 12-d

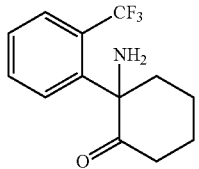 [SMILES: NC1(c2ccccc2C(F)(F)F)CCCCC1=O]

Using the compound 12-c (500 mg, 1.74 mmol) as a raw material, the method described in step d in Example 1 was conducted accordingly to obtain 480 mg of pale yellow oily liquid crude product, which was directly cast into the reaction in next step without purification. MS (M+H)+: 258.1

Step e: Preparation of 12-e

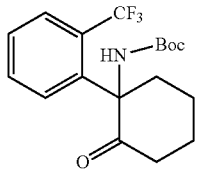 [SMILES: CC(C)(C)OC(=O)NC1(c2ccccc2C(F)(F)F)CCCCC1=O]

Using the crude compound 12-d (480 mg crude product) as a raw material, the method described in step e in Example 1 was conducted accordingly to obtain 367 mg of colorless oily liquid, yield: 59.0% (two steps together). ¹H NMR (400 MHz, CDCl₃) δ 8.05 (d, J=7.6 Hz, 1H), 7.74 (d, J=7.9 Hz, 1H), 7.65 (t, J=7.7 Hz, 1H), 7.47 (dd, J=17.4, 9.9 Hz, 1H), 6.47 (s, 1H), 3.85 (d, J=11.8 Hz, 1H), 2.42 (d, J=11.6 Hz, 1H), 2.35-2.25 (m, 1H), 2.04 (s, 1H), 1.81 (s, 4H), 1.31 (s, 9H). MS (M+H)+: 358.1

Step f: Preparation of 12-f

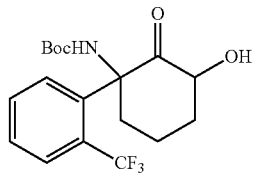 [SMILES: CC(C)(C)OC(=O)NC1(c2ccccc2C(F)(F)F)CCCC(O)C1=O]

Use compound 12-e (230 mg, 0.64 mmol) as a raw material, the method described in step f in Example 1 was conducted accordingly to obtain 121 mg of colorless oily liquid, yield: 50.4%. ¹H NMR (400 MHz, CDCl₃) δ 8.04 (d, J=7.6 Hz, 1H), 7.77 (d, J=7.8 Hz, 1H), 7.67 (t, J=7.6 Hz, 1H), 7.48 (t, J=7.6 Hz, 1H), 6.52 (s, 1H), 4.10 (dd, J=12.0, 6.3 Hz, 1H), 4.01 (d, J=14.4 Hz, 1H), 3.25 (d, J=5.5 Hz, 1H), 2.38 (ddd, J=12.5, 6.6, 3.2 Hz, 1H), 1.79 (d, J=7.6 Hz, 2H), 1.74-1.64 (m, 1H), 1.55 (dd, J=7.4, 4.4 Hz, 1H), 1.30 (s, 9H). MS (M+H)+: 374.1

Step g: Preparation of Compound 12

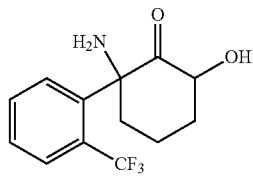 [SMILES: NC1(c2ccccc2C(F)(F)F)CCCC(O)C1=O]

Using the compound 12-f (102 mg, 0.27 mmol) as a raw material, the method described in step g in Example 1 was conducted accordingly to obtain 68 mg of colorless oily liquid, yield: 90.7%. ¹H NMR (400 MHz, CDCl₃) δ 7.78 (dd, J=16.6, 8.0 Hz, 2H), 7.67 (t, J=7.6 Hz, 1H), 7.50 (t, J=7.6 Hz, 1H), 4.18 (dd, J=11.6, 6.9 Hz, 1H), 3.03 (d, J=12.3 Hz, 1H), 2.35 (ddd, J=12.4, 6.6, 3.1 Hz, 1H), 1.77-1.59 (m, 3H), 1.56-1.47 (m, 1H). MS (M+H)+: 274.1

Example 13: Preparation of 2-amino-6-hydroxy-2-(4-(trifluoromethyl)phenyl)cyclohexane-1-one (Compound 13)

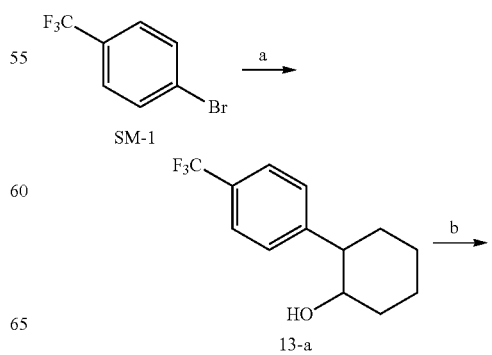

-continued

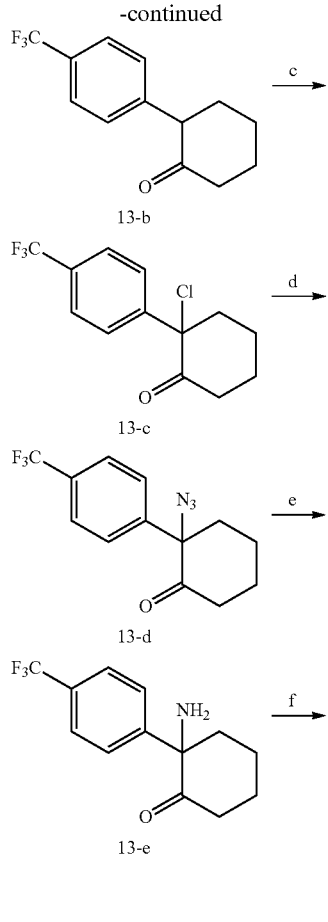

13-b 13-c 13-d 13-e 13-f 13-g

Compound 13

Step a: Preparation of 13-a

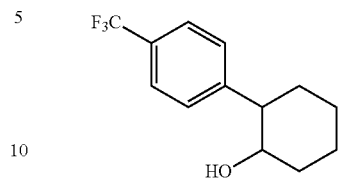

Using 4-trifluoromethyl bromobenzene (10 g, 44.44 mmoL) and epoxycyclohexane (4.8 g, 48.9 mmoL) as raw materials, the method described in step a in Example 1 was conducted accordingly to obtain 9.61 g of colorless oily liquid, yield: 88.5%. $^1$H NMR (400 MHz, CDCl$_3$) δ 7.59 (d, J=8.1 Hz, 2H), 7.37 (d, J=8.0 Hz, 2H), 3.70 (td, J=9.9, 4.2 Hz, 1H), 2.56-2.47 (m, 1H), 2.15-2.09 (m, 1H), 1.89-1.82 (m, 2H), 1.82-1.74 (m, 1H), 1.48-1.34 (m, 4H). MS(M+Na)$^+$: 267.

Step b: Preparation of 13-b

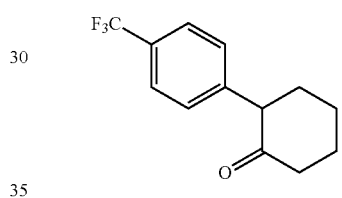

Using the compound 13-a (9.61 g, 39.34 mmol) as a raw material, the method described in step b in Example 1 was conducted accordingly to obtain 4.78 g of white solid, yield: 50.2%. $^1$H NMR (400 MHz, CDCl$_3$) δ 7.59 (d, J=8.1 Hz, 2H), 7.26 (s, 2H), 3.67 (dd, J=12.3, 5.4 Hz, 1H), 2.59-2.43 (m, 2H), 2.29 (ddd, J=12.7, 5.5, 3.1 Hz, 1H), 2.19 (dq, J=6.0, 3.5 Hz, 1H), 2.07-1.95 (m, 2H), 1.91-1.79 (m, 2H). MS (M+H)$^+$: 243.

Step c: Preparation of 13-c

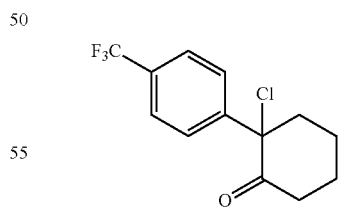

Using the compound 13-b (2 g, 8.26 mmol) as a raw material, the method described in step c in Example 2 was conducted accordingly to obtain 1.33 g of light yellow oily liquid, yield: 58.2%. $^1$H NMR (400 MHz, CDCl$_3$) δ 7.65 (d, J=8.3 Hz, 2H), 7.55 (d, J=8.4 Hz, 2H), 3.07-2.99 (m, 1H), 2.81-2.71 (m, 1H), 2.53-2.40 (m, 2H), 2.13 (ddd, J=17.9, 9.2, 4.5 Hz, 1H), 2.06-2.01 (m, 1H), 1.93-1.81 (m, 2H). MS (M+Na)+: 299.

Step d: Preparation of 13-d

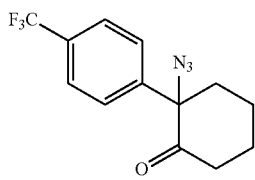 [SMILES: [N-]=[N+]=NC1(c2ccc(C(F)(F)F)cc2)CCCCC1=O]

Using the compound 13-c (1.33 g, 4.81 mmol) as a raw material, the method described in step d in Example 2 was conducted accordingly to obtain 907 mg of pale yellow oily liquid, yield: 66.6%. $^1$H NMR (400 MHz, CDCl$_3$) δ 7.79-7.65 (m, 2H), 7.50-7.37 (m, 2H), 2.74-2.67 (m, 1H), 2.63 (dtd, J=14.1, 4.6, 1.6 Hz, 1H), 2.36 (ddd, J=14.1, 11.6, 5.9 Hz, 1H), 2.05 (ddd, J=11.7, 9.8, 3.6 Hz, 1H), 1.97-1.92 (m, 1H), 1.92-1.86 (m, 1H), 1.86-1.80 (m, 1H), 1.72-1.60 (m, 1H). MS (M+Na)$^+$: 306.

Step e: Preparation of 13-e

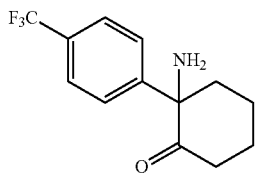 [SMILES: NC1(c2ccc(C(F)(F)F)cc2)CCCCC1=O]

Using the compound 13-d (907 mg, 3.2 mmol) as a raw material, the method described in step e in Example 2 was conducted accordingly to obtain 700 mg of pale yellow oily liquid, which was directly cast into the reaction in next step without purification. MS (M+H)$^+$: 280

Step f: Preparation of 13-f

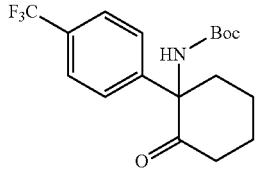 [SMILES: CC(C)(C)OC(=O)NC1(c2ccc(C(F)(F)F)cc2)CCCCC1=O]

Using crude compound 13-e (700 mg crude product) as a raw material, the method described in step e in Example 1 was conducted accordingly to obtain 798 mg of yellow oily liquid, yield: 69.8% (two steps together). $^1$H NMR (400 MHz, CDCl$_3$) δ 7.62 (d, J=8.2 Hz, 2H), 7.46 (d, J=8.1 Hz, 2H), 6.40 (s, 1H), 3.64 (d, J=12.2 Hz, 1H), 2.44 (d, J=13.3 Hz, 1H), 2.24-2.18 (m, 1H), 2.02 (dd, J=10.8, 4.8 Hz, 1H), 1.89 (d, J=11.0 Hz, 2H), 1.78 (dd, J=20.7, 11.4 Hz, 2H), 1.31 (s, 9H). MS (M+Na)$^+$: 380.

Step g: Preparation of 13-g

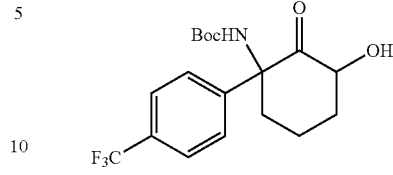

Using the compound 13-f (400 mg, 1.12 mmol) as a raw material, the method described in step f in Example 1 was conducted accordingly to obtain 87 mg of colorless oily substance, yield: 20.8%. $^1$H NMR (400 MHz, CDCl$_3$) δ 7.64 (d, J=8.2 Hz, 2H), 7.44 (d, J=8.2 Hz, 2H), 6.40 (s, 1H), 4.02 (dd, J=11.9, 6.6 Hz, 1H), 3.72 (s, 1H), 3.32 (s, 1H), 2.38 (ddd, J=12.5, 6.5, 2.9 Hz, 1H), 2.00-1.88 (m, 3H), 1.66-1.58 (m, 1H), 1.31 (s, 9H). MS (M+Na)$^+$: 396

Step h: Preparation of Compound 13

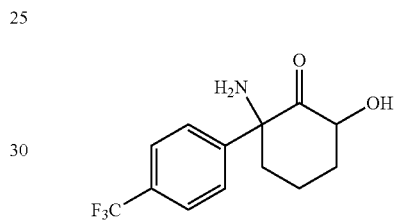

The compound 13-g (1.5 g, 4.02 mmol) was dissolved in DCM (15 mL), 4M HCl 1,4-dioxane solution (2 mL) was added, and mixture was stirred at room temperature for 1.5 hours. A large amount of white solid were precipitated, and solvent was rotary evaporated, the residue was neutralized with saturated NaHCO$_3$ (20 ml). Ethyl acetate was added for extraction (10 mL×3), the organic phases were combined, and washed with saturated NaCl solution, dried with anhydrous sodium sulfate, filtered, and subjected to column chromatography (PE/EA=2/1) to obtain 880 mg of colorless oil, yield: 80.1%. $^1$H NMR (400 MHz, CD$_3$OD) δ 7.73 (d, J=8.1 Hz, 2H), 7.50 (d, J=8.1 Hz, 2H), 4.09 (dd, J=12.2, 6.5 Hz, 1H), 2.91 (d, J=12.1 Hz, 1H), 2.24 (dd, J=9.3, 5.7 Hz, 1H), 1.82 (dd, J=18.8, 8.5 Hz, 2H), 1.74-1.58 (m, 2H). MS (M+H)$^+$: 296.1

Example 14: Preparation of (2R,6R)-2-amino-6-hydroxy-2-(4-(trifluoromethyl)phenyl)cyclohexane-1-one (Compound 14)

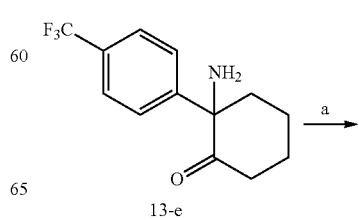

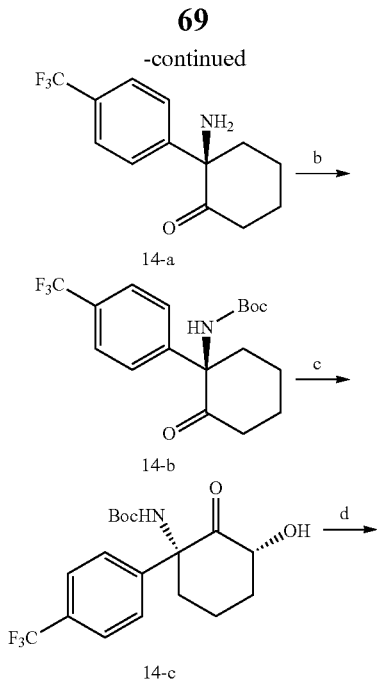

14-a 14-b 14-c

Compound 14

Step a: Preparation of 14-a

The compound 13-e (3.57 g, 13.88 mmol) was dissolved in methanol (80 ml), and a methanol solution of R-(−)-mandelic acid (2.32 g, 15.26 mmol) was added with stirring. After the addition, the mixture was reacted at room temperature overnight. The reaction solution was dried by rotary evaporation, and acetone (40 ml) was added, and beat at room temperature for 30 minutes and then filtered with suction to obtain 5.1 g of white solid. THF (70 ml) was added into the white solid. The mixture was heated to reflux until it was completely dissolved, and naturally cooled down to room temperature, and the solid was slowly precipitated out in the system, filtered and dried to obtain 2.72 g of white solid. The same operation was repeated twice to obtain 1.54 g of white solid, ee value >99%. The obtained white solid was adjusted to have a pH of about 9 with 1.0M NaOH, and extracted with EA (15 ml×3). The organic phases were combined, washed with saturated brine, dried with anhydrous sodium sulfate, and rotary evaporated to obtain 998 mg of colorless oil.

Step b: Preparation of 14-b

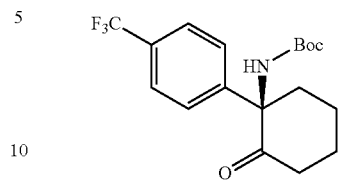

Using the compound 14-a (998 mg, 3.88 mmol) as a raw material, the method described in step e in Example 1 was conducted accordingly to obtain 1.09 g of white solid, yield: 78.6%. $^1$H NMR (400 MHz, CDCl$_3$) δ 7.62 (d, J=8.3 Hz, 2H), 7.47 (d, J=8.1 Hz, 2H), 6.41 (s, 1H), 3.65 (d, J=12.5 Hz, 1H), 2.44 (d, J=13.2 Hz, 1H), 2.24 (s, 1H), 2.00 (t, J=14.5 Hz, 1H), 1.90 (d, J=10.9 Hz, 2H), 1.79 (dd, J=20.7, 11.4 Hz, 2H), 1.39-1.25 (m, 9H). MS (M+Na)$^+$: 380.

Step c: Preparation of 14-c

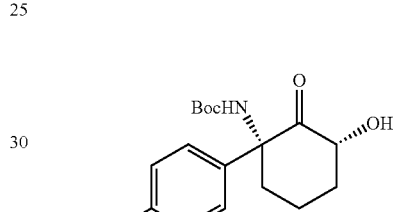

Using the compound 14-b (600 mg, 1.68 mmol) as a raw material, the method described in step f in Example 1 was conducted accordingly to obtain 223 mg of white foam, yield: 35.6%. $^1$H NMR (400 MHz, CDCl$_3$) δ 7.64 (d, J=8.2 Hz, 2H), 7.45 (d, J=8.2 Hz, 2H), 6.40 (s, 1H), 4.07-3.97 (m, 1H), 3.74 (d, J=11.6 Hz, 1H), 3.34 (d, J=4.7 Hz, 1H), 2.38 (ddd, J=12.4, 6.5, 3.0 Hz, 1H), 2.00-1.86 (m, 3H), 1.62 (td, J=12.6, 4.4 Hz, 1H), 1.32 (s, 9H). MS (M+Na)$^+$: 396

Step d: Preparation of Compound 14

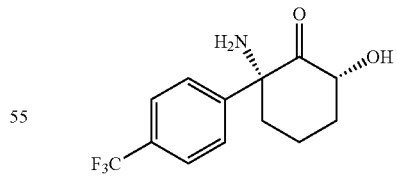

Using the compound 14-c (180 mg, 0.48 mmol) as a raw material, the method described in step g in Example 1 was conducted accordingly to obtain 122 mg of colorless oily liquid, yield: 92.4%, ee>99%. $^1$H NMR (400 MHz, CD$_3$OD) δ 7.73 (d, J=8.1 Hz, 2H), 7.50 (d, J=8.1 Hz, 2H), 4.09 (dd, J=12.2, 6.5 Hz, 1H), 2.91 (d, J=12.1 Hz, 1H), 2.24 (dd, J=9.3, 5.7 Hz, 1H), 1.82 (dd, J=18.8, 8.5 Hz, 2H), 1.74-1.58 (m, 2H). MS (M+Na)$^+$: 296.1

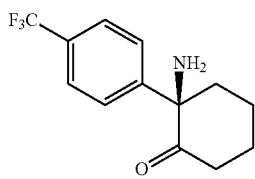 [SMILES: N[C@@]1(c2ccc(C(F)(F)F)cc2)CCCCC1=O]

Example 15: Preparation of (2S,6S)-2-amino-6-hydroxy-2-(4-(trifluoromethyl)phenyl)cyclohexane-1-one (compound 15)

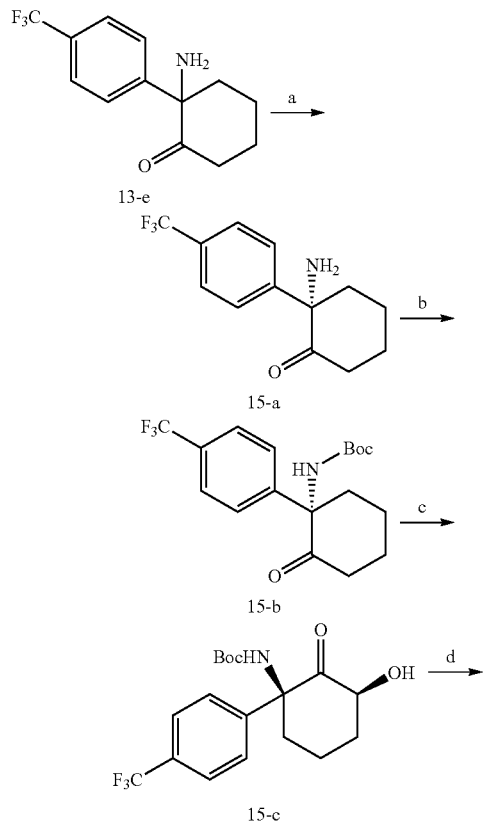

Step a: Preparation of 15-a

The compound 13-e (4.7 g, 18.27 mmol) was dissolved in methanol (100 ml), and the methanol solution of S-(+)-mandelic acid (3.06 g, 20.11 mmol) was added with stirring. After the addition, the mixture was reacted at room temperature overnight. The reaction solution was dried via rotary evaporation, and acetone (100 ml) was added. The mixture beat at room temperature for 30 minutes and then filtered with suction to obtain 7.4 g of white solid. THF (100 ml) was added to the white solid. The mixture was heated to reflux until it was completely dissolved, and naturally cooled down to room temperature, and solid was slowly precipitated out from the system, filtered and dried to obtain 4.6 g of white solid. The same operation was repeated three times to obtain 1.57 g of white solid, ee value >99%. The obtained white solid was adjusted to have a pH of about 9 with 1.0M NaOH, and extracted with EA (20 ml×3). The organic phases were combined, washed with saturated brine, dried with anhydrous sodium sulfate, and rotary evaporated to obtain 940 mg of colorless oil.

Step b: Preparation of 15-b

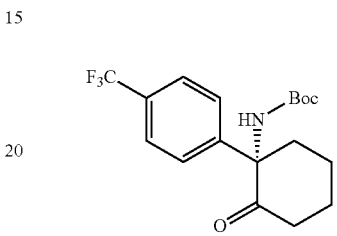

Using the compound 15-a (940 mg, 3.65 mmol) as a raw material, the method described in step e in Example 1 was conducted accordingly to obtain 1.13 g of white solid, yield: 86.5%. $^1$H NMR (400 MHz, CDCl$_3$) δ 7.62 (d, J=8.3 Hz, 2H), 7.47 (d, J=8.1 Hz, 2H), 6.41 (s, 1H), 3.65 (d, J=12.4 Hz, 1H), 2.44 (d, J=13.2 Hz, 1H), 2.24 (s, 1H), 2.04-1.98 (m, 1H), 1.90 (d, J=10.9 Hz, 2H), 1.84-1.69 (m, 2H), 1.26 (s, 9H). MS (M+Na)$^+$: 380.

Step c: Preparation of 15-c

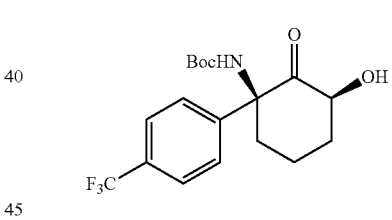

Using the compound 15-b (600 mg, 1.68 mmol) as a raw material, the method described in step f in Example 1 was conducted accordingly to obtain 232 mg of white foam, yield: 37.0%. $^1$H NMR (400 MHz, CDCl$_3$) δ 7.64 (d, J=8.3 Hz, 2H), 7.44 (d, J=8.2 Hz, 2H), 6.40 (s, 1H), 4.02 (s, 1H), 3.73 (d, J=12.0 Hz, 1H), 3.36 (s, 1H), 2.37 (ddd, J=12.4, 6.4, 2.9 Hz, 1H), 1.99-1.82 (m, 3H), 1.60 (dd, J=12.6, 4.5 Hz, 1H), 1.38-1.25 (m, 9H). MS (M+Na)$^+$: 396.

Step d: Preparation of Compound 15

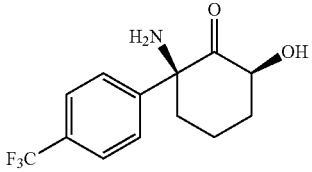 [SMILES: N[C@]1(c2ccc(C(F)(F)F)cc2)CCC[C@H](O)C1=O]

Using the compound 15-c (180 mg, 0.48 mmol) as a raw material, the method described in step g in Example 1 was conducted accordingly to obtain 125 mg of colorless oily liquid, yield: 94.7%, ee>99%. $^1$H NMR (400 MHz, CD$_3$OD) δ 7.73 (d, J=8.1 Hz, 2H), 7.50 (d, J=8.1 Hz, 2H), 4.09 (dd, J=12.2, 6.5 Hz, 1H), 2.91 (d, J=12.1 Hz, 1H), 2.24 (dd, J=9.3, 5.7 Hz, 1H), 1.82 (dd, J=18.8, 8.5 Hz, 2H), 1.74-1.58 (m, 2H). MS (M+H)$^+$: 274.

Example 16: Preparation of 2-amino-6-hydroxy-2-(3-(trifluoromethyl)phenyl)cyclohexane-1-one (Compound 16)

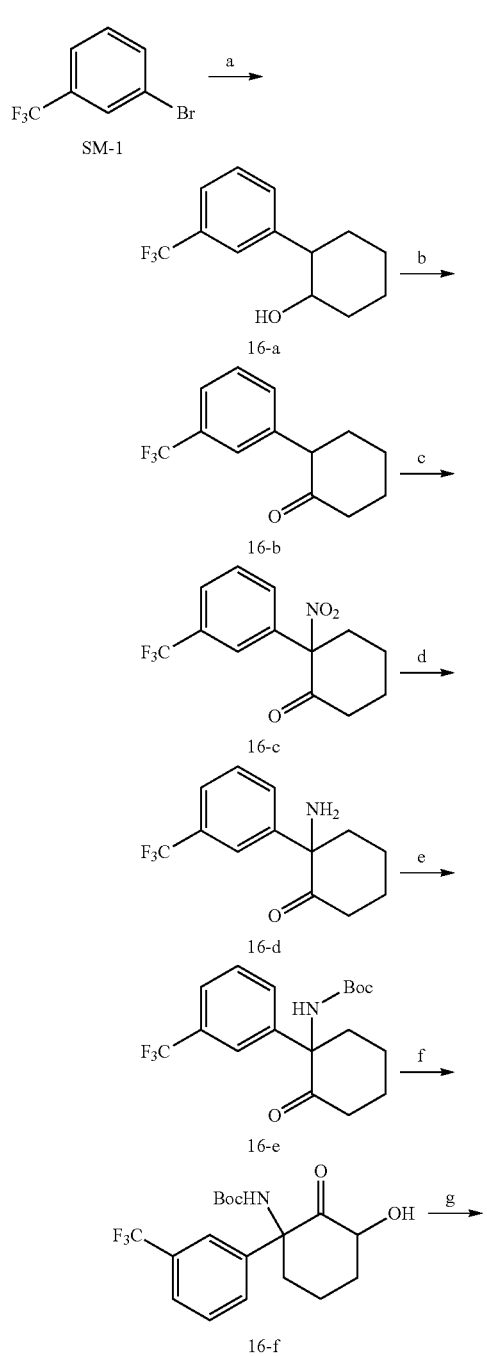

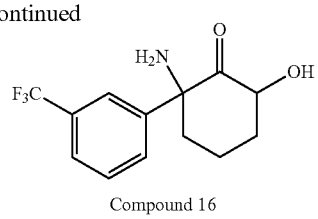

Compound 16

Step a: Preparation of 16-a

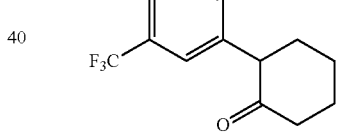

Using 3-trifluoromethyl bromobenzene (10 g, 44.44 mmoL) and epoxycyclohexane (4.8 g, 48.9 mmoL) as raw materials, the method described in step a in Example 1 was conducted accordingly to obtain 8.8 g of yellow oily liquid, yield: 81.03%. $^1$H NMR (400 MHz, CDCl$_3$) δ 7.50 (s, 1H), 7.48-7.44 (m, 1H), 7.40 (d, J=5.1 Hz, 2H), 3.60 (td, J=10.0, 4.1 Hz, 1H), 2.51-2.41 (m, 1H), 2.09-1.99 (m, 1H), 1.84 (dd, J=12.4, 1.8 Hz, 2H), 1.75 (d, J=12.1 Hz, 1H), 1.53-1.43 (m, 1H), 1.41-1.27 (m, 3H). MS (M+Na)$^+$: 267.1

Step b: Preparation of 16-b

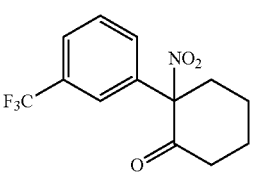 [SMILES: O=C1CCCCC1(c1cccc(C(F)(F)F)c1)[N+](=O)[O-]]

Using the compound 16-a (8.8 g, 36.03 mmol) as a raw material, the method described in step b in Example 1 was conducted accordingly to obtain 3.8 g of light yellow oil, yield: 43.5%. $^1$H NMR (400 MHz, CDCl$_3$) δ 7.52 (d, J=7.7 Hz, 1H), 7.45 (t, J=7.7 Hz, 1H), 7.39 (s, 1H), 7.33 (d, J=7.6 Hz, 1H), 3.68 (dd, J=12.4, 5.4 Hz, 1H), 2.56-2.42 (m, 2H), 2.30 (ddd, J=12.7, 5.3, 3.1 Hz, 1H), 2.23-2.15 (m, 1H), 2.02 (dt, J=9.7, 4.2 Hz, 2H), 1.84 (t, J=11.3 Hz, 2H). MS (M+Na)$^+$: 243.1

Step c: Preparation of 16-c

Using the compound 16-b (3.0 g, 12.38 mmol) as a raw material, the method described in step c in Example 1 was conducted accordingly to obtain 1.43 g of pale yellow oily substance, yield: 40.2%. $^1$H NMR (400 MHz, CDCl$_3$) δ 7.72 (d, J=7.8 Hz, 1H), 7.59 (d, J=3.5 Hz, 2H), 7.53 (d, J=7.8 Hz, 1H), 3.17 (ddd, J=11.1, 8.1, 3.5 Hz, 1H), 2.81-2.68 (m, 2H), 2.61-2.51 (m, 1H), 2.03-1.82 (m, 4H). MS (M+Na)$^+$: 310.1

Step d: Preparation of 16-d

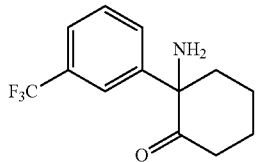 [SMILES: NC1(c2cccc(C(F)(F)F)c2)CCCCC1=O]

Using the compound 16-c (1.3 g, 4.52 mmol) as a raw material, the method described in step d in Example 1 was conducted accordingly to obtain 1.08 g of pale yellow oily liquid crude product, which was directly cast into the reaction in next step without purification. MS (M+H)$^+$: 258.1

Step e: Preparation of 16-e

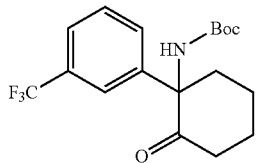 [SMILES: CC(C)(C)OC(=O)NC1(c2cccc(C(F)(F)F)c2)CCCCC1=O]

Using the crude compound 16-d (1.08 g crude product) as a raw material, the method described in step e in Example 1 was conducted accordingly to obtain 729 mg of colorless oily liquid, yield: 45.1% (two steps together). $^1$H NMR (400 MHz, CDCl$_3$) δ 7.64-7.43 (m, 4H), 6.35 (s, 1H), 3.57 (d, J=12.5 Hz, 1H), 2.51-2.42 (m, 1H), 2.21 (dd, J=10.4, 4.8 Hz, 1H), 2.00 (d, J=12.9 Hz, 1H), 1.92 (d, J=13.9 Hz, 2H), 1.84-1.75 (m, 2H), 1.32 (s, 9H). MS (M+H)$^+$: 358.1

Step f: Preparation of 16-f

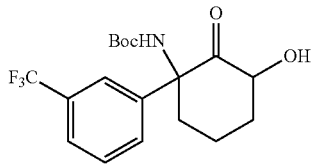

Use compound 16-e (400 mg, 1.12 mmol) as a raw material, the method described in step f in Example 1 was conducted accordingly to obtain 124 mg of colorless oily liquid, yield: 29.7%. $^1$H NMR (400 MHz, CDCl$_3$) δ 7.58-7.51 (m, 4H), 6.36 (s, 1H), 4.03 (dd, J=11.0, 6.9 Hz, 1H), 3.69 (s, 1H), 2.43-2.35 (m, 2H), 1.93 (d, J=18.0 Hz, 3H), 1.68-1.57 (m, 1H), 1.31 (s, 9H). MS (M+H)$^+$: 375.

Step g: Preparation of Compound 16

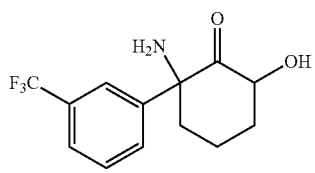 [SMILES: NC1(c2cccc(C(F)(F)F)c2)CCCC(O)C1=O]

Using the compound 16-f (117 mg, 0.31 mmol) as a raw material, the method described in step g in Example 1 was conducted accordingly to obtain 79 mg of colorless oily liquid, yield: 91.9%. $^1$H NMR (400 MHz, CDCl$_3$) δ 7.60 (d, J=7.8 Hz, 1H), 7.53 (t, J=7.6 Hz, 2H), 7.38 (d, J=7.7 Hz, 1H), 4.17 (dd, J=11.8, 7.0 Hz, 1H), 2.94-2.87 (m, 1H), 2.39 (ddd, J=12.1, 6.9, 2.8 Hz, 1H), 1.87-1.51 (m, 4H). MS (M+H)$^+$: 274.1.

Example 17: Preparation of 2-amino-2-(3,4-dimethoxyphenyl)-6-hydroxycyclohexane-1-one (Compound 17)

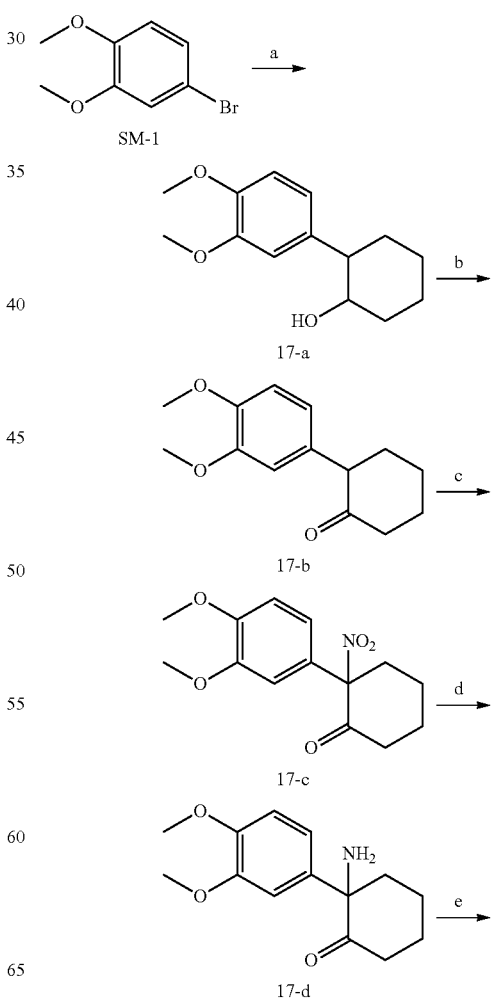

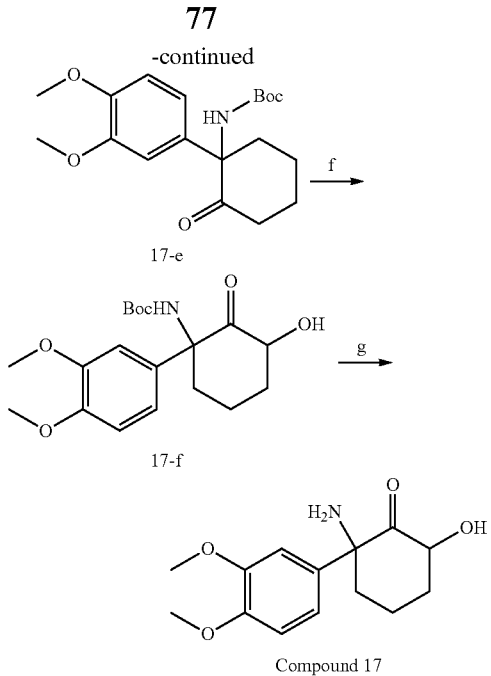

17-e 17-f

Compound 17

Step a: Preparation of 17-a

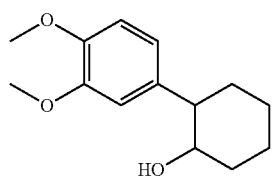 [SMILES: COc1ccc(C2CCCCC2O)cc1OC]

Using 3,4-dimethoxybromobenzene (10 g, 46.1 mmoL) and epoxycyclohexane (4.8 g, 48.9 mmol) as raw materials, the method described in step a in Example 1 was conducted accordingly to obtain 8.25 g of yellow oily liquid, yield: 75.8%. $^1$H NMR (400 MHz, CDCl$_3$) δ 6.78 (ddd, J=11.7, 8.9, 4.9 Hz, 3H), 3.87 (s, 3H), 3.84 (s, 3H), 3.58 (td, J=10.0, 4.2 Hz, 1H), 2.39-2.30 (m, 1H), 2.09 (dd, J=5.4, 4.0 Hz, 1H), 1.88-1.79 (m, 2H), 1.73 (dd, J=16.2, 13.5 Hz, 2H), 1.51-1.41 (m, 1H), 1.40-1.31 (m, 2H). MS (M+Na)$^+$: 259

Step b: Preparation of 17-b

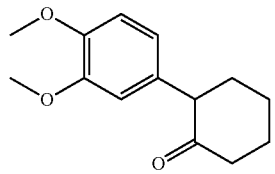 [SMILES: COc1ccc(C2CCCCC2=O)cc1OC]

Using the compound 17-a (6 g, 25.39 mmol) as a raw material, the method described in step b in Example 1 was conducted accordingly to obtain 4.82 g of colorless oil, yield: 80.9%. $^1$H NMR (400 MHz, CDCl$_3$) δ 6.83 (d, J=8.2 Hz, 1H), 6.69 (dd, J=8.2, 1.9 Hz, 1H), 6.65 (d, J=1.9 Hz, 1H), 3.85 (s, 6H), 3.56 (dd, J=12.0, 5.5 Hz, 1H), 2.55-2.39 (m, 2H), 2.30-2.22 (m, 1H), 2.14 (ddd, J=13.1, 7.4, 3.8 Hz, 1H), 2.00 (ddd, J=12.3, 7.5, 3.6 Hz, 2H), 1.82 (ddd, J=11.7, 8.3, 3.6 Hz, 2H). MS (M+Na)$^+$: 235

Step c: Preparation of 17-c

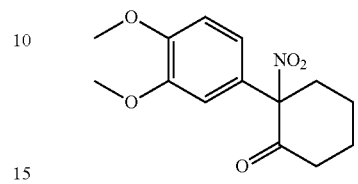

Using the compound 17-b (1.65 g, 7.04 mmol) as a raw material, the method described in step c in Example 1 was conducted accordingly to obtain 428 mg of pale yellow solid, yield: 21.8%. $^1$H NMR (400 MHz, CDCl$_3$) δ 6.94 (dt, J=13.9, 5.2 Hz, 2H), 6.80 (d, J=2.0 Hz, 1H), 3.91 (s, 3H), 3.87 (s, 3H), 3.06 (ddd, J=14.2, 10.9, 3.5 Hz, 1H), 2.86 (dd, J=14.3, 3.3 Hz, 1H), 2.66 (dt, J=14.0, 5.7 Hz, 1H), 2.55 (ddd, J=12.0, 9.2, 4.6 Hz, 1H), 1.94 (ddd, J=11.9, 7.6, 2.8 Hz, 3H), 1.84-1.75 (m, 1H). MS (M+H)$^+$: 280

Step d: Preparation of 17-d

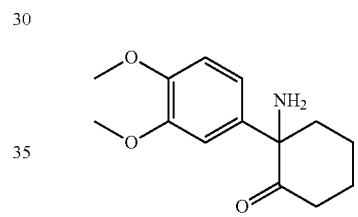

Using the compound 17-c (428 mg, 1.53 mmol) as a raw material, the method described in step d in Example 1 was conducted accordingly to obtain 213 mg of pale yellow oily liquid crude product, which was directly cast into the reaction in next step without purification. MS (M+H)$^+$: 258.1

Step e: Preparation of 17-e

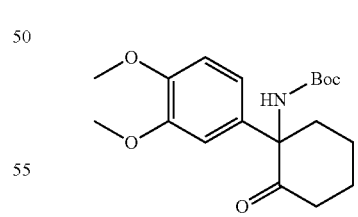

Using the crude compound 17-d (213 mg crude product) as a raw material, the method described in step e in Example 1 was conducted accordingly to obtain 230 mg of colorless oily liquid, yield: 43.0% (two steps together). $^1$H NMR (400 MHz, CDCl$_3$) δ 6.98 (d, J=7.8 Hz, 1H), 6.85 (d, J=8.4 Hz, 1H), 6.74 (s, 1H), 6.25 (s, 1H), 3.87 (s, 3H), 3.84 (s, 3H), 3.52 (d, J=13.3 Hz, 1H), 2.36 (dd, J=23.7, 10.7 Hz, 2H), 1.98 (s, 2H), 1.85 (s, 2H), 1.78-1.68 (m, 1H), 1.33 (s, 9H). MS (M+Na)$^+$: 372

Step f: Preparation of 17-f

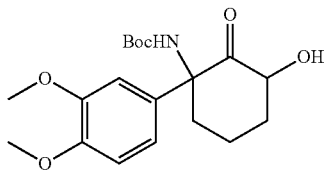 [SMILES: COc1ccc(C2(NC(=O)OC(C)(C)C)CCCC(O)C2=O)cc1OC]

Using the compound 17-e (230 mg, 0.66 mmol) as a raw material, the method described in step f in Example 1 was conducted accordingly to obtain 134 mg of white solid, yield: 55.8%. $^1$H NMR (400 MHz, CDCl$_3$) δ 6.92 (dd, J=8.4, 1.8 Hz, 1H), 6.85 (d, J=8.4 Hz, 1H), 6.72 (d, J=1.5 Hz, 1H), 6.09 (s, 1H), 4.11-4.06 (m, 1H), 3.87 (s, 3H), 3.85 (s, 3H), 3.49 (d, J=10.4 Hz, 1H), 2.34 (ddd, J=12.4, 6.5, 3.0 Hz, 1H), 2.09 (d, J=3.2 Hz, 1H), 1.87 (s, 2H), 1.66-1.57 (m, 1H), 1.34 (s, 9H). MS (M+Na)$^+$: 388

Step g: Preparation of Compound 17

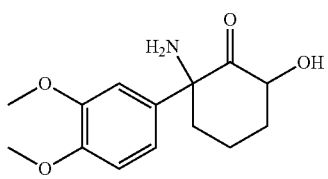 [SMILES: COc1ccc(C2(N)CCCC(O)C2=O)cc1OC]

Using the compound 17-f (130 mg, 0.36 mmol) as a raw material, the method described in step g in Example 1 was conducted accordingly to obtain 72 mg of colorless oily liquid, yield: 76.6%. $^1$H NMR (400 MHz, CDCl$_3$) δ 6.85 (d, J=8.2 Hz, 1H), 6.75-6.70 (m, 2H), 4.25 (dd, J=12.2, 7.0 Hz, 1H), 3.87 (s, 3H), 3.86 (s, 3H), 2.87-2.79 (m, 1H), 2.35 (ddd, J=12.3, 6.7, 3.0 Hz, 1H), 1.80-1.69 (m, 3H), 1.57-1.48 (m, 1H). MS (M+H)$^+$: 266.

Example 18: Preparation of 2-amino-2-(3,5-dimethoxyphenyl)-6-hydroxycyclohexane-1-one (Compound 18)

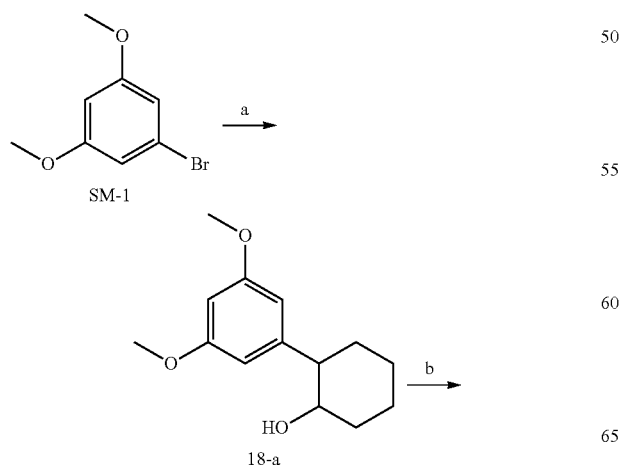

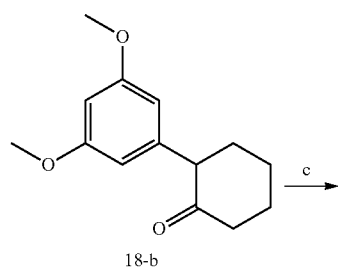

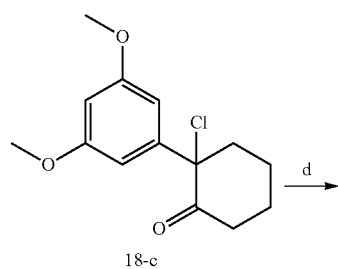

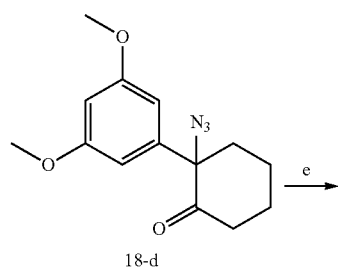

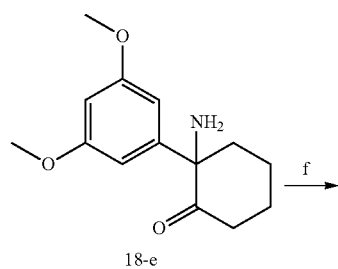

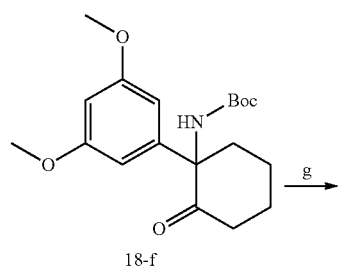

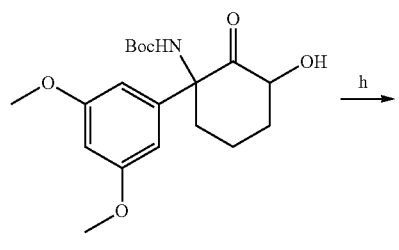

-continued

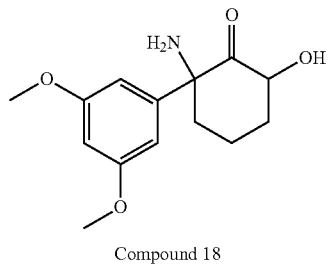

Compound 18

Step c: Preparation of 18-c

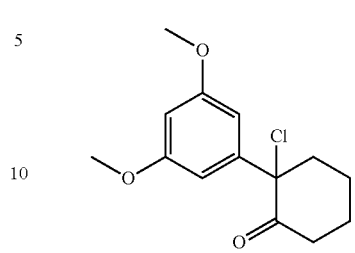

Using the compound 18-b (5.44 g, 23.2 mmol) as a raw material, the method described in step c in Example 2 was conducted accordingly to obtain 1.29 g of light yellow oily liquid, yield: 20.7%. $^1$H NMR (400 MHz, CDCl$_3$) δ 6.52 (d, J=2.2 Hz, 2H), 6.42 (t, J=2.2 Hz, 1H), 3.79 (d, J=7.5 Hz, 6H), 2.95 (ddd, J=14.4, 5.6, 3.6 Hz, 1H), 2.78 (dt, J=11.9, 5.2 Hz, 1H), 2.47-2.36 (m, 2H), 2.30-2.20 (m, 1H), 1.92-1.83 (m, 3H). MS (M+Na)$^+$: 291.0

Step a: Preparation of 18-a

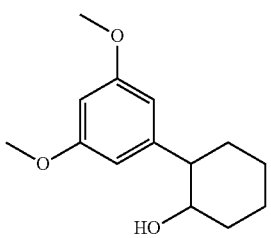 [SMILES: COc1cc(OC)cc(C2CCCCC2O)c1]

Using 3,5-dimethoxybromobenzene (11.8 g, 54.36 mmoL) and epoxycyclohexane (6.2 g, 63.17 mmol) as raw materials, the method described in step a in Example 1 was conducted accordingly to obtain 9.9 g of colorless oily liquid, yield: 77.1%. $^1$H NMR (400 MHz, CDCl$_3$) δ 6.41 (d, J=2.2 Hz, 2H), 6.35 (t, J=2.2 Hz, 1H), 3.78 (s, 6H), 3.67-3.59 (m, 1H), 2.41-2.33 (m, 1H), 2.10 (dd, J=8.2, 3.6 Hz, 1H), 1.89-1.82 (m, 2H), 1.78-1.72 (m, 1H), 1.51-1.29 (m, 4H). MS (M+H)$^+$: 237.

Step b: Preparation of 18-b

Step d: Preparation of 18-d

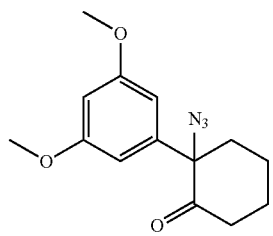

Using the compound 18-c (1.29 g, 4.8 mmol) as a raw material, the method described in step d in Example 2 was conducted accordingly to obtain 1.05 g of pale yellow oily liquid, yield: 79.4%. $^1$H NMR (400 MHz, CDCl$_3$) δ 6.47 (t, J=2.1 Hz, 1H), 6.42 (d, J=2.1 Hz, 2H), 3.79 (s, 6H), 2.72 (dd, J=14.4, 3.3 Hz, 1H), 2.52 (dd, J=14.9, 3.1 Hz, 1H), 2.47-2.37 (m, 1H), 1.95 (ddd, J=12.7, 7.9, 3.2 Hz, 2H), 1.85 (d, J=5.9 Hz, 1H), 1.72 (s, 2H). MS (M+Na)$^+$: 298.

Step e: Preparation of 18-e

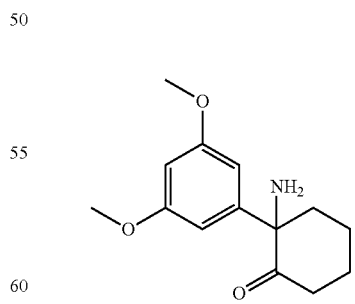

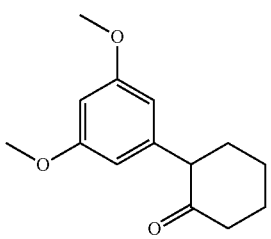 [SMILES: COc1cc(OC)cc(C2CCCCC2=O)c1]

Using the compound 18-a (9.9 g, 41.89 mmol) as a raw material, the method described in step b in Example 1 was conducted accordingly to obtain 5.44 g of white solid, yield: 55.4%. $^1$H NMR (400 MHz, CDCl$_3$) δ 6.37 (t, J=2.3 Hz, 1H), 6.30 (d, J=2.2 Hz, 2H), 3.77 (s, 6H), 3.55 (dd, J=11.9, 5.4 Hz, 1H), 2.56-2.49 (m, 1H), 2.48-2.39 (m, 1H), 2.30-2.21 (m, 1H), 2.15-2.10 (m, 1H), 2.04-1.96 (m, 2H), 1.86-1.77 (m, 2H). MS (M+H)$^+$: 235.

Using the compound 18-d (1.05 g, 3.81 mmol) as a raw material, the method described in step e in Example 2 was conducted accordingly to obtain 1.17 g of pale yellow oily liquid, which was directly cast into the reaction in next step without purification. MS (M+H)$^+$: 250

Step f: Preparation of 18-f

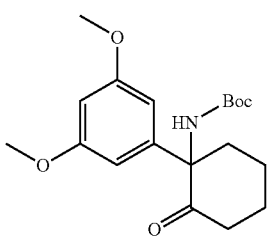 [SMILES: COc1cc(OC)cc(C2(NC(=O)OC(C)(C)C)CCCCC2=O)c1]

Using the crude compound 18-e (1.17 g crude product) as a raw material, the method described in step e in Example 1 was conducted accordingly to obtain 1.22 g of yellow oily liquid, yield: 87.8% (two steps together). $^1$H NMR (400 MHz, CDCl$_3$) δ 6.49 (s, 2H), 6.37 (t, J=2.0 Hz, 1H), 6.21 (s, 1H), 3.77 (s, 6H), 3.48 (d, J=12.5 Hz, 1H), 2.35 (dd, J=28.6, 12.8 Hz, 2H), 1.99 (d, J=8.4 Hz, 2H), 1.87 (d, J=13.9 Hz, 2H), 1.77-1.68 (m, 1H), 1.34 (s, 9H). MS (M+Na)$^+$: 372.

Step g: Preparation of 18-g

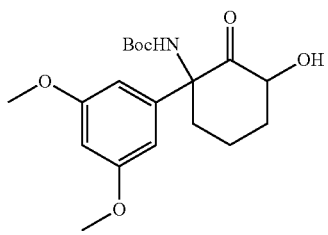 [SMILES: COc1cc(OC)cc(C2(NC(=O)OC(C)(C)C)CCCC(O)C2=O)c1]

Using the compound 18-f (400 mg, 1.14 mmol) as a raw material, the method described in step f in Example 1 was conducted accordingly to obtain 155 mg of yellow oil, yield: 37.1%. $^1$H NMR (400 MHz, CDCl$_3$) δ 6.44 (s, 2H), 6.39 (s, 1H), 6.04 (s, 1H), 4.08 (d, J=11.6 Hz, 1H), 3.77 (s, 7H), 3.41 (s, 1H), 2.33 (s, 1H), 1.86 (s, 1H), 1.62 (d, J=7.7 Hz, 3H), 1.34 (s, 9H). MS (M+Na)$^+$: 388

Step h: Preparation of Compound 18

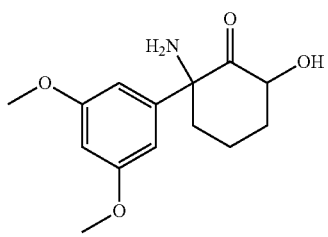 [SMILES: COc1cc(OC)cc(C2(N)CCCC(O)C2=O)c1]

Using the compound 18-g (155 mg, 0.42 mmol) as a raw material, the method described in step g in Example 1 was conducted accordingly to obtain 103 mg of colorless oily liquid, yield: 92.0%. $^1$H NMR (400 MHz, CDCl$_3$) δ 6.39 (t, J=2.1 Hz, 1H), 6.34 (d, J=2.1 Hz, 2H), 4.23 (dd, J=12.3, 7.0 Hz, 1H), 3.78 (s, 6H), 2.84-2.77 (m, 1H), 2.34 (ddd, J=12.7, 6.9, 3.0 Hz, 1H), 1.79-1.74 (m, 2H), 1.73-1.67 (m, 1H), 1.51 (ddd, J=12.4, 8.6, 3.8 Hz, 1H). MS(M+H)$^+$: 266.

Example 19: Preparation of 2-amino-2-(4-chloro-2-fluorophenyl)-6-hydroxycyclohexane-1-one (Compound 19)

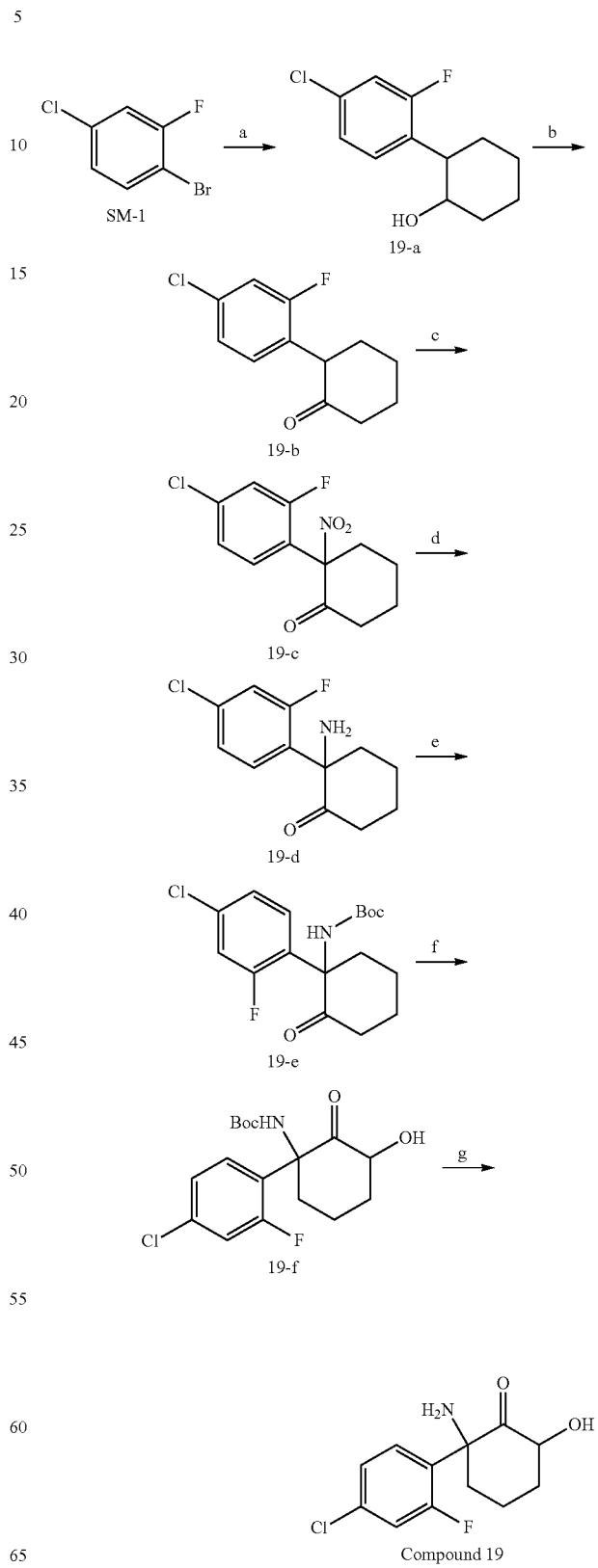

Step a: Preparation of 19-a

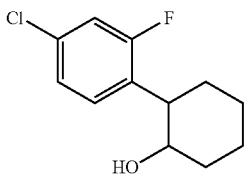 [SMILES: OC1CCCCC1c1ccc(Cl)cc1F]

Using 2-fluoro-4-chlorobromobenzene (5 g, 23.9 mmoL) and epoxycyclohexane (2.6 g, 26.5 mmol) as raw materials, the method described in step a in Example 1 was conducted accordingly to obtain 4.49 g of pale yellow solid, yield: 82.2%. $^1$H NMR (400 MHz, CDCl$_3$) δ 7.20 (t, J=8.0 Hz, 1H), 7.11 (dd, J=8.3, 2.0 Hz, 1H), 7.06 (dd, J=10.0, 2.0 Hz, 1H), 3.72 (td, J=9.6, 4.4 Hz, 1H), 2.81-2.73 (m, 1H), 2.15-2.07 (m, 1H), 1.86-1.82 (m, 1H), 1.77 (ddd, J=13.8, 5.3, 2.4 Hz, 2H), 1.50 (dd, J=12.2, 2.8 Hz, 1H), 1.43-1.32 (m, 3H). MS (M+Na)$^+$: 251

Step b: Preparation of 19-b

Using the compound 19-a (4.24 g, 18.54 mmol) as a raw material, the method described in step b in Example 1 was conducted accordingly to obtain 2.68 g of white solid, yield: 63.8%. $^1$H NMR (400 MHz, CDCl$_3$) δ 7.15-7.04 (m, 3H), 3.80 (dd, J=12.9, 5.4 Hz, 1H), 2.59-2.41 (m, 2H), 2.21 (dddd, J=15.4, 12.5, 5.7, 2.9 Hz, 2H), 2.06-1.95 (m, 2H), 1.87-1.74 (m, 2H). MS (M+H)$^+$: 227.

Step c: Preparation of 19-c

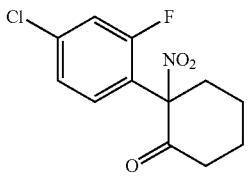 [SMILES: O=C1CCCCC1(c1ccc(Cl)cc1F)[N+](=O)[O-]]

Using the compound 19-b (1.66 g, 7.32 mmol) as a raw material, the method described in step c in Example 1 was conducted accordingly to obtain 797 mg of white solid, yield: 40.1%. $^1$H NMR (400 MHz, CDCl$_3$) δ 7.23 (d, J=1.5 Hz, 1H), 7.21-7.14 (m, 2H), 3.00-2.84 (m, 2H), 2.78-2.68 (m, 1H), 2.64-2.54 (m, 1H), 2.02-1.84 (m, 3H), 1.76-1.64 (m, 1H). MS (M+Na)$^+$: 294.

Step d: Preparation of 19-d

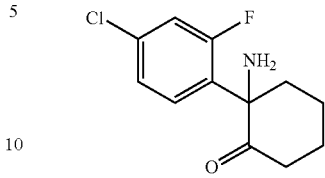

Using the compound 19-c (756 mg, 2.78 mmol) as a raw material, the method described in step d in Example 1 was conducted accordingly to obtain 699 mg of pale yellow oily liquid crude product, which was directly cast into the reaction in next step without purification. MS (M+H)$^+$: 258.1

Step e: Preparation of 19-e

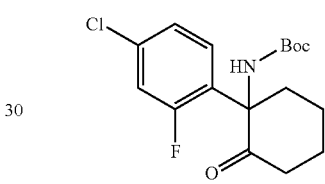

Using the crude compound 19-d (699 mg crude product) as a raw material, the method described in step e in Example 1 was conducted accordingly to obtain 768 mg of colorless oily liquid, yield: 80.8% (two steps together). $^1$H NMR (400 MHz, CDCl$_3$) δ 7.65 (s, 1H), 7.20 (d, J=8.3 Hz, 1H), 7.11-7.03 (m, 1H), 6.46 (s, 1H), 3.72 (s, 1H), 2.45 (d, J=12.2 Hz, 1H), 2.39-2.28 (m, 1H), 2.08-1.98 (m, 1H), 1.83-1.64 (m, 4H), 1.32 (s, 9H). MS (M+Na)$^+$: 364.

Step f: Preparation of 19-f

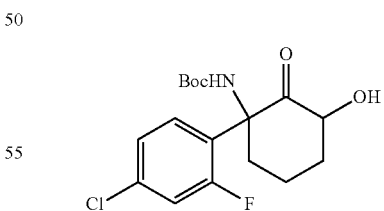

Using the compound 19-e (350 mg, 1.02 mmol) as a raw material, the method described in step f in Example 1 was conducted accordingly to obtain 176 mg of white solid, yield: 48.1%. $^1$H NMR (400 MHz, CDCl$_3$) δ 7.65 (s, 1H), 7.22 (d, J=7.3 Hz, 1H), 7.08 (dd, J=11.0, 2.0 Hz, 1H), 6.48 (s, 1H), 4.17 (dd, J=11.5, 7.0 Hz, 1H), 3.80 (s, 1H), 3.34 (s, 1H), 2.39 (ddd, J=12.2, 6.7, 3.4 Hz, 1H), 1.69-1.58 (m, 4H), 1.33 (s, 9H). MS (M+Na)$^+$: 380

Step g: Preparation of Compound 19

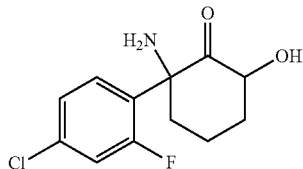 [SMILES: NC1(c2ccc(Cl)cc2F)CCCC(O)C1=O]

Using the compound 19-f (100 mg, 0.28 mmol) as a raw material, the method described in step g in Example 1 was conducted accordingly to obtain 65 mg of colorless oily liquid, yield: 90.3%. $^1$H NMR (400 MHz, CDCl$_3$) δ 7.42 (t, J=8.4 Hz, 1H), 7.24 (dd, J=8.6, 1.4 Hz, 1H), 7.11 (dd, J=11.0, 2.0 Hz, 1H), 4.22 (dd, J=11.7, 7.0 Hz, 1H), 2.85 (dd, J=6.9, 4.2 Hz, 1H), 2.37 (ddd, J=12.2, 6.9, 3.3 Hz, 1H), 1.76 (dd, J=6.5, 3.7 Hz, 1H), 1.63 (t, J=8.3 Hz, 2H), 1.48 (dd, J=12.3, 4.4 Hz, 1H). MS (M+H)$^+$: 258.

Example 20: Preparation of 2-amino-2-(5-chloro-2-fluorophenyl)-6-hydroxycyclohexane-1-one (Compound 20)

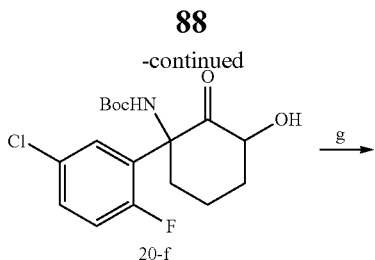

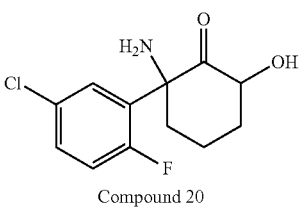

Compound 20

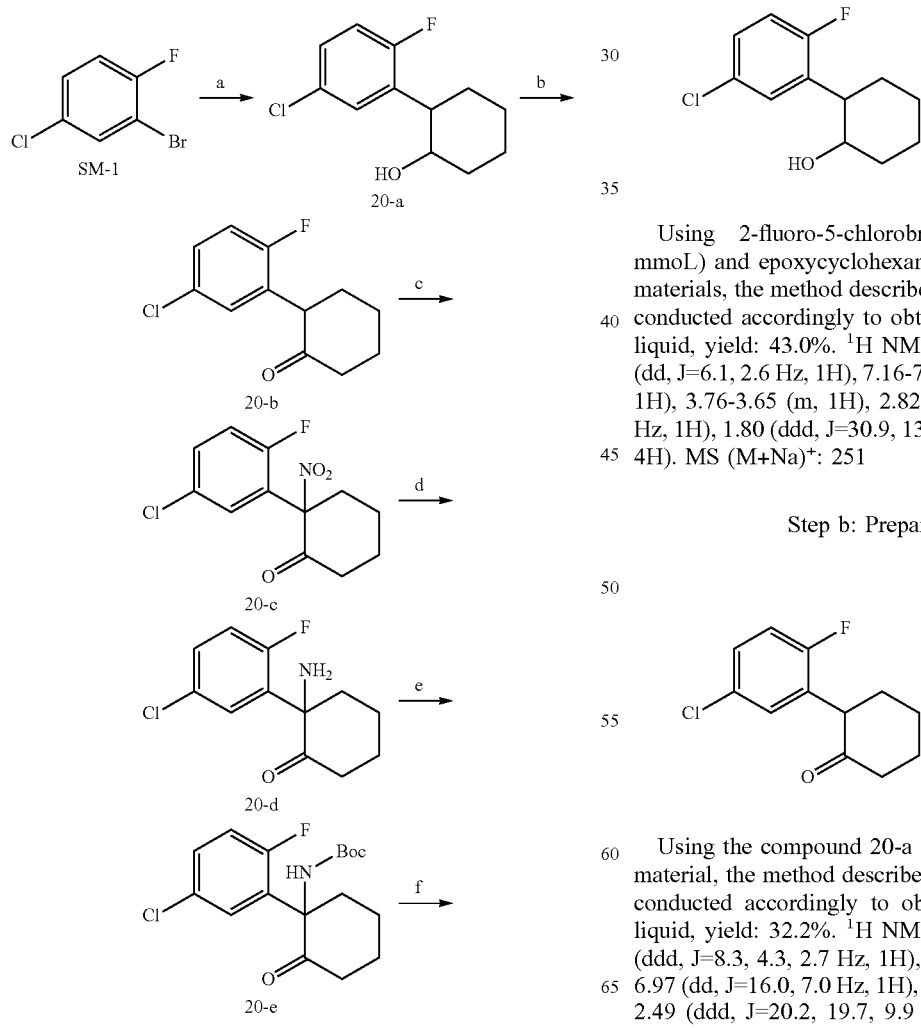

Step a: Preparation of 20-a

Using 2-fluoro-5-chlorobromobenzene (10 g, 47.8 mmoL) and epoxycyclohexane (5.6 g, 57.1 mmol) as raw materials, the method described in step a in Example 1 was conducted accordingly to obtain 4.7 g of pale yellow oily liquid, yield: 43.0%. $^1$H NMR (400 MHz, CDCl$_3$) δ 7.24 (dd, J=6.1, 2.6 Hz, 1H), 7.16-7.12 (m, 1H), 6.97 (t, J=9.2 Hz, 1H), 3.76-3.65 (m, 1H), 2.82-2.74 (m, 1H), 2.11 (d, J=8.9 Hz, 1H), 1.80 (ddd, J=30.9, 13.4, 3.2 Hz, 3H), 1.43-1.28 (m, 4H). MS (M+Na)$^+$: 251

Step b: Preparation of 20-b

Using the compound 20-a (4.7 g, 20.55 mmol) as a raw material, the method described in step b in Example 1 was conducted accordingly to obtain 1.5 g of colorless oily liquid, yield: 32.2%. $^1$H NMR (400 MHz, CDCl$_3$) δ 7.19 (ddd, J=8.3, 4.3, 2.7 Hz, 1H), 7.13 (dd, J=6.1, 2.6 Hz, 1H), 6.97 (dd, J=16.0, 7.0 Hz, 1H), 3.80 (dd, J=13.0, 5.4 Hz, 1H), 2.49 (ddd, J=20.2, 19.7, 9.9 Hz, 2H), 2.29-2.15 (m, 2H), 2.08-1.96 (m, 2H), 1.85-1.74 (m, 2H). MS (M+H)$^+$: 227.

Step c: Preparation of 20-c

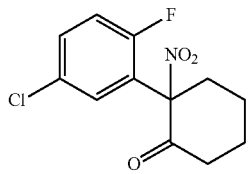 [SMILES: O=C1CCCCC1(c1cc(Cl)ccc1F)[N+](=O)[O-]]

Using the compound 20-b (1.5 g, 6.62 mmol) as a raw material, the method described in step c in Example 1 was conducted accordingly to obtain 550 mg of yellow oily liquid, yield: 30.6%. $^1$H NMR (400 MHz, CDCl$_3$) δ 7.42 (ddd, J=8.7, 4.2, 2.6 Hz, 1H), 7.21 (dd, J=6.3, 2.5 Hz, 1H), 7.13 (dd, J=10.5, 8.9 Hz, 1H), 2.90 (ddd, J=10.4, 8.0, 4.2 Hz, 2H), 2.77-2.70 (m, 1H), 2.63-2.55 (m, 1H), 2.00-1.94 (m, 2H), 1.92-1.84 (m, 1H), 1.73 (ddd, J=13.8, 9.0, 4.5 Hz, 1H). MS (M+Na)$^+$: 294.

Step d: Preparation of 20-d

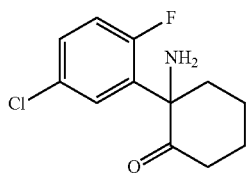 [SMILES: NC1(c2cc(Cl)ccc2F)CCCCC1=O]

Using the compound 20-c (650 mg, 2.39 mmol) as a raw material, the method described in step d in Example 1 was conducted accordingly to obtain 600 mg of pale yellow oily liquid crude product, which was directly cast into the reaction in next step without purification. MS (M+H)$^+$: 258.1

Step e: Preparation of 20-e

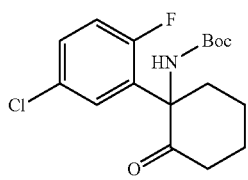 [SMILES: CC(C)(C)OC(=O)NC1(c2cc(Cl)ccc2F)CCCCC1=O]

Using the crude compound 20-d (600 mg crude product) as a raw material, the method described in step e in Example 1 was conducted accordingly to obtain 420 mg of pale yellow solid, yield: 51.3% (two steps together). $^1$H NMR (400 MHz, CDCl$_3$) δ 7.63 (s, 1H), 7.26 (s, 1H), 6.98 (dd, J=10.4, 8.9 Hz, 1H), 6.98 (dd, J=10.4, 8.9 Hz, 1H), 6.38 (s, 1H), 6.38 (s, 1H), 3.66 (s, 1H), 2.47 (d, J=11.8 Hz, 1H), 2.33 (td, J=12.0, 5.8 Hz, 1H), 2.01 (d, J=19.9 Hz, 1H), 1.77 (dt, J=22.1, 8.7 Hz, 4H), 1.31 (d, J=18.2 Hz, 9H). MS (M+H)$^+$: 342.

Step f: Preparation of 20-f

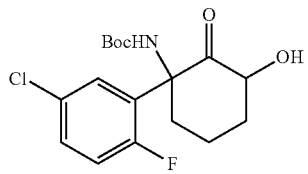 [SMILES: CC(C)(C)OC(=O)NC1(c2cc(Cl)ccc2F)CCCC(O)C1=O]

Using the compound 20-e (510 mg, 1.49 mmol) as a raw material, the method described in step f in Example 1 was conducted accordingly to obtain 280 mg of white solid, yield: 52.4%. $^1$H NMR (400 MHz, CDCl$_3$) δ 7.66 (s, 1H), 7.33-7.27 (m, 1H), 7.03-6.95 (m, 1H), 6.46 (s, 1H), 4.17 (dd, J=11.8, 5.9 Hz, 1H), 3.79 (s, 1H), 3.35 (d, J=5.5 Hz, 1H), 2.41 (ddd, J=12.3, 6.5, 3.0 Hz, 1H), 1.83 (d, J=10.9 Hz, 1H), 1.70 (d, J=12.8 Hz, 2H), 1.51 (dd, J=12.6, 7.8 Hz, 1H), 1.33 (s, 9H). MS (M+Na)$^+$: 380.

Step g: Preparation of Compound 20

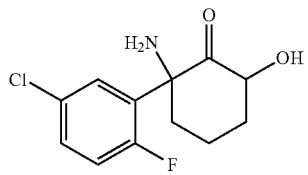 [SMILES: NC1(c2cc(Cl)ccc2F)CCCC(O)C1=O]

Using the compound 20-f (100 mg, 0.28 mmol) as a raw material, the method described in step g in Example 1 was conducted accordingly to obtain 58 mg of colorless oily liquid, yield: 80.6%. $^1$H NMR (400 MHz, CDCl$_3$) δ 7.45 (dd, J=6.6, 2.5 Hz, 1H), 7.31 (ddd, J=8.7, 4.3, 2.6 Hz, 1H), 7.03 (dd, J=10.5, 8.8 Hz, 1H), 4.23 (dd, J=11.8, 6.9 Hz, 1H), 2.85-2.78 (m, 1H), 2.42-2.35 (m, 1H), 1.81-1.75 (m, 1H)), 1.70-1.62 (m, 2H), 1.54-1.43 (m, 1H). MS (M+H)$^+$: 258.

Example 21: Preparation of 2-amino-2-(2-fluoro-5-(trifluoromethoxy)phenyl)-6-hydroxycyclohexane-1-one (Compound 21)

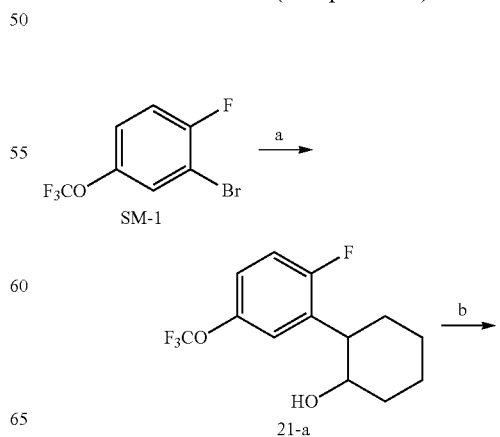

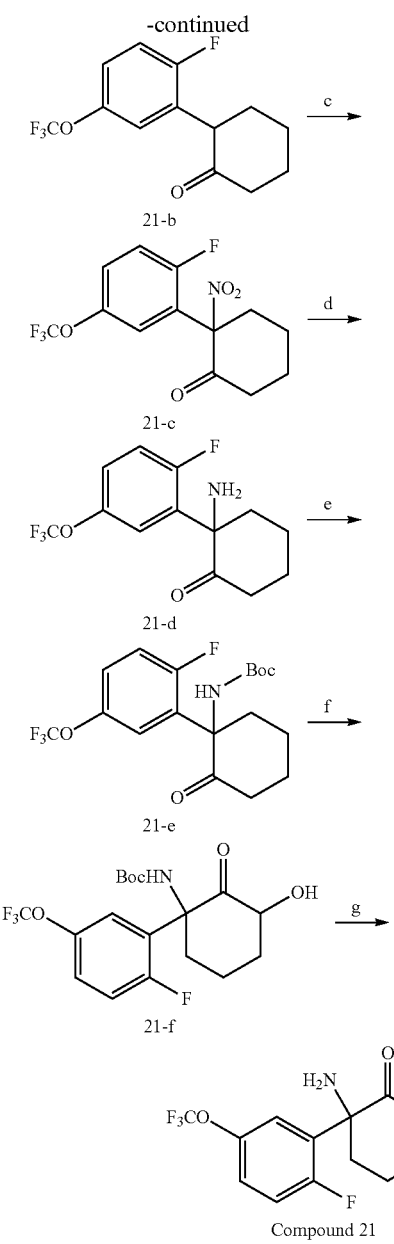

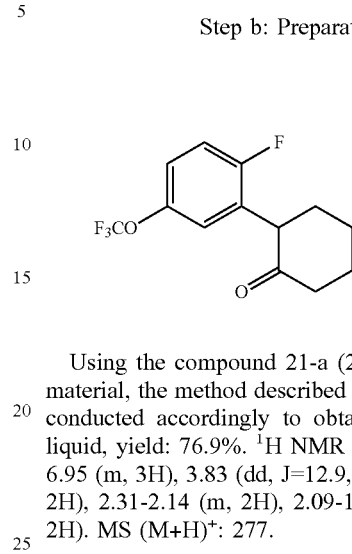

Compound 21

Step a: Preparation of 21-a

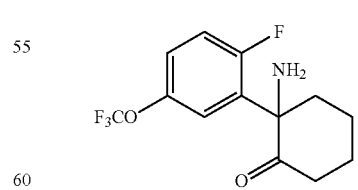

Using 2-fluoro-5-(trifluoromethoxy)bromobenzene (2.88 g, 11.1 mmoL) and epoxycyclohexane (1.38 g, 14.1 mmol) as raw materials, the method described in step a in Example 1 was conducted accordingly to obtain 2.2 g of colorless oily liquid, yield: 71.2%. $^1$H NMR (400 MHz, CDCl$_3$) δ 7.13 (d, J=6.2 Hz, 1H), 7.07-7.03 (m, 2H), 3.72 (s, 1H), 2.86-2.77 (m, 1H), 2.13 (dd, J=9.2, 4.1 Hz, 1H), 1.88-1.81 (m, 2H), 1.80-1.75 (m, 1H), 1.39 (ddd, J=15.4, 7.3, 3.5 Hz, 4H). MS (M+H)$^+$: 279

Step b: Preparation of 21-b

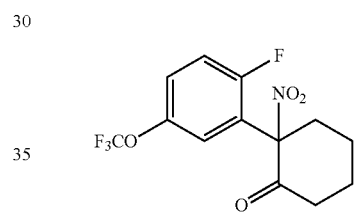

Using the compound 21-a (2.1 g, 7.55 mmol) as a raw material, the method described in step b in Example 1 was conducted accordingly to obtain 1.6 g of colorless oily liquid, yield: 76.9%. $^1$H NMR (400 MHz, CDCl$_3$) δ 7.14-6.95 (m, 3H), 3.83 (dd, J=12.9, 5.4 Hz, 1H), 2.61-2.43 (m, 2H), 2.31-2.14 (m, 2H), 2.09-1.94 (m, 2H), 1.88-1.77 (m, 2H). MS (M+H)$^+$: 277.

Step c: Preparation of 21-c

Using the compound 21-b (175 mg, 0.63 mmol) as a raw material, the method described in step c in Example 1 was conducted accordingly to obtain 90 mg of yellow oily liquid, yield: 44.1%. $^1$H NMR (400 MHz, CDCl$_3$) δ 7.35 (d, J=9.0 Hz, 1H), 7.25-7.18 (m, 1H), 7.09 (dd, J=5.7, 2.7 Hz, 1H), 3.03-2.94 (m, 1H), 2.88-2.80 (m, 1H), 2.76 (dd, J=13.5, 6.8 Hz, 1H), 2.65-2.56 (m, 1H), 1.99 (dt, J=12.9, 6.4 Hz, 2H), 1.89 (dd, J=15.4, 7.8 Hz, 1H), 1.80-1.67 (m, 1H). MS (M+Na)$^+$: 344.

Step d: Preparation of 21-d

Using the compound 21-c (320 mg, 1.0 mmol) as a raw material, the method described in step d in Example 1 was conducted accordingly to obtain 321 mg of pale yellow oily liquid crude product, which was directly cast into the reaction in next step without purification. MS (M+H)$^+$: 292

Step e: Preparation of 21-e

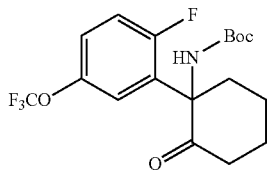 [SMILES: CC(C)(C)OC(=O)NC1(c2cc(OC(F)(F)F)ccc2F)CCCCC1=O]

Using the crude compound 21-d (321 mg crude product) as a raw material, the method described in step e in Example 1 was conducted accordingly to obtain 275 mg of pale yellow solid, yield: 70.5% (two steps together). $^1$H NMR (400 MHz, CDCl$_3$) δ 7.56 (s, 1H), 7.22-7.15 (m, 1H), 7.09-7.02 (m, 1H), 6.36 (s, 1H), 3.64 (s, 1H), 2.49 (d, J=12.6 Hz, 1H), 2.35 (dd, J=14.8, 9.4 Hz, 1H), 2.04 (s, 1H), 1.88-1.68 (m, 4H), 1.32 (s, 9H). MS (M+Na)$^+$: 414.

Step f: Preparation of 21-f

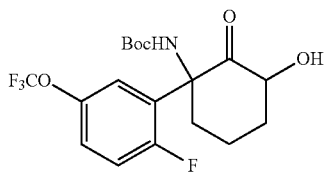 [SMILES: CC(C)(C)OC(=O)NC1(c2cc(OC(F)(F)F)ccc2F)CCCC(O)C1=O]

Using the compound 21-e (220 mg, 0.56 mmol) as a raw material, the method described in step f in Example 1 was conducted accordingly to obtain 68 mg of white solid, yield: 29.7%. $^1$H NMR (400 MHz, CDCl$_3$) δ 7.60 (s, 1H), 7.22 (d, J=8.4 Hz, 1H), 7.07 (t, J=9.6 Hz, 1H), 6.46 (s, 1H), 4.23-4.11 (m, 1H), 3.79 (s, 1H), 3.35 (d, J=5.5 Hz, 1H), 2.46-2.37 (m, 1H), 1.83 (d, J=7.3 Hz, 1H), 1.69 (d, J=11.8 Hz, 2H), 1.54-1.46 (m, 1H), 1.32 (s, 9H). MS (M+Na)$^+$: 430.

Step g: Preparation of Compound 21

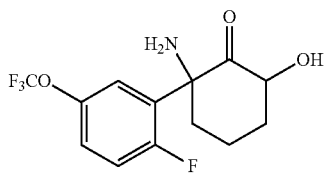 [SMILES: NC1(c2cc(OC(F)(F)F)ccc2F)CCCC(O)C1=O]

Using the compound 21-f (68 mg, 0.17 mmol) as a raw material, the method described in step g in Example 1 was conducted accordingly to obtain 42 mg of colorless oily liquid, yield: 82.4%. $^1$H NMR (400 MHz, CDCl$_3$) δ 7.35 (dd, J=6.0, 2.7 Hz, 1H), 7.25-7.20 (m, 1H), 7.15-7.08 (m, 1H), 4.22 (dd, J=11.7, 6.9 Hz, 1H), 2.84-2.77 (m, 1H), 2.39 (ddd, J=12.5, 6.7, 3.0 Hz, 1H), 1.79 (dd, J=8.5, 4.6 Hz, 1H), 1.67 (d, J=12.2 Hz, 2H), 1.52 (td, J=12.2, 4.2 Hz, 1H). MS (M+H)$^+$: 308.

Example 22: Preparation of 2-amino-2-(2-fluoro-3-(trifluoromethoxy)phenyl)-6-hydroxycyclohexane-1-one (Compound 22)

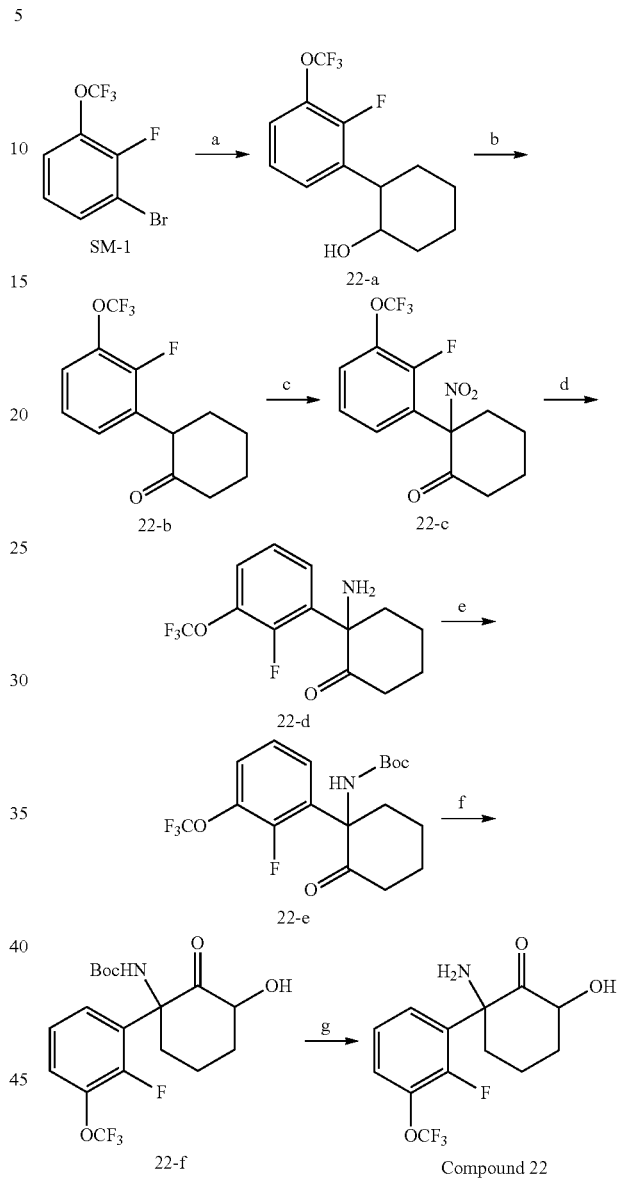

Step a: Preparation of 22-a

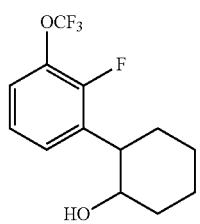 [SMILES: OC1CCCCC1c1cccc(OC(F)(F)F)c1F]

Using 2-fluoro-3-(trifluoromethoxy)bromobenzene (8.2 g, 31.7 mmoL) and epoxycyclohexane (3.52 g, 35.9 mmol) as raw materials, the method described in step a in Example 1 was conducted accordingly to obtain 8.1 g of colorless oily liquid, yield: 92.0%. $^1$H NMR (400 MHz, CDCl$_3$) δ 7.25-7.20 (m, 1H), 7.17 (dd, J=11.0, 4.4 Hz, 1H), 7.12 (dd, J=11.8, 4.7 Hz, 1H), 3.77 (s, 1H), 2.92-2.81 (m, 1H), 2.19-2.11 (m, 1H), 1.92-1.82 (m, 2H), 1.77 (dd, J=11.6, 2.3 Hz, 1H), 1.45-1.34 (m, 4H). MS (M+H)$^+$: 279

Step b: Preparation of 22-b

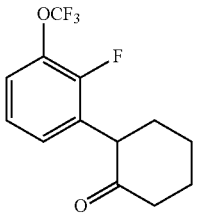

Using the compound 22-a (7 g, 25.2 mmol) as a raw material, the method described in step b in Example 1 was conducted accordingly to obtain 4.5 g of white solid, yield: 64.8%. $^1$H NMR (400 MHz, CDCl$_3$) δ 7.24-7.19 (m, 1H), 7.14-7.08 (m, 2H), 3.89 (dd, J=12.8, 5.4 Hz, 1H), 2.61-2.44 (m, 2H), 2.33-2.16 (m, 2H), 2.00 (ddd, J=15.5, 10.0, 3.1 Hz, 2H), 1.92-1.74 (m, 2H). MS(M+H)$^+$: 277.1

Step c: Preparation of 22-c

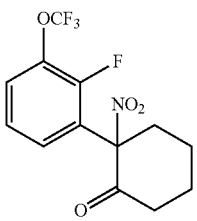 [SMILES: O=C1CCCCC1(c1cccc(OC(F)(F)F)c1F)[N+](=O)[O-]]

Using the compound 22-b (430 mg, 1.56 mmol) as a raw material, the method described in step c in Example 1 was conducted accordingly to obtain 113 mg of yellow oily liquid, yield: 22.6%. $^1$H NMR (400 MHz, CDCl$_3$) δ 7.44 (t, J=7.7 Hz, 1H), 7.26 (td, J=8.0, 1.4 Hz, 1H), 7.18-7.13 (m, 1H), 3.03-2.94 (m, 1H), 2.88 (ddd, J=14.6, 7.2, 3.6 Hz, 1H), 2.79-2.71 (m, 1H), 2.61 (dt, J=14.2, 7.2 Hz, 1H), 2.02-1.94 (m, 2H), 1.91-1.82 (m, 1H), 1.79-1.70 (m, 1H). MS (M+Na)$^+$: 344.

Step d: Preparation of 22-d

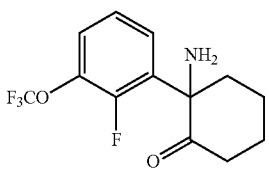 [SMILES: NC1(c2cccc(OC(F)(F)F)c2F)CCCCC1=O]

Using the compound 22-c (110 mg, 0.34 mmol) as a raw material, the method described in step d in Example 1 was conducted accordingly to obtain 121 mg of pale yellow oily liquid crude product, which was directly cast into the reaction in next step without purification. MS (M+H)$^+$: 292

Step e: Preparation of 22-e

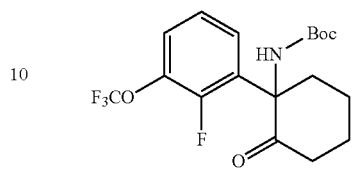

Using the crude compound 22-d (121 mg crude product) as a raw material, the method described in step e in Example 1 was conducted accordingly to obtain 68 mg of white solid, yield: 50.7% (two steps together). $^1$H NMR (400 MHz, CDCl$_3$) δ 7.66 (s, 1H), 7.29 (t, J=6.5 Hz, 1H), 7.21 (d, J=7.9 Hz, 1H), 6.47 (s, 1H), 3.71 (s, 1H), 2.49 (d, J=11.6 Hz, 1H), 2.32 (dd, J=14.7, 9.2 Hz, 1H), 2.05 (d, J=9.0 Hz, 1H), 1.78 (d, J=33.2 Hz, 4H), 1.32 (s, 9H). MS(M+Na)$^+$: 414.1

Step f: Preparation of 22-f

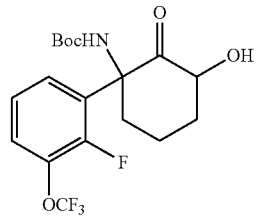 [SMILES: CC(C)(C)OC(=O)NC1(c2cccc(OC(F)(F)F)c2F)CCCC(O)C1=O]

Using the compound 22-e (283 mg, 0.72 mmol) as a raw material, the method described in step f in Example 1 was conducted accordingly to obtain 106 mg of white solid, yield: 36.0%. $^1$H NMR (400 MHz, CDCl$_3$) δ 7.66 (s, 1H), 7.31 (t, J=7.5 Hz, 1H), 7.25-7.20 (m, 1H), 6.52 (s, 1H), 4.15 (dd, J=11.6, 6.9 Hz, 1H), 3.81 (s, 1H), 3.35 (s, 1H), 2.40 (ddd, J=12.0, 6.6, 3.3 Hz, 1H), 1.81 (s, 1H), 1.71 (t, J=9.2 Hz, 2H), 1.57-1.50 (m, 1H), 1.31 (s, 9H). MS(M+Na)$^+$: 430.0

Step g: Preparation of Compound 22

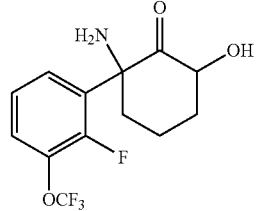 [SMILES: NC1(c2cccc(OC(F)(F)F)c2F)CCCC(O)C1=O]

Using the compound 22-f (101 mg, 0.25 mmol) as a raw material, the method described in step g in Example 1 was conducted accordingly to obtain 64 mg of light yellow oily liquid, yield: 84.2%. $^1$H NMR (400 MHz, CD$_3$OD) δ 7.65-7.59 (m, 1H), 7.46 (t, J=7.7 Hz, 1H), 7.38 (td, J=8.1, 1.3 Hz, 1H), 4.18 (dd, J=11.7, 6.6 Hz, 1H), 2.95-2.88 (m, 1H), 2.26 (ddd, J=9.8, 6.4, 2.9 Hz, 1H), 1.80 (ddd, J=11.8, 6.1, 3.4 Hz, 1H), 1.76-1.65 (m, 2H), 1.63-1.52 (m, 1H). MS (M+H)$^+$: 308.

Example 23: Preparation of (2R,6R)-2-amino-2-(2-fluoro-3-(trifluoromethoxy)phenyl)-6-hydroxycyclohexane-1-one (Compound 23)

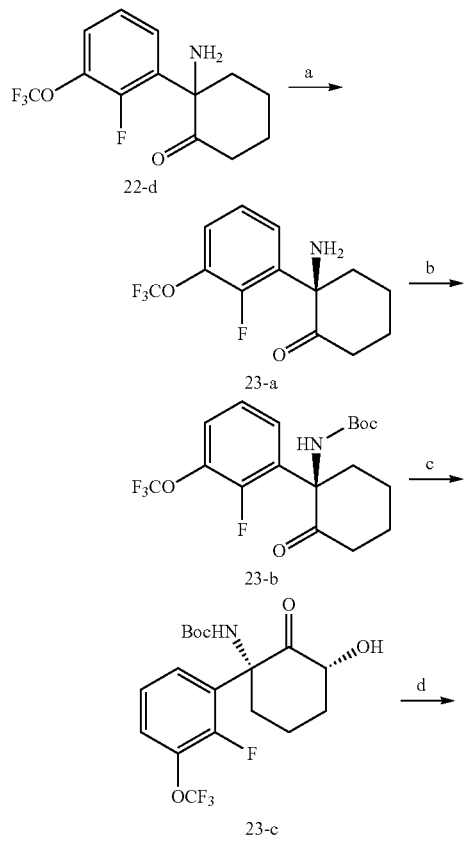

Step a: Preparation of 23-a

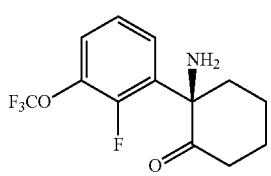 [SMILES: N[C@@]1(c2cccc(OC(F)(F)F)c2F)CCCCC1=O]

The compound 22-d (4 g, 13.73 mmol) was dissolved in methanol (80 ml), and the methanol solution of L-(+)-tartaric acid (2.3 g, 15.32 mmol) (60 ml) was added with stirring. After adding, the mixture was reacted at room temperature overnight, and a large amount of white solid were precipitated out. The reaction solution was dried via rotary evaporation, the obtained white solid was dissolved in refluxing acetone (1.2 L). The solution was cooled to room temperature naturally, and a white solid was gradually precipitated, filtered and dried to obtain 3.68 g of white solid. The same operation was repeated twice to obtain 950 mg of white solid, ee value >98%. The obtained white solid was adjusted to have a pH of about 9 with 1.0M NaOH, and extracted with EA (15 ml×3). The organic phases were combined, washed with saturated brine, dried with anhydrous sodium sulfate, and rotary evaporated to obtain 650 mg of colorless oil.

Step b: Preparation of 23-b

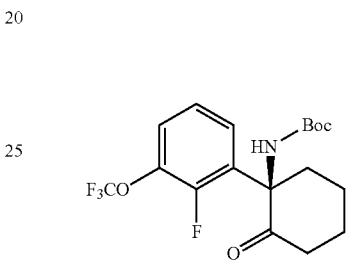

Using the compound 23-a (645 mg, 2.2 mmol) as a raw material, the method described in step e in Example 1 was conducted accordingly to obtain 814 mg of colorless gum, yield: 93.9%. $^1$H NMR (400 MHz, CDCl$_3$) δ 7.67 (s, 1H), 7.26 (dt, J=27.3, 7.9 Hz, 2H), 6.47 (s, 1H), 3.70 (s, 1H), 2.49 (d, J=12.0 Hz, 1H), 2.33 (dt, J=17.5, 8.7 Hz, 1H), 2.09-1.99 (m, 1H), 1.78 (d, J=33.9 Hz, 4H), 1.32 (s, 9H). MS (M+Na)$^+$: 414.

Step c: Preparation of 23-c

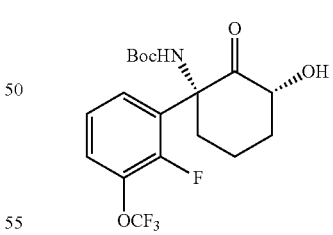

Using the compound 23-b (414 mg, 1.06 mmol) as a raw material, the method described in step f in Example 1 was conducted accordingly to obtain 164 mg of white solid, yield: 38.0%. $^1$H NMR (400 MHz, CDCl$_3$) δ 7.66 (s, 1H), 7.31 (t, J=7.6 Hz, 1H), 7.27-7.19 (m, 1H), 6.53 (s, 1H), 4.15 (s, 1H), 3.82 (s, 1H), 3.36 (d, J=4.2 Hz, 1H), 2.41 (ddd, J=12.2, 6.6, 3.3 Hz, 1H), 1.81 (s, 1H), 1.76-1.64 (m, 2H), 1.56 (td, J=12.2, 4.7 Hz, 1H), 1.31 (s, 9H). MS (M+Na)$^+$: 430

Step d: Preparation of Compound 23

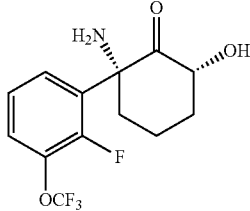 [SMILES: N[C@@]1(c2cccc(OC(F)(F)F)c2F)CCC[C@@H](O)C1=O]

Using the compound 23-c (220 mg, 0.54 mmol) as a raw material, the method described in step g in Example 1 was conducted accordingly to obtain 148 mg of colorless oily liquid, yield: 89.2%, ee>99%. $^1$H NMR (400 MHz, CD$_3$OD) δ 7.65-7.59 (m, 1H), 7.46 (t, J=7.7 Hz, 1H), 7.38 (td, J=8.1, 1.3 Hz, 1H), 4.18 (dd, J=11.7, 6.6 Hz, 1H), 2.95-2.88 (m, 1H), 2.26 (ddd, J=9.8, 6.4, 2.9 Hz, 1H), 1.80 (ddd, J=11.8, 6.1, 3.4 Hz, 1H), 1.76-1.65 (m, 2H), 1.63-1.52 (m, 1H). MS (M+H)$^+$: 308.

Example 24: Preparation of (2S,6S)-2-amino-2-(2-fluoro-3-(trifluoromethoxy)phenyl)-6-hydroxycyclohexane-1-one (Compound 24)

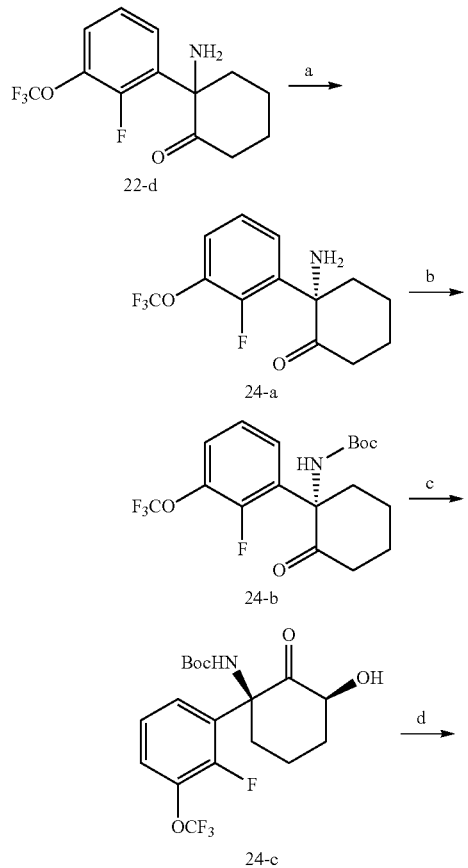

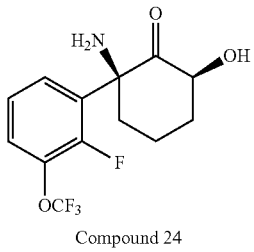

Compound 24

Step a: Preparation of 24-a

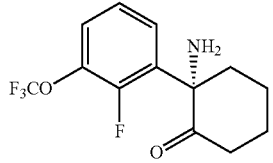

The compound 22-d (4.97 g, 17.08 mmol) was dissolved in methanol (100 ml), and the methanol solution of D-(−)-tartaric acid (2.69 g, 17.93 mmol) was added with stirring After adding, the mixture was reacted at room temperature overnight, and a large amount of white solid were precipitated out. The reaction solution was dried via rotary evaporation, the obtained white solid was dissolved in refluxing acetone (1.2 L) the solution was cooled to room temperature naturally, and a white solid was gradually precipitated, filtered and dried to obtain 4.5 g of white solid. The same operation was repeated twice to obtain 995 mg of white solid, ee value >98%. The obtained white solid was adjusted to have a pH of about 9 with 1.0M NaOH, and extracted with EA (20 ml×3). The organic phases were combined, washed with saturated brine, dried with anhydrous sodium sulfate, and rotary evaporated to obtain 647 mg of colorless oil.

Step b: Preparation of 24-b

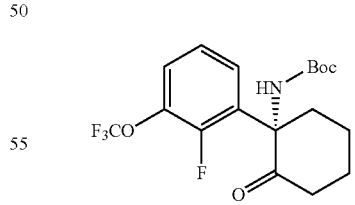

Using the compound 24-a (645 mg, 2.2 mmol) as a raw material, the method described in step e in Example 1 was conducted accordingly to obtain 765 mg of white solid, yield: 88.3%. $^1$H NMR (400 MHz, CDCl$_3$) δ 7.66 (s, 1H), 7.29 (t, J=7.5 Hz, 1H), 7.22 (t, J=8.0 Hz, 1H), 6.47 (s, 1H), 3.70 (s, 1H), 2.48 (d, J=12.1 Hz, 1H), 2.33 (dt, J=17.3, 8.6 Hz, 1H), 2.05 (dd, J=5.9, 3.1 Hz, 1H), 1.78 (d, J=34.1 Hz, 4H), 1.32 (s, 9H). MS (M+Na)$^+$: 414.

Step c: Preparation of 24-c

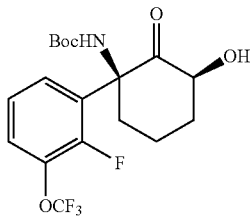 [SMILES: CC(C)(C)OC(=O)N[C@]1(c2cccc(OC(F)(F)F)c2F)CCC[C@H](O)C1=O]

Using the compound 24-b (420 mg, 1.07 mmol) as a raw material, the method described in step f in Example 1 was conducted accordingly to obtain 150 mg of white foam, yield: 34.3%. $^1$H NMR (400 MHz, CDCl$_3$) δ 7.66 (s, 1H), 7.31 (t, J=7.6 Hz, 1H), 7.24 (dd, J=8.7, 7.9 Hz, 1H), 6.53 (s, 1H), 4.15 (dd, J=11.9, 7.6 Hz, 1H), 3.82 (s, 1H), 3.36 (s, 1H), 2.41 (ddd, J=12.2, 6.6, 3.3 Hz, 1H), 1.81 (s, 1H), 1.76-1.65 (m, 2H), 1.60-1.52 (m, 1H), 1.31 (s, 9H). MS (M+Na)$^+$: 430.

Step d: Preparation of Compound 24

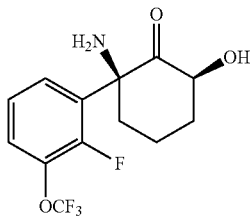 [SMILES: N[C@]1(c2cccc(OC(F)(F)F)c2F)CCC[C@H](O)C1=O]

Using the compound 24-c (122 mg, 0.3 mmol) as a raw material, the method described in step g in Example 1 was conducted accordingly to obtain 79 mg of white solid, yield: 85.9%, ee >99%. $^1$H NMR (400 MHz, CD$_3$OD) δ 7.65-7.59 (m, 1H), 7.46 (t, J=7.7 Hz, 1H), 7.38 (td, J=8.1, 1.3 Hz, 1H), 4.18 (dd, J=11.7, 6.6 Hz, 1H), 2.95-2.88 (m, 1H), 2.26 (ddd, J=9.8, 6.4, 2.9 Hz, 1H), 1.80 (ddd, J=11.8, 6.1, 3.4 Hz, 1H), 1.76-1.65 (m, 2H), 1.63-1.52 (m, 1H). MS (M+H)$^+$: 308.

Example 25: Preparation of 2-amino-2-(3-fluoro-4-(trifluoromethyl)phenyl)-6-hydroxycyclohexane-1-one (Compound 25)

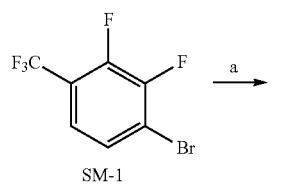
SM-1

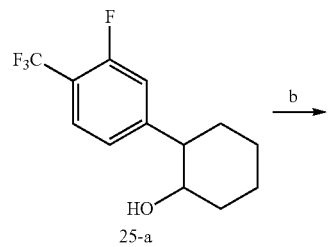
25-a

-continued

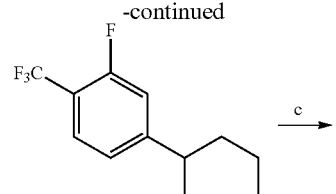
25-b

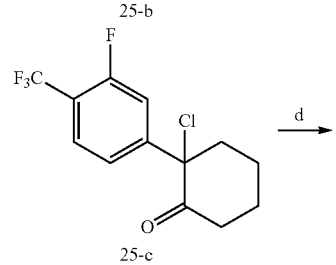
25-c

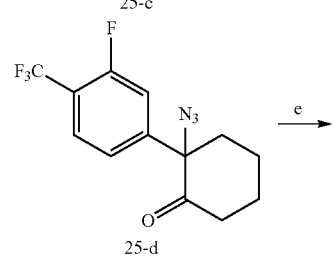
25-d

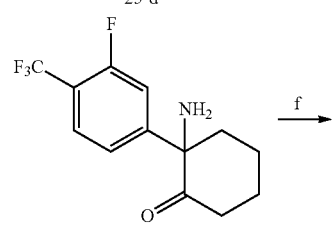
25-e

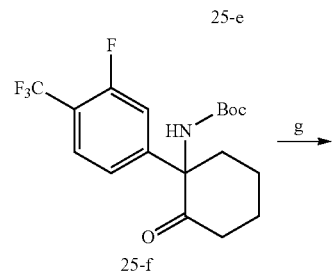
25-f

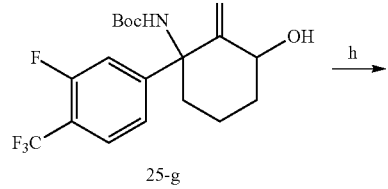
25-g

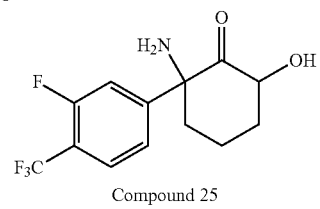
Compound 25

Step a: Preparation of 25-a

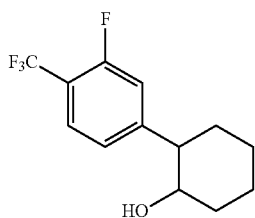 [SMILES: OC1CCCCC1c1ccc(C(F)(F)F)c(F)c1]

Using 3-fluoro-4-trifluoromethylbromobenzene (10 g, 41.2 mmoL) and epoxycyclohexane (4.2 g, 42.8 mmol) as raw materials, the method described in step a in Example 1 was conducted accordingly to obtain 9.2 g of yellow oily liquid, yield: 85.3%. NMR (400 MHz, CDCl$_3$) δ 7.55 (t, J=7.7 Hz, 1H), 7.12 (dd, J=12.8, 10.3 Hz, 2H), 3.67 (td, J=9.8, 4.6 Hz, 1H), 2.56-2.47 (m, 1H), 2.17-2.10 (m, 1H), 1.91-1.83 (m, 2H), 1.81-1.75 (m, 1H), 1.47-1.36 (m, 4H). MS (M+H)$^+$: 263.

Step b: Preparation of 25-b

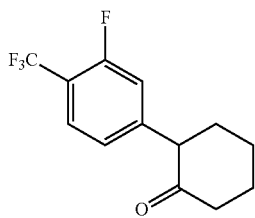 [SMILES: O=C1CCCCC1c1ccc(C(F)(F)F)c(F)c1]

Using the compound 25-a (9.2 g, 35.1 mmol) as a raw material, the method described in step b in Example 1 was conducted accordingly to obtain 6.8 g of yellow solid, yield: 74.5%. $^1$H NMR (400 MHz, CDCl$_3$) δ 7.55 (t, J=7.8 Hz, 1H), 7.03-6.96 (m, 2H), 3.66 (dd, J=12.1, 5.0 Hz, 1H), 2.51 (dt, J=12.5, 10.1 Hz, 2H), 2.34-2.25 (m, 1H), 2.20 (ddd, J=8.9, 6.2, 2.9 Hz, 1H), 2.06-1.94 (m, 2H), 1.86-1.79 (m, 2H). MS (M+H)$^+$: 261.

Step c: Preparation of 25-c

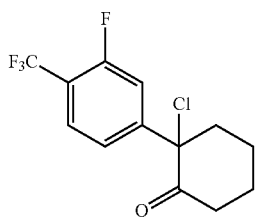 [SMILES: O=C1CCCCC1(Cl)c1ccc(C(F)(F)F)c(F)c1]

Using the compound 25-b (2.5 g, 9.6 mmol) as a raw material, the method described in step c in Example 2 was conducted accordingly to obtain 1.42 g of light yellow oily liquid, yield: 50.2%. $^1$H NMR (400 MHz, CDCl$_3$) δ 7.62 (t, J=7.8 Hz, 1H), 7.31 (t, J=9.9 Hz, 2H), 3.09 (ddd, J=14.4, 10.9, 5.5 Hz, 1H), 2.68-2.59 (m, 1H), 2.53-2.41 (m, 2H), 2.19 (ddd, J=10.1, 8.6, 3.3 Hz, 1H), 2.14-2.05 (m, 1H), 1.92-1.83 (m, 2H). MS (M+Na)$^+$: 317.0

Step d: Preparation of 25-d

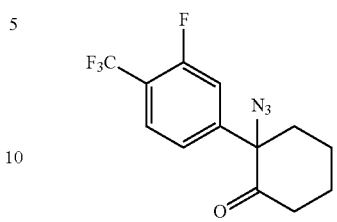

Using the compound 25-c (1.42 g, 4.82 mmol) as a raw material, the method described in step d in Example 2 was conducted accordingly to obtain 986 mg of pale yellow oily liquid, yield: 67.9%. $^1$H NMR (400 MHz, CDCl$_3$) δ 7.70 (t, J=7.8 Hz, 1H), 7.19 (t, J=9.5 Hz, 2H), 2.72-2.64 (m, 1H), 2.63-2.55 (m, 1H), 2.37 (ddd, J=14.4, 10.7, 5.6 Hz, 1H), 2.09 (ddd, J=14.4, 11.0, 3.4 Hz, 1H), 2.00-1.84 (m, 3H), 1.73-1.65 (m, 1H). MS (M+Na)$^+$: 324.

Step e: Preparation of 25-e

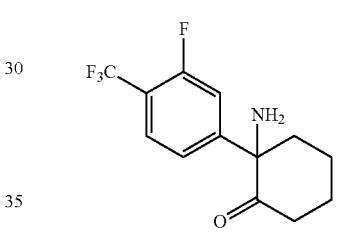

Using the compound 25-d (986 mg, 3.27 mmol) as a raw material, the method described in step e in Example 2 was conducted accordingly to obtain 913 mg of pale yellow oily liquid, which was directly cast into the reaction in next step without purification. MS (M+H)$^+$: 276

Step f: Preparation of 25-f

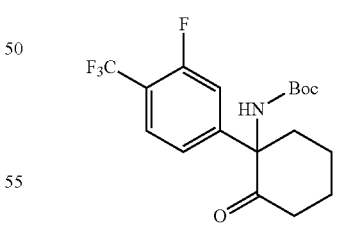

Using the crude compound 25-d (913 mg crude product) as a raw material, the method described in step e in Example 1 was conducted accordingly to obtain 1.01 g of white solid, yield: 82.2% (two steps together). $^1$H NMR (400 MHz, CDCl$_3$) δ 7.60 (t, J=7.8 Hz, 1H), 7.22 (d, J=11.5 Hz, 2H), 6.38 (s, 1H), 3.55 (d, J=12.3 Hz, 1H), 2.48 (d, J=12.5 Hz, 1H), 2.23 (dd, J=16.9, 11.4 Hz, 1H), 2.08-1.99 (m, 1H), 1.89 (d, J=11.2 Hz, 2H), 1.79 (s, 2H), 1.34 (s, 9H). MS (M+Na)$^+$: 398.

Step g: Preparation of 25-g

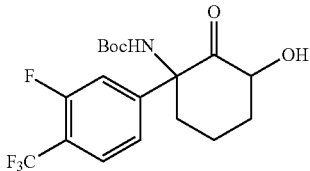

Using the compound 25-f (400 mg, 1.06 mmol) as a raw material, the method described in step f in Example 1 was conducted accordingly to obtain 178 mg of colorless oil, yield: 42.7%. $^1$H NMR (400 MHz, CDCl$_3$) δ 7.62 (t, J=7.8 Hz, 1H), 7.20 (d, J=10.8 Hz, 2H), 6.43 (s, 1H), 4.02 (dd, J=11.6, 5.7 Hz, 1H), 3.71 (d, J=12.7 Hz, 1H), 3.32 (d, J=4.7 Hz, 1H), 2.40 (ddd, J=12.2, 6.5, 3.1 Hz, 1H), 1.92 (dd, J=14.1, 10.3 Hz, 2H), 1.87-1.76 (m, 1H), 1.67-1.60 (m, 1H), 1.33 (s, 9H). MS (M+Na)$^+$: 414.

Step h: Preparation of Compound 25

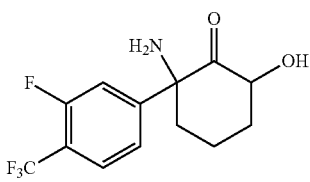 [SMILES: NC1(c2ccc(C(F)(F)F)c(F)c2)CCCC(O)C1=O]

Using the compound 25-g (78 mg, 0.2 mmol) as a raw material, the method described in step g in Example 1 was conducted accordingly to obtain 50 mg of colorless oily liquid, yield: 86.2%. $^1$H NMR (400 MHz, CDCl$_3$) δ 7.64 (t, J=7.8 Hz, 1H), 7.14 (d, J=11.3 Hz, 1H), 7.07 (d, J=8.2 Hz, 1H), 4.16 (dd, J=11.8, 7.0 Hz, 1H), 2.86-2.79 (m, 1H), 2.43-2.36 (m, 1H), 1.78 (dd, J=13.6, 2.9 Hz, 2H), 1.72-1.55 (m, 2H). MS (M+H)$^+$: 292.

Example 26: Preparation of 2-amino-2-(2-fluoro-3-(trifluoromethyl)phenyl)-6-hydroxycyclohexane-1-one (Compound 26)

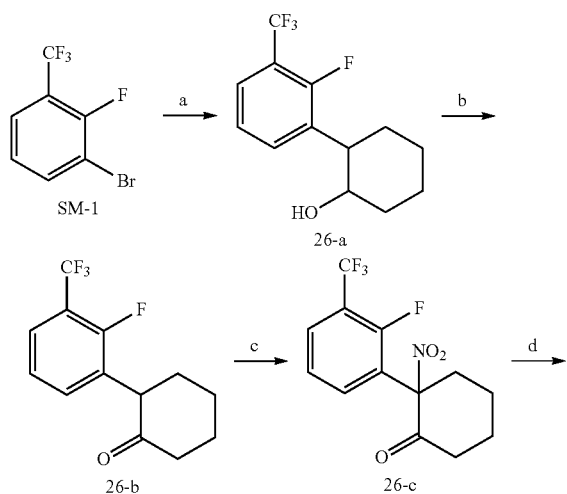

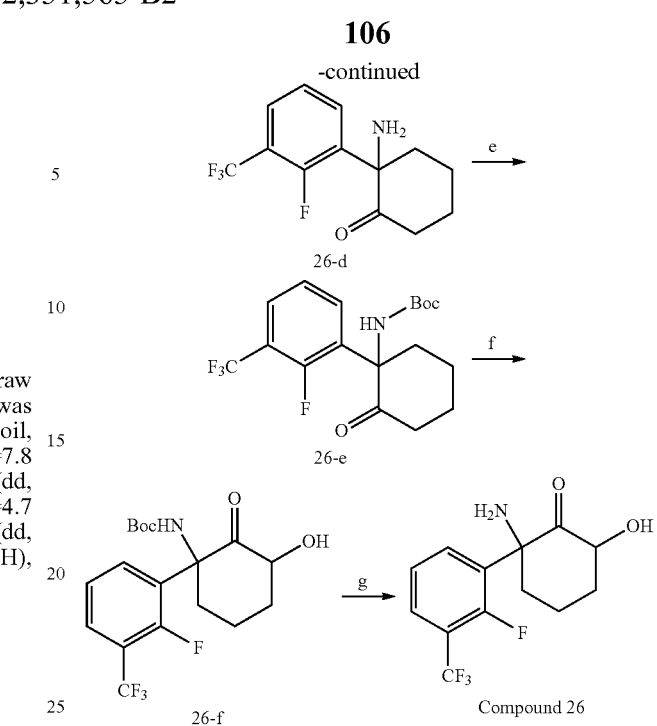

Step a: Preparation of 26-a

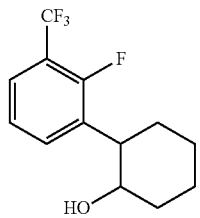

Using 2-fluoro-3-trifluoromethylbromobenzene (5 g, 20.58 mmoL) and epoxycyclohexane (2.2 g, 22.4 mmol) as raw materials, the method described in step a in Example 1 was conducted accordingly to obtain 4.7 g of yellow oily liquid, yield: 87.1%. $^1$H NMR (400 MHz, CDCl$_3$) δ 7.48 (dd, J=14.4, 7.0 Hz, 2H), 7.21 (t, J=7.8 Hz, 1H), 3.82-3.71 (m, 1H), 2.94-2.85 (m, 1H), 2.18-2.12 (m, 1H), 1.90-1.84 (m, 2H), 1.80-1.75 (m, 1H), 1.52 (d, J=12.8 Hz, 1H), 1.42 (dd, J=8.4, 6.5 Hz, 2H), 1.38-1.32 (m, 1H). MS (M+H)$^+$: 263

Step b: Preparation of 26-b

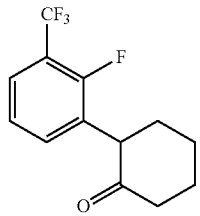

Using the compound 26-a (5 g, 19.1 mmol) as a raw material, the method described in step b in Example 1 was conducted accordingly to obtain 2.7 g of white solid, yield: 54.4%. $^1$H NMR (400 MHz, CDCl$_3$) δ 7.51 (t, J=7.2 Hz, 1H), 7.38 (t, J=7.0 Hz, 1H), 7.22 (t, J=7.8 Hz, 1H), 3.94 (dd, J=12.9, 5.3 Hz, 1H), 2.61-2.48 (m, 2H), 2.31-2.18 (m, 2H), 2.02 (dd, J=19.3, 5.9 Hz, 2H), 1.90-1.78 (m, 2H). MS (M+H)$^+$: 261

Step c: Preparation of 26-c

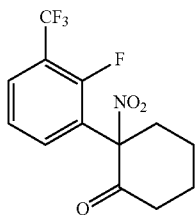

Using the compound 26-b (2.1 g, 8.07 mmol) as a raw material, the method described in step c in Example 1 was conducted accordingly to obtain 830 mg of pale yellow oily substance, yield: 33.7%. $^1$H NMR (400 MHz, CDCl$_3$) δ 7.73 (dd, J=9.9, 4.5 Hz, 1H), 7.42-7.32 (m, 2H), 3.05-2.97 (m, 1H), 2.92-2.84 (m, 1H), 2.82-2.73 (m, 1H), 2.67-2.58 (m, 1H), 2.00 (dd, J=10.6, 5.5 Hz, 2H), 1.91-1.82 (m, 1H), 1.81-1.71 (m, 1H). MS (M+Na)$^+$: 328.

Step d: Preparation of 26-d

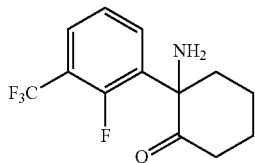 [SMILES: NC1(c2cccc(C(F)(F)F)c2F)CCCCC1=O]

Using the compound 26-c (740 mg, 2.42 mmol) as a raw material, the method described in step d in Example 1 was conducted accordingly to obtain 603 mg of yellow oily liquid crude product, which was directly cast into the reaction in next step without purification. MS (M+H)$^+$: 276

Step e: Preparation of 26-e

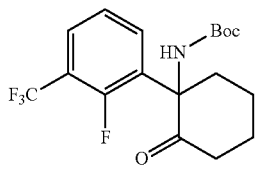 [SMILES: CC(C)(C)OC(=O)NC1(c2cccc(C(F)(F)F)c2F)CCCCC1=O]

Using the crude compound 26-d (603 mg crude product) as a raw material, the method described in step e in Example 1 was conducted accordingly to obtain 632 mg of colorless oily liquid, yield: 69.4% (two steps together). $^1$H NMR (400 MHz, CDCl$_3$) δ 7.96 (s, 1H), 7.59 (t, J=7.1 Hz, 1H), 7.32 (t, J=7.8 Hz, 1H), 6.50 (s, 1H), 3.73 (s, 1H), 2.50 (d, J=12.5 Hz, 1H), 2.33 (dd, J=15.1, 9.5 Hz, 1H), 2.09-1.98 (m, 2H), 1.85-1.76 (m, 2H), 1.70 (s, 1H), 1.32 (s, 9H). MS (M+H)$^+$: 376

Step f: Preparation of 26-f

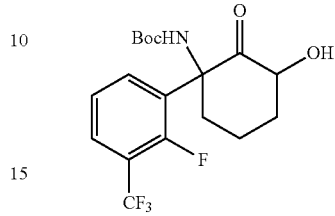

Using the compound 26-e (220 mg, 0.59 mmol) as a raw material, the method described in step f in Example 1 was conducted accordingly to obtain 85 mg of white solid, yield: 37.1%. $^1$H NMR (400 MHz, CDCl$_3$) δ 7.96 (s, 1H), 7.62 (t, J=7.0 Hz, 1H), 7.34 (t, J=7.9 Hz, 1H), 6.55 (s, 1H), 4.20-4.14 (m, 1H), 3.84 (s, 1H), 3.38 (d, J=5.3 Hz, 1H), 2.40 (dd, J=12.9, 6.0 Hz, 1H), 2.22 (t, J=7.6 Hz, 1H), 2.02-1.98 (m, 2H), 1.83 (d, J=9.8 Hz, 1H), 1.32 (s, 9H). MS (M+Na)$^+$: 414

Step g: Preparation of Compound 26

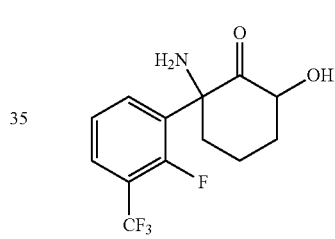

Using the compound 26-f (81 mg, 0.21 mmol) as a raw material, the method described in step g in Example 1 was conducted accordingly to obtain 50 mg of light yellow oily liquid, yield: 83.3%. $^1$H NMR (400 MHz, CDCl$_3$) δ 7.70 (t, J=7.4 Hz, 1H), 7.63 (t, J=7.1 Hz, 1H), 7.36 (t, J=7.9 Hz, 1H), 4.23 (dd, J=11.4, 7.0 Hz, 1H), 2.95-2.85 (m, 1H), 2.39 (ddd, J=12.3, 6.9, 2.8 Hz, 1H), 1.80 (dd, J=7.6, 4.4 Hz, 1H), 1.70-1.60 (m, 2H), 1.52 (ddd, J=24.7, 12.3, 4.2 Hz, 1H). MS (M+H)$^+$: 292.

Example 27: Preparation of 2-amino-2-(3-fluoro-2-(trifluoromethyl)phenyl)-6-hydroxycyclohexane-1-one (Compound 27)

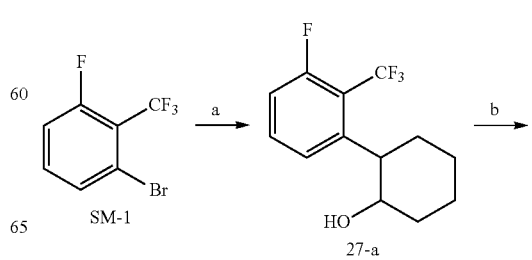

-continued

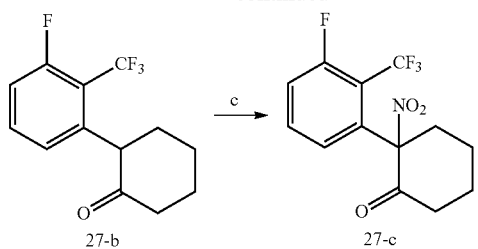

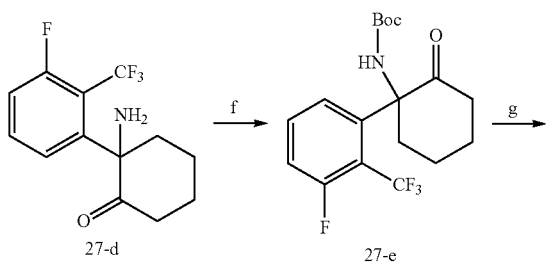

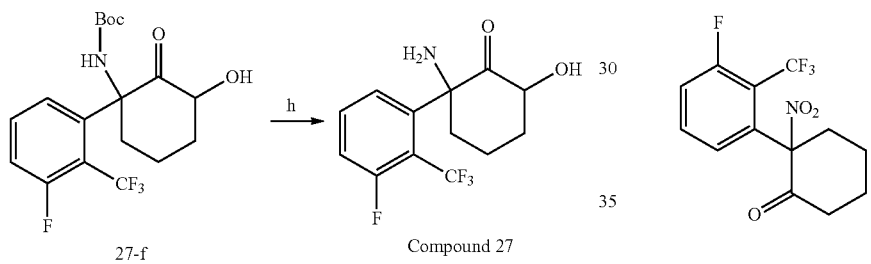

Step a: Preparation of 27-a

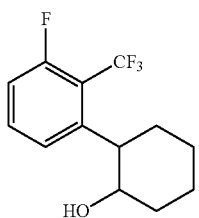 [SMILES: OC1CCCCC1c1cccc(F)c1C(F)(F)F]

Using 3-fluoro-2-trifluoromethylbromobenzene (10 g, 41.2 mmoL) and epoxycyclohexane (4.2 g, 42.8 mmol) as raw materials, the method described in step a in Example 1 was conducted accordingly to obtain 6.9 g of pale yellow oily liquid, yield: 63.9%. $^1$H NMR (400 MHz, CDCl$_3$) δ 7.55-7.47 (m, 1H), 7.31-7.26 (m, 1H), 7.11-7.00 (m, 1H), 3.86 (d, J=25.5 Hz, 1H), 2.99 (t, J=8.6 Hz, 1H), 2.17 (t, J=8.7 Hz, 1H), 1.94-1.83 (m, 2H), 1.79-1.72 (m, 1H), 1.40 (dt, J=18.3, 12.1 Hz, 4H). MS (M+H)$^+$: 263.

Step b: Preparation of 27-b

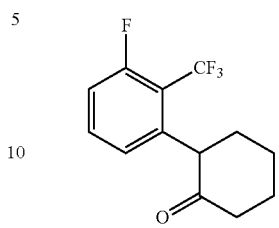

Using the compound 27-a (6.9 g, 26.3 mmol) as a raw material, the method described in step b in Example 1 was conducted accordingly to obtain 4.9 g of yellow solid, yield: 71.6%. $^1$H NMR (400 MHz, CDCl$_3$) δ 7.48 (dd, J=8.0, 5.4 Hz, 1H), 7.09 (dd, J=13.4, 6.0 Hz, 2H), 4.10 (dd, J=12.7, 5.6 Hz, 1H), 2.61-2.44 (m, 2H), 2.35-2.17 (m, 2H), 2.09-1.95 (m, 2H), 1.93-1.76 (m, 2H). MS (M+H)$^+$: 261.

Step c: Preparation of 27-c

Using the compound 27-b (1.5 g, 5.76 mmol) as a raw material, the method described in step c in Example 1 was conducted accordingly to obtain 430 mg of light yellow oily liquid, yield: 24.4%. $^1$H NMR (400 MHz, CDCl$_3$) δ 7.55 (td, J=8.2, 5.8 Hz, 1H), 7.33-7.27 (m, 1H), 6.86 (d, J=8.1 Hz, 1H), 3.12 (d, J=15.4 Hz, 1H), 2.78-2.72 (m, 2H), 2.63-2.53 (m, 1H), 2.10-2.02 (m, 1H), 1.93-1.82 (m, 2H), 1.77 (ddd, J=14.7, 7.6, 3.4 Hz, 1H). MS (M+Na)$^+$: 328.

Step d: Preparation of 27-d

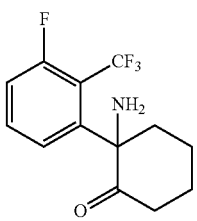 [SMILES: NC1(c2cccc(F)c2C(F)(F)F)CCCCC1=O]

Using the compound 27-c (950 mg, 3.11 mmol) as a raw material, the method described in step d in Example 1 was conducted accordingly to obtain 920 mg of pale yellow oily liquid, which was directly cast into the reaction in next step without purification. MS (M+H)$^+$: 276

Step e: Preparation of 27-e

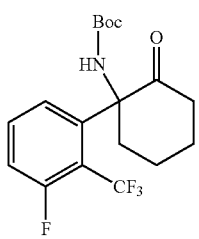 [SMILES: CC(C)(C)OC(=O)NC1(c2cccc(F)c2C(F)(F)F)CCCCC1=O]

Using the crude compound 27-d (920 mg crude product) as a raw material, the method described in step e in Example 1 was conducted accordingly to obtain 980 mg of white solid, yield: 83.9% (two steps together). $^1$H NMR (400 MHz, CDCl$_3$) δ 7.68 (d, J=7.6 Hz, 1H), 7.57 (dd, J=13.8, 7.9 Hz, 1H), 7.24-7.16 (m, 1H), 6.02 (s, 1H), 3.31 (s, 1H), 2.61-2.48 (m, 2H), 2.35 (ddd, J=12.0, 9.5, 5.4 Hz, 1H), 2.10-1.93 (m, 3H), 1.83 (d, J=5.0 Hz, 1H), 1.33 (s, 9H). MS (M+Na)$^+$: 398.

Step f: Preparation of 27-f

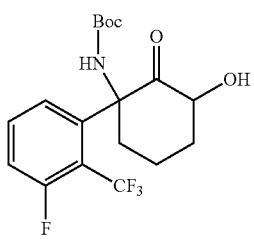 [SMILES: CC(C)(C)OC(=O)NC1(c2cccc(F)c2C(F)(F)F)CCCC(O)C1=O]

Using the compound 27-e (400 mg, 1.06 mmol) as a raw material, the method described in step f in Example 1 was conducted accordingly to obtain 178 mg of colorless oil, yield: 42.7%. $^1$H NMR (400 MHz, CDCl$_3$) δ 7.83 (d, J=7.3 Hz, 1H), 7.63 (dd, J=13.9, 8.2 Hz, 1H), 7.23 (d, J=8.9 Hz, 1H), 6.45 (s, 1H), 4.11-4.06 (m, 1H), 3.94 (s, 1H), 3.19 (d, J=6.7 Hz, 1H), 2.39 (ddd, J=11.9, 6.3, 3.2 Hz, 1H), 1.74 (dd, J=19.2, 11.2 Hz, 3H), 1.40 (t, J=10.5 Hz, 1H), 1.32 (s, 9H). MS (M+Na)+: 414.

Step g: Preparation of Compound 27

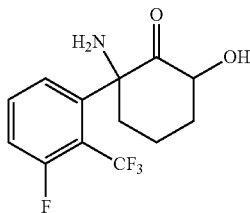 [SMILES: NC1(c2cccc(F)c2C(F)(F)F)CCCC(O)C1=O]

Using the compound 27-f (78 mg, 0.2 mmol) as a raw material, the method described in step g in Example 1 was conducted accordingly to obtain 50 mg of light yellow oily liquid, yield: 86.2%. $^1$H NMR (400 MHz, CDCl$_3$) δ 7.59 (dt, J=15.4, 6.8 Hz, 2H), 7.26-7.17 (m, 1H), 4.19 (dd, J=9.2, 6.4 Hz, 1H), 2.81 (dd, J=14.3, 2.8 Hz, 1H), 2.26 (dd, J=9.3, 3.2 Hz, 1H), 1.87-1.78 (m, 1H), 1.72 (dd, J=14.6, 3.7 Hz, 1H), 1.62 (dd, J=19.6, 10.9 Hz, 2H). MS (M+H)$^+$: 292.

Example 28: Preparation of 2-amino-2-(4-chloro-3-(trifluoromethoxy)phenyl)-6-hydroxycyclohexane-1-one (Compound 28)

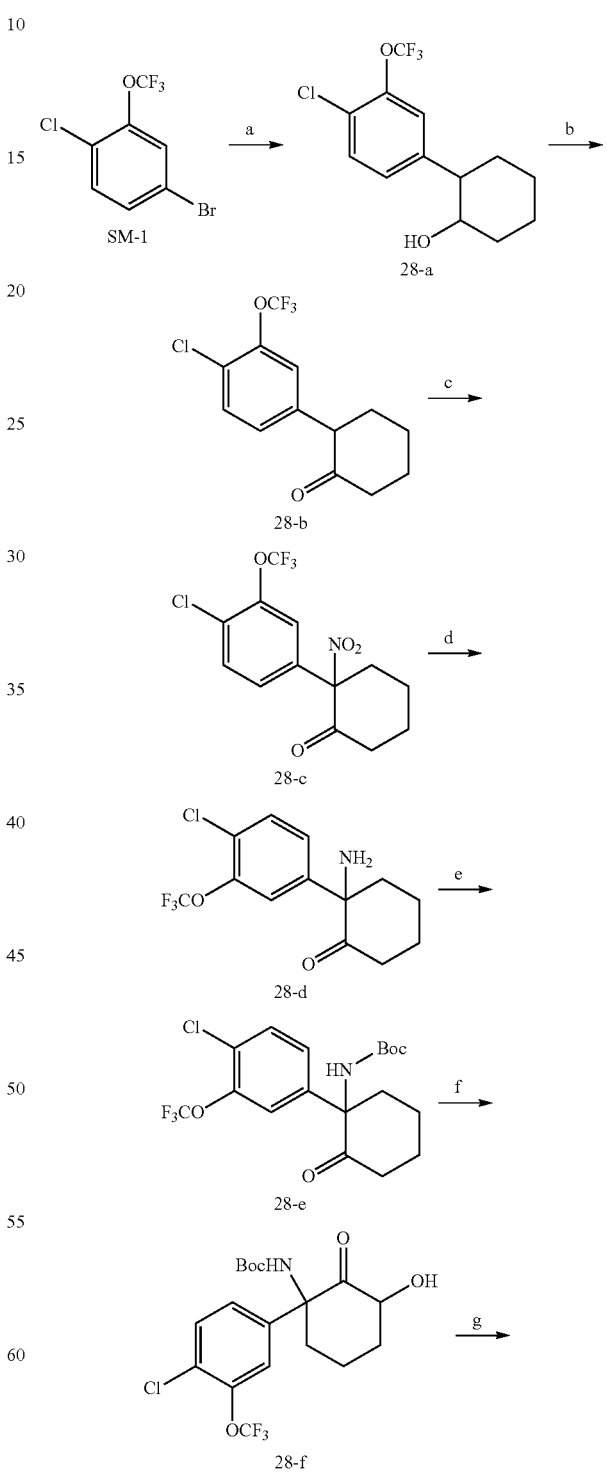

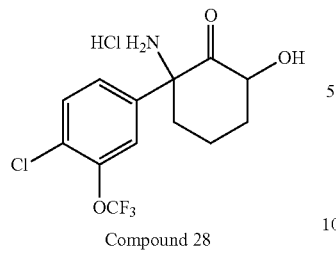

Compound 28

Step a: Preparation of 28-a

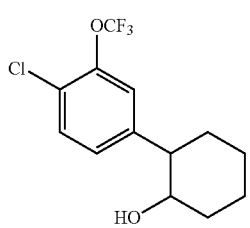 [SMILES: OC1CCCCC1c1ccc(Cl)c(OC(F)(F)F)c1]

Using 4-chloro-3-trifluoromethoxybromobenzene (8.5 g, 30.86 mmoL) and epoxycyclohexane (3.2 g, 32.6 mmol) as raw materials, the method described in step a in Example 1 was conducted accordingly to obtain 5.4 g of yellow oily liquid, yield: 59.4%. NMR (400 MHz, CDCl$_3$) δ 7.41 (d, J=8.2 Hz, 1H), 7.21 (s, 1H), 7.14 (dd, J=8.3, 2.0 Hz, 1H), 3.61 (dd, J=12.9, 5.5 Hz, 1H), 2.49-2.39 (m, 1H), 2.13-2.05 (m, 1H), 1.89-1.82 (m, 2H), 1.77 (dd, J=9.3, 6.3 Hz, 1H), 1.47-1.36 (m, 4H). MS (M+H)$^+$: 295.

Step b: Preparation of 28-b

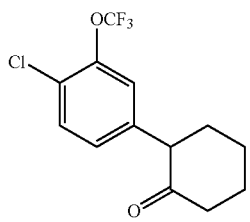 [SMILES: O=C1CCCCC1c1ccc(Cl)c(OC(F)(F)F)c1]

Using the compound 28-a (5.37 g, 18.22 mmol) as a raw material, the method described in step b in Example 1 was conducted accordingly to obtain 5.08 g of yellow oily liquid, yield: 95.2%. $^1$H NMR (400 MHz, CDCl$_3$) δ 7.41 (d, J=8.3 Hz, 1H), 7.10 (s, 1H), 7.03 (dd, J=8.3, 1.9 Hz, 1H), 3.61 (dd, J=12.3, 5.4 Hz, 1H), 2.57-2.44 (m, 2H), 2.28 (ddd, J=11.8, 5.1, 2.7 Hz, 1H), 2.22-2.14 (m, 1H), 2.05-1.91 (m, 2H), 1.86-1.77 (m, 2H). MS (M+H)$^+$: 293

Step c: Preparation of 28-c

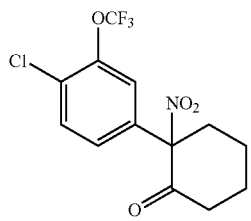 [SMILES: O=C1CCCCC1(c1ccc(Cl)c(OC(F)(F)F)c1)[N+](=O)[O-]]

Using the compound 28-b (3.9 g, 13.32 mmol) as a raw material, the method described in step c in Example 1 was conducted accordingly to obtain 1.47 g of pale yellow oily substance, yield: 32.7%. $^1$H NMR (400 MHz, CDCl$_3$) δ 7.57 (d, J=8.5 Hz, 1H), 7.31 (s, 1H), 7.24 (dd, J=9.0, 2.7 Hz, 1H), 3.15 (ddd, J=10.7, 7.7, 3.5 Hz, 1H), 2.76-2.60 (m, 2H), 2.59-2.51 (m, 1H), 2.05-1.98 (m, 1H), 1.96-1.80 (m, 3H). MS (M+Na)+: 360.

Step d: Preparation of 28-d

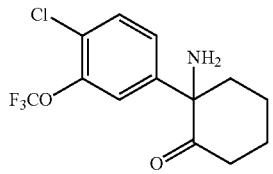 [SMILES: NC1(c2ccc(Cl)c(OC(F)(F)F)c2)CCCCC1=O]

Using the compound 28-c (1.47 g, 4.35 mmol) as a raw material, the method described in step d in Example 1 was conducted accordingly to obtain 1.5 g of colorless oily liquid crude product, which was directly cast into the reaction in next step without purification. MS (M+H)$^+$: 308

Step e: Preparation of 28-e

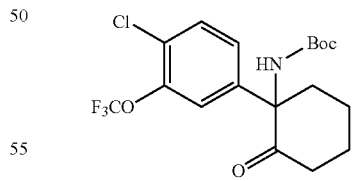

Using the crude compound 28-d (1.5 g crude product) as a raw material, the method described in step e in Example 1 was conducted accordingly to obtain 1.17 g of white solid, yield: 65.9% (two steps together). $^1$H NMR (400 MHz, CDCl$_3$) δ 7.46 (d, J=8.4 Hz, 1H), 7.30 (s, 1H), 7.26 (s, 1H), 6.32 (s, 1H), 3.49 (d, J=12.5 Hz, 1H), 2.47 (d, J=12.8 Hz, 1H), 2.23 (d, J=13.5 Hz, 1H), 2.02 (s, 1H), 1.94-1.86 (m, 2H), 1.78 (d, J=10.6 Hz, 2H), 1.32 (s, 9H). MS (M+Na)$^+$: 430

Step f: Preparation of 28-f

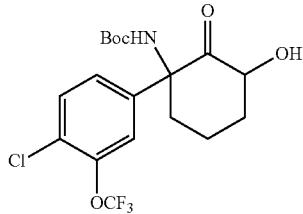 [SMILES: CC(C)(C)OC(=O)NC1(c2ccc(Cl)c(OC(F)(F)F)c2)CCCC(O)C1=O]

Using the compound 28-e (370 mg, 0.91 mmol) as a raw material, the method described in step f in Example 1 was conducted accordingly to obtain 103 mg of colorless oil, yield: 26.8%. $^1$H NMR (400 MHz, CDCl$_3$) δ 7.48 (d, J=8.4 Hz, 1H), 7.30 (d, J=7.8 Hz, 1H), 7.20 (d, J=5.8 Hz, 1H), 6.36 (s, 1H), 4.05 (s, 1H), 3.64 (s, 1H), 3.31 (s, 1H), 2.39 (ddd, J=12.4, 6.5, 3.1 Hz, 1H), 1.94-1.87 (m, 2H), 1.77 (d, J=15.2 Hz, 1H), 1.66-1.61 (m, 1H), 1.31 (s, 9H). MS (M+Na)$^+$: 446

Step g: Preparation of Compound 28

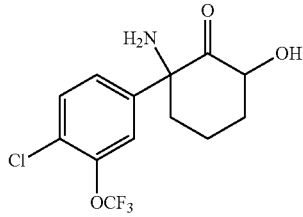 [SMILES: NC1(c2ccc(Cl)c(OC(F)(F)F)c2)CCCC(O)C1=O]

Using the compound 28-f (100 mg, 0.24 mmol) as a raw material, the method described in step g in Example 1 was conducted accordingly to obtain 58 mg of pale yellow oily liquid, yield: 76.3%. $^1$H NMR (400 MHz, CDCl$_3$) δ 7.50 (d, J=8.4 Hz, 1H), 7.23 (s, 1H), 7.07 (dd, J=8.4, 2.1 Hz, 1H), 4.16 (dd, J=11.8, 7.0 Hz, 1H), 2.84-2.75 (m, 1H), 2.42-2.34 (m, 1H), 1.77 (dd, J=20.4, 9.5 Hz, 2H), 1.60 (ddd, J=23.2, 12.9, 3.3 Hz, 2H). MS (M+H)+: 324.

Example 29: Preparation of 2-amino-6-hydroxy-2-(2,3,6-trifluorophenyl)cyclohexane-1-one (Compound 29)

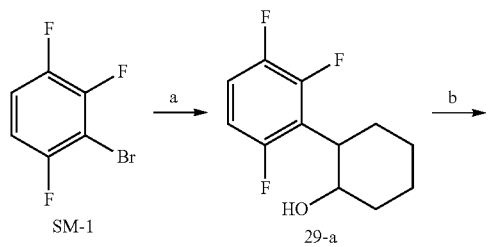

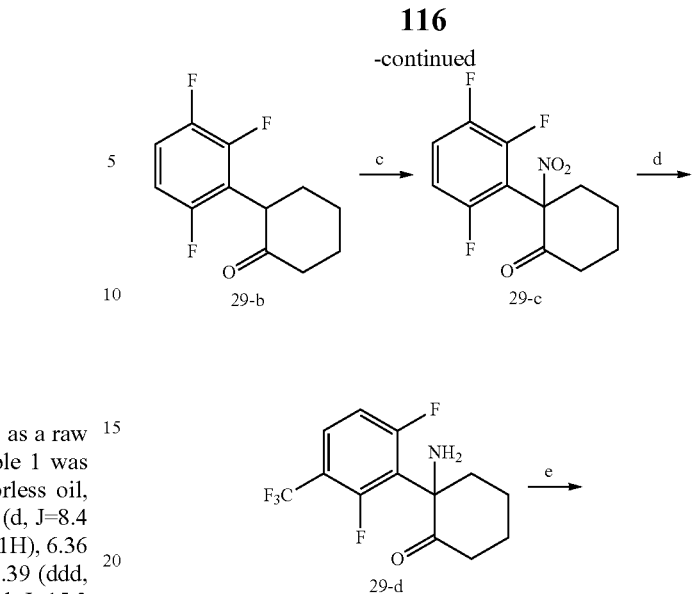

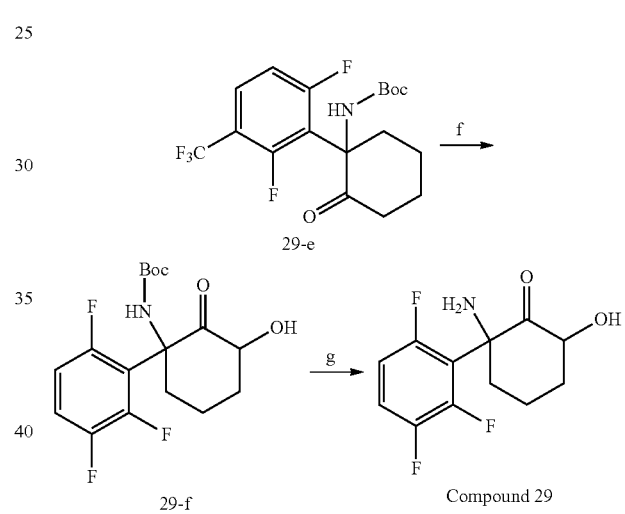

Step a: Preparation of 29-a

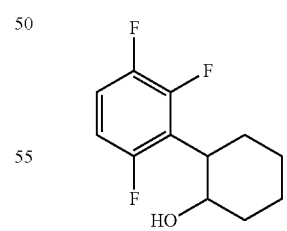

Using 2,3,6-trifluorobromobenzene (5 g, 23.7 mmoL) and epoxycyclohexane (3 g, 30.6 mmol) as raw materials, the method described in step a in Example 1 was conducted accordingly to obtain 4.3 g of colorless oily liquid, yield: 78.8%. $^1$H NMR (400 MHz, CDCl$_3$) δ 7.03-6.94 (m, 1H), 6.79 (tdd, J=9.4, 3.8, 2.2 Hz, 1H), 4.00 (s, 1H), 3.01-2.90 (m, 1H), 2.16-2.08 (m, 1H), 1.88-1.78 (m, 3H), 1.45-1.29 (m, 4H). MS (M+H)$^+$: 231.

Step b: Preparation of 29-b

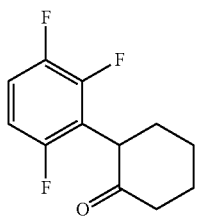 [SMILES: O=C1CCCCC1c1c(F)ccc(F)c1F]

Using the compound 29-a (5.46 g, 23.7 mmol) as a raw material, the method described in step b in Example 1 was conducted accordingly to obtain 4.5 g of yellow oily liquid, yield: 83.1%. $^1$H NMR (400 MHz, CDCl$_3$) δ 7.04 (ddd, J=18.3, 9.2, 5.0 Hz, 1H), 6.80 (tdd, J=9.2, 3.7, 2.2 Hz, 1H), 3.92 (dd, J=12.3, 6.5 Hz, 1H), 2.65-2.56 (m, 1H), 2.47-2.28 (m, 2H), 2.18 (ddd, J=8.0, 5.7, 3.2 Hz, 2H), 2.04-1.99 (m, 1H), 1.81 (ddd, J=11.4, 7.2, 4.8 Hz, 2H). MS (M+H)$^+$: 229.1

Step c: Preparation of 29-c

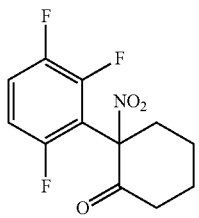 [SMILES: O=C1CCCCC1(c1c(F)ccc(F)c1F)[N+](=O)[O-]]

Using the compound 29-b (2.1 g, 9.2 mmol) as a raw material, the method described in step c in Example 1 was conducted accordingly to obtain 780 mg of pale yellow oily substance, yield: 31.0%. $^1$H NMR (400 MHz, CDCl$_3$) δ 7.33 (qd, J=8.9, 4.8 Hz, 1H), 7.02-6.93 (m, 1H), 3.29 (ddd, J=15.2, 5.5, 2.5 Hz, 1H), 2.86-2.75 (m, 2H), 2.69-2.58 (m, 1H), 2.03 (ddd, J=17.0, 10.3, 4.1 Hz, 2H), 1.90 (dd, J=10.3, 4.4 Hz, 1H), 1.60 (t, J=11.8 Hz, 1H). MS (M+Na)$^+$: 296.

Step d: Preparation of 29-d

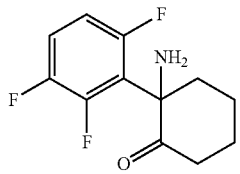 [SMILES: NC1(c2c(F)ccc(F)c2F)CCCCC1=O]

Using the compound 29-c (799 mg, 2.92 mmol) as a raw material, the method described in step d in Example 1 was conducted accordingly to obtain 647 mg of colorless oily liquid crude product, which was directly cast into the reaction in next step without purification. MS (M+H)$^+$: 244

Step e: Preparation of 29-e

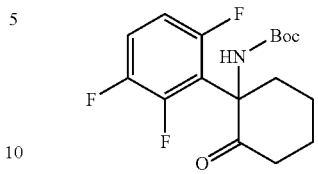

Using the crude compound 29-d (647 mg crude product) as a raw material, the method described in step e in Example 1 was conducted accordingly to obtain 681 mg of yellow solid, yield: 68.1% (two steps together). $^1$H NMR (400 MHz, CDCl$_3$) δ 7.14 (qd, J=8.9, 4.9 Hz, 1H), 6.91-6.80 (m, 1H), 6.48 (s, 1H), 3.79 (d, J=32.4 Hz, 1H), 2.60-2.45 (m, 1H), 2.40 (td, J=12.1, 5.8 Hz, 1H), 2.15-2.05 (m, 1H), 1.96-1.81 (m, 1H), 1.76 (dt, J=27.0, 13.4 Hz, 2H), 1.62-1.50 (m, 1H), 1.34 (s, 9H). MS (M+Na)$^+$: 366

Step f: Preparation of 29-f

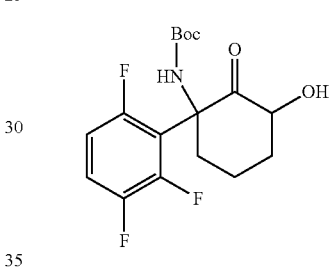

Using the compound 29-e (200 mg, 0.58 mmol) as a raw material, the method described in step f in Example 1 was conducted accordingly to obtain 84 mg of white solid, yield: 40.2%. $^1$H NMR (400 MHz, CDCl$_3$) δ 7.22-7.11 (m, 1H), 6.90-6.80 (m, 1H), 6.46 (s, 1H), 4.28-4.19 (m, 1H), 3.89 (s, 1H), 3.30 (d, J=5.9 Hz, 1H), 2.44 (ddd, J=12.4, 6.4, 3.3 Hz, 1H), 1.91-1.80 (m, 1H), 1.73 (dd, J=27.7, 14.1 Hz, 1H), 1.56-1.48 (m, 2H), 1.35 (s, 9H). MS (M+Na)$^+$: 382

Step g: Preparation of Compound 29

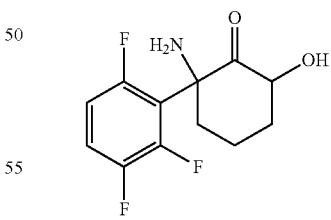

Using the compound 29-f (84 mg, 0.23 mmol) as a raw material, the method described in step g in Example 1 was conducted accordingly to obtain 55 mg of colorless oily liquid, yield: 91.7%. $^1$H NMR (400 MHz, CDCl$_3$) δ 7.17 (qd, J=9.0, 4.9 Hz, 1H), 6.93-6.84 (m, 1H), 4.31 (dd, J=11.5, 7.1 Hz, 1H), 3.22 (dd, J=14.0, 2.6 Hz, 1H), 2.41 (ddd, J=12.4, 6.8, 3.0 Hz, 1H), 1.86-1.80 (m, 1H), 1.60 (dd, J=27.0, 13.5 Hz, 1H), 1.48 (dt, J=13.3, 9.6 Hz, 2H). MS (M+H)$^+$: 260.1.

Example 30: Preparation of 2-amino-6-hydroxy-2-(2,3,5-trifluorophenyl)cyclohexane-1-one (Compound 30)

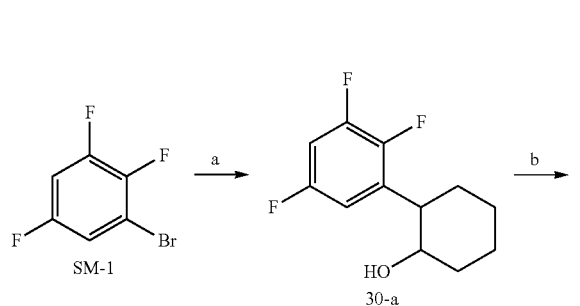

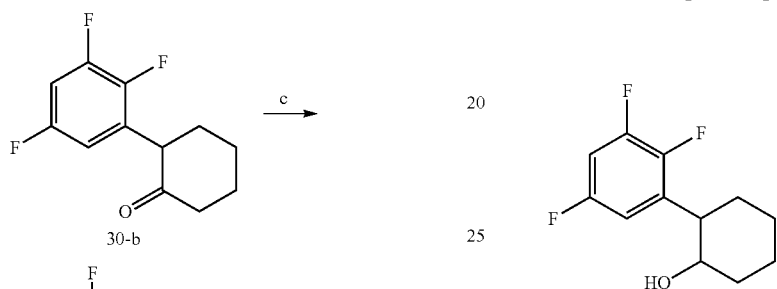

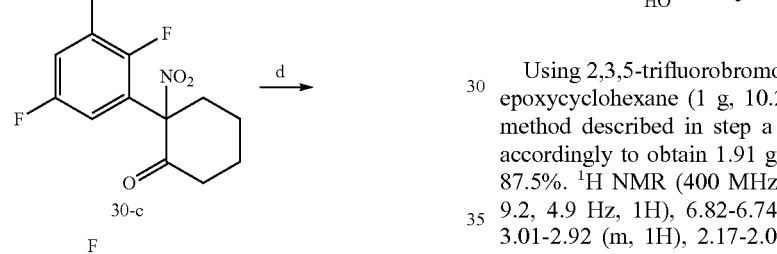

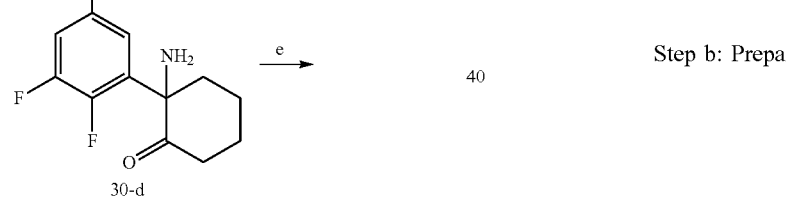

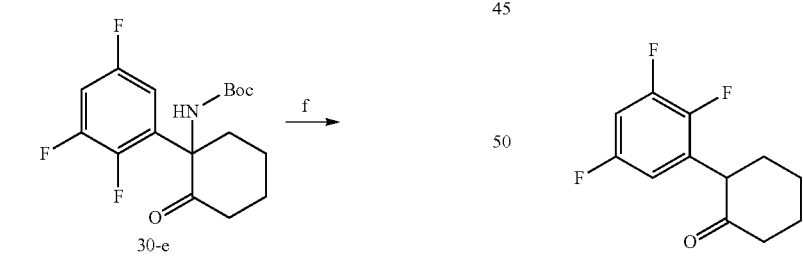

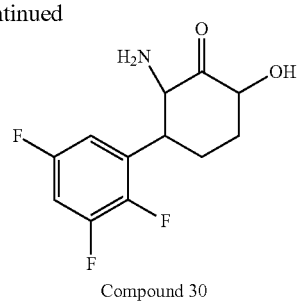

Compound 30

Step a: Preparation of 30-a

Using 2,3,5-trifluorobromobenzene (2 g, 9.48 mmoL) and epoxycyclohexane (1 g, 10.2 mmol) as raw materials, the method described in step a in Example 1 was conducted accordingly to obtain 1.91 g of colorless oily liquid, yield: 87.5%. $^1$H NMR (400 MHz, CDCl$_3$) δ 6.98 (ddd, J=18.2, 9.2, 4.9 Hz, 1H), 6.82-6.74 (m, 1H), 4.04-3.93 (m, 1H), 3.01-2.92 (m, 1H), 2.17-2.08 (m, 1H), 1.81 (ddd, J=11.3, 9.2, 5.4 Hz, 3H), 1.47-1.25 (m, 4H). MS (M+Na)$^+$: 253.1.

Step b: Preparation of 30-b

Using the compound 30-a (1.84 g, 8.0 mmol) as a raw material, the method described in step b in Example 1 was conducted accordingly to obtain 1.15 g of white solid, yield: 63.0%. $^1$H NMR (400 MHz, CDCl$_3$) δ 7.04 (ddd, J=18.3, 9.2, 5.0 Hz, 1H), 6.81 (tdd, J=9.2, 3.7, 2.2 Hz, 1H), 3.93 (dd, J=12.2, 6.5 Hz, 1H), 2.66-2.58 (m, 1H), 2.49-2.38 (m, 1H), 2.24-2.12 (m, 3H), 2.02 (dd, J=8.0, 6.2 Hz, 1H), 1.82 (ddd, J=12.1, 7.5, 5.0 Hz, 2H). MS (M+H)$^+$: 229.1

Step c: Preparation of 30-c

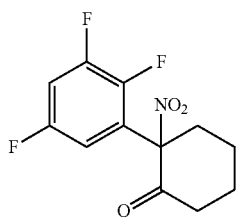 [SMILES: O=C1CCCCC1(c1cc(F)cc(F)c1F)[N+](=O)[O-]]

Using the compound 30-b (1.07 g, 4.69 mmol) as a raw material, the method described in step c in Example 1 was conducted accordingly to obtain 487 mg of pale yellow oily substance, yield: 38.0%. $^1$H NMR (400 MHz, CDCl$_3$) δ 7.33 (qd, J=9.0, 4.8 Hz, 1H), 7.02-6.93 (m, 1H), 3.27 (ddt, J=14.4, 4.9, 2.7 Hz, 1H), 2.85-2.73 (m, 2H), 2.68-2.57 (m, 1H), 2.07-1.96 (m, 2H), 1.94-1.86 (m, 1H), 1.67-1.56 (m, 1H). MS (M+Na)$^+$: 296.

Step d: Preparation of 30-d

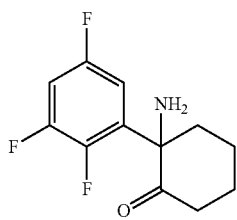 [SMILES: NC1(c2cc(F)cc(F)c2F)CCCCC1=O]

Using the compound 30-c (450 mg, 1.65 mmol) as a raw material, the method described in step d in Example 1 was conducted accordingly to obtain 370 mg of colorless oily liquid crude product, which was directly cast into the reaction in next step without purification. MS (M+H)$^+$: 244.1

Step e: Preparation of 30-e

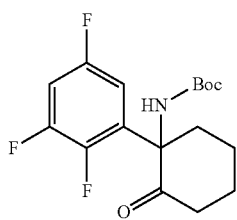 [SMILES: CC(C)(C)OC(=O)NC1(c2cc(F)cc(F)c2F)CCCCC1=O]

Using the crude compound 30-d (370 mg crude product) as a raw material, the method described in step e in Example 1 was conducted accordingly to obtain 365 mg of white solid, yield: 64.5% (two steps together). $^1$H NMR (400 MHz, CDCl$_3$) δ 7.14 (ddd, J=17.8, 9.0, 4.9 Hz, 1H), 6.85 (tdd, J=9.3, 3.9, 2.2 Hz, 1H), 6.48 (s, 1H), 3.83 (s, 1H), 2.48 (t, J=6.8 Hz, 1H), 2.40 (td, J=12.1, 5.7 Hz, 1H), 2.08 (ddd, J=17.9, 9.0, 5.9 Hz, 1H), 1.87 (d, J=8.5 Hz, 1H), 1.79-1.68 (m, 2H), 1.53-1.47 (m, 1H), 1.34 (s, 9H). MS (M+Na)$^+$: 366

Step f: Preparation of 30-f

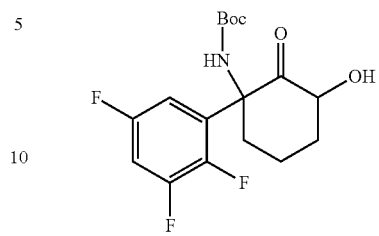

Using the compound 30-e (355 mg, 1.03 mmol) as a raw material, the method described in step f in Example 1 was conducted accordingly to obtain 240 mg of white solid, yield: 64.5%. $^1$H NMR (400 MHz, CDCl$_3$) δ 7.16 (qd, J=9.0, 4.9 Hz, 1H), 6.86 (tdd, J=9.4, 3.9, 2.2 Hz, 1H), 6.46 (s, 1H), 4.23 (dd, J=11.5, 7.1 Hz, 1H), 3.89 (s, 1H), 3.30 (s, 1H), 2.43 (dtd, J=12.9, 6.5, 3.3 Hz, 1H), 1.86 (dd, J=9.5, 5.4 Hz, 1H), 1.73 (dd, J=28.0, 14.1 Hz, 1H), 1.54-1.44 (m, 2H), 1.34 (s, 9H). MS (M+Na)$^+$: 382.1

Step g: Preparation of Compound 30

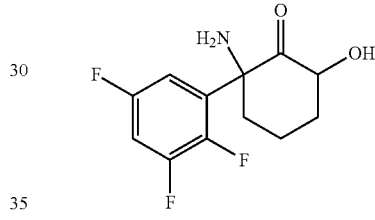

Using the compound 30-f (210 mg, 0.58 mmol) as a raw material, the method described in step g in Example 1 was conducted accordingly to obtain 138 mg of colorless oily liquid, yield: 91.4%. $^1$H NMR (400 MHz, CDCl$_3$) δ 7.16 (qd, J=9.0, 4.9 Hz, 1H), 6.92-6.85 (m, 1H), 4.31 (dd, J=11.5, 7.1 Hz, 1H), 3.22 (dd, J=14.0, 2.6 Hz, 1H), 2.41 (ddd, J=12.4, 6.9, 3.0 Hz, 1H), 1.88-1.79 (m, 1H), 1.60 (dd, J=27.0, 13.5 Hz, 1H), 1.54-1.41 (m, 2H). (M+H)$^+$: 260.0.

Example 31: Preparation of 2-amino-6-hydroxy-2-(2,4,6-trifluorophenyl)cyclohexane-1-one (Compound 31)

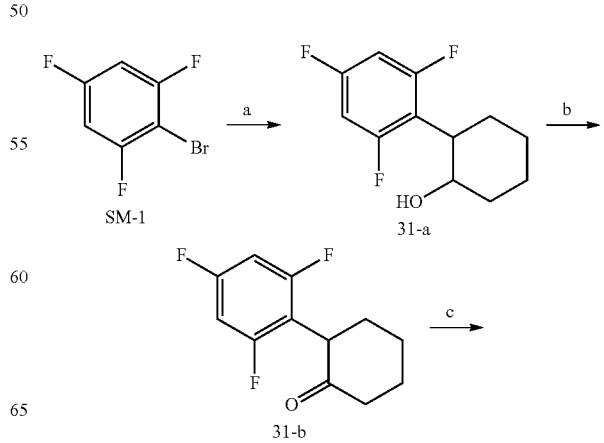

-continued

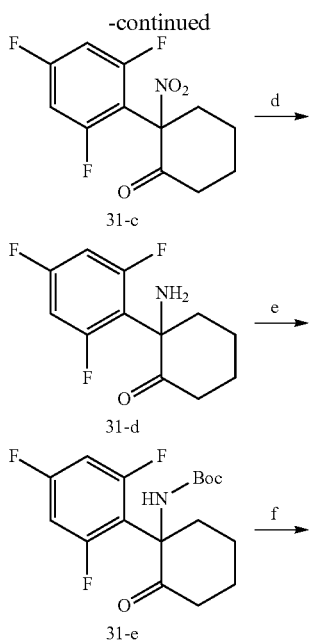

31-c 31-d 31-e 31-f

Compound 31

Step a: Preparation of 31-a

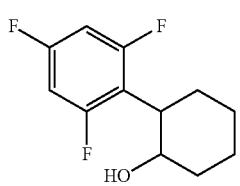 [SMILES: OC1CCCCC1c1c(F)cc(F)cc1F]

Using 2,4,6-trifluorobromobenzene (8 g, 37.9 mmoL) and epoxycyclohexane (3.96 g, 40.3 mmol) as raw materials, the method described in step a in Example 1 was conducted accordingly to obtain 4.57 g of colorless oily liquid, yield: 52.3%. $^1$H NMR (400 MHz, CDCl$_3$) δ 6.67-6.58 (m, 2H), 3.94 (s, 1H), 2.88 (td, J=11.2, 4.3 Hz, 1H), 2.15-2.08 (m, 1H), 1.85-1.75 (m, 3H), 1.44-1.27 (m, 4H). MS (M+Na)$^+$: 253.1.

Step b: Preparation of 31-b

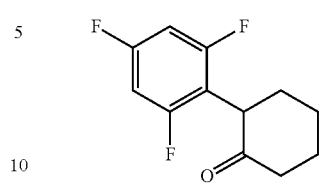

Using the compound 31-a (4.56 g, 19.8 mmol) as a raw material, the method described in step b in Example 1 was conducted accordingly to obtain 2.75 g of colorless oily liquid, yield: 60.8%. $^1$H NMR (400 MHz, CDCl$_3$) δ 6.64 (t, J=8.5 Hz, 2H), 3.85 (dd, J=12.6, 6.3 Hz, 1H), 2.64-2.55 (m, 1H), 2.40 (td, J=13.8, 5.7 Hz, 1H), 2.21-2.10 (m, 3H), 2.00 (ddd, J=9.8, 6.2, 2.9 Hz, 1H), 1.83-1.74 (m, 2H). MS (M+H)$^+$: 229.

Step c: Preparation of 31-c

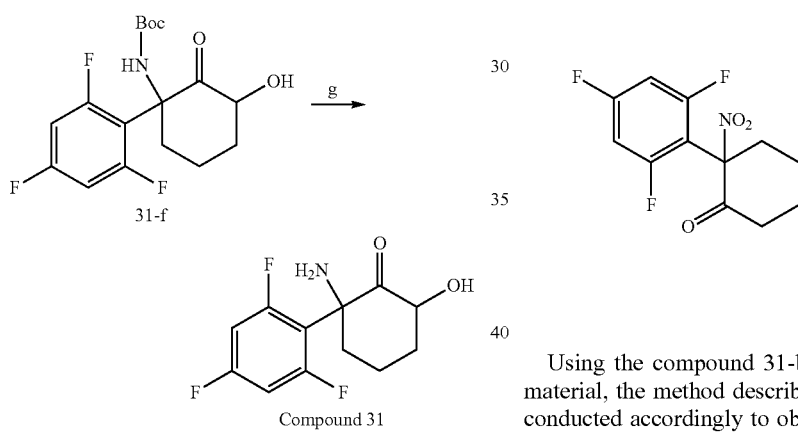

Using the compound 31-b (2.6 g, 11.4 mmol) as a raw material, the method described in step c in Example 1 was conducted accordingly to obtain 1.05 g of pale yellow oily substance, yield: 33.7%. $^1$H NMR (400 MHz, CDCl$_3$) δ 6.83-6.76 (m, 2H), 3.25 (ddd, J=14.3, 4.7, 2.7 Hz, 1H), 2.74 (dd, J=11.2, 6.2 Hz, 2H), 2.61 (dd, J=12.0, 6.2 Hz, 1H), 2.10-1.95 (m, 3H), 1.92-1.84 (m, 1H). MS (M+Na)$^+$: 296.

Step d: Preparation of 31-d

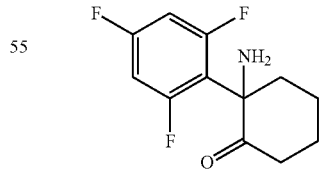

Using the compound 31-c (1.03 g, 3.77 mmol) as a raw material, the method described in step d in Example 1 was conducted accordingly to obtain 1.05 g of pale yellow oily liquid crude product, which was directly cast into the reaction in next step without purification. MS (M+H)$^+$: 244.1

Step e: Preparation of 31-e

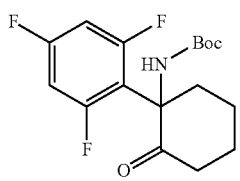 [SMILES: CC(C)(C)OC(=O)NC1(c2c(F)cc(F)cc2F)CCCCC1=O]

Using the crude compound 31-d (1.05 g crude product) as a raw material, the method described in step e in Example 1 was conducted accordingly to obtain 870 mg of white solid, yield: 67.2% (two steps together). $^1$H NMR (400 MHz, CDCl$_3$) δ 6.68 (dd, J=9.7, 8.5 Hz, 2H), 6.47 (s, 1H), 3.79 (s, 1H), 2.50-2.37 (m, 2H), 2.12-2.05 (m, 1H), 1.83 (dd, J=10.4, 7.6 Hz, 1H), 1.75 (dd, J=18.7, 6.9 Hz, 2H), 1.53-1.48 (m, 1H), 1.34 (s, 9H). MS (M+Na)$^+$: 366

Step f: Preparation of 31-f

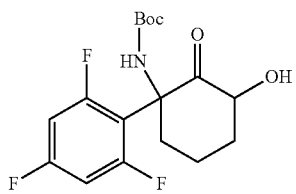

Using the compound 31-e (470 mg, 1.37 mmol) as a raw material, the method described in step f in Example 1 was conducted accordingly to obtain 77 mg of colorless oil, yield: 15.6%. $^1$H NMR (400 MHz, CDCl$_3$) δ 6.73-6.64 (m, 2H), 6.44 (s, 1H), 4.30-4.20 (m, 1H), 3.85 (s, 1H), 3.29 (d, J=6.1 Hz, 1H), 2.43 (ddd, J=12.7, 6.5, 3.4 Hz, 1H), 1.88-1.80 (m, 1H), 1.70 (d, J=13.4 Hz, 1H), 1.54-1.47 (m, 2H), 1.35 (s, 9H). MS (M+Na)$^+$: 382.1

Step g: Preparation of Compound 31

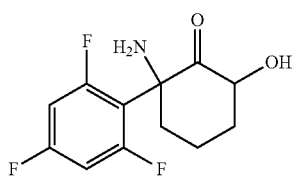 [SMILES: NC1(c2c(F)cc(F)cc2F)CCCC(O)C1=O]

Using the compound 31-f (70 mg, 0.19 mmol) as a raw material, the method described in step g in Example 1 was conducted accordingly to obtain 43 mg of colorless oily liquid, yield: 86%. NMR (400 MHz, CDCl$_3$) δ 6.71 (dd, J=9.8, 8.5 Hz, 2H), 4.30 (dd, J=11.2, 7.2 Hz, 1H), 3.18 (dd, J=13.9, 2.5 Hz, 1H), 2.40 (ddd, J=10.4, 6.9, 3.0 Hz, 1H), 1.85-1.77 (m, 1H), 1.57 (dd, J=26.9, 13.7 Hz, 1H), 1.51-1.39 (m, 2H). (M+H)$^+$: 260.

Example 32: Preparation of 2-amino-6-hydroxy-2-o-tolylcyclohexane-1-one hydrochloride (Compound 32)

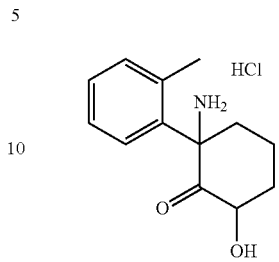

Compound 1 (30 mg, 0.14 mmol) was dissolved in 5 ml ethyl acetate, 4M HCl 1,4-dioxane solution (1 mL) was added dropwise under stirring conditions. A large amount of white solid were precipitated out. The mixture was stirred at room temperature for 30 min, and filtered. The filter cake was washed with ethyl acetate and dried to obtain 32 mg of white solid, yield: 91.4%, purity: 99.5%. $^1$H NMR (400 MHz, CD$_3$OD) δ 7.71 (dd, J=5.5, 3.8 Hz, 1H), 7.46-7.41 (m, 2H), 7.37-7.32 (m, 1H), 4.25 (dd, J=11.8, 6.8 Hz, 1H), 3.27-3.19 (m, 1H), 2.35-2.27 (m, 1H), 2.24 (s, 3H), 1.95-1.77 (m, 3H), 1.66 (ddd, J=24.5, 12.2, 4.5 Hz, 1H). MS(M+H)$^+$: 220.1

Example 33: Preparation of 2-amino-6-hydroxy-2-m-tolylcyclohexane-1-one hydrochloride (Compound 33)

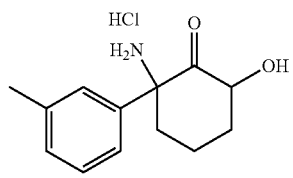 [SMILES: Cl ; Cc1cccc(C2(N)CCCC(O)C2=O)c1]

Using the compound 2 (30 mg, 0.14 mmol) as a raw material, the method described in Example 32 was conducted accordingly to obtain 30 mg of white solid, yield: 85.7%. Purity: 99.2%. $^1$H NMR (400 MHz, CD$_3$OD) δ 7.45 (t, J=7.6 Hz, 1H), 7.35 (d, J=7.6 Hz, 1H), 7.25 (d, J=8.8 Hz, 2H), 4.25 (dd, J=12.2, 6.8 Hz, 1H), 3.11 (dd, J=13.7, 2.8 Hz, 1H), 2.41 (s, 3H), 2.29 (ddd, J=12.2, 6.5, 2.9 Hz, 1H), 2.06-1.91 (m, 2H), 1.88-1.76 (m, 1H), 1.69 (td, J=12.4, 3.8 Hz, 1H). MS (M+H)$^+$: 220.1.

Example 34: Preparation of 2-amino-6-hydroxy-2-m-fluorophenylcyclohexane-1-one hydrochloride (Compound 34)

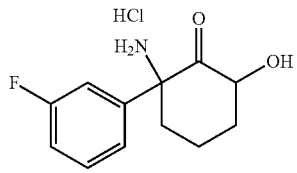 [SMILES: Cl ; NC1(c2cccc(F)c2)CCCC(O)C1=O]

Using the compound 3 (30 mg, 0.13 mmol) as a raw material, the method described in Example 32 was conducted accordingly to obtain 28 mg of white solid, yield: 80.2%. Purity: 99.5%. $^1$H NMR (400 MHz, CD$_3$OD) δ 7.60 (d, J=6.3 Hz, 1H), 7.31 (d, J=1.9 Hz, 1H), 7.25 (d, J=7.4 Hz, 2H), 4.25 (dd, J=12.2, 6.7 Hz, 1H), 3.13-3.03 (m, 1H), 2.37-2.26 (m, 1H), 2.02 (d, J=13.5 Hz, 2H), 1.88-1.63 (m, 2H). MS (M+H)$^+$: 224.

Example 35: Preparation of 2-amino-6-hydroxy-2-p-fluorophenylcyclohexane-1-one hydrochloride (Compound 35)

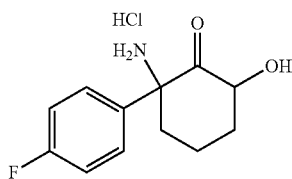

Using the compound 4 (50 mg, 0.22 mmol) as a raw material, the method described in Example 32 was conducted accordingly to obtain 52 mg of white solid, yield: 89.6%. Purity: 99.28%. $^1$H NMR (400 MHz, CD$_3$OD) δ 7.51-7.45 (m, 2H), 7.35-7.28 (m, 2H), 4.24 (dd, J=12.1, 6.7 Hz, 1H), 3.09 (dd, J=13.9, 2.8 Hz, 1H), 2.31 (ddd, J=12.3, 6.6, 2.9 Hz, 1H), 2.09-2.00 (m, 1H), 1.99-1.91 (m, 1H), 1.82 (ddd, J=13.8, 8.5, 3.0 Hz, 1H), 1.71 (ddd, J=16.5, 9.7, 3.2 Hz, 1H). MS (M+H)$^+$: 224.

Example 36: Preparation of 2-amino-6-hydroxy-2-(2-methoxyphenyl)cyclohexane-1-one hydrochloride (Compound 36)

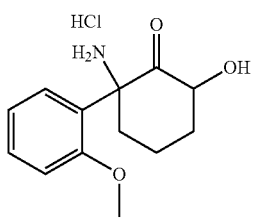 [SMILES: Cl ; COc1ccccc1C1(N)CCCC(O)C1=O]

Using the compound 5 (43 mg, 0.18 mmol) as a raw material, the method described in Example 32 was conducted accordingly to obtain 46 mg of white solid, yield: 92%. Purity: 98.7%. $^1$H NMR (400 MHz, CD$_3$OD) δ 7.66 (dd, J=7.9, 1.2 Hz, 1H), 7.57-7.51 (m, 1H), 7.17 (dd, J=16.0, 8.1 Hz, 2H), 4.15 (dd, J=12.0, 6.6 Hz, 1H), 3.81 (s, 3H), 3.08 (dd, J=12.8, 2.1 Hz, 1H), 2.25 (ddd, J=9.3, 5.7, 2.9 Hz, 1H), 1.93-1.73 (m, 3H), 1.56 (qd, J=12.4, 4.7 Hz, 1H). MS (M+H)$^+$: 236.1

Example 37: Preparation of 2-amino-6-hydroxy-2-(3-methoxyphenyl)cyclohexane-1-one hydrochloride (Compound 37)

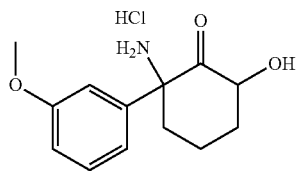 [SMILES: Cl ; COc1cccc(C2(N)CCCC(O)C2=O)c1]

Using the compound 6 (50 mg, 0.21 mmol) as a raw material, the method described in Example 32 was conducted accordingly to obtain 55 mg of white solid, yield: 94.8%. Purity: 97.2%. $^1$H NMR (400 MHz, CD$_3$OD) δ 7.49 (t, J=8.1 Hz, 1H), 7.10 (dd, J=8.3, 2.1 Hz, 1H), 7.01 (dd, J=7.8, 1.2 Hz, 1H), 6.93 (t, J=2.1 Hz, 1H), 4.26 (dd, J=12.3, 6.8 Hz, 1H), 3.84 (s, 3H), 3.08 (dd, J=13.7, 2.8 Hz, 1H), 2.33-2.26 (m, 1H), 1.99 (d, J=12.7 Hz, 3H), 1.86-1.77 (m, 1H), 1.69 (d, J=4.1 Hz, 1H). MS (M+H)$^+$: 236.

Example 38: Preparation of 2-amino-6-hydroxy-2-(3-trifluoromethoxyphenyl)cyclohexane-1-one hydrochloride (Compound 38)

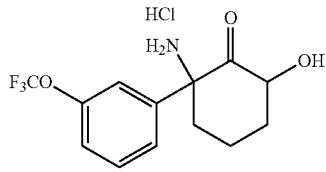 [SMILES: Cl ; NC1(c2cccc(OC(F)(F)F)c2)CCCC(O)C1=O]

Using the compound 7 (50 mg, 0.17 mmol) as a raw material, the method described in Example 32 was conducted accordingly to obtain 50 mg of white solid, yield: 89.3%. Purity: 97.2%. $^1$H NMR (400 MHz, CD$_3$OD) δ 7.70 (t, J=8.1 Hz, 1H), 7.50 (d, J=8.4 Hz, 1H), 7.45 (d, J=7.9 Hz, 1H), 7.38 (s, 1H)), 4.23 (dd, J=12.0, 6.7 Hz, 1H), 3.10 (dd, J=14.0, 2.7 Hz, 1H), 2.32 (ddd, J=12.0, 6.6, 2.8 Hz, 1H), 2.06-1.93 (m, 2H), 1.85-1.65 (m, 2H). MS (M+H)$^+$: 290.1

Example 39: Preparation of 6-hydroxy-2-methyl-amino-2-(3-trifluoromethoxyphenyl)cyclohexane-1-one hydrochloride (Compound 39)

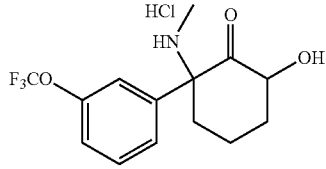 [SMILES: CNC1(c2cccc(OC(F)(F)F)c2)CCCC(O)C1=O ; Cl]

Compound 7 (150 mg, 0.52 mmol) was dissolved in a mixed solvent of EA (3 mL) and MeOH (3 ml) under Ar protection. Pd/C (120 mg) and p-methoxybenzaldehyde (314 mg, 2.31 mmol) were added. After H$_2$ replacement, the mixture was reacted at 50° C. for 2 days. After the raw materials were reacted completely, the mixture was filtered, 4M HCl 1,4-dioxane solution (0.5 mL) was added under stirring at room temperature. The mixture was stirred for 30 min, the solvent rotary evaporated to dryness, and ethyl acetate (10 mL) was added. A large amount of white solid was precipitated, and filtered. The obtained solid was beat with DCM (10 ml), filtered, and the filter cake was washed with DCM, the obtained white solid was prepared by HPLC, and 35 mg of white solid was obtained after freeze-drying. The white solid was dissolved in 10 ml saturated NaHCO$_3$ solution, extracted with EA (8 ml×3). The organic phases were combined, washed with saturated brine, dried over anhydrous sodium sulfate, filtered, evaporated under reduced pressure to remove the low boiling solvent, and the resulted residue was dissolved in 5 ml ethyl acetate, 4M HCl 1,4-dioxane solution (0.5 mL) was added dropwise under stirring conditions. A large amount of white solid were precipitated out and filtered, and the white solid obtained was dried to obtain 42 mg of white solid, yield: 23.9%, purity: 98.2%. $^1$H NMR (400 MHz, CD$_3$OD) δ 7.74 (t, J=8.1 Hz, 1H), 7.56 (d, J=8.3 Hz, 1H), 7.46 (d, J=7.9 Hz, 1H), 7.40 (s, 1H), 4.19 (dd, J=11.9, 6.7 Hz, 1H), 3.28-3.23 (m, 1H), 2.34 (s, 3H), 2.34-2.28 (m, 1H), 2.08-2.03 (m, 1H), 1.95 (dd, J=13.5, 3.7 Hz, 1H), 1.82-1.67 (m, 2H). MS (M+H)$^+$: 304.

Example 40: Preparation of 2-(dimethylamino)-6-hydroxy-2-(3-trifluoromethoxyphenyl)cyclohexane-1-one hydrochloride (Compound 40)

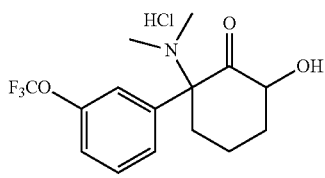 [SMILES: CN(C)C1(c2cccc(OC(F)(F)F)c2)CCCC(O)C1=O ; Cl]

The compound 7 (200 mg, 0.69 mmol) was dissolved in a mixed solvent of EA (5 mL) and MeOH (5 ml) under Ar protection. Pd/C (60 mg) and formaldehyde (3 ml) were added, the mixture was reacted at room temperature for 6 h after hydrogen replacement. After the raw materials were reacted completely, the mixture was filtered, and 4M HCl 1,4-dioxane solution (0.5 mL) was added under stirring at room temperature. The mixture was stirred for 30 min, the solvent was rotary evaporated to dryness, and ethyl acetate (10 mL) was added. A large amount of white solid were precipitated, and filtered. The obtained solid was beat with ethyl acetate (10 ml), rinsed, and dried to obtain 122 mg of colored solid, yield: 49.8%, purity: 97.5%. $^1$H NMR (400 MHz, CD$_3$OD) δ 7.74 (t, J=8.2 Hz, 1H), 7.56 (d, J=8.2 Hz, 1H), 7.45 (d, J=7.9 Hz, 1H), 7.40 (s, 1H)), 4.19 (dd, J=11.7, 6.8 Hz, 1H), 3.27-3.20 (m, 1H), 2.38 (s, 6H), 2.33-2.28 (m, 1H), 2.08-2.03 (m, 1H), 1.95 (dd, J=13.5, 3.7 Hz, 1H), 1.83-1.64 (m, 2H). MS (M+H)$^+$: 318.

Example 41: Preparation of 2-ethylamino-6-hydroxy-2-(3-trifluoromethoxyphenyl)cyclohexane-1-one hydrochloride (Compound 41)

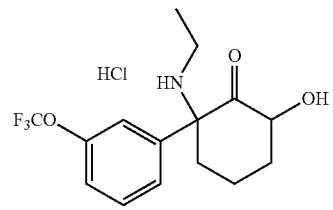 [SMILES: CCNC1(c2cccc(OC(F)(F)F)c2)CCCC(O)C1=O ; Cl]

Using the compound 8 (50 mg, 0.16 mmol) as a raw material, the method described in Example 32 was conducted accordingly to obtain 49 mg of white solid, yield: 87.5%. Purity: 95.5%. $^1$H NMR (400 MHz, CD$_3$OD) δ 7.72 (t, J=8.1 Hz, 1H), 7.54 (d, J=8.3 Hz, 1H), 7.47 (d, J=7.6 Hz, 1H), 7.40 (s, 1H)), 4.20 (dd, J=11.9, 6.7 Hz, 1H), 3.28-3.19 (m, 1H), 2.87 (td, J=14.5, 7.2 Hz, 1H), 2.51 (dd, J=10.1, 7.3 Hz, 1H), 2.30 (dd, J=11.8, 2.8 Hz, 1H), 2.02 (d, J=10.3 Hz, 2H), 1.82-1.63 (m, 2H), 1.23 (t, J=7.2 Hz, 3H). MS (M+H)$^+$: 318.

Example 42: Preparation of 2-amino-2-(3-chloro-2-fluorophenyl)-6-hydroxycyclohexane-1-one hydrochloride (Compound 42)

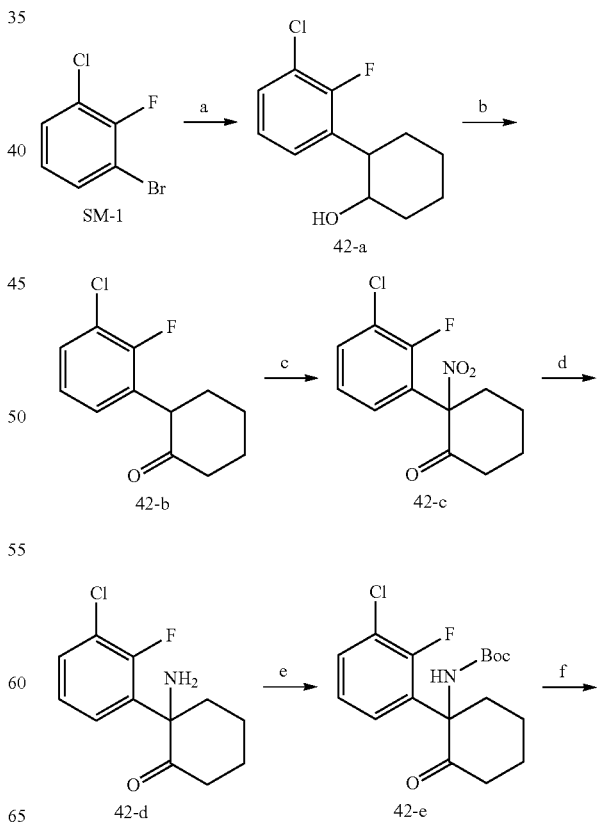

-continued

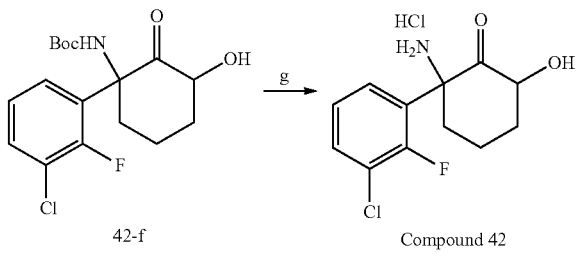

42-f       Compound 42

Step a: Preparation of 42-a

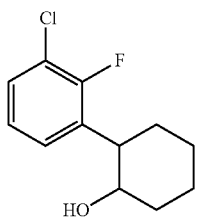 [SMILES: OC1CCCCC1c1cccc(Cl)c1F]

Using 2-fluoro-3-chloro-bromobenzene (8.36 g, 39.9 mmoL) and epoxycyclohexane (4.8 g, 48.9 mmol) as raw materials, the method described in step a in Example 1 was conducted accordingly to obtain 8.0 g of yellow oil liquid, yield: 87.6%. $^1$H NMR (400 MHz, CDCl$_3$) δ 7.29-7.23 (m, 1H), 7.20-7.14 (m, 1H), 7.05 (t, J=7.8 Hz, 1H), 3.76 (td, J=9.7, 4.3 Hz, 1H), 2.88-2.78 (m, 1H), 2.16-2.08 (m, 1H), 1.90-1.81 (m, 2H), 1.80-1.71 (m, 1H), 1.58-1.47 (m, 2H), 1.42-1.36 (m, 2H). MS (M+H)$^+$: 229.1

Step b: Preparation of 42-b

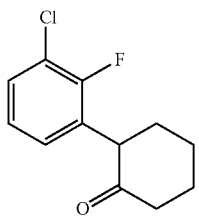

Using the compound 42-a (4 g, 17.49 mmol) as a raw material, the method described in step b in Example 1 was conducted accordingly to obtain 2.6 g of yellow oily liquid, yield: 65.6%. $^1$H NMR (400 MHz, CDCl$_3$) δ 7.31-7.26 (m, 1H), 7.05 (dd, J=4.3, 2.8 Hz, 2H), 3.85 (dd, J=12.8, 5.6 Hz, 1H), 2.59-2.42 (m, 2H), 2.29-2.14 (m, 2H), 2.03-1.95 (m, 2H), 1.81 (dt, J=11.7, 9.5 Hz, 2H). MS (M+H)$^+$: 227.0

Step c: Preparation of 42-c

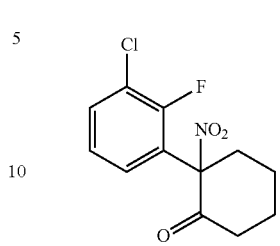

Using the compound 42-b (2.6 g, 11.5 mmol) as a raw material, the method described in step c in Example 1 was conducted accordingly to obtain 500 mg of white solid, yield: 16%. $^1$H NMR (400 MHz, CDCl$_3$) δ 7.57-7.49 (m, 1H), 7.19 (dd, J=8.8, 8.1 Hz, 1H), 7.14-7.09 (m, 1H), 3.01-2.85 (m, 2H), 2.81-2.70 (m, 1H), 2.68-2.57 (m, 1H), 1.98 (dt, J=13.3, 6.5 Hz, 2H), 1.92-1.82 (m, 1H), 1.78-1.69 (m, 1H). MS (M-NO2)$^+$: 225.1

Step d: Preparation of 42-d

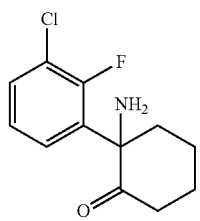 [SMILES: NC1(c2cccc(Cl)c2F)CCCCC1=O]

Using the compound 42-c (500 mg, 1.84 mmol) as a raw material, the method described in step d in Example 1 was conducted accordingly to obtain 500 mg of crude yellow oily liquid, which was directly cast into the reaction in next step without purification. MS (M+H)$^+$: 242.1

Step e: Preparation of 42-e

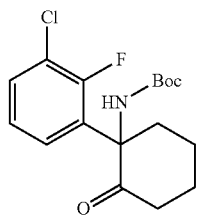 [SMILES: CC(C)(C)OC(=O)NC1(c2cccc(Cl)c2F)CCCCC1=O]

Using crude compound 42-d (500 mg crude product) as a raw material, the method described in step e in Example 1 was conducted accordingly to obtain 350 mg of yellow oily liquid, yield: 55.6% (two steps together). $^1$H NMR (400 MHz, CDCl$_3$) δ 7.63 (s, 1H), 7.40-7.34 (m, 1H), 7.15 (t, J=7.9 Hz, 1H), 6.48 (s, 1H), 3.74 (s, 1H), 2.47 (d, J=11.0 Hz, 1H), 2.39-2.29 (m, 1H), 2.04 (d, J=4.1 Hz, 1H), 1.84-1.66 (m, 4H), 1.32 (s, 9H). MS (M+Na)$^+$: 364.1

Step f: Preparation of 42-f

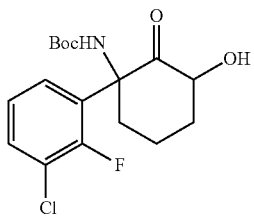 [SMILES: CC(C)(C)OC(=O)NC1(c2cccc(Cl)c2F)CCCC(O)C1=O]

Using the compound 42-e (341 mg, 1 mmol) as a raw material, the method described in step f in Example 1 was conducted accordingly to obtain 100 mg of colorless oil, yield: 27.9%. $^1$H NMR (400 MHz, CDCl$_3$) δ 7.62 (s, 1H), 7.40 (t, J=7.4 Hz, 1H), 7.17 (t, J=8.0 Hz, 1H), 6.51 (s, 1H), 4.17 (dd, J=11.9, 7.0 Hz, 1H), 3.83 (s, 1H), 3.37 (s, 1H), 2.39 (ddd, J=11.8, 6.5, 3.0 Hz, 1H), 1.74-1.62 (m, 3H), 1.58-1.49 (m, 1H), 1.32 (s, 9H). MS (M+Na)$^+$: 380.

Step g: Preparation of Compound 42

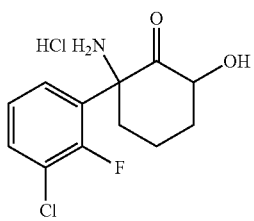

Compound 42-f (100 mg, 0.28 mmol) was dissolved in DCM (3 mL), and 4M HCl 1,4-dioxane solution (1 mL) was added. A white solid was gradually precipitated out, the mixture was stirred at room temperature for 1.5 hours, and the solvent was rotary evaporated to dryness. 8 ml of ethyl acetate was added to the residue and the mixture was stirred at room temperature for 30 min and filtered, and the filter cake was dried to obtain 40 mg of white solid, yield: 48.8%. Purity: 99.28%. $^1$H NMR (400 MHz, CD$_3$OD) δ 7.85-7.56 (m, 2H), 7.50-7.29 (m, 1H), 4.41-4.18 (m, 1H), 3.13 (dt, J=22.7, 10.0 Hz, 1H), 2.44-2.22 (m, 1H), 2.09-1.82 (m, 2H), 1.81-1.53 (m, 2H). MS (M+H)$^+$: 258.0.

Example 43: Preparation of 2-amino-2-(2,6-difluorophenyl)-6-hydroxycyclohexane-1-one hydrochloride (Compound 43)

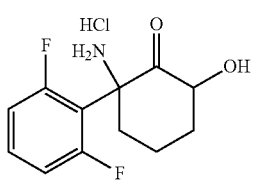 [SMILES: NC1(c2c(F)cccc2F)CCCC(O)C1=O ; Cl]

Using the compound 10 (40 mg, 0.16 mmol) as a raw material, the method described in Example 32 was conducted accordingly to obtain 42 mg of white solid, yield: 91.3%. Purity: 99.4%. $^1$H NMR (400 MHz, CD$_3$OD) δ 7.67 (tt, J=8.4, 6.2 Hz, 1H), 7.21 (dd, J=10.8, 8.6 Hz, 2H), 4.42 (dd, J=11.4, 7.0 Hz, 1H), 3.36 (dd, J=8.2, 5.5 Hz, 1H), 2.39-2.30 (m, 1H), 2.02-1.93 (m, 1H), 1.81 (dd, J=24.5, 10.9 Hz, 1H), 1.74-1.57 (m, 2H). MS (M+H)$^+$: 278.0

Example 44: Preparation of 2-amino-2-(2,3-difluorophenyl)-6-hydroxycyclohexane-1-one hydrochloride (Compound 44)

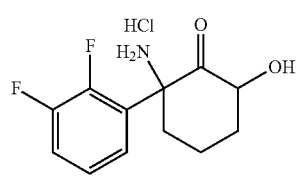 [SMILES: NC1(c2cccc(F)c2F)CCCC(O)C1=O ; Cl]

Using the compound 11 (40 mg, 0.16 mmol) as a raw material, the method described in Example 32 was conducted accordingly to obtain 40 mg of white solid, yield: 87.0%. Purity: 98.1%. $^1$H NMR (400 MHz, CD$_3$OD) δ 7.57-7.49 (m, 2H), 7.47-7.40 (m, 1H), 4.37 (dd, J=11.0, 6.9 Hz, 1H), 3.19-3.10 (m, 1H), 2.33 (ddd, J=12.2, 6.5, 2.7 Hz, 1H), 2.04-1.89 (m, 2H), 1.80-1.59 (m, 2H). MS (M+H)$^+$: 242.1.

Example 45: Preparation of 2-amino-6-hydroxy-2-(2-(trifluoromethyl)phenyl)cyclohexane-1-one hydrochloride (Compound 45)

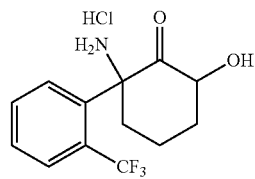 [SMILES: NC1(c2ccccc2C(F)(F)F)CCCC(O)C1=O ; Cl]

Using the compound 12 (48 mg, 0.18 mmol) as a raw material, the method described in Example 32 was conducted accordingly to obtain 49 mg of white solid, yield: 90.7%. Purity: 94.3%. $^1$H NMR (400 MHz, CD$_3$OD) δ 8.05 (d, J=8.0 Hz, 1H), 8.00 (d, J=7.8 Hz, 1H), 7.91 (t, J=7.7 Hz, 1H), 7.80 (t, J=7.7 Hz, 1H), 4.27 (dd, J=11.6, 6.8 Hz, 1H), 3.37 (dd, J=14.4, 2.6 Hz, 1H), 2.30 (ddd, J=9.6, 6.2, 2.9 Hz, 1H), 2.01 (dd, J=13.5, 3.5 Hz, 1H), 1.95-1.88 (m, 1H), 1.78 (ddd, J=24.0, 11.8, 3.0 Hz, 1H), 1.67 (ddd, J=16.8, 12.1, 4.2 Hz, 1H). MS (M+H)$^+$: 274.1.

Example 46: Preparation of 2-amino-6-hydroxy-2-(4-(trifluoromethyl)phenyl)cyclohexane-1-one hydrochloride (Compound 46)

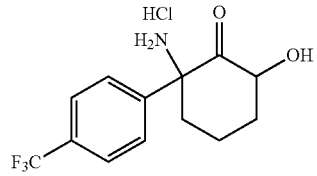 [SMILES: NC1(c2ccc(C(F)(F)F)cc2)CCCC(O)C1=O ; Cl]

Using the compound 13 (30 mg, 0.11 mmol) as a raw material, the method described in Example 32 was conducted accordingly to obtain 28 mg of white solid, yield: 82.4%. Purity: 96.4%. $^1$H NMR (400 MHz, CD$_3$OD) δ 7.90 (d, J=8.3 Hz, 2H), 7.67 (d, J=8.3 Hz, 2H), 4.24 (dd, J=11.9, 6.7 Hz, 1H), 3.16 (dd, J=14.0, 2.5 Hz, 1H), 2.32 (ddd, J=12.0, 6.6, 2.8 Hz, 1H), 2.10 (td, J=13.6, 3.9 Hz, 1H), 1.99 (dd, J=9.8, 5.9 Hz, 1H), 1.76 (ddd, J=19.9, 15.9, 8.4 Hz, 2H). MS (M+H)$^+$: 274.

Example 47: Preparation of 2-amino-6-hydroxy-2-(4-(trifluoromethyl)phenyl)cyclohexane-1-one methanesulfonate (Compound 47)

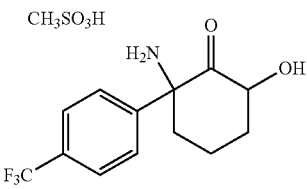

Compound 13 (40 mg, 0.15 mmol) was dissolved in DCM (3 mL), and a solution of methanesulfonic acid (14 mg, 0.15 mmol) in DCM was added dropwise under stirring. After adding, the mixture was stirred at room temperature for 1.5 hours, and a large amount of white solid was precipitated, and directly filtered. The filter cake was washed with DCM and dried to obtain 42 mg of white solid powder, yield: 77.8%, purity: 99.2%. Melting point: 177° C.-181° C. $^1$H NMR (400 MHz, CD$_3$OD) δ 7.90 (d, J=8.4 Hz, 2H), 7.68 (d, J=8.3 Hz, 2H), 4.24 (dd, J=12.0, 6.7 Hz, 1H), 3.17 (dd, J=14.0, 2.6 Hz, 1H), 2.70 (s, 3H), 2.32 (ddd, J=12.0, 6.6, 2.8 Hz, 1H), 2.10 (td, J=13.5, 3.9 Hz, 1H), 2.04-1.95 (m, 1H), 1.87-1.65 (m, 2H). MS (M+H)$^+$: 274.

Example 48: Preparation of 2-amino-6-hydroxy-2-(4-(trifluoromethyl)phenyl)cyclohexane-1-one sulfate (Compound 48)

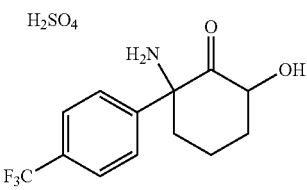

The compound 13 (40 mg, 0.15 mmol) was dissolved in DCM (3 mL), and sulfuric acid (14 mg, 0.15 mmol) in DCM was added dropwise under stirring. After adding, the mixture was stirred at room temperature for 1.5 hours. The system was a colorless and transparent liquid, the low boiling solvent was evaporated off under reduced pressure, and ethyl acetate (7 ml) was added to the residue. The mixture was beat, and a large amount of white solid was precipitated, filtered, washed with ethyl acetate, and dried to obtain 46 mg of white solid powder, yield: 85.2%, purity: 98.2%. Melting point: 206.5° C.-208.7° C. $^1$H NMR (400 MHz, CD$_3$OD) δ 7.90 (d, J=8.4 Hz, 2H), 7.68 (d, J=8.3 Hz, 2H), 4.24 (dd, J=11.9, 6.7 Hz, 1H), 3.18 (dd, J=14.0, 2.3 Hz, 1H), 2.32 (ddd, J=12.0, 6.6, 2.8 Hz, 1H), 2.10 (td, J=13.5, 3.8 Hz, 1H), 2.04-1.95 (m, 1H), 1.87-1.65 (m, 2H). MS (M+H)$^+$: 274.

Example 49: Preparation of 2-amino-6-hydroxy-2-(4-(trifluoromethyl)phenyl)cyclohexane-1-one oxalate (compound 49)

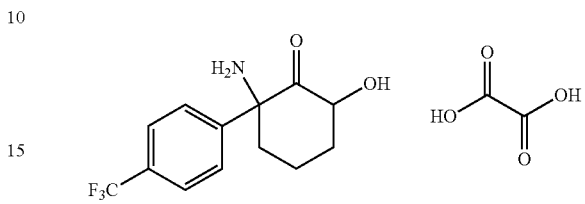

The compound 13 (50 mg, 0.18 mmol) was dissolved in DCM (4 mL), and the methanol solution of oxalic acid dihydrate (24 mg, 0.18 mmol) was added dropwise under stirring. After adding, the mixture was stirred at room temperature for 1.5 hours. The system was a colorless and transparent liquid, the low boiling solvent was evaporated off under reduced pressure, and ethyl acetate (7 ml) was added to the residue. The mixture was beat, and a large amount of white solid was precipitated, filtered, washed with ethyl acetate, and dried to obtain 58 mg of white solid powder, yield: 87.9%, purity: 98.6%. $^1$H NMR (400 MHz, CD$_3$OD) δ 7.88 (d, J=8.2 Hz, 2H), 7.67 (d, J=8.2 Hz, 2H), 4.23 (dd, J=11.8, 6.7 Hz, 1H), 3.18 (d, J=12.2 Hz, 1H), 2.31 (dd, J=9.1, 6.5 Hz, 1H), 2.16-2.06 (m, 1H), 1.97 (s, 1H), 1.73 (ddd, J=20.3, 16.4, 10.7 Hz, 2H). MS (M+H)$^+$: 274.

Example 50: Preparation of (2R,6R)-2-amino-6-hydroxy-2-(4-(trifluoromethyl)phenyl)cyclohexane-1-one hydrochloride (Compound 50)

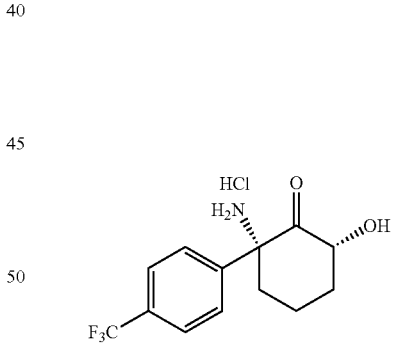

Using compound 14 (180 mg, 0.48 mmol) as a raw material, the method described in Example 32 was conducted accordingly to obtain 65 mg of white solid, yield: 43.6%, purity 97.7%, ee>99%, [α]$_D^{20}$: −165° (c 0.2, H$_2$O). $^1$H NMR (400 MHz, CD$_3$OD) δ 7.90 (d, J=8.4 Hz, 2H), 7.67 (d, J=8.3 Hz, 2H), 4.24 (dd, J=12.0, 6.7 Hz, 1H), 3.16 (dd, J=14.0, 2.6 Hz, 1H), 2.32 (ddd, J=12.0, 6.6, 2.8 Hz, 1H), 2.09 (tt, J=10.5, 5.1 Hz, 1H), 2.02-1.96 (m, 1H), 1.86-1.65 (m, 2H). MS (M+Na)$^+$: 296.1

Example 51: Preparation of (2S,6S)-2-amino-6-hydroxy-2-(4-(trifluoromethyl)phenyl)cyclohexane-1-one hydrochloride (Compound 51)

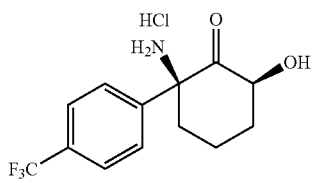 [SMILES: N[C@]1(c2ccc(C(F)(F)F)cc2)CCC[C@H](O)C1=O ; Cl]

Using compound 15 (180 mg, 0.48 mmol) as a raw material, the method described in Example 32 was conducted accordingly to obtain 117 mg of white solid, yield: 78.5%, purity 98.9%, ee>99%, $[\alpha]_D^{20}$: +154° (c 0.2, H$_2$O). $^1$H NMR (400 MHz, CD$_3$OD) δ 7.90 (d, J=8.4 Hz, 2H), 7.67 (d, J=8.3 Hz, 2H), 4.24 (dd, J=12.0, 6.7 Hz, 1H), 3.16 (dd, J=14.0, 2.7 Hz, 1H), 2.32 (ddd, J=12.1, 6.6, 2.9 Hz, 1H), 2.09 (td, J=13.5, 3.9 Hz, 1H), 2.03-1.94 (m, 1H), 1.87-1.65 (m, 2H). MS (M+H)$^+$: 274.

Example 52: Preparation of 2-amino-6-hydroxy-2-(3-(trifluoromethyl)phenyl)cyclohexane-1-one hydrochloride (Compound 52)

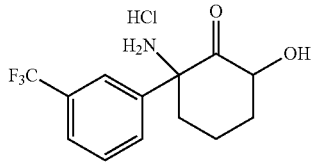 [SMILES: NC1(c2cccc(C(F)(F)F)c2)CCCC(O)C1=O ; Cl]

Using compound 16 (60 mg, 0.22 mmol) as a raw material, the method described in Example 32 was conducted accordingly to obtain 59 mg of white solid, yield: 86.8%. Purity: 97.4%. $^1$H NMR (400 MHz, CD$_3$OD) δ7.88 (d, J=7.6 Hz, 1H), 7.81 (t, J=7.7 Hz, 1H), 7.76 (d, J=8.0 Hz, 1H), 7.72 (s, 1H), 4.23 (dd, J=11.9, 6.7 Hz, 1H), 3.17 (dd, J=14.0, 2.7 Hz, 1H), 2.36-2.28 (m, 1H), 2.10 (td, J=13.6, 3.9 Hz, 1H), 2.03-1.97 (m, 1H), 1.84-1.58 (m, 2H). MS (M+H)$^+$: 274.1.

Example 53: Preparation of 3-(1-amino-3-hydroxy-2-oxocyclohexane)benzonitrile trifluoroacetate (Compound 53)

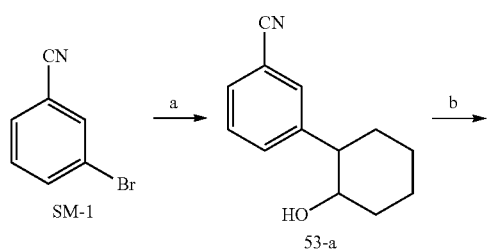

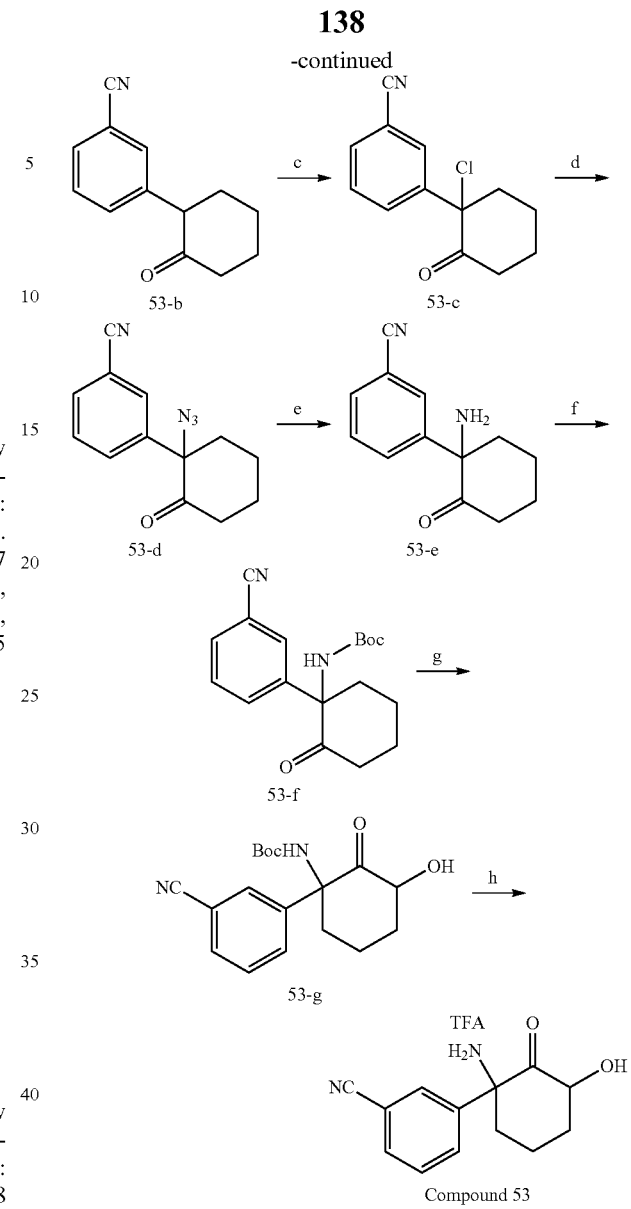

Step a: Preparation of 53-a

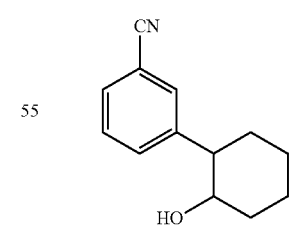

Using m-bromobenzonitrile (10 g, 54.94 mmol) and epoxycyclohexane (5.8 g, 59.09 mmol) as raw materials, the method described in step a in Example 1 was conducted accordingly to obtain 6.7 g of colorless oily liquid, yield: 60.6%. $^1$H NMR (400 MHz, CDCl$_3$) δ 7.55 (s, 1H), 7.54-7.47 (m, 2H), 7.42 (t, J=7.6 Hz, 1H), 3.66 (td, J=9.9, 4.3 Hz, 1H), 2.53-2.44 (m, 1H), 2.15-2.07 (m, 1H), 1.81 (ddd, J=15.6, 9.7, 5.3 Hz, 3H), 1.49-1.37 (m, 4H). MS(M+H)+: 202

Step b: Preparation of 53-b

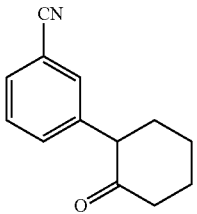 [SMILES: N#Cc1cccc(C2CCCCC2=O)c1]

Using compound 53-a (6.25 g, 31.05 mmol) as a raw material, the method described in step b in Example 1 was conducted accordingly to obtain 5.54 g of white solid, yield: 89.5%. $^1$H NMR (400 MHz, CDCl$_3$) δ 7.55 (d, J=7.7 Hz, 1H), 7.47-7.40 (m, 2H), 7.37 (d, J=8.1 Hz, 1H), 3.65 (dd, J=12.4, 5.3 Hz, 1H), 2.59-2.45 (m, 2H), 2.33-2.25 (m, 1H), 2.20 (ddd, J=12.9, 5.9, 2.8 Hz, 1H), 2.00 (ddd, J=15.4, 8.8, 2.5 Hz, 2H), 1.88-1.77 (m, 2H). MS(M+H)+: 200

Step c: Preparation of 53-c

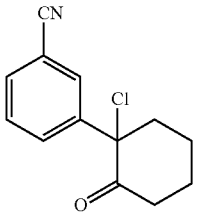 [SMILES: N#Cc1cccc(C2(Cl)CCCCC2=O)c1]

Using compound 53-b (3.0 g, 15.06 mmol) as a raw material, the method described in step c in Example 2 was conducted accordingly to obtain 1.92 g of pale yellow oily liquid, yield: 60.8%. $^1$H NMR (400 MHz, CDCl$_3$) δ 7.75 (d, J=1.5 Hz, 1H), 7.68-7.60 (m, 2H), 7.51 (d, J=7.9 Hz, 1H), 3.11 (ddd, J=14.3, 11.0, 5.7 Hz, 1H), 3.02-2.79 (m, 2H), 2.62 (dd, J=10.2, 4.0 Hz, 1H), 2.19 (ddd, J=11.9, 6.0, 2.6 Hz, 1H), 2.12-2.06 (m, 1H), 1.90-1.84 (m, 2H). MS (M+H)+: 234

Step d: Preparation of 53-d

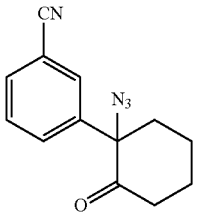 [SMILES: N#Cc1cccc(C2(N=[N+]=[N-])CCCCC2=O)c1]

Using compound 53-c (3.3 g, 14.1 mmol) as a raw material, the method described in step d in Example 2 was conducted accordingly to obtain 2.1 g of pale yellow oily liquid, yield: 61.9%. $^1$H NMR (400 MHz, CDCl$_3$) δ 7.70 (d, J=7.5 Hz, 1H), 7.64 (s, 1H), 7.58 (t, J=7.7 Hz, 1H), 7.54-7.51 (m, 1H), 2.72-2.58 (m, 2H), 2.36 (dt, J=13.9, 5.6 Hz, 1H), 2.11 (ddd, J=14.2, 10.9, 3.4 Hz, 1H), 2.01-1.91 (m, 3H), 1.68 (d, J=10.5 Hz, 1H). MS (M+Na)+: 263.

Step e: Preparation of 53-e

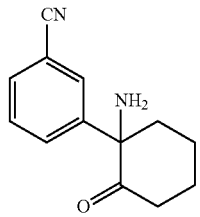 [SMILES: N#Cc1cccc(C2(N)CCCCC2=O)c1]

Using compound 53-d (800 g, 3.33 mmol) as a raw material, the method described in step e in Example 2 was conducted accordingly to obtain 636 mg of pale yellow oily liquid, which was directly cast into the reaction in next step without purification. MS (M+H)+: 215

Step f: Preparation of 53-f

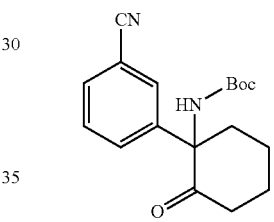

Using the crude compound 53-e (636 mg crude) as a raw material, the method described in step e in Example 1 was conducted accordingly to obtain 728 mg of off-white solid, yield: 69.5% (two steps together). $^1$H NMR (400 MHz, CDCl$_3$) δ 7.68-7.54 (m, 3H), 7.48 (t, J=7.8 Hz, 1H), 6.36 (s, 1H), 3.55 (d, J=12.2 Hz, 1H), 2.47 (d, J=12.6 Hz, 1H), 2.19 (d, J=12.4 Hz, 1H), 2.03 (d, J=5.8 Hz, 1H), 1.95-1.86 (m, 2H), 1.83-1.75 (m, 2H), 1.32 (s, 9H). MS (M+Na)+: 337

Step g: Preparation of 53-g

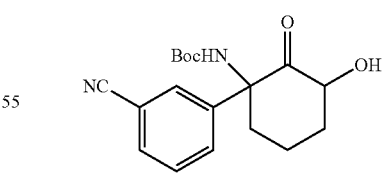

Using compound 53-f (303 mg, 0.96 mmol) as a raw material, the method described in step f in Example 1 was conducted accordingly to obtain 101 mg of white solid, yield: 31.8%. $^1$H NMR (400 MHz, CDCl$_3$) δ 7.61 (d, J=8.7 Hz, 2H), 7.51 (dd, J=17.3, 9.8 Hz, 2H), 6.41 (s, 1H), 4.01 (s, 1H), 3.70 (s, 1H), 3.33 (d, J=4.4 Hz, 1H), 2.40 (ddd, J=12.2, 6.5, 3.2 Hz, 1H), 1.92 (dt, J=14.3, 7.1 Hz, 2H), 1.65-1.58 (m, 2H), 1.30 (s, 9H). MS (M+Na)+: 353

Step h: Preparation of Compound 53

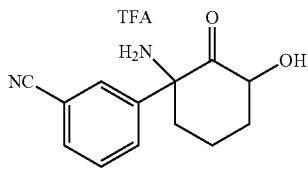 [SMILES: N#Cc1cccc(C2(N)CCCC(O)C2=O)c1]

Using compound 53-g (40 mg, 0.12 mmol) as a raw material and using trifluoroacetic acid (0.5 ml) as acid for deprotection, the method described in step g in Example 42 was conducted accordingly to obtain 23 mg of white solid, yield: 54.8%. Purity: 98.9%. $^1$H NMR (400 MHz, CD$_3$OD) δ 7.96-7.91 (m, 1H), 7.84 (s, 1H), 7.76 (dd, J=4.8, 1.2 Hz, 2H), 4.24 (dd, J=11.9, 6.7 Hz, 1H), 3.15 (dd, J=14.0, 2.6 Hz, 1H), 2.35-2.29 (m, 1H), 2.08 (td, J=13.6, 3.9 Hz, 1H), 2.03-1.95 (m, 1H), 1.84-1.65 (m, 2H). MS (M+H)$^+$: 231.

Example 54: Preparation of 2-amino-2-(3,4-dimethoxyphenyl)-6-hydroxycyclohexane-1-one hydrochloride (Compound 54)

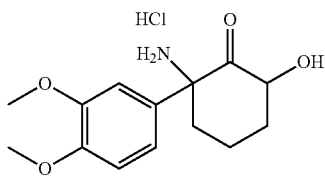 [SMILES: Cl ; COc1ccc(C2(N)CCCC(O)C2=O)cc1OC]

Using compound 17 (80 mg, 0.30 mmol) as a raw material, the method described in Example 32 was conducted accordingly to obtain 88 mg of white solid, yield: 96.7%. Purity: 99.3%. $^1$H NMR (400 MHz, CD$_3$OD) δ 7.11 (d, J=8.5 Hz, 1H), 7.04 (dd, J=8.5, 2.3 Hz, 1H), 6.87 (d, J=2.2 Hz, 1H), 4.29 (dd, J=12.4, 6.7 Hz, 1H), 3.87 (s, 3H), 3.86 (s, 3H), 3.08 (dd, J=13.6, 2.7 Hz, 1H), 2.30 (ddd, J=12.5, 6.4, 2.9 Hz, 1H), 2.06-1.93 (m, 2H), 1.92-1.80 (m, 1H), 1.68 (qd, J=12.6, 4.3 Hz, 1H). MS (M+H)$^+$: 266.

Example 55: Preparation of 2-amino-2-(3,5-dimethoxyphenyl)-6-hydroxycyclohexane-1-one hydrochloride (Compound 55)

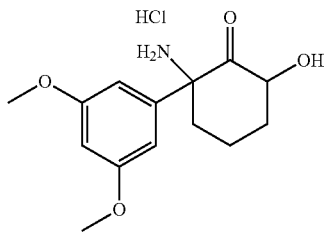 [SMILES: Cl ; COc1cc(OC)cc(C2(N)CCCC(O)C2=O)c1]

Using compound 18 (65 mg, 0.24 mmol) as a raw material, the method described in Example 32 was conducted accordingly to obtain 65 mg of white solid, yield: 87.8%. Purity: 96.5%. $^1$H NMR (400 MHz, MeOD) δ 6.64 (d, J=1.9 Hz, 1H), 6.53 (d, J=2.0 Hz, 2H), 4.28 (dd, J=12.4, 6.7 Hz, 1H), 3.86-3.77 (m, 6H), 3.04 (dd, J=13.6, 2.6 Hz, 1H), 2.30 (ddd, J=12.5, 6.4, 3.0 Hz, 1H), 1.99 (ddd, J=14.1, 11.4, 4.7 Hz, 2H), 1.88 (dt, J=27.8, 8.6 Hz, 1H), 1.66 (ddd, J=25.2, 12.6, 4.2 Hz, 1H). MS(M+H)$^+$: 266

Example 56: Preparation of 2-amino-2-(4-chloro-2-fluorophenyl)-6-hydroxycyclohexane-1-one hydrochloride (Compound 56)

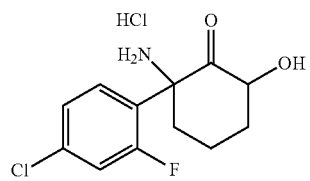 [SMILES: Cl ; NC1(c2ccc(Cl)cc2F)CCCC(O)C1=O]

Using compound 19 (100 mg, 0.39 mmol) as a raw material, the method described in Example 32 was conducted accordingly to obtain 110 mg of white solid, yield: 96.5%. Purity: 99.4%. $^1$H NMR (400 MHz, CD$_3$OD) δ 7.76 (t, J=8.5 Hz, 1H), 7.49 (dd, J=8.5, 2.0 Hz, 1H), 7.45 (dd, J=11.3, 2.1 Hz, 1H), 4.34 (dd, J=11.1, 6.9 Hz, 1H), 3.13 (dd, J=13.7, 2.6 Hz, 1H), 2.37-2.28 (m, 1H), 1.96 (ddd, J=14.9, 10.1, 3.3 Hz, 2H), 1.68 (ddd, J=15.8, 13.0, 3.4 Hz, 2H). MS (M+H)$^+$: 258.

Example 57: Preparation of 2-amino-2-(5-chloro-2-fluorophenyl)-6-hydroxycyclohexane-1-one hydrochloride (Compound 57)

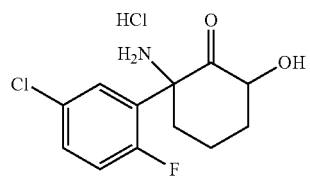

Using compound 20 (100 mg, 0.39 mmol) as a raw material, the method described in Example 32 was conducted accordingly to obtain 102 mg of white solid, yield: 89.5%. Purity: 98.5%. $^1$H NMR (400 MHz, CD$_3$OD) δ 7.76 (dd, J=6.5, 2.5 Hz, 1H), 7.64 (ddd, J=8.8, 4.3, 2.6 Hz, 1H), 7.33 (dd, J=10.9, 8.9 Hz, 1H), 4.34 (dd, J=11.4, 6.7 Hz, 1H), 3.11 (dd, J=14.0, 2.6 Hz, 1H), 2.33 (ddd, J=12.0, 6.8, 2.9 Hz, 1H), 1.98 (ddd, J=27.5, 12.2, 4.7 Hz, 2H), 1.78-1.59 (m, 2H). MS (M+H)$^+$: 258.

Example 58: Preparation of 2-amino-2-(2-fluoro-5-(trifluoromethoxy)phenyl)-6-hydroxycyclohexane-1-one hydrochloride (Compound 58)

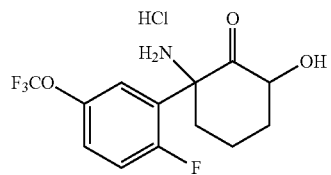 [SMILES: Cl ; NC1(c2cc(OC(F)(F)F)ccc2F)CCCC(O)C1=O]

Using compound 21 (68 mg, 0.22 mmol) as a raw material, the method described in Example 32 was conducted accordingly to obtain 65 mg of white solid, yield: 85.5%. Purity: 99.6%. $^1$H NMR (400 MHz, CD$_3$OD) δ 7.69 (dd, J=6.0, 2.8 Hz, 1H), 7.61 (dd, J=8.6, 3.5 Hz, 1H), 7.45 (dd, J=10.5, 9.2 Hz, 1H), 4.33 (dt, J=15.1, 7.6 Hz, 1H), 3.10 (dd, J=14.0, 2.8 Hz, 1H), 2.39-2.29 (m, 1H), 2.06-1.90 (m, 2H), 1.79-1.59 (m, 2H). MS (M+H)$^+$: 308.

Example 59: Preparation of 2-amino-2-(2-fluoro-3-(trifluoromethoxy)phenyl)-6-hydroxycyclohexane-1-one hydrochloride (Compound 59)

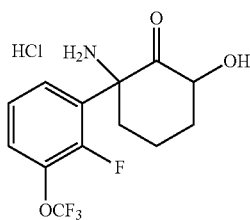 [SMILES: NC1(c2cccc(OC(F)(F)F)c2F)CCCC(O)C1=O ; Cl]

Compound 22 (30 mg, 0.098 mmol) was dissolved in DCM (3 mL), 4M HCl 1,4-dioxane solution (0.3 mL) was added, and the mixture was stirred at room temperature for 1.5 hours. A large amount of white solid was precipitated out. The solvent was rotary evaporated to dryness, 10 ml ethyl acetate was added. The mixture was beat, filtered. The filter cake was with ethyl acetate, and dried to obtain 27 mg of white solid powder, yield:

80.4%, purity: 96.2%. Melting point: 188° C.-191.4° C. $^1$H NMR (400 MHz, CD$_3$OD) δ 7.80-7.74 (m, 1H), 7.70 (t, J=7.9 Hz, 1H), 7.54 (td, J=8.2, 1.5 Hz, 1H), 4.33 (dd, J=11.2, 6.5 Hz, 1H), 3.16 (dd, J=13.8, 2.5 Hz, 1H), 2.39-2.28 (m, 1H), 2.06-1.91 (m, 2H), 1.78-1.59 (m, 2H). MS (M+H)$^+$: 308

Example 60: Preparation of 2-amino-2-(2-fluoro-3-(trifluoromethoxy)phenyl)-6-hydroxycyclohexane-1-one methanesulfonate (Compound 60)

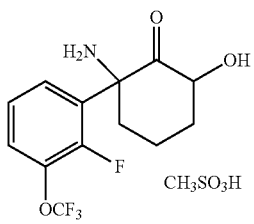

Compound 22 (53 mg, 0.17 mmol) was dissolved in DCM (3 mL), and a solution of methanesulfonic acid (17 mg, 0.17 mmol) in DCM was added dropwise under stirring. After adding, the mixture was stirred at room temperature for 1.5 hours, and a large amount of white solid were precipitated, and directly filtered. The filter cake was washed with DCM and dried to obtain 67 mg of white solid powder, yield: 96.3%, purity: 99.4%. Melting point: 172.1° C.-176.9° C. $^1$H NMR (400 MHz, CD$_3$OD) δ 7.76 (t, J=7.4 Hz, 1H), 7.70 (t, J=7.8 Hz, 1H), 7.54 (td, J=8.2, 1.3 Hz, 1H), 4.33 (dd, J=11.1, 6.5 Hz, 1H), 3.15 (dd, J=13.7, 2.3 Hz, 1H), 2.69 (s, 3H), 2.38-2.28 (m, 1H), 2.05-1.89 (m, 2H), 1.79-1.59 (m, 2H). MS(M+H)$^+$: 308

Example 61: Preparation of 2-amino-2-(2-fluoro-3-(trifluoromethoxy)phenyl)-6-hydroxycyclohexane-1-one sulfate (Compound 61)

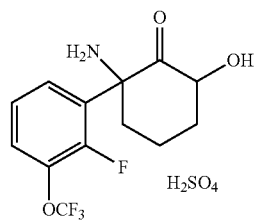

The compound 22 (53 mg, 0.17 mmol) was dissolved in DCM (3 mL), and sulfuric acid (17 mg, 0.17 mmol) in DCM was added dropwise under stirring. After adding, the mixture was stirred at room temperature for 1.5 hours. The system was a colorless and transparent liquid, the low boiling solvent was evaporated off under reduced pressure, and ethyl acetate (7 ml) was added to the residue. The mixture was beat, and a large amount of white solid was precipitated, filtered, washed with ethyl acetate, and dried to obtain 47 mg of white solid powder, yield: 67.2%, purity: 99.0%. Melting point: 172.1° C.-179° C. $^1$H NMR (400 MHz, CD$_3$OD) δ 7.80 (dd, J=10.8, 4.0 Hz, 1H), 7.68 (t, J=7.8 Hz, 1H), 7.53 (td, J=8.2, 1.3 Hz, 1H), 4.32 (dd, J=10.5, 6.9 Hz, 1H), 3.19 (dd, J=14.0, 2.6 Hz, 1H), 2.36-2.28 (m, 1H), 2.06-1.89 (m, 2H), 1.77-1.60 (m, 2H). MS(M+H)$^+$: 308

Example 62: Preparation of 2-amino-2-(2-fluoro-3-(trifluoromethoxy)phenyl)-6-hydroxycyclohexane-1-one oxalate (Compound 62)

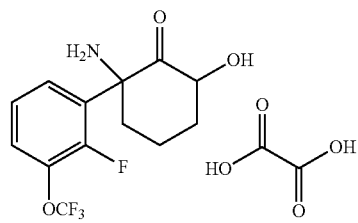

The compound 22 (43 mg, 0.14 mmol) was dissolved in DCM (4 mL), and the methanol solution of oxalic acid dihydrate (18 mg, 0.14 mmol) was added dropwise under stirring. After adding, the mixture was stirred at room temperature for 1.5 hours. The system was a colorless and transparent liquid, the low boiling solvent was evaporated off under reduced pressure, and ethyl acetate (7 ml) was added to the residue. The mixture was beat, and a large amount of white solid was precipitated, filtered, washed with ethyl acetate, and dried to obtain 53 mg of white solid powder, yield: 95.3%, purity: 91.5%. $^1$H NMR (400 MHz, CD$_3$OD) δ 7.76 (t, J=7.1 Hz, 1H), 7.68 (t, J=7.8 Hz, 1H), 7.52 (t, J=7.9 Hz, 1H), 4.32 (dd, J=11.1, 6.7 Hz, 1H), 3.16 (d, J=14.2 Hz, 1H), 2.37-2.29 (m, 1H), 2.04-1.90 (m, 2H), 1.67 (dt, J=13.0, 11.9 Hz, 2H). MS(M+H)$^+$: 308

Example 63: Preparation of 2-amino-2-(2-fluoro-3-(trifluoromethoxy)phenyl)-6-hydroxycyclohexane-1-one benzoate (Compound 63)

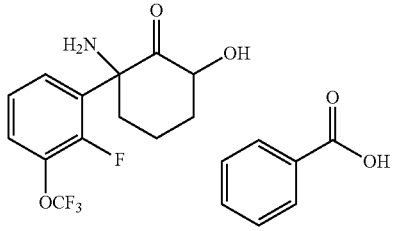

The compound 22 (50 mg, 0.16 mmol) was dissolved in DCM (4 mL), and benzoic acid (20 mg, 0.16 mmol) in DCM was added dropwise under stirring. After adding, the mixture was stirred at room temperature for 1.5 hours. The system was a colorless and transparent liquid, the low boiling solvent was evaporated off under reduced pressure, and ethyl acetate (7 ml) was added to the residue. The mixture was beat, and a large amount of white solid was precipitated, filtered, washed with ethyl acetate, and dried to obtain 51 mg of white solid powder, yield: 95.3%, purity: 99.2%. $^1$H NMR (400 MHz, CD$_3$OD) δ 8.01-7.96 (m, 2H), 7.64 (dd, J=10.7, 4.0 Hz, 1H), 7.52 (q, J=7.8 Hz, 2H), 7.45-7.38 (m, 3H), 4.21 (dd, J=11.5, 6.6 Hz, 1H), 3.01-2.92 (m, 1H), 2.31-2.22 (m, 1H), 1.84-1.55 (m, 4H). MS (M+H)$^+$: 308

Example 64: Preparation of (2R,6R)-2-amino-2-(2-fluoro-3-(trifluoromethoxy)phenyl)-6-hydroxycyclohexane-1-one hydrochloride (Compound 64)

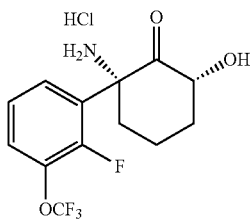 [SMILES: N[C@@]1(c2cccc(OC(F)(F)F)c2F)CCC[C@@H](O)C1=O ; Cl]

Using compound 23 (220 mg, 0.72 mmol) as a raw material, the method described in Example 32 was conducted accordingly to obtain 228 mg of white solid, yield: 92.7%, purity 99.9%, ee>99%, [α]$_D^{20}$: −119° (c 0.15, H$_2$O), melting point: 204.1° C.-205.2° C. $^1$H NMR (400 MHz, CD$_3$OD) δ 7.76 (dd, J=10.8, 4.0 Hz, 1H), 7.70 (t, J=7.8 Hz, 1H), 7.53 (td, J=8.2, 1.4 Hz, 1H), 4.33 (dd, J=11.2, 6.6 Hz, 1H), 3.15 (dd, J=13.7, 2.4 Hz, 1H), 2.33 (dd, J=9.1, 6.7 Hz, 1H), 2.03-1.91 (m, 2H), 1.69 (ddd, J=19.7, 15.2, 8.6 Hz, 2H). MS (M+H)$^+$: 308

Example 65: Preparation of (2S,6S)-2-amino-2-(2-fluoro-3-(trifluoromethoxy)phenyl)-6-hydroxycyclohexane-1-one hydrochloride (Compound 65)

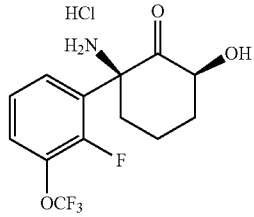 [SMILES: N[C@]1(c2cccc(OC(F)(F)F)c2F)CCC[C@H](O)C1=O ; Cl]

Using compound 23 (220 mg, 0.72 mmol) as a raw material, the method described in Example 32 was conducted accordingly to obtain 198 mg of white solid, yield: 80.5%, purity 97.9%, ee>99%, [α]$_D^{20}$: +126° (c 0.15, H$_2$O), melting point: 199.9° C.-202.6° C. $^1$H NMR (400 MHz, CD$_3$OD) δ 7.76 (dd, J=10.8, 4.0 Hz, 1H), 7.70 (t, J=7.8 Hz, 1H), 7.54 (td, J=8.2, 1.4 Hz, 1H), 4.33 (dd, J=11.2, 6.6 Hz, 1H), 3.15 (dd, J=13.8, 2.5 Hz, 1H), 2.38-2.28 (m, 1H), 2.04-1.90 (m, 2H), 1.67 (ddd, J=21.5, 16.5, 11.3 Hz, 2H). MS (M+H)$^+$: 308.

Example 66: Preparation of 2-amino-2-(3-fluoro-4-(trifluoromethyl)phenyl)-6-hydroxycyclohexane-1-one hydrochloride (Compound 66)

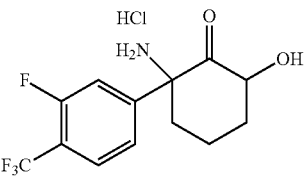

Using compound 25 (78 mg, 0.27 mmol) as a raw material, the method described in Example 32 was conducted accordingly to obtain 80 mg of white solid, yield: 90.9%. Purity: 96.6%. $^1$H NMR (400 MHz, CD$_3$OD) δ 7.93 (t, J=7.9 Hz, 1H), 7.54 (d, J=11.4 Hz, 1H), 7.45 (d, J=8.2 Hz, 1H), 4.26 (dd, J=12.0, 6.7 Hz, 1H), 3.12 (dd, J=14.0, 2.6 Hz, 1H), 2.37-2.29 (m, 1H), 2.09 (td, J=13.6, 3.9 Hz, 1H), 1.99 (d, J=15.4 Hz, 1H), 1.87-1.64 (m, 2H). MS (M+H)$^+$: 292.

Example 67: Preparation of 2-amino-2-(2-fluoro-3-(trifluoromethyl)phenyl)-6-hydroxycyclohexane-1-one hydrochloride (Compound 67)

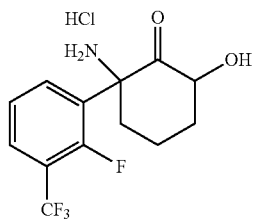 [SMILES: NC1(c2cccc(C(F)(F)F)c2F)CCCC(O)C1=O ; Cl]

Using compound 26 (80 mg, 0.27 mmol) as a raw material, the method described in Example 32 was conducted accordingly to obtain 78 mg of white solid, yield: 86.7%. Purity: 99.1%. ¹H NMR (400 MHz, CD₃OD) δ 8.07 (t, J=7.3 Hz, 1H), 7.96 (t, J=7.1 Hz, 1H), 7.63 (t, J=8.0 Hz, 1H), 4.33 (dt, J=14.0, 7.1 Hz, 1H), 3.18 (dd, J=13.9, 2.6 Hz, 1H), 2.38-2.29 (m, 1H), 2.07-1.91 (m, 2H), 1.80-1.59 (m, 2H). MS (M+H)⁺: 292.

Example 68: Preparation of 2-amino-2-(3-fluoro-2-(trifluoromethyl)phenyl)-6-hydroxycyclohexane-1-one hydrochloride (Compound 68)

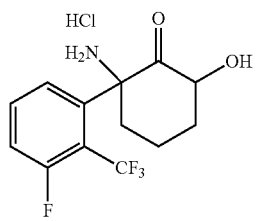 [SMILES: NC1(c2cccc(F)c2C(F)(F)F)CCCC(O)C1=O ; Cl]

Using compound 27 (78 mg, 0.27 mmol) as a raw material, the method described in Example 32 was conducted accordingly to obtain 75 mg of white solid, yield: 85.2%. Purity: 96.6%. ¹H NMR (400 MHz, CD₃OD) δ 7.98-7.85 (m, 2H), 7.67-7.59 (m, 1H), 4.29 (dd, J=10.8, 6.9 Hz, 1H), 3.34 (s, 1H), 2.29 (dd, J=12.1, 5.3 Hz, 1H), 2.04-1.96 (m, 1H), 1.88 (dd, J=6.6, 3.6 Hz, 1H), 1.65 (dd, J=14.1, 6.8 Hz, 2H). MS (M+H)⁺: 292.

Example 69: Preparation of 2-amino-2-(3-chloro-5-(trifluoromethoxy)phenyl)-6-hydroxycyclohexane-1-one hydrochloride (Compound 69)

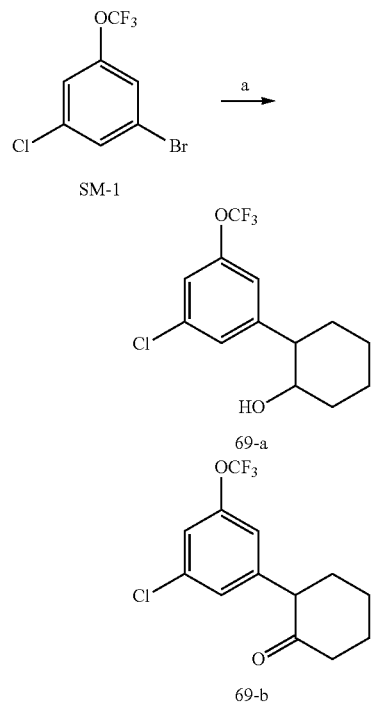

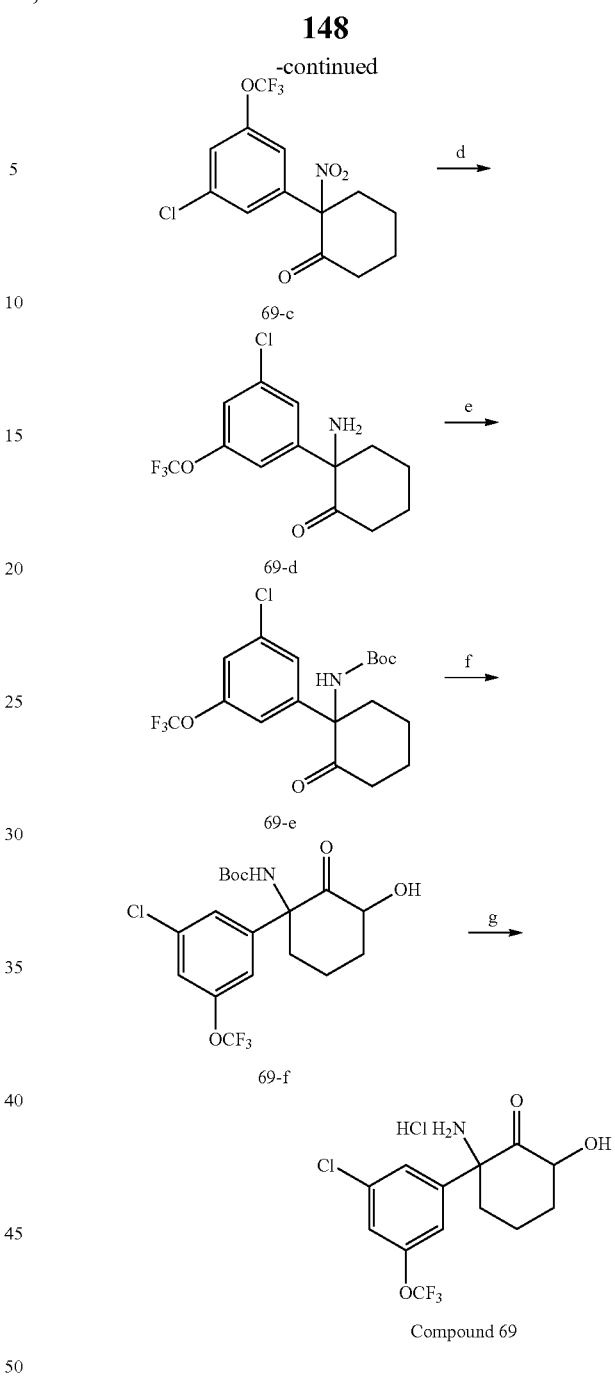

Step a: Preparation of 69-a

Using 3-chloro-5-trifluoromethoxybromobenzene (5 g, 18.15 mmoL) and epoxycyclohexane (2.1 g, 21.4 mmol) as raw materials, the method described in step a in Example 1 was conducted accordingly to obtain 4.2 g of yellow oily liquid, yield: 78.5%. $^1$H NMR (400 MHz, CDCl$_3$) δ 7.20 (d, J=4.5 Hz, 1H), 7.08 (d, J=20.0 Hz, 1H), 7.01 (s, 1H), 3.70-3.58 (m, 1H), 2.57-2.37 (m, 1H), 2.17-2.05 (m, 1H), 1.86 (d, J=9.4 Hz, 2H), 1.78 (d, J=12.4 Hz, 1H), 1.48-1.35 (m, 4H). MS (M+H)$^+$: 295.

Step b: Preparation of 69-b

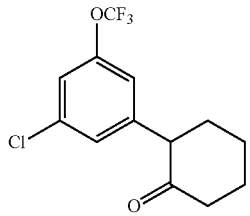 [SMILES: O=C1CCCCC1c1cc(Cl)cc(OC(F)(F)F)c1]

Using compound 69-a (1.05 g, 3.56 mmol) as a raw material, the method described in step b in Example 1 was conducted accordingly to obtain 884 mg of yellow oily liquid, yield: 84.8%. $^1$H NMR (400 MHz, CDCl$_3$) δ 7.13 (s, 1H), 7.08 (s, 1H), 6.90 (s, 1H), 3.60 (dd, J=12.3, 5.4 Hz, 1H), 2.55 (dd, J=16.8, 3.0 Hz, 1H), 2.51-2.41 (m, 1H), 2.33-2.25 (m, 1H), 2.23-2.14 (m, 1H), 2.05-1.99 (m, 1H), 1.98-1.89 (m, 1H), 1.87-1.77 (m, 2H). MS (M+H)$^+$: 293

Step c: Preparation of 69-c

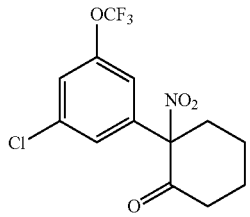 [SMILES: O=C1CCCCC1(c1cc(Cl)cc(OC(F)(F)F)c1)[N+](=O)[O-]]

Using compound 69-b (1 g, 3.42 mmol) as a raw material, the method described in step c in Example 1 was conducted accordingly to obtain 500 mg of pale yellow oil, yield: 43.3%. MS (M+Na)$^+$: 360.

Step d: Preparation of 69-d

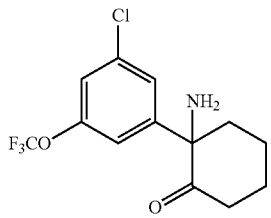 [SMILES: NC1(c2cc(Cl)cc(OC(F)(F)F)c2)CCCCC1=O]

Using the compound 69-c (500 mg, 1.48 mmol) as a raw material, the method described in step d in Example 1 was conducted accordingly to obtain 275 mg of crude yellow oily liquid, which was directly cast into the reaction in next step without purification. MS (M+H)$^+$: 308

Step e: Preparation of 69-e

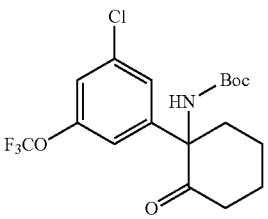 [SMILES: CC(C)(C)OC(=O)NC1(c2cc(Cl)cc(OC(F)(F)F)c2)CCCCC1=O]

Using crude compound 69-d (275 mg crude product) as a raw material, the method described in step e in Example 1 was conducted accordingly to obtain 220 mg of colorless oily liquid, yield: 36.4% (two steps together). $^1$H NMR (400 MHz, CDCl$_3$) δ 7.27 (s, 1H), 7.18 (s, 1H), 7.11 (s, 1H), 6.28 (s, 1H), 3.44 (s, 1H), 2.49 (d, J=12.7 Hz, 1H), 2.31-2.21 (m, 1H), 2.02 (s, 1H), 1.92 (t, J=11.5 Hz, 2H), 1.80 (d, J=9.0 Hz, 2H), 1.32 (d, J=11.3 Hz, 9H). MS (M+Na)$^+$: 430

Step f: Preparation of 69-f

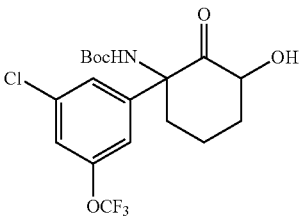 [SMILES: CC(C)(C)OC(=O)NC1(c2cc(Cl)cc(OC(F)(F)F)c2)CCCC(O)C1=O]

Using the compound 69-e (220 mg, 0.54 mmol) as a raw material, the method described in step f in Example 1 was conducted accordingly to obtain 36 mg of colorless oil, yield: 15.7%. $^1$H NMR (400 MHz, CDCl$_3$) δ 7.19 (dd, J=16.5, 8.2 Hz, 2H), 7.09 (s, 1H), 6.36 (s, 1H), 4.09-4.00 (m, 1H), 3.62 (s, 1H), 3.33 (s, 1H), 2.40 (ddd, J=12.3, 6.5, 3.0 Hz, 1H), 1.96-1.89 (m, 2H), 1.63-1.59 (m, 2H), 1.32 (s, 9H). MS (M+Na)$^+$: 446

Step g: Preparation of Compound 69

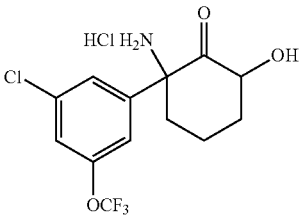

Using compound 69-f (36 mg, 0.085 mmol) as a raw material, the method described in step g in Example 42 to obtain 10 mg of white solid, yield: 33.3%. Purity: 94.4%. $^1$H NMR (400 MHz, CD$_3$OD) δ 7.60 (d, J=11.0 Hz, 1H), 7.50 (s, 1H), 7.34 (s, 1H), 4.25 (dd, J=11.8, 6.7 Hz, 1H), 3.08 (dt, J=11.0, 5.5 Hz, 1H), 2.37-2.29 (m, 1H), 2.10-1.97 (m, 2H), 1.82-1.66 (m, 2H). MS (M+H)$^+$: 324.

Example 70: Preparation of 2-amino-2-(4-chloro-3-(trifluoromethoxy)phenyl)-6-hydroxycyclohexane-1-one hydrochloride (Compound 70)

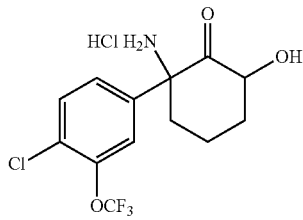

Using compound 28 (100 mg, 0.32 mmol) as a raw material, the method described in Example 32 was conducted accordingly to obtain 102 mg of white solid, yield: 91.1%. Purity: 95.9%. $^1$H NMR (400 MHz, CD$_3$OD) δ 7.82 (d, J=8.4 Hz, 1H), 7.50 (s, 1H), 7.47 (dd, J=8.4, 2.3 Hz, 1H), 4.25 (dd, J=11.9, 6.8 Hz, 1H), 3.08 (dd, J=14.1, 2.6 Hz, 1H), 2.37-2.28 (m, 1H), 2.09-1.96 (m, 2H), 1.81-1.67 (m, 2H). MS (M+H)$^+$: 324.

Example 71: Preparation of 2-amino-6-hydroxy-2-(2,3,6-trifluorophenyl)cyclohexane-1-one hydrochloride (Compound 71)

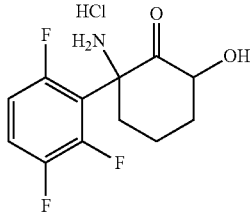 [SMILES: Cl ; NC1(c2c(F)ccc(F)c2F)CCCC(O)C1=O]

Using compound 29 (84 mg, 0.32 mmol) as a raw material, the method described in Example 32 was conducted accordingly to obtain 88 mg of white solid, yield: 91.7%. Purity: 97.7%. $^1$H NMR (400 MHz, CD$_3$OD) δ 7.63 (qd, J=9.3, 4.9 Hz, 1H), 7.28-7.20 (m, 1H), 4.46 (dd, J=11.5, 7.0 Hz, 1H), 3.39-3.32 (m, 1H), 2.37 (ddd, J=12.0, 6.9, 2.7 Hz, 1H), 2.04-1.95 (m, 1H), 1.90-1.78 (m, 1H), 1.77-1.58 (m, 2H). MS (M+H)$^+$: 260.1.

Example 72: Preparation of 2-amino-6-hydroxy-2-(2,3,5-trifluorophenyl)cyclohexane-1-one hydrochloride (Compound 72)

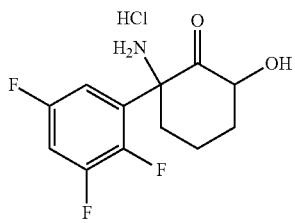 [SMILES: Cl ; NC1(c2cc(F)cc(F)c2F)CCCC(O)C1=O]

Using compound 30 (210 mg, 0.81 mmol) as a raw material, the method described in Example 32 was conducted accordingly to obtain 223 mg of white solid, yield: 92.9%. Purity: 99.1%. $^1$H NMR (400 MHz, CD$_3$OD) δ 7.62 (qd, J=9.3, 4.9 Hz, 1H), 7.28-7.19 (m, 1H), 4.45 (dd, J=11.5, 7.0 Hz, 1H), 3.38-3.31 (m, 1H), 2.36 (ddd, J=12.1, 6.9, 2.7 Hz, 1H), 2.00 (dd, J=9.7, 6.9 Hz, 1H), 1.88-1.58 (m, 3H). MS (M+H)$^+$: 260.0

Example 73: Preparation of 2-amino-6-hydroxy-2-(2,4,6-trifluorophenyl)cyclohexane-1-one hydrochloride (Compound 73)

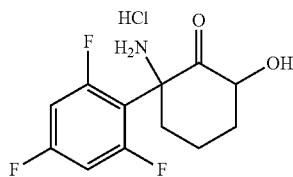 [SMILES: Cl ; NC1(c2c(F)cc(F)cc2F)CCCC(O)C1=O]

Using compound 31 (70 mg, 0.27 mmol) as a raw material, the method described in Example 32 was conducted accordingly to obtain 70 mg of white solid, yield: 87.5%. Purity: 98.5%. $^1$H NMR (400 MHz, CD$_3$OD) δ 7.20-7.12 (m, 2H), 4.45 (dd, J=11.3, 7.0 Hz, 1H), 2.40-2.32 (m, 1H), 2.01-1.94 (m, 1H), 1.79 (dd, J=26.0, 13.3 Hz, 2H), 1.72-1.57 (m, 2H). MS (M+H)$^+$: 260.

Example 74: Preparation of 3-amino-3-(2-chlorophenyl)-5-hydroxytetrahydro-4H-pyran-4-one hydrochloride (Compound 74)

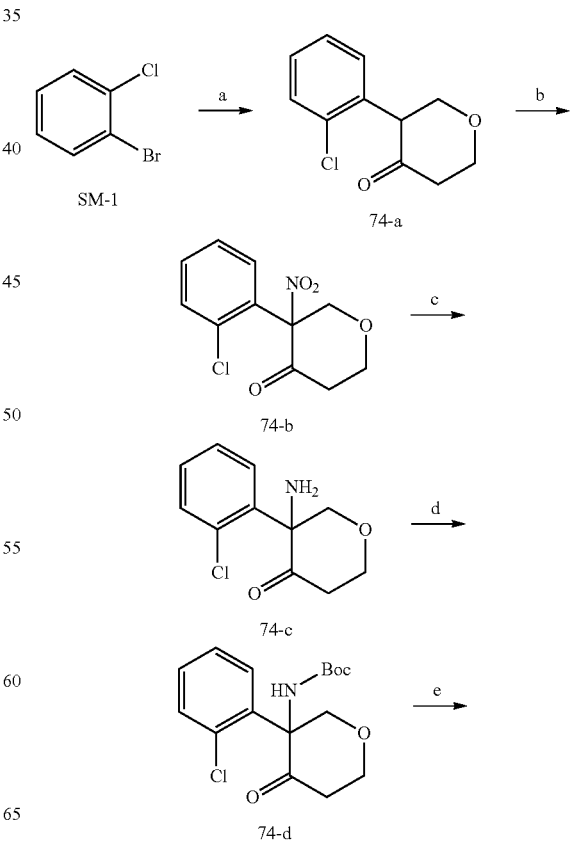

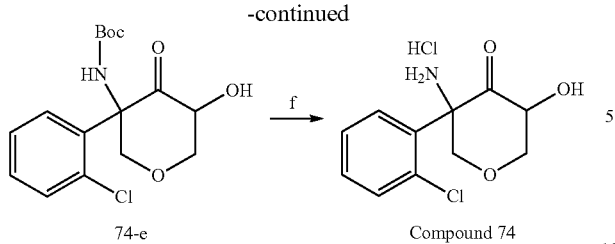

74-e → Compound 74

Step a: Preparation of 74-a

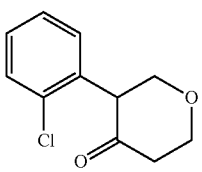 [SMILES: O=C1CCOCC1c1ccccc1Cl]

Under Ar protection, O-chlorobromobenzene (5 g, 26.12 mmol) and tetrahydro-4H-pyran-4-one (2.88 g, 28.76 mmol) were dissolved in toluene (150 mL), and Cs$_2$CO$_3$ (21.3 g, 65.38 mmol) was added. Pd$_2$(dba)$_3$ (719 mg, 0.78 mmol) and Xantphos (728 mg, 1.26 mmol) were added separately, and the mixture was stirred at 80° C. overnight. After the reaction was completed, it was filtered and the filter cake was washed with ethyl acetate. The obtained filtrate was evaporated under reduced pressure to remove the low boiling solvent, and the obtained crude product was subjected to column chromatography (PE:EA=20:1) to obtain 945 mg of yellow oily liquid, yield: 17.2%. $^1$H NMR (400 MHz, CDCl$_3$) δ 7.43-7.38 (m, 1H), 7.26 (s, 3H), 4.42-4.25 (m, 3H), 3.96-3.81 (m, 2H), 2.83 (ddd, J=14.8, 12.2, 7.1 Hz, 1H), 2.60-2.51 (m, 1H). MS (M+H)$^+$: 211.

Step b: Preparation of 74-b

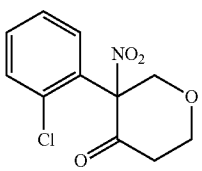

Using compound 74-a (569 mg, 2.7 mmol) as a raw material, the method described in step c in Example 1 was conducted accordingly to obtain 285 mg of pale yellow oil, yield: 41.3%. $^1$H NMR (400 MHz, CDCl$_3$) δ 7.48 (dd, J=7.8, 1.5 Hz, 1H), 7.42-7.33 (m, 2H), 7.11 (dd, J=7.7, 1.7 Hz, 1H), 4.86 (s, 2H), 4.22 (ddd, J=11.0, 6.5, 4.2 Hz, 1H), 4.09 (ddd, J=11.5, 9.4, 4.3 Hz, 1H), 3.01 (ddd, J=15.9, 9.4, 6.6 Hz, 1H), 2.85-2.77 (m, 1H). MS (M+Na)+: 278.

Step c: Preparation of 74-c

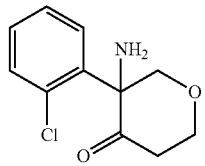 [SMILES: NC1(c2ccccc2Cl)COCCC1=O]

Using compound 74-b (285 mg, 1.11 mmol) as a raw material, the method described in step d in Example 1 was conducted accordingly to obtain 249 mg of crude light yellow oily liquid, which was directly cast into the reaction in next step without purification. MS (M+Na)$^+$: 248.

Step d: Preparation of 74-d

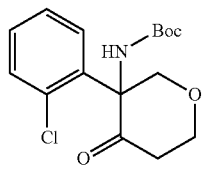 [SMILES: CC(C)(C)OC(=O)NC1(c2ccccc2Cl)COCCC1=O]

Using the crude compound 74-c (249 mg) as a raw material, the method described in step e in Example 1 was conducted accordingly to obtain 233 mg of white solid, yield: 64.2% (two steps together). $^1$H NMR (400 MHz, CDCl$_3$) δ 8.01 (d, J=7.1 Hz, 1H), 7.39 (dd, J=9.8, 5.8 Hz, 1H), 7.32 (t, J=6.9 Hz, 1H), 7.30-7.26 (m, 1H), 6.53 (s, 1H), 5.57 (d, J=11.1 Hz, 1H), 4.33-4.25 (m, 1H), 3.77-3.68 (m, 1H), 3.42 (d, J=12.1 Hz, 1H), 2.66 (td, J=12.2, 7.1 Hz, 1H), 2.41-2.31 (m, 1H), 1.30 (d, J=12.8 Hz, 9H). MS (M+Na)$^+$: 348.

Step e: Preparation of 74-e

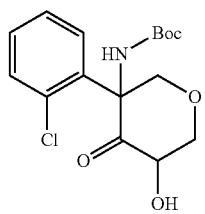 [SMILES: CC(C)(C)OC(=O)NC1(c2ccccc2Cl)COCC(O)C1=O]

Using compound 74-d (301 mg, 0.92 mmol) as a raw material, the method described in step f in Example 1 was conducted accordingly to obtain 125 mg of white solid, yield: 39.6%. $^1$H NMR (400 MHz, CDCl$_3$) δ 7.93 (s, 1H), 7.42-7.28 (m, 3H), 6.50 (s, 1H), 5.61 (s, 1H), 4.41-4.34 (m, 1H), 4.27-4.19 (m, 1H), 3.39 (d, J=12.2 Hz, 1H), 3.32 (d, J=6.0 Hz, 1H), 3.24 (t, J=10.2 Hz, 1H), 1.25 (s, 9H). MS (M+Na)$^+$: 364.

Step f: Preparation of Compound 74

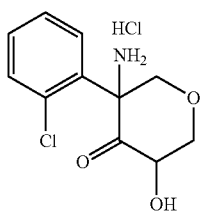

Using compound 74-e (50 mg, 0.15 mmol) as a raw material, the method described in step g in Example 42 was conducted accordingly to obtain 31 mg of white solid, yield: 75.6%. Purity: 98.5%. $^1$H NMR (400 MHz, CD$_3$OD) δ 7.96-7.91 (m, 1H), 7.61-7.54 (m, 3H), 5.16 (d, J=12.1 Hz, 1H), 4.40-4.27 (m, 2H), 3.67 (d, J=12.2 Hz, 1H), 3.41 (t, J=9.4 Hz, 1H). MS (M+H)$^+$: 242.

Example 75: Preparation of 2-amino-2-(2-chlorophenyl)-5-hydroxycyclopentane-1-one hydrochloride (Compound 75)

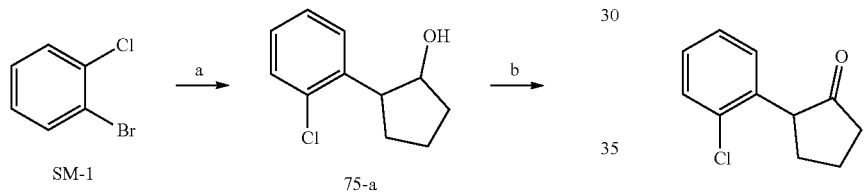

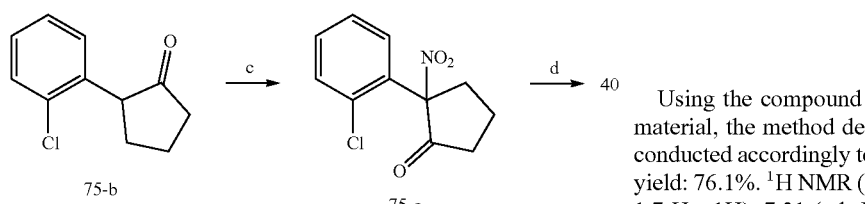

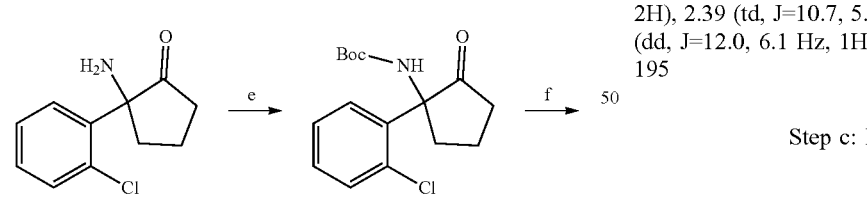

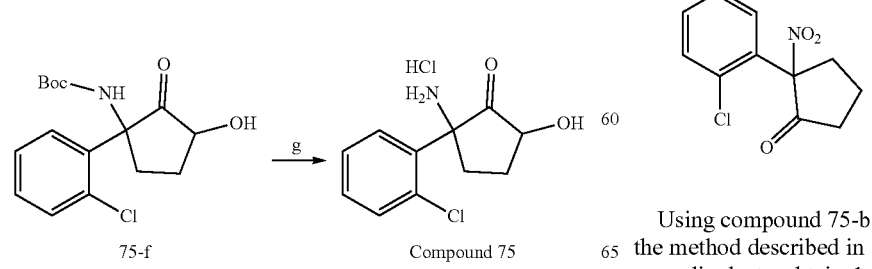

Step a: Preparation of 75-a

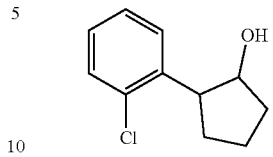

Using o-chlorobromobenzene (14.9 g, 77.8 mmoL) and epoxycyclopentane (7.3 g, 86.8 mmol) as raw materials, the method described in step a in Example 1 was conducted accordingly to obtain 13.6 g of colorless oily liquid, yield: 88.9%. $^1$H NMR (400 MHz, CDCl$_3$) δ 7.38 (dd, J=7.9, 0.7 Hz, 1H), 7.29-7.22 (m, 2H), 7.15 (ddd, J=7.9, 6.8, 2.3 Hz, 1H), 4.33 (q, J=6.4 Hz, 1H), 3.51-3.43 (m, 1H), 2.32-2.21 (m, 1H), 2.09 (ddt, J=12.8, 8.1, 6.3 Hz, 1H), 1.93 (ddd, J=16.3, 8.3, 3.6 Hz, 1H), 1.86-1.64 (m, 3H). MS (M+H)$^+$: 197.

Step b: Preparation of 75-b

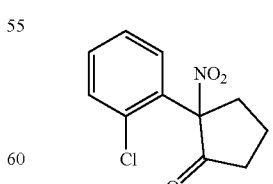

Using the compound 75-a (13.5 g, 68.6 mmol) as a raw material, the method described in step b in Example 1 was conducted accordingly to obtain 10.2 g of yellow oily liquid, yield: 76.1%. $^1$H NMR (400 MHz, CDCl$_3$) δ 7.37 (dd, J=7.5, 1.7 Hz, 1H), 7.21 (pd, J=7.3, 1.7 Hz, 2H), 7.10 (dd, J=7.2, 2.1 Hz, 1H), 3.72 (dd, J=11.7, 8.8 Hz, 1H), 2.55-2.47 (m, 2H), 2.39 (td, J=10.7, 5.5 Hz, 1H), 2.23-2.15 (m, 1H), 2.09 (dd, J=12.0, 6.1 Hz, 1H), 2.01-1.93 (m, 1H). MS (M+H)$^+$: 195

Step c: Preparation of 75-c

Using compound 75-b (5 g, 25.7 mmol) as a raw material, the method described in step c in Example 1 was conducted accordingly to obtain 1.5 g of pale yellow oily substance, yield: 24.4%. MS (M+Na)$^+$: 262.

Step d: Preparation of 75-d

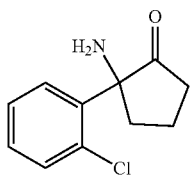 [SMILES: NC1(c2ccccc2Cl)CCCC1=O]

Using compound 75-c (1.5 g, 6.26 mmol) as a raw material, the method described in step d in Example 1 was conducted accordingly to obtain 525 mg of yellow oily liquid, yield: 40.1%. $^1$H NMR (400 MHz, CDCl$_3$) δ 7.79 (dd, J=7.7, 1.5 Hz, 1H), 7.28 (dddd, J=20.1, 15.0, 8.1, 1.3 Hz, 3H), 2.77-2.56 (m, 3H), 2.19-2.09 (m, 2H), 1.94-1.86 (m, 1H). MS (M+H)$^+$: 210.

Step e: Preparation of 75-e

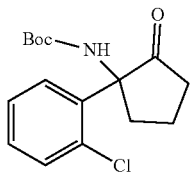 [SMILES: CC(C)(C)OC(=O)NC1(c2ccccc2Cl)CCCC1=O]

Using compound 75-d (525 mg, 2.5 mmol) as a raw material, the method described in step e in Example 1 was conducted accordingly to obtain 560 mg of white solid, yield: 72.2%. $^1$H NMR (400 MHz, CDCl$_3$) δ 7.42 (dd, J=6.7, 1.6 Hz, 1H), 7.27-7.20 (m, 3H), 5.25 (s, 1H), 2.84 (s, 2H), 2.61-2.45 (m, 2H), 2.09-2.00 (m, 1H), 1.77-1.66 (m, 1H), 1.42 (s, 9H). MS (M+Na)$^+$: 332

Step f: Preparation of 75-f

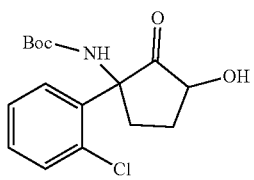 [SMILES: CC(C)(C)OC(=O)NC1(c2ccccc2Cl)CCC(O)C1=O]

Using the compound 75-e (1.06 g, 3.42 mmol) as a raw material, the method described in step f in Example 1 was conducted accordingly to obtain 230 mg of colorless oil, yield: 20.7%. $^1$H NMR (400 MHz, CDCl$_3$) δ 7.42 (dd, J=6.1, 2.3 Hz, 1H), 7.26-7.22 (m, 3H), 5.30 (s, 1H), 4.44 (t, J=8.7 Hz, 1H), 2.92 (s, 1H), 2.72 (dd, J=14.6, 7.9 Hz, 1H), 2.35-2.25 (m, 1H), 2.16-2.07 (m, 1H), 1.41 (s, 9H). MS (M+Na)$^+$: 348

Step g: Preparation of Compound 75

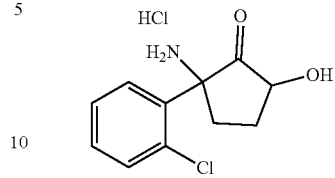

Using compound 75-f (120 mg, 0.37 mmol) as a raw material, the method described in step g in Example 42 to obtain 43 mg of white solid, yield: 44.3%. Purity: 96.4%. $^1$H NMR (400 MHz, CD$_3$OD) δ 7.60 (dd, J=7.9, 1.3 Hz, 1H), 7.49 (td, J=7.7, 1.6 Hz, 1H), 7.44 (td, J=7.7, 1.4 Hz, 1H), 7.29 (dd, J=7.8, 1.5 Hz, 1H), 4.75 (t, J=9.4 Hz, 1H), 2.84 (ddd, J=14.9, 9.4, 7.9 Hz, 1H), 2.64 (ddd, J=14.8, 8.3, 4.2 Hz, 1H), 2.44-2.33 (m, 1H), 2.03-1.90 (m, 1H). MS (M+H)$^+$: 226.

Example 76: Preparation of 2-amino-2-(2-chlorophenyl)-7-hydroxycycloheptan-1-one hydrochloride (Compound 76)

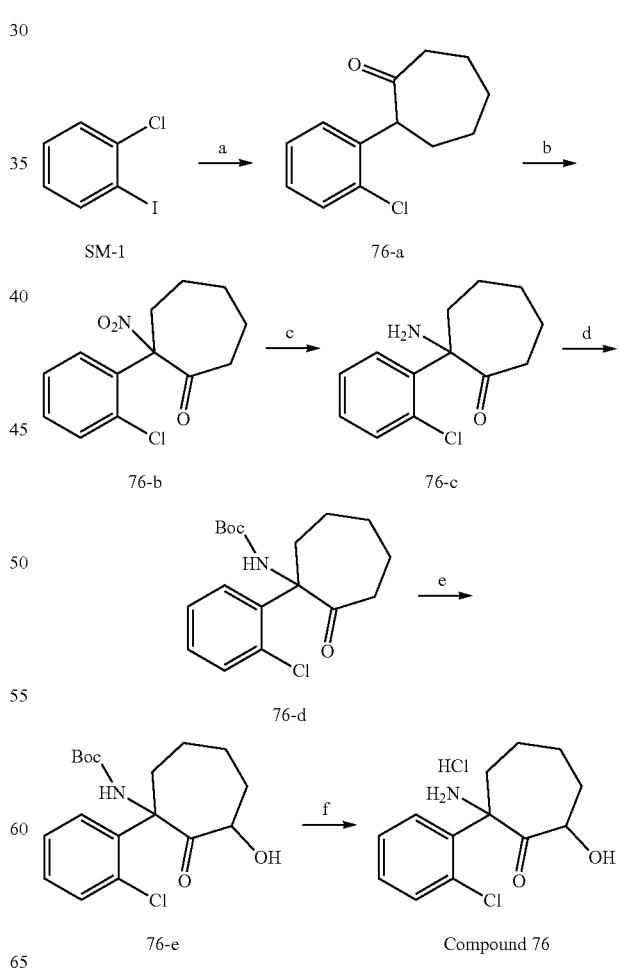

Step a: Preparation of 76-a

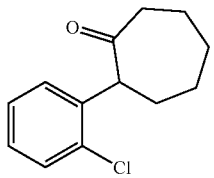 [SMILES: O=C1CCCCCC1c1ccccc1Cl]

Using o-chloroiodobenzene (4 g, 16.78 mmol) and cycloheptanone (3.76 g, 33.52 mmol) as raw materials, the method described in step a in Example 74 was conducted accordingly to obtain 1.39 g of yellow oily liquid, yield: 37.2%. $^1$H NMR (400 MHz, CDCl$_3$) δ 7.34 (d, J=7.9 Hz, 1H), 7.26 (s, 1H), 7.25 (s, 1H), 7.20-7.14 (m, 1H), 4.34 (dd, J=11.0, 2.5 Hz, 1H), 3.74 (t, J=6.5 Hz, 1H), 2.79 (ddd, J=9.4, 7.2, 2.8 Hz, 1H), 2.63 (ddd, "J=15.6, 11.5, 4.1 Hz, 1H), 2.52-2.47 (m, 1H), 2.02-1.95 (m, 2H), 1.85 (dd, J=6.6, 3.1 Hz, 1H), 1.73-1.64 (m, 3H). MS (M+H)$^+$: 223.

Step b: Preparation of 76-b

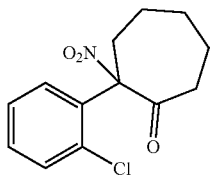 [SMILES: O=C1CCCCCC1(c1ccccc1Cl)[N+](=O)[O-]]

Using compound 76-a (400 mg, 1.8 mmol) as a raw material, the method described in step c in Example 1 was conducted accordingly to obtain 146 mg of pale yellow oil, yield: 30.4%. NMR (400 MHz, CDCl$_3$) δ 7.52-7.44 (m, 1H), 7.34 (dtd, J=20.2, 7.5, 1.5 Hz, 2H), 7.16 (dd, J=7.7, 1.6 Hz, 1H), 3.71-3.53 (m, 1H), 2.96-2.84 (m, 1H), 2.75 (td, J=12.2, 2.7 Hz, 1H), 2.30 (dd, J=15.8, 10.3 Hz, 1H), 2.16-1.98 (m, 1H), 1.98-1.83 (m, 2H), 1.81-1.67 (m, 2H), 1.48-1.34 (m, 1H). MS (M+Na)$^+$: 290.1.

Step c: Preparation of 76-c

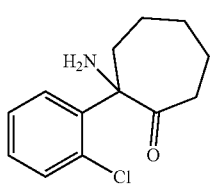 [SMILES: NC1(c2ccccc2Cl)CCCCCC1=O]

Using compound 76-b (146 mg, 0.54 mmol) as a raw material, the method described in step d in Example 1 was conducted accordingly to obtain 152 mg of crude light yellow oily liquid, which was directly cast into the reaction in next step without purification. MS (M+H)$^+$: 238.1

Step d: Preparation of 76-d

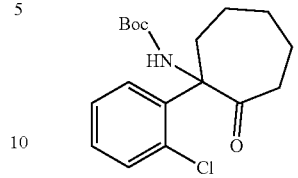

Using the crude compound 76-c (152 mg) as a raw material, the method described in step e in Example 1 was conducted accordingly to obtain 120 mg of pale yellow oily liquid, yield: 65.2% (two steps together). $^1$H NMR (400 MHz, CDCl$_3$) δ 7.77 (s, 1H), 7.40-7.35 (m, 2H), 7.30-7.28 (m, 1H), 6.40 (s, 1H), 3.36 (m, 2H), 3.25 (s, 1H), 1.73-1.65 (m, 2H), 1.63-1.55 (m, 2H), 1.50-1.42 (dd, J=14.0, 6.9 Hz, 1H), 1.40-1.37 (m, 2H), 1.32 (s, 9H). MS (M+Na)$^+$: 360.1.

Step e: Preparation of 76-e

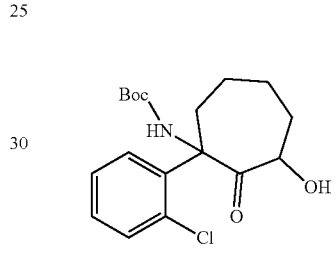

Using compound 76-d (120 mg, 0.36 mmol) as a raw material, the method described in step f in Example 1 was conducted accordingly to obtain 53 mg of pale yellow oily liquid, yield: 42.1%. $^1$H NMR (400 MHz, CDCl$_3$) δ 7.79 (s, 1H), 7.40-7.33 (m, 2H), 7.32-7.27 (m, 1H), 6.45 (s, 1H), 4.40 (d, J=4.1 Hz, 1H), 3.48 (d, J=3.5 Hz, 1H), 3.31 (s, 1H), 1.93-1.80 (m, 3H), 1.76-1.68 (m, 1H), 1.62 (dd, J=14.0, 6.9 Hz, 1H), 1.49-1.37 (m, 2H), 1.32 (s, 9H). MS (M+Na)$^+$: 376.1.

Step f: Preparation of Compound 76

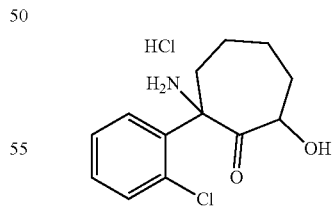

Using compound 76-e (47 mg, 0.13 mmol) as a raw material, the method described in step g in Example 42 was conducted accordingly to obtain 20 mg of white solid, yield: 51.9%. Purity: 99.2%. $^1$H NMR (400 MHz, CD$_3$OD) δ 7.72-7.67 (m, 1H), 7.64-7.59 (m, 1H), 7.55 (qd, J=7.4, 3.5 Hz, 2H), 4.60-4.51 (m, 1H)), 2.67 (ddd, J=15.2, 6.4, 2.9 Hz, 1H), 2.47-2.25 (m, 1H), 2.10-1.89 (m, 1H), 1.81-1.68 (m, 3H), 1.65-1.49 (m, 2H). MS (M+H)$^+$: 254.1.

Example 77: Preparation of 2-amino-2-(4-fluoro-2-(trifluoromethyl)phenyl)-6-hydroxycyclohexane-1-one hydrochloride (Compound 77)

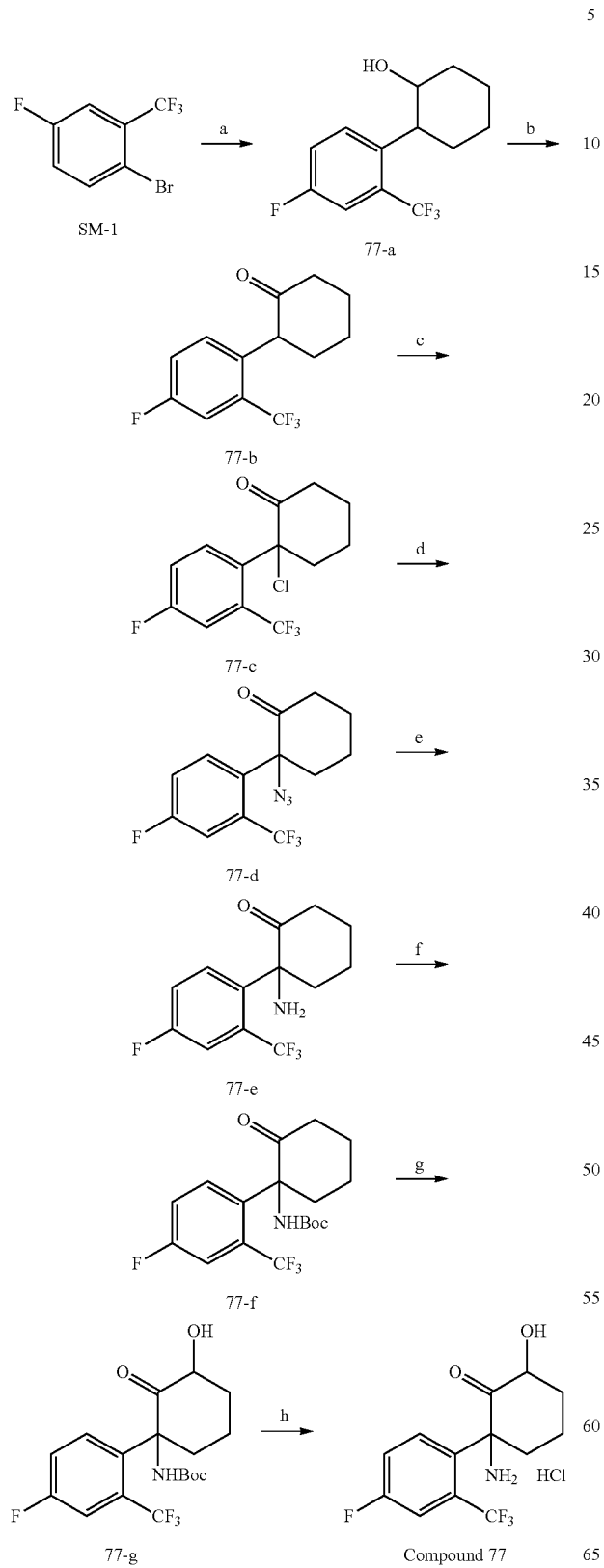

Step a: Preparation of 77-a

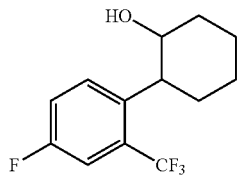 [SMILES: OC1CCCCC1c1ccc(F)cc1C(F)(F)F]

Using 1-bromo-4-fluoro-2-(trifluoromethyl)benzene (7.2 g, 29.63 mmol) and epoxycyclohexane (3.2 g, 32.6 mmol) as raw materials, the method described in step a in Example 1 was conducted accordingly to obtain 6.5 g of colorless oily liquid, yield: 83.6%. $^1$H NMR (400 MHz, CDCl$_3$) δ 7.48 (dd, J=8.6, 5.4 Hz, 1H), 7.36 (dd, J=9.3, 2.7 Hz, 1H), 7.25 (dt, J=8.2, 3.9 Hz, 1H), 3.83-3.74 (m, 1H), 2.88 (t, J=9.6 Hz, 1H), 2.16 (dd, J=5.9, 2.5 Hz, 1H), 1.79-1.64 (m, 3H), 1.47-1.29 (m, 5H). MS (M+1)$^+$: 263.

Step b: Preparation of 77-b

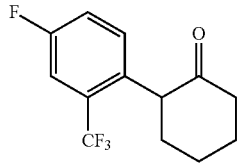

Using compound 77-a (6.5 g, 24.78 mmol) as a raw material, the method described in step b in Example 1 was conducted accordingly to obtain 5.3 g of pale yellow solid, yield: 82.2%. $^1$H NMR (400 MHz, CDCl$_3$) δ 7.37-7.28 (m, 2H), 7.23 (dd, J=8.5, 2.4 Hz, 1H), 4.02 (dd, J=12.2, 5.0 Hz, 1H), 2.58-2.48 (m, 2H), 2.29-2.20 (m, 2H), 2.00-1.74 (m, 4H). MS(M+H)$^+$: 261.

Step c: Preparation of 77-c

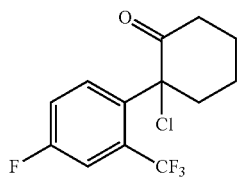 [SMILES: O=C1CCCCC1(Cl)c1ccc(F)cc1C(F)(F)F]

Using compound 77-b (2.0 g, 7.68 mmol) as a raw material, the method described in step c in Example 2 was conducted accordingly to obtain 0.49 g of pale yellow oily liquid, yield: 21.7%. $^1$H NMR (400 MHz, CDCl$_3$) δ 8.11 (dd, J=9.0, 5.4 Hz, 1H), 7.39 (dd, J=9.0, 2.7 Hz, 1H), 7.31-7.27 (m, 1H), 3.07 (ddd, J=16.4, 13.5, 6.4 Hz, 1H), 2.59-2.37 (m, 3H), 2.21-2.05 (m, 2H), 1.86 (dd, J=11.9, 6.4 Hz, 2H). MS (M+H)$^+$: 295.

Step d: Preparation of 77-d

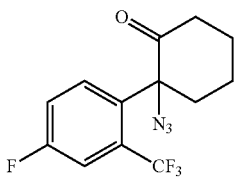

Using compound 77-c (0.49 g, 1.66 mmol) as a raw material, the method described in step d in Example 2 was conducted accordingly to obtain 38 mg of pale yellow oily liquid, yield: 7.6%. $^1$H NMR (400 MHz, CDCl$_3$) δ 7.60-7.48 (m, 2H), 7.39 (d, J=11.0 Hz, 1H), 2.70 (dd, J=13.3, 7.7 Hz, 1H), 2.58 (dd, J=12.7, 7.5 Hz, 1H), 2.47-2.37 (m, 1H), 2.02 (dd, J=11.5, 4.6 Hz, 3H), 1.75 (s, 1H), 1.63 (dd, J=14.6, 7.3 Hz, 1H). MS (M+H)$^+$: 302.

Step e: Preparation of 77-e

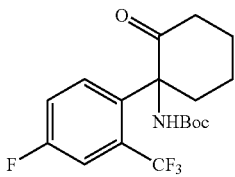 [SMILES: CC(C)(C)OC(=O)NC1(c2ccc(F)cc2C(F)(F)F)CCCCC1=O]

Using compound 77-d (150 mg, 0.5 mmol) as a raw material, the method described in step e in Example 2 was conducted accordingly to obtain 140 mg of pale yellow oily liquid, which was directly cast into the reaction in next step without purification. MS (M+H)$^+$: 276.

Step f: Preparation of 77-f

Using the crude compound 77-e (140 mg crude) as a raw material, the method described in step e in Example 1 was conducted accordingly to obtain 115 mg of white solid, yield: 61.5% (two steps together). $^1$H NMR (400 MHz, CDCl$_3$) δ 7.86 (m, 1H), 7.49 (m, 1H), 7.32 (d, J=9.5 Hz, 1H), 6.48 (s, 1H), 3.74 (m, 1H), 2.48 (m, 1H), 2.32 (m, 1H), 1.78 (m, 5H), 1.26 (s, 9H). MS (M+H)$^+$: 376

Step g: Preparation of 77-g

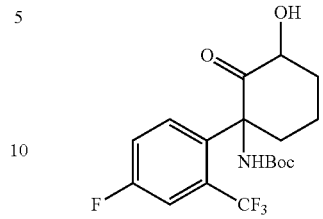

Using the compound 77-f (28 mg, 0.07 mmol) as a raw material, the method described in step f in Example 1 was conducted accordingly to obtain 9 mg of colorless oil, yield: 30.8%. $^1$H NMR (400 MHz, CDCl$_3$) δ 7.86 (s, 1H), 7.50 (d, J=8.2 Hz, 1H), 7.32 (d, J=10.8 Hz, 1H), 6.52 (s, 1H), 4.19-4.09 (m, 1H), 3.85 (s, 1H), 3.35 (d, J=5.5 Hz, 1H), 2.46-2.36 (m, 1H), 1.82 (dd, J=11.3, 6.9 Hz, 1H), 1.75-1.64 (m, 2H), 1.55 (dd, J=12.5, 4.2 Hz, 1H), 1.32 (s, 9H). MS (M+Na)$^+$: 414

Step h: Preparation of Compound 77

Using compound 77-g (24 mg, 0.06 mmol) as a raw material, the method described in step g in Example 42 was conducted accordingly to obtain 10 mg of white solid, yield: 49.8%. Purity: 96.6%. $^1$H NMR (400 MHz, CD$_3$OD) δ 8.00 (t, J=7.9 Hz, 1H), 7.78 (d, J=8.2 Hz, 1H), 7.72 (d, J=11.3 Hz, 1H), 4.34 (dd, J=11.2, 6.9 Hz, 1H), 3.18 (dd, J=13.8, 2.4 Hz, 1H), 2.38-2.26 (m, 1H), 2.08-1.90 (m, 2H), 1.82-1.59 (m, 2H). MS (M+H)$^+$: 292.

Example 78: Preparation of 5-(1-amino-3-hydroxy-2-oxocyclohexyl)-2-trifluoromethylbenzonitrile oxalate (Compound 78)

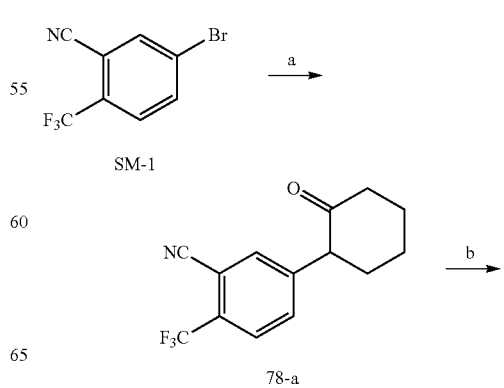

-continued

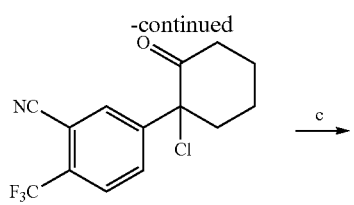

78-b

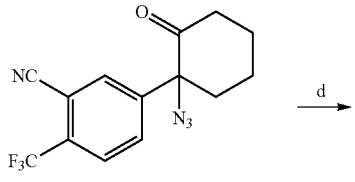

78-c

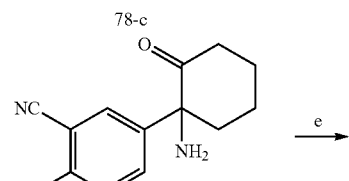

78-d

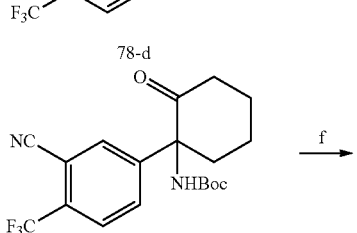

78-e

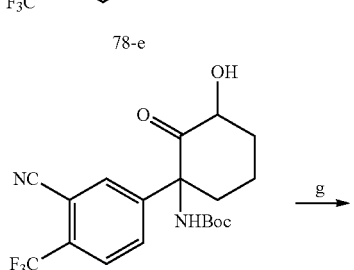

78-f

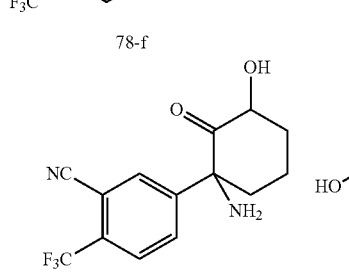

Compound 78

Step a: Preparation of 78-a

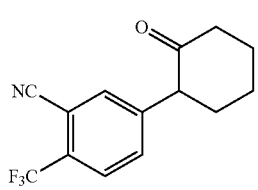 [SMILES: N#Cc1cc(C2CCCCC2=O)ccc1C(F)(F)F]

Using 5-bromo-2-trifluoromethyl benzonitrile (2 g, 8.0 mmol) and cyclohexanone (1.6 g, 16 mmol) as raw materials, the method described in step a in Example 74 was conducted accordingly to obtain 1.2 g of pale white solid, yield: 56.1%. $^1$H NMR (400 MHz, CDCl$_3$) δ 7.88-7.78 (m, 2H), 7.65 (d, J=8.2 Hz, 1H), 3.98 (dd, J=12.6, 5.4 Hz, 1H), 2.67-2.54 (m, 1H), 2.50-2.40 (m, 1H), 2.33-2.24 (m, 1H), 2.23-2.14 (m, 1H), 2.10-1.98 (m, 2H), 1.97-1.74 (m, 2H). MS (M+H)$^+$: 268.

Step b: Preparation of 78-b

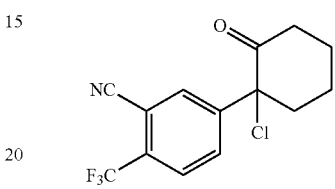

Using compound 78-a (1.2 g, 4.5 mmol) as a raw material, the method described in step c in Example 2 was conducted accordingly to obtain 1.1 g of light yellow solid, yield: 81.5%. $^1$H NMR (400 MHz, CDCl$_3$) δ 7.96 (d, J=17.5 Hz, 1H), 7.80 (s, 2H), 3.19 (d, J=12.8 Hz, 1H), 2.51 (d, J=20.2 Hz, 3H), 2.22 (dd, J=32.5, 10.3 Hz, 2H), 1.88 (dd, J=35.5, 13.3 Hz, 2H). MS (M+H)$^+$: 302.

Step c: Preparation of 78-c

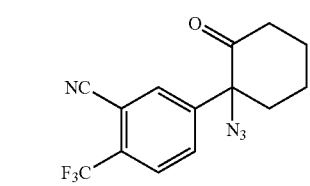

Using compound 78-b (1.4 g, 4.6 mmol) as a raw material, the method described in step d in Example 2 was conducted accordingly to obtain 0.7 g of pale yellow oily liquid, yield: 49%. $^1$H NMR (400 MHz, CDCl$_3$) δ 7.87 (d, J=8.3 Hz, 1H), 7.81 (s, 1H), 7.65 (d, J=8.4 Hz, 1H), 2.84-2.73 (m, 1H), 2.42 (ddd, J=19.6, 18.4, 11.5 Hz, 2H), 2.26-2.14 (m, 1H), 2.11-1.87 (m, 4H). MS (M+H)$^+$: 309.

Step d: Preparation of 78-d

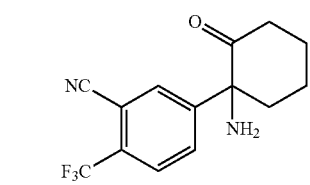

Using the compound 78-c (0.7 g, 2.3 mmol) as a raw material, the method described in step e in Example 2 was conducted accordingly to obtain 0.5 g of crude yellow solid, which was directly cast into the reaction in next step without purification. MS (M+H)$^+$: 283.

Step e: Preparation of 78-e

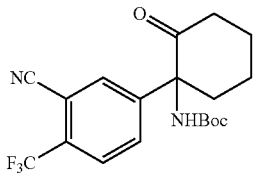 [SMILES: CC(C)(C)OC(=O)NC1(c2ccc(C(F)(F)F)c(C#N)c2)CCCCC1=O]

Using the crude compound 78-d (0.5 g crude) as a raw material, the method described in step e in Example 1 was conducted accordingly to obtain 0.6 g of white solid, yield: 69.1% (two steps together). $^1$H NMR (400 MHz, CDCl$_3$) δ 7.79 (d, J=8.1 Hz, 2H), 7.74 (s, 1H), 6.31 (s, 1H), 3.45 (d, J=13.9 Hz, 1H), 2.55 (d, J=13.5 Hz, 1H), 2.26-2.16 (m, 1H), 2.04 (d, J=6.6 Hz, 1H), 1.99-1.76 (m, 4H), 1.34 (s, 9H). MS (M+H)$^+$: 383.

Step f: Preparation of 78-f

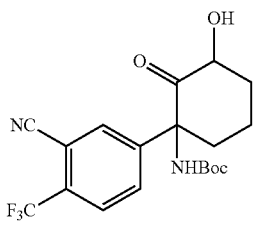

Using compound 78-e (0.28 g, 0.73 mmol) as a raw material, the method described in step f in Example 1 was conducted accordingly to obtain 78 mg of white solid, yield: 26.7%. $^1$H NMR (400 MHz, CDCl$_3$) δ 7.80 (dd, J=10.8, 7.2 Hz, 2H), 7.70 (s, 1H), 6.49 (s, 1H), 3.99 (s, 1H), 3.77 (d, J=12.2 Hz, 1H), 3.29 (d, J=3.8 Hz, 1H), 2.47-2.37 (m, 1H), 1.93 (dd, J=27.8, 14.2 Hz, 2H), 1.78-1.61 (m, 2H), 1.32 (s, 9H). MS (M+H)$^+$: 399.

Step g: Preparation of Compound 78

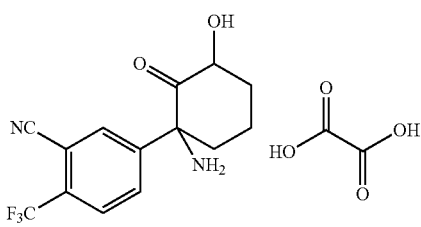

Compound 78-f (85 mg, 0.2 mmol) was dissolved in DCM (10 mL), and trifluoroacetic acid (1 ml) was added under ice-bath conditions. The mixture was stirred at room temperature for 1 h, followed by TLC. After the reaction of the raw materials was completed, the low boiling solvent was removed by rotary evaporation. Saturated sodium bicarbonate aqueous solution (15 mL) was added to the residue, and the mixture was extracted with ethyl acetate (10 ml×3). The organic phases were combined, washed with water (10 ml) and saturated brine (10 ml), dried with anhydrous sodium sulfate, and rotary evaporated to remove the low boiling solvent to obtain 60 mg of white solid. The obtained solid was dissolved in methanol (10 ml), oxalic acid dihydrate (25.2 mg, 0.20 mmol) was added, and the mixture was stirred at room temperature for 16 h. The methanol was removed by rotary evaporation, and a small amount of methanol (0.2 mL) and ethyl acetate (6 mL) were added to beat. A white solid was precipitated, filtered, and the solid was washed with ethyl acetate and dried to obtain 41 mg of white solid, yield: 49.4%, purity: 94.8%. $^1$H NMR (400 MHz, CD$_3$OD) δ 8.13-8.04 (m, 2H), 7.95 (d, J=8.4 Hz, 1H), 4.23 (dd, J=11.4, 7.0 Hz, 1H), 3.18 (d, J=13.2 Hz, 1H), 2.32 (s, 1H), 2.10 (dd, J=24.3, 11.2 Hz, 1H), 1.96 (d, J=8.1 Hz, 2H), 1.80-1.69 (m, 2H). MS (M+H)$^+$: 299.

Example 79: Preparation of 4-(1-amino-3-hydroxy-2-oxocyclohexyl)-3-fluorobenzonitrile oxalate (Compound 79)

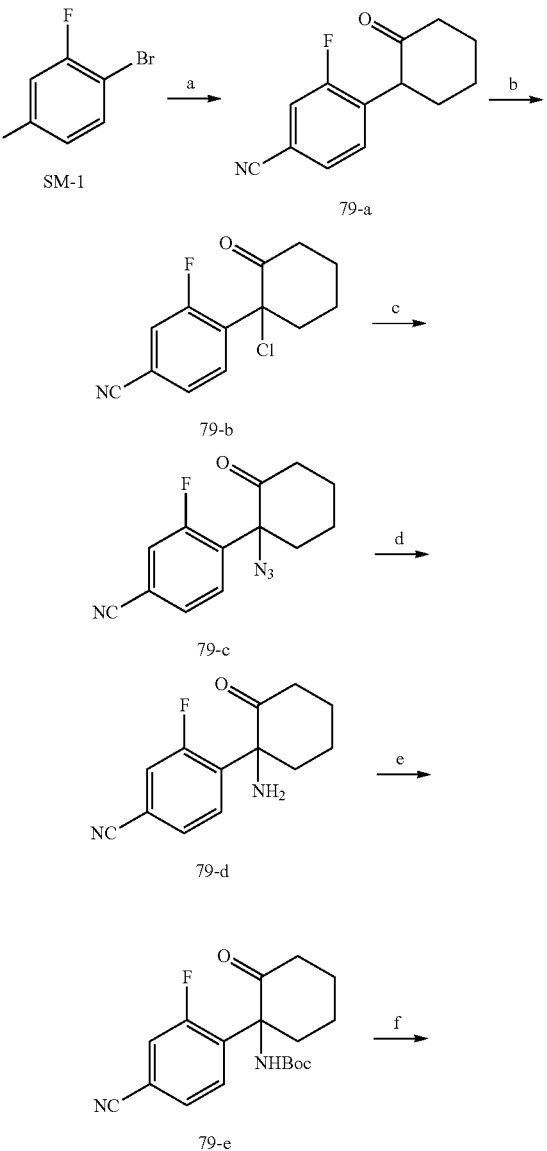

-continued

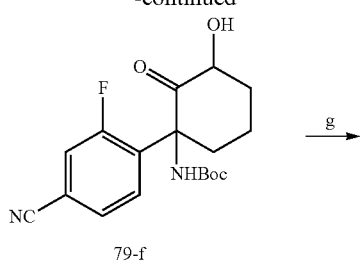

79-f

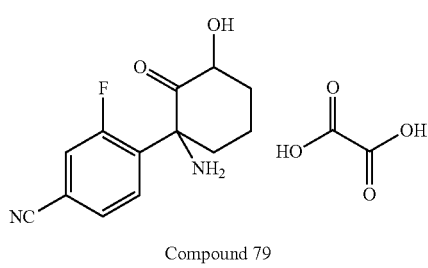

Compound 79

Step a: Preparation of 79-a

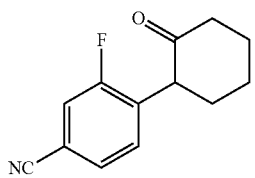 [SMILES: N#Cc1ccc(C2CCCCC2=O)c(F)c1]

Using 4-bromo-3-fluorobenzonitrile (2 g, 10 mmol) and cyclohexanone (1.96 g, 20 mmol) as raw materials, the method described in step a in Example 74 was conducted accordingly to obtain 1.5 g of pale white solid, yield: 69.1%. $^1$H NMR (400 MHz, CDCl$_3$) δ 7.46-7.42 (m, 1H), 7.34 (dd, J=9.5, 1.4 Hz, 1H), 7.29 (t, J=7.4 Hz, 1H), 3.90 (dd, J=13.0, 5.3 Hz, 1H), 2.52 (ddd, J=20.1, 19.3, 9.9 Hz, 2H), 2.24 (dtdd, J=11.5, 8.6, 5.4, 2.8 Hz, 2H), 2.11-1.95 (m, 2H), 1.91-1.76 (m, 2H). MS (M+H)$^+$: 218.

Step b: Preparation of 79-b

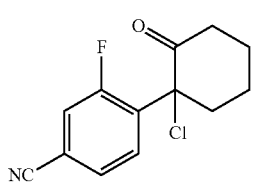 [SMILES: N#Cc1ccc(C2(N=[N+]=[N-])CCCCC2=O)c(F)c1]

Using compound 79-a (1.5 g, 6.9 mmol) as a raw material, the method described in step c in Example 2 was conducted accordingly to obtain 0.6 g of white solid, yield: 34.5%. $^1$H NMR (400 MHz, CDCl$_3$) δ 7.86 (t, J=7.8 Hz, 1H), 7.55-7.49 (m, 1H), 7.37 (dd, J=10.7, 1.4 Hz, 1H), 3.15-3.01 (m, 1H), 2.63-2.48 (m, 2H), 2.37 (dd, J=14.7, 3.3 Hz, 1H), 2.21-2.07 (m, 2H), 1.94-1.83 (m, 2H). MS (M+H)$^+$: 252.

Step c: Preparation of 79-c

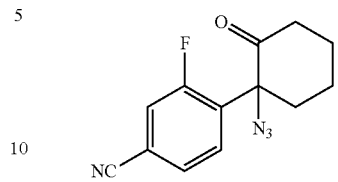

Using compound 79-b (0.69 g, 2.7 mmol) as a raw material, the method described in step d in Example 2 was conducted accordingly to obtain 0.35 g of pale yellow oily liquid, yield: 49.4%. $^1$H NMR (400 MHz, CDCl$_3$) δ 7.56 (t, J=4.5 Hz, 2H), 7.42 (d, J=10.5 Hz, 1H), 2.72 (ddd, J=16.2, 10.4, 5.8 Hz, 1H), 2.58 (dt, J=9.0, 4.8 Hz, 1H), 2.33 (ddd, J=16.9, 10.1, 5.4 Hz, 1H), 2.10-2.02 (m, 2H), 1.95-1.87 (m, 2H), 1.76 (dd, J=10.4, 4.8 Hz, 1H). MS (M+H)$^+$: 259.

Step d: Preparation of 79-d

Using the compound 79-c (345 mg, 1.3 mmol) as a raw material, the method described in step e in Example 2 was conducted accordingly to obtain 310 mg of crude yellow solid, which was directly cast into the reaction in next step without purification. MS (M+H)$^+$: 233.

Step e: Preparation of 79-e

Using the crude compound 79-d (0.31 g crude) as a raw material, the method described in step e in Example 1 was conducted accordingly to obtain 285 mg of white solid, yield: 64% (two steps together). $^1$H NMR (400 MHz, CDCl$_3$) δ 7.84 (s, 1H), 7.53 (d, J=7.9 Hz, 1H), 7.34 (t, J=10.8 Hz, 1H), 6.42 (s, 1H), 3.67 (s, 1H), 2.48 (t, J=16.3 Hz, 1H), 2.35-2.20 (m, 1H), 2.05 (d, J=7.5 Hz, 1H), 1.91-1.78 (m, 2H), 1.70 (t, J=18.3 Hz, 2H), 1.32 (s, 9H). MS (M+H)$^+$: 333.

Step f: Preparation of 79-f

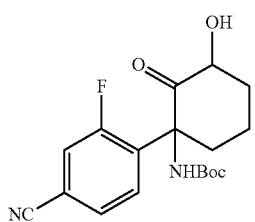 [SMILES: CC(C)(C)OC(=O)NC1(c2ccc(C#N)cc2F)CCCC(O)C1=O]

Using compound 79-e (0.27 g, 0.81 mmol) as a raw material, the method described in step f in Example 1 was conducted accordingly to obtain 76 mg of white solid, yield: 26.8%. $^1$H NMR (400 MHz, CDCl$_3$) δ 7.86 (s, 1H), 7.54 (d, J=8.2 Hz, 1H), 7.36 (d, J=10.5 Hz, 1H), 6.51 (s, 1H), 4.17-4.04 (m, 1H), 3.82 (s, 1H), 3.32 (d, J=5.6 Hz, 1H), 2.46-2.36 (m, 1H), 1.84 (d, J=11.3 Hz, 1H), 1.76-1.60 (m, 2H), 1.32 (s, 9H). MS (M+H)$^+$: 349.

Step g: Preparation of Compound 79

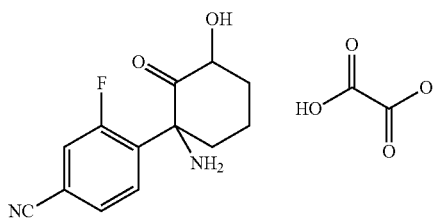

Using compound 79-f (74 mg, 0.21 mmol) as a raw material, the method described in step g of Example 78 was conducted accordingly to obtain 50 mg of white solid, yield: 66.6%, purity: 96.7%. $^1$H NMR (400 MHz, CD$_3$OD) δ 7.93 (t, J=8.0 Hz, 1H), 7.77 (dd, J=13.8, 4.2 Hz, 2H), 4.30 (dd, J=10.8, 6.8 Hz, 1H), 3.13 (d, J=13.5 Hz, 1H), 2.29 (d, J=8.7 Hz, 1H), 1.95 (dt, J=18.6, 9.1 Hz, 2H), 1.76-1.56 (m, 2H). MS (M+H)$^+$: 249.

Example 80: Preparation of 4-(1-amino-3-hydroxy-2-oxocyclohexyl)benzonitrile oxalate (Compound 80)

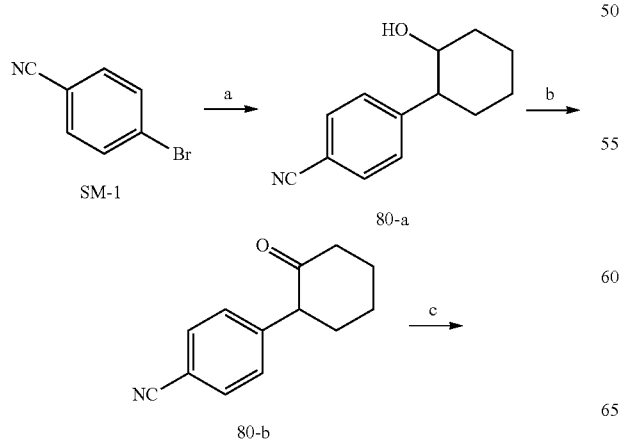

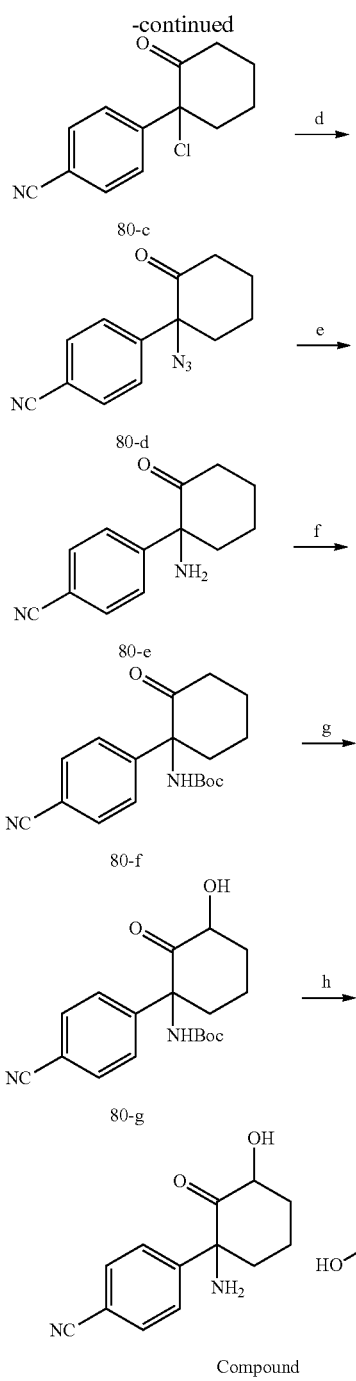

Step a: Preparation of 80-a

Using p-bromobenzonitrile (10 g, 55 mmol) and epoxycyclohexane (5.9 g, 60.4 mmol) as raw materials, the method described in step a in Example 1 was conducted accordingly to obtain 8.5 g of white solid, yield: 76.8%. ¹H NMR (400 MHz, CDCl₃) δ 7.62 (d, J=8.3 Hz, 2H), 7.37 (d, J=8.2 Hz, 2H), 3.75-3.64 (m, 1H), 2.57-2.48 (m, 1H), 2.17-2.09 (m, 1H), 1.83 (ddd, J=25.5, 13.8, 2.6 Hz, 3H), 1.45-1.34 (m, 4H). MS (M+1)⁺: 202.

Step b: Preparation of 80-b

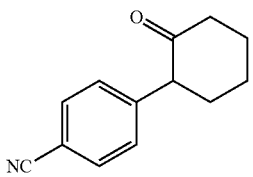 [SMILES: N#Cc1ccc(C2CCCCC2=O)cc1]

Using compound 80-a (8.5 g, 42.2 mmol) as a raw material, the method described in step b in Example 1 was conducted accordingly to obtain 6.4 g of white solid, yield: 76.2%. 1H NMR (400 MHz, CDCl₃) δ 7.62 (d, J=8.3 Hz, 2H), 7.24 (d, J=8.3 Hz, 2H), 3.67 (dd, J=12.5, 5.3 Hz, 1H), 2.60-2.42 (m, 2H), 2.33-2.14 (m, 2H), 2.07-1.93 (m, 2H), 1.91-1.75 (m, 2H). MS(M+H)⁺: 200.

Step c: Preparation of 80-c

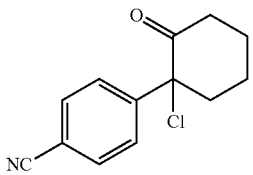

Using compound 80-b (3.0 g, 15 mmol) as a raw material, the method described in step c in Example 2 was conducted accordingly to obtain 3 g of pale yellow oily liquid, yield: 85.2%. ¹H NMR (400 MHz, CDCl₃) δ 7.72-7.67 (m, 2H), 7.58-7.52 (m, 2H), 3.15-3.03 (m, 1H), 2.74-2.61 (m, 1H), 2.54-2.40 (m, 2H), 2.22-2.14 (m, 1H), 2.14-2.02 (m, 1H), 1.92-1.81 (m, 2H). MS (M+H)⁺: 234.

Step d: Preparation of 80-d

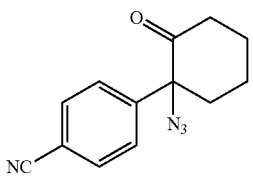 [SMILES: N#Cc1ccc(C2(N=[N+]=[N-])CCCCC2=O)cc1]

Using compound 80-c (1 g, 4.28 mmol) as a raw material, the method described in step d in Example 2 was conducted accordingly to obtain 575 mg of pale yellow oily liquid, yield: 55.9%. ¹H NMR (400 MHz, CDCl₃) δ 7.76 (d, J=8.5 Hz, 2H), 7.43 (d, J=8.4 Hz, 2H), 2.71-2.58 (m, 2H), 2.35 (ddd, J=14.3, 10.8, 5.6 Hz, 1H), 2.08 (ddd, J=14.4, 11.1, 3.4 Hz, 1H), 2.01-1.80 (m, 3H), 1.65 (tt, J=6.7, 6.2 Hz, 1H). MS (M+H)⁺: 241.

Step e: Preparation of 80-e

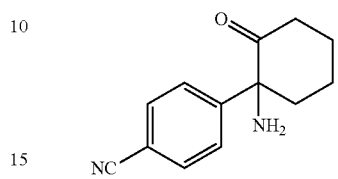

Using compound 80-d (500 mg, 2.08 mmol) as a raw material, the method described in step e in Example 2 was conducted accordingly to obtain 450 mg of pale yellow oily liquid, which was directly cast into the reaction in next step without purification. MS (M+H)⁺: 215.

Step f: Preparation of 80-f

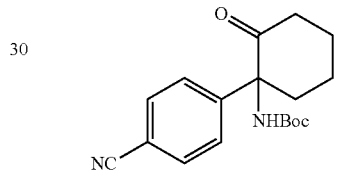

Using the crude compound 80-e (450 mg crude product) as a raw material, the method described in step e in Example 1 was conducted accordingly to obtain 472 mg of colorless oil, yield: 72.2% (two steps together). ¹H NMR (400 MHz, CDCl₃) δ 7.66 (d, J=8.5 Hz, 2H), 7.46 (d, J=8.3 Hz, 2H), 6.41 (s, 1H), 3.60 (d, J=12.1 Hz, 1H), 2.46 (d, J=12.5 Hz, 1H), 2.20 (s, 1H), 2.04 (d, J=3.8 Hz, 1H), 1.83 (dd, J=36.1, 11.8 Hz, 4H), 1.31 (s, 9H). MS (M+H)⁺: 315.

Step g: Preparation of 80-g

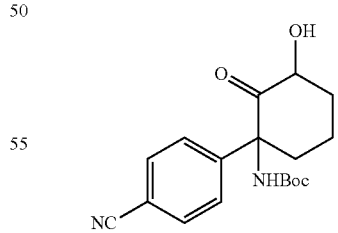

Using compound 80-f (300 mg, 0.95 mmol) as a raw material, the method described in step f in Example 1 was conducted accordingly to obtain 68 mg of white solid, yield: 21.6%. ¹H NMR (400 MHz, CDCl₃) δ 7.68 (d, J=8.4 Hz, 2H), 7.44 (d, J=8.4 Hz, 2H), 6.43 (s, 1H), 4.00 (m, 1H), 3.72 (m, 1H), 3.31 (m, 1H), 2.39 (m, 1H), 1.91 (m, 2H), 1.61 (m, 2H), 1.25 (s, 9H). MS (M+Na)⁺: 353.

Step h: Preparation of Compound 80

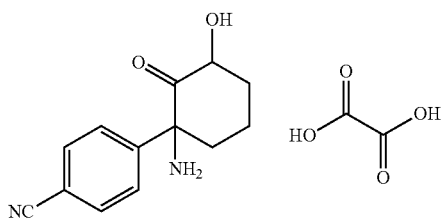 [SMILES: N#Cc1ccc(C2(N)CCCC(O)C2=O)cc1 ; O=C(O)C(=O)O]

Using compound 80-g (64 mg, 0.19 mmol) as a raw material, the method described in step g in Example 78 was conducted accordingly to obtain 30 mg of white solid, yield: 48%. Purity: 96.5%. $^1$H NMR (400 MHz, CD$_3$OD) δ 7.91 (d, J=8.1 Hz, 2H), 7.62 (d, J=8.2 Hz, 2H), 4.19 (dd, J=11.7, 6.7 Hz, 1H), 3.11 (d, J=13.5 Hz, 1H), 2.30 (s, 1H), 2.07 (d, J=13.4 Hz, 1H), 1.96 (d, J=12.1 Hz, 1H), 1.83-1.62 (m, 2H). MS (M+H)$^+$: 231.

Biological evaluation

The invention is further described below in conjunction with test examples, but these examples are not intended to limit the scope of the invention.

Test Example 1 Evaluation of the Antidepressant Activity of the Compound of the Present Invention in a Forced Swimming Experiment Via Intraperitoneal Administration to Mice The forced-swimming test is currently the most widely used classic method to evaluate the antidepressant effects of compounds in rodents. The test is a method of behavioral despair (behavioral despair is the core symptom of depression), by placing the animal in a confined environment (such as water) in which the animal struggles and tries to escape without being able to escape, thereby providing an unavoidable oppressive environment, and after a period of time, the animal shows a typical "immobile state". The time in immobile state of experimental animal is observed and recorded, which can be used to evaluate the effect of antidepressant compounds.

1.1 Experimental Purpose 1 h and 24 h after a single intraperitoneal administration of 10 mg/kg, forced swimming tests were respectively carried out to investigate the effects of different compounds on depression-like behaviors of C57 mice.

1.2 Experimental Protocol

1) Animal

Experimental animals were 6-week aged C57 mice, male, and C57 mice were purchased from Shanghai SLAC Laboratory Animal Co., Ltd., with a body weight of 20.45±0.19 g. Before the experiment, they arrived at the Animal Feeding Center of Shanghai Institute of Materia Medica, Chinese Academy of Sciences (Animal Production License: SCXK9 [Shanghai]2004-0002, usage license: SYXK[Shanghai] 2003-0029), and adapted for 3 days or more in animal facilities. They were bred at 6 animals/cage. The breeding environment was room temperature 23±0.2° C., with 12/12 hours alternation of day and night. Before the behavioral test, the animals should be moved to the behavioral test operation room 2 hours in advance to adapt to the environment and reduce their tension.

2) Animal Grouping

Animal grouping information and related dosing information are shown in Table 2.

TABLE 2

Animal grouping and dosing information

| Group | Quantity | Mode of administration | Injection dose (mg/kg) | Injection volume (ml/kg) |
|---|---|---|---|---|
| Blank control group | 10 | Intraperitoneal injection | 0.9% NaCl | 10 |
| Fluoxetine | 10 | Intraperitoneal injection | 10 | 10 |
| Ketamine | 10 | Intraperitoneal injection | 10 | 10 |
| (2R,6R)-HNK | 10 | Intraperitoneal injection | 10 | 10 |
| Compound of the invention | 10 | Intraperitoneal injection | 10 | 10 |

3) Experimental Steps

Preparation of the test product: each test compound was accurately weighed and dissolved in 0.9% NaCl solution, mixed thoroughly, and prepared as a 1 mg/ml solution, set aside.

24 hours before the administration, the mice were placed in a cylindrical tank to adapt to the aquatic environment for 10 min. On the day of the behavioral test, the animals were respectively administered intraperitoneally once at 1 h and 24 h before the behavioral test. The mice were placed individually into a cylindrical glass tank with a height of 30 cm and a diameter of 20 cm. The water depth in the tank was 15 cm, so that the animals could not escape from the glass tank and their feet and tails could not touch the bottom of the tank, the water temperature was 23° C.-25° C. A 6 minute video was taken after the mouse entered into water. Since most animals were very active in the first two minutes, the immobility time in the following 4 minute were calculated (criterion of immobility: the mouse stops struggling in the water, stays still and has small limbs movement to maintain balance or to keep a floating state).

4) Test Result

The antidepressant effect of a compound was evaluated by the ability of the compound to reduce the immobility time of the animal in the forced swimming test as compared with the blank group. The shorter the immobility time of the animal to be tested, the higher the inhibition rate and the stronger the antidepressant activity.

Inhibition rate$_{1\,h}$(%)=immobility time$_{(blank,\,1\,h)}$−immobility time$_{(administration,\,1\,h)}$/immobility time$_{(blank,\,1\,h)}$×100%

Inhibition rate$_{24\,h}$(%)=immobility time$_{(blank,\,24\,h)}$−immobility time$_{(administration,\,24\,h)}$/immobility time$_{(blank,\,24\,h)}$×100%

TABLE 3

Results of antidepressant activity of compounds of the present invention administered intraperitoneally to mice

| Compound | 1 h inhibition rate (%) | 24 h inhibition rate (%) |
|---|---|---|
| 39 | 46.6 ± 1.0 | 49.1 ± 3.7 |
| 44 | 36.5 ± 2.9 | 53.5 ± 0.2 |
| 45 | 33.0 ± 4.1 | 44.5 ± 2.2 |
| 46 | 34.7 ± 4.1 | 43.5 ± 0.0 |
| 53 | 50.9 ± 2.0 | 39.6 ± 3.2 |
| 59 | 32.0 ± 2.2 | 40.3 ± 4.9 |
| 71 | 24.2 ± 4.7 | 57.4 ± 4.4 |
| 73 | 38.6 ± 6.0 | 36.9 ± 3.9 |
| Fluoxetine | −4.6 ± 2.3 | 4.6 ± 1.8 |
| Ketamine | 29.2 ± 4.6 | 35.4 ± 7.9 |
| (2R,6R)-HNK | 31.1 ± 4.0 | 27.4 ± 3.9 |
| Comparative compound 1 | 17.4 ± 0.2 | 10.6 ± 1.2 |

The structure of comparative compound 1 is

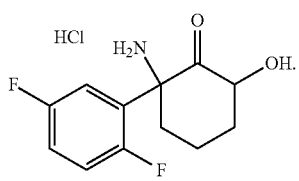

The structure of (2R, 6R)-HNK is

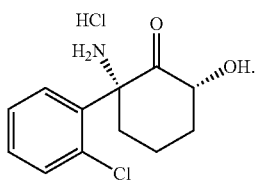 [SMILES: Cl ; N[C@@]1(c2ccccc2Cl)CCC[C@@H](O)C1=O]

It can be seen from Table 3 that the traditional antidepressant fluoxetine has no obvious antidepressant effect for 1 hour and 24 hours in the forced swimming experiment, which shows that fluoxetine does not have fast-acting antidepressant effects, that is consistent with clinical results. It is reported in the literature that the comparative compound 1 has only 17.4% and 10.6% inhibition rates for immobility time at 1 hour and 24 hours, which are far lower than those of the compound of the present invention. The compounds of the present invention are same as ketamine, and both can quickly exert an antidepressant effect after 1 hour of intraperitoneal administration. More prominently, the 1 hour antidepressant activity of the compounds of the present invention (inhibition rate of 32.0%-50.9%) is significantly better than the positive control drug ketamine (inhibition rate of 29.2%), especially the antidepressant activity of the compounds of the present invention is greatly better than that of the lead compound (2R, 6R)-HNK (inhibition rate of 31.1%). The 24-hour antidepressant activity proves that the compounds of the present invention have long-lasting antidepressant activity, and are also significantly better than the positive control drug ketamine, and have a greater increase than that of the lead compound (2R, 6R)-HNK (inhibition rate 27.4%).

In summary, the above experimental results show that the compounds of the present invention have rapid, long-lasting and stronger antidepressant activity compared with the existing compounds.

Test Example 2. Evaluation of the Antidepressant Activity of the Compounds of the Present Invention in a Forced Swimming Experiment Via Oral Administration to Mice 2.1 Experimental Purpose 1 h and 24 h after a single oral administration of 20 mg/kg, forced swimming experiments were then carried out to investigate the effects of different compounds on depression-like behavior in C57 mice.

2.2 Experimental Program

1) Animal

Experimental animals were 6-week aged C57 mice, male, C57 mice were purchased from Shanghai SLAC Laboratory Animal Co., Ltd., with a body weight of 20.45±0.19 g. Before the experiment, they arrived at the Animal Feeding Center of Shanghai Institute of Materia Medica, Chinese Academy of Sciences (Animal Production License: SCXK9 [Shanghai]2004-0002, usage license: SYXK[Shanghai] 2003-0029), and adapted for 3 days or more in animal facilities. They were bred at 6 animals/cage. The breeding environment was room temperature 23±0.2° C., with 12/12 hours alternation of day and night. Before the behavioral test, the animals should be moved to the behavioral test operation room 2 hours in advance to adapt to the environment and reduce their tension.

2) Animal Grouping

Animal grouping information and related dosing information are shown in Table 4.

TABLE 4

Animal grouping and dosing information

| Group | Quantity | Mode of administration | Dose of administration (mg/kg) | Dosing volume (ml/kg) |
|---|---|---|---|---|
| Blank control group | 10 | intragastrically | 0.9% NaCl | 10 |
| Fluoxetine | 10 | intragastrically | 20 | 10 |
| Ketamine | 10 | intraperitoneally | 10 | 10 |
| (2R,6R)-HNK | 10 | intragastrically | 20 | 10 |
| Compound of the invention | 10 | intragastrically | 20 | 10 |

3) Experimental Steps

Preparation of the test product: each test compound was accurately weighed and dissolved in 0.9% NaCl solution, mixed thoroughly, and prepared into 1 mg/ml and 2 mg/ml solutions respectively, and set aside.

24 hours before the administration, the mice were placed in a cylindrical tank to adapt to the aquatic environment for 10 min. On the day of the behavioral test, the animals were respectively administered intragastrically once at 1 h and 24 h before the behavioral test. The mice were placed individually into a cylindrical glass tank with a height of 30 cm and a diameter of 20 cm. The water depth in the tank was 15 cm, so that the animals could not escape from the glass tank and their feet and tails could not touch the bottom of the tank, the water temperature was 23° C.-25° C. A 6 minute video was taken after the mouse entered into water. Since most animals were very active in the first two minutes, the immobility time in the following 4 minute were calculated (criterion of immobility: the mouse stops struggling in the water, stays still and has small limbs movement to maintain balance or to keep a floating state).

4) Test Result

The antidepressant effect of a compound was evaluated by the ability of the compound to reduce the immobility time of the animal in the forced swimming test as compared with the blank group.

Inhibition rate$_{1\,h}$(%)=immobility time$_{(blank,\,1\,h)}$−immobility time$_{(administration,\,1\,h)}$/immobility time$_{(blank,\,1\,h)}$×100%

Inhibition rate$_{24h}$(%)=immobility time$_{(blank,\,24\,h)}$−immobility time$_{(administration,\,24\,h)}$/immobility time$_{(blank,\,24\,h)}$×100%

TABLE 5

Results of the antidepressant activity of compounds of the present invention after oral administration in mice

| Compound | 1 h inhibition rate (%) | 24 h inhibition rate (%) |
|---|---|---|
| 44 | 27.3 ± 1.2 | 22.3 ± 2.3 |
| 46 | 31.2 ± 4.7 | 32.3 ± 1.5 |
| 50 | 34.5 ± 3.1 | 35.6 ± 3.6 |
| 51 | 66.9 ± 0.3 | 38.6 ± 2.1 |
| 59 | 28.6 ± 1.8 | 36.1 ± 1.6 |
| 64 | 36.5 ± 5.3 | 34.5 ± 1.0 |
| 65 | 23.8 ± 0.6 | 32.0 ± 2.9 |
| Fluoxetine | 2.2 ± 1.2 | 1.8 ± 1.3 |
| Ketamine (intraperitoneally) | 22.7 ± 0.2 | 25.1 ± 2.7 |
| (2R,6R)-HNK | 18.4 ± 1.6 | 19.6 ± 4.4 |

The oral absorption of ketamine is poor, and the oral curative effect is not good. As a result, injection is used clinically. However, when the current clinical research is used for rapid antidepressant treatment, nasal administration is compelled to be used, which brings inconvenience to clinical use.

It can be seen from Table 5 that in the forced swimming experiment, oral administration of traditional antidepressant fluoxetine, like intraperitoneal administration, no antidepressant effect was shown for 1 hour and 24 hours, indicating that fluoxetine does not have any fast-acting antidepressant effect, which is consistent with clinical results. In the case of oral administration of the compounds of the present invention to mice, all of them can significantly reduce the immobility time of mice in forced swimming at 1 h and 24 h, and show fast, long-lasting and strong antidepressant effects.

Compared with the positive control drug ketamine and the lead compound (2R, 6R)-HNK, the compounds of the present invention have a significant increase in antidepressant activity and have obvious advantages.

The compounds of the present invention are effective orally, and can be made into an oral dosage form in the future, which is another significant advantage of the compounds of the present invention over ketamine.

Test Example 3. In Vivo Pharmacokinetic Experiment of the Compounds of the Present Invention in Mice Healthy male C57 mice were randomly divided into groups with 3 mice in each group, and the test compounds were administrated intragastrically or by intravenous injection. See Table 6 below for specific arrangements:

TABLE 6 pharmacokinetic experiment dosing protocol for C57 mice in vivo:

| Compound | Route of administration | Dose of administration (mg/kg) | Dosing volume (ml/kg) |
|---|---|---|---|
| 50 | Intragastrically (p.o.) | 20 | 10 |
| 50 | Intravenous (i.v.) | 5 | 5 |
| 51 | Intragastrically | 20 | 10 |
| 51 | Intravenous | 5 | 5 |
| 64 | intragastrically | 20 | 10 |
| 64 | intravenous | 5 | 5 |
| 2R,6R-HNK | intragastrically | 20 | 10 |
| 2R,6R-HNK | intravenous | 5 | 5 |

Each test compound was dissolved in physiological saline to prepare a certain concentration of solution for administration.

One day before administration, the mice were fasted and allowed to drink freely for 12-14 h. The mice were fed 4 h after administration.

0.030 mL of blood was took from each animal each time through the orbit, and anticoagulated with EDTAK$_2$. The collection time points were as follows: in PO group, 5 min, 15 min, 30 min, 1 h, 2 h, 4 h, 6 h, 8 h, 24 h after administration of test substance; in IV group, 2 min, 5 min, 15 min, 30 min, 1 h, 2 h, 4 h, 6 h, 8 h, 24 h after administration of test substance. After blood samples were collected, they were placed on ice and centrifuged to separate the plasma within 30 minutes (centrifugation conditions: 5000 rpm, 10 minutes, 4° C.). The sample were stored at −80° C. before analysis.

TABLE 7 pharmacokinetic data in mice

| Compound | dose (mg/kg) | T$_{1/2}$ (h) | T$_{max}$ (h) | C$_{max}$ (ng/mL) | AUC$_{0-t}$ (ngh/mL) | AUC$_{0-\infty}$ (ngh/mL) | MRT (h) | CL (ml/min/Kg) | Vss (L/Kg) | F (%) |
|---|---|---|---|---|---|---|---|---|---|---|
| 50 | 20 (p.o.) | 4.16 | 0.11 | 8098 | 13548 | 13624 | 2.49 | | | 112 |
| 50 | 5 (i.v.) | 1.67 | | | 3022 | 3075 | 1.29 | 27.2 | 2.1 | |
| 51 | 20 (p.o.) | 4.09 | 0.0833 | 7519 | 17539 | 17877 | 3.59 | | | 68.0 |
| 51 | 5 (i.v.) | 1.79 | | | 6471 | 6567 | 1.23 | 13.5 | 0.98 | |
| 64 | 20 (p.o.) | 3.98 | 0.0833 | 11891 | 12708 | 12816 | 2.08 | | | 66.2 |
| 64 | 5 (i.v.) | 0.87 | | | 4817 | 4838 | 0.88 | 17.2 | 0.91 | |

TABLE 7-continued pharmacokinetic data in mice

| Compound | dose (mg/kg) | $T_{1/2}$ (h) | $T_{max}$ (h) | $C_{max}$ (ng/mL) | $AUC_{0-t}$ (ngh/mL) | $AUC_{0-\infty}$ (ngh/mL) | MRT (h) | CL (ml/min/Kg) | Vss (L/Kg) | F (%) |
|---|---|---|---|---|---|---|---|---|---|---|
| 2R,6R-HNK | 20 (p.o.) | 0.93 | 0.0833 | 7177 | 5589 | 5599 | 0.875 | | | 66.8 |
| 2R,6R-HNK | 5 (i.v.) | 0.34 | | | 2085 | 2096 | 0.39 | 40.7 | 0.94 | |

Good metabolic property in vivo is the material basis for the pharmacological activity of compounds and one of the most critical indicators of druggability. It can be seen from Table 7 that, as compared with the lead compound 2R, 6R-HNK, the compounds of the present invention have a prolonged oral half-life ($T_{1/2}$) by more than 4 times, and a 2-3 times increase in drug plasma exposure (AUC), wherein the maximum blood drug concentration ($C_{max}$) is also significantly increased, and the intravenous clearance rate (CL) is reduced by 2-3 times (if the clearance rate is low, it is conducive to the drug's efficacy).

Therefore, as seen from the above table, the compounds of the present invention have significantly better metabolic characteristics than those of lead compound 2R, 6R-HNK, and have better druggability.

Test Example 4. In Vivo Pharmacokinetic Experiment of the Compounds of the Present Invention in Rats Healthy male SD rats were randomly divided into groups with 3 rats in each group, and the test compounds were administrated intragastrically or by intravenous injection. See Table 8 below for specific arrangements:

TABLE 8 pharmacokinetic experiment dosing protocol for SD Rat in vivo:

| Compound | Route of administration | Dose of administration (mg/kg) | Dosing volume (ml/kg) |
|---|---|---|---|
| 50 | p.o. | 10 | 10 |
| 50 | p.o. | 100 | 10 |
| 50 | i.v. | 10 | 5 |
| 51 | p.o. | 20 | 10 |
| 51 | i.v. | 5 | 5 |

Each test compound was dissolved in physiological saline to prepare a certain concentration of solution for administration.

One day before administration, the rats were fasted and allowed to drink freely for 12-14 h. The rats were fed 4 h after administration. 0.030 mL of blood was took from each animal each time through the orbit, and anticoagulated with $EDTAK_2$ anticoagulation. The collection time points were as follows: in PO group, 5 min, 10 min, 15 min, 30 min, 1 h, 2 h, 4 h, 6 h, 8 h, 24 h after administration of test substance; in IV group, 2 min, 5 min, 15 min, 30 min, 1 h, 2 h, 4 h, 6 h, 8 h, 24 h after administration of test substance. After blood samples were collected, they were placed on ice and centrifuged to separate the plasma within 30 minutes (centrifugation conditions: 5000 rpm, 10 minutes, 4° C.). The sample were stored at −80° C. before analysis.

TABLE 9 pharmacokinetic data in rats:

| Compound | dose (mg/kg) | $T_{1/2}$ (h) | $T_{max}$ (h) | $C_{max}$ (ng/mL) | $AUC_{0-t}$ (ngh/mL) | $AUC_{0-\infty}$ (ngh/mL) | MRT (h) | CL (ml/min/Kg) | Vss (L/Kg) | F (%) |
|---|---|---|---|---|---|---|---|---|---|---|
| 50 | 100 (p.o.) | 4.86 | 0.67 | 17328 | 85478 | 87916 | 5.47 | | | 77.8 |
|  | 10 (p.o.) | 5.73 | 0.31 | 3109 | 9060 | 9533 | 6.29 | | | 82.5 |
|  | 10 (i.v.) | 4.84 | | | 10976 | 11306 | 4.56 | 14.8 | 4.03 | |
| 51 | 20 (p.o.) | 4.74 | 0.33 | 9351 | 68383 | 70298 | 6.21 | | | 86 |
|  | 5 (i.v.) | 5.6 | | | 19871 | 20688 | 6.15 | 4.03 | 1.49 | |
| 2R,6R-HNK (literature) [a] | 10 (p.o.) | 6.9 | 0.167 | 1500 | | 2650 | | | | 42 |
|  | 10 (i.v.) | 8.0 | | | | 6270 | | 27 | 7.5 | |

[a] Journal of Psychopharmacology, 2019, 33, 12-24.

It can be seen from Table 9 that, compared with 2R, 6R-HNK reported in the literature, the compounds of the present invention have significantly improved the drug plasma exposure (AUC), maximum blood concentration ($C_{max}$) and oral bioavailability (F), while the intravenous clearance rate (CL) is significantly reduced, indicating that the compounds of the present invention have significantly better rat metabolic characteristics than those of the lead compound 2R, 6R-HNK and have better druggability.

Test Example 5. Study of Distribution of Compounds of the Present Invention in Mouse Brain Tissue Healthy male C57 mice were randomly divided into groups with 3 mice in each group, and the test compound was administrated intragastrically. See Table 10 below for specific arrangements:

TABLE 10 dosing protocol for C57 mice brain tissue distribution experiment

| Compound | Route of administration | Dose of administration (mg/kg) | Dosing volume (ml/kg) |
|---|---|---|---|
| 50 | p.o. | 20 | 10 |
| 51 | p.o. | 20 | 10 |

TABLE 10-continued dosing protocol for C57 mice brain tissue distribution experiment

| Compound | Route of administration | Dose of administration (mg/kg) | Dosing volume (ml/kg) |
|---|---|---|---|
| 51 | p.o. | 10 | 5 |
| 64 | p.o. | 10 | 5 |

Each test compound was dissolved in physiological saline to prepare a certain concentration of solution for administration.

One day before administration, the mice were fasted and allowed to drink freely for 12-14 h. The mice were fed 4 h after administration.

After the animals were bled, the brain tissue was collected. After washing, 50% ice methanol was added for homogenate at 1:4 (m/v). The collection time points was 10 min, 15 min, 30 min, 1 h, 2 h after administration of the test substance; 30.0 μL of tissue sample was taken (the sample was taken out from the refrigerator at −80° C., vortexed for 30 seconds after natural melting at room temperature) and added into a 1.5 mL centrifuge tube. 300.0 μL internal standard solution (30 ng/mL Buspiroflavone acetonitrile solution) was added, the mixture was vortex for 60 seconds and then centrifuged for 3 minutes (centrifugal force was 12000 rpm); 75 μL of the supernatant was taken and transferred to 96-well injection plate loaded with equal volume of water, shaken and mixed well, and subjected to LC-MS/MS analysis, wherein injection volume was 10 μL.

TABLE 11 brain tissue distribution experimental data for compounds of the present invention in C57 mouse

| Compound | Dose (mg/kg) | Brain tissue concentration (ng/g) | $AUC_{0-\infty}$ ($h \cdot ng \cdot g^{-1}$) | $T_{1/2}$ (h) |
|---|---|---|---|---|
| 50 | 20 (intragastrically) | 19364 (10 min) | 18509 | 1.44 |
| 51 | 20 (p.o.) | 23536 (10 min) | 46324 | 1.36 |
| 51 | 10 (p.o.) | 5094 (15 min) | | |
| 64 | 10 (p.o.) | 5743 (30 min) | | |
| Ketamine [a] | 30 (intraperitoneally) | 1929 | | |
| 2R,6R-HNK [b] | 10 (intraperitoneally) | 2562 | | |
| 2R,6R-HNK [c] | 50 (p.o.) | 6490-8600 (10 min) | 2850-5190 | 0.7 |

[a] Journal of Pharmaceutical and Biomedical Analysis, 2018, 148, 288-297;
[b] 1) Nature, 2016, 533, 481-486;
2) Nature, 2017, 546, E1-E5.
[c] Journal of Psychopharmacology, 2019, 33, 12-24.

As a drug for treatment of depression, as a central nervous system disease, it is necessary for the drug to be distributed into the CNS system such as brain tissue, and the amount of drug entering the brain tissue directly determines its therapeutic effect. Under normal circumstances, the absorption degree of intraperitoneal injection is significantly better than that of oral administration. However, it can be seen from Table 11 that, when administered orally at 10 mg/kg, the concentration of the compounds of the present invention in the brain tissue is increased by two folds or more as compared with that of the lead compound 2R, 6R-HNK administered intraperitoneally. Furthermore, the brain drug half-life (T1/2) of the compounds of the present invention is increased by 100% or more as compared with that of 2R, 6R-HNK. 10 min after oral administration, the drug concentration of 20 mg/kg of the compound of the present invention in the brain tissue is significantly increased by 2-3 folds than that of 50 mg/kg of the lead compound 2R, 6R-HNK. The brain drug exposure (AUC) is also significantly increased. Meanwhile, the maximum drug concentration of the compounds of invention in the brain tissue is also significantly higher than that of the positive drug ketamine administered intraperitoneally.

Therefore, it can be seen from the above table that, as compared to the positive drug ketamine and the lead compound 2R, 6R-HNK, the compounds of the present invention have advantages in brain tissue distribution and have better druggability.

Test Example 6. hERG Potassium Channel Inhibition Experiment of Compounds of the Present Invention 6.1 Experimental Purpose Fully automatic patch clamps were used to test the blocking effect of the compounds of the present invention on the hERG potassium current on a stable cell line transfected with hERG potassium channels.

6.2 Experimental Methods 6.2.1 Cell Preparation

CHO-hERG cells were cultured in 175 $cm^2$ culture flask. When the cell grew to 60-80% confluence, the culture medium was removed. The cells were washed with 7 ml PBS (Phosphate Buffered Saline) once, and then 3 ml Detachin was added to digest.

After the digestion was completed, 7 ml culture medium was added to neutralize. The mixture was centrifuged, and after the supernatant was removed, 5 ml culture medium was added to resuspend to ensure the cell density was $2 \times 10^6$-$5 \times 10^6$/ml.

6.2.2. Solution Preparation

TABLE 12 composition of intracellular fluid and extracellular fluid

| Reagent | Extracellular fluid (mM) | Intracellular fluid (mM) |
|---|---|---|
| $CaCl_2$ | 2 | 5.374 |
| $MgCl_2$ | 1 | 1.75 |

TABLE 12-continued composition of intracellular fluid and extracellular fluid

| Reagent | Extracellular fluid (mM) | Intracellular fluid (mM) |
|---|---|---|
| KCl | 4 | 120 |
| NaCl | 145 | — |
| glucose | 10 | — |
| HEPES | 10 | 10 |
| EGTA | — | 5 |
| $Na_2ATP$ | — | 4 |
| pH | 7.4 | 7.25 |

6.2.3 Electrophysiological Recording Process

Single-cell high-impedance sealing and whole-cell mode formation were all automatically completed by using the Qpatch instrument. After the recording mode was obtained, the cell was clamped at −80 millivolts. Before +40 millivolt depolarization stimulation for 5 seconds was given, −50 millivolt pre-voltage for 50 millisecond was first given, then repolarized to −50 millivolt for 5 seconds, and then returned to −80 millivolt. This voltage stimulus was applied every 15 seconds. After recording for 2 min, extracellular fluid was given, and recording was conducted for 5 min, and then the dosing process started. The compound concentration started from the lowest test concentration, and each test concentration was given for 2.5 min. After all concentrations were continuously given, 3 µM of the positive control compound Cisapride was given. At least 3 cells per concentration (n≥3) were tested.

6.2.4 Compound Preparation 20 mM compound mother liquor was diluted with extracellular fluid. 5 µL of 20 mM compound mother liquor was taken and added into 2495 µL extracellular fluid, so that it was diluted 500 times to 40 µM, and was then serially diluted 3 times in an extracellular fluid containing 0.2% DMSO to obtain the final concentration to be tested.

The highest tested concentration was 40 µM, and the concentrations were in order as follows: 40, 13.33, 4.44, 1.48, 0.49, 0.16 µM, totally 6 concentrations.

The content of DMSO in the final test concentration did not exceed 0.2%. This concentration of DMSO had no effect on the hERG potassium channel.

6.3 Data Analysis

Experimental data were analyzed by XLFit software.

6.4 Experimental Results

The blocking effect of the compounds of the present invention on the hERG potassium current was determined by the above test, and the measured results were shown in Table 13.

TABLE 13 blocking effect of compounds of the present invention on the hERG potassium current

| Compound | $IC_{50}$ (µM) |
|---|---|
| 44 | >40 |
| 45 | >40 |

TABLE 13-continued blocking effect of compounds of the present invention on the hERG potassium current

| Compound | $IC_{50}$ (µM) |
|---|---|
| 46 | >40 |
| 51 | >40 |
| 64 | >40 |
| 73 | >40 |
| Cispride | 0.05 |

The hERG potassium channel inhibition test is the most basic test for evaluating the cardiac safety of compounds. It can be seen from Table 13 that the compounds of the present invention have no obvious inhibitory effect on the hERG potassium channel, indicating that the compounds of the present invention have a low risk of cardiotoxicity.

All literatures mentioned in the present invention are incorporated by reference herein, as if each is individually incorporated by reference. Additionally, it should be understood that after reading the above teaching, many variations and modifications may be made by the skilled in the art, and these equivalents also fall within the scope as defined by the appended claims.

The invention claimed is:

1. A compound represented by the following general formula (I), or a tautomer, an enantiomer, a diastereomer, a racemate or a mixture thereof, or a pharmaceutically acceptable salt thereof;

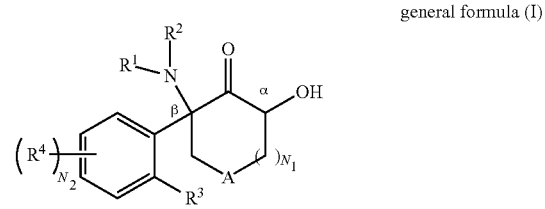

general formula (I)

wherein,
A is $CH_2$;
$N_1$ is 1 and $N_2$ is 0, 1, 2, 3 or 4;
$R^1$ and $R^2$ are each independently hydrogen, or $C_1$-$C_6$ alkyl, and the above-mentioned alkyl can be independently substituted by 1 to 2 substituents selected from the group consisting of halogen, hydroxyl, amino, cyano, $C_1$-$C_4$ alkyl, $C_1$-$C_4$ haloalkyl, $C_1$-$C_4$ alkoxy, and $C_1$-$C_4$ haloalkoxy;
$R^3$ is hydrogen, $C_1$-$C_6$ alkyl, $C_1$-$C_6$ haloalkyl, $C_1$-$C_6$ alkoxy, $C_1$-$C_6$ haloalkoxy or halogen; and when A is $CH_2$ and $N_1$ is 1, $R^3$ is not chlorine;
each $R^4$ is independently hydrogen, $C_1$-$C_6$ alkyl, $C_1$-$C_6$ haloalkyl, $C_1$-$C_6$ alkoxy, $C_1$-$C_6$ haloalkoxy, halogen, or cyano, wherein the halogen is fluorine, bromine or iodine; and $R^3$ and $R^4$ are not hydrogen at the same time; or when $R^3$ is fluorine, not all of the substituents at other positions of the benzene ring are hydrogen or position 5 of the benzene ring is not fluorine; and
the stereo configuration of α- or β-position carbon atom is each independently R, S or (R, S).

2. The compound of claim 1, or a tautomer, an enantiomer, a diastereomer, a racemate or a mixture thereof, or a pharmaceutically acceptable salt thereof, wherein the compound is a compound represented by general formula (I-A), or (I-B):

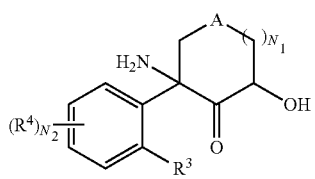

general formula (I-A) compound
  wherein, in formula (I-A), A, $N_1$, $N_2$, $R^3$ and $R^4$ are as defined in claim 1;

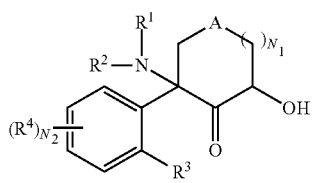

general formula (I-B) compound
  wherein, in formula (I-B), A, $N_1$, $N_2$, $R^3$ and $R^4$ are as defined in claims 1, $R^1$ and $R^2$ are each independently hydrogen or $C_1$-$C_6$ alkyl, and the above alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, and $C_1$-$C_4$ haloalkoxy,
general formula (I-C) compound.

3. The compound of claim 1, or a tautomer, an enantiomer, a diastereomer, a racemate, or a mixture thereof, or a pharmaceutically acceptable salt thereof, wherein $R^1$ and $R^2$ are each independently hydrogen, methyl, or ethyl.

4. The compound of claim 1, or a tautomer, an enantiomer, a diastereomer, a racemate, or a mixture thereof, or a pharmaceutically acceptable salt thereof, wherein
  $R^3$ is hydrogen;
  $R^4$ is $C_1$-$C_6$ haloalkyl.

5. The compound of claim 1, or a tautomer, an enantiomer, a diastereomer, a racemate, or a mixture thereof, or a pharmaceutically acceptable salt thereof, wherein
  $R^3$ is halogen;
  $R^4$ is $C_1$-$C_6$ haloalkoxy.

6. The compound of claim 1, or a tautomer, an enantiomer, a diastereomer, a racemate, or a mixture thereof, or a pharmaceutically acceptable salt thereof, wherein $R^3$ is hydrogen, fluorine, methyl, trifluoromethyl or trifluoromethoxy.

7. The compound of claim 1, or a tautomer, an enantiomer, a diastereomer, a racemate, or a mixture thereof, or a pharmaceutically acceptable salt thereof, wherein $R^4$ is hydrogen, fluorine, methyl, methoxy, trifluoromethyl, trifluoromethoxy or cyano.

8. A pharmaceutical composition which comprises a compound of claim 1, or a tautomer, an enantiomer, a diastereomer, a racemate or a mixture thereof, or a pharmaceutically acceptable salt thereof; and a pharmaceutically acceptable carrier or excipient.

9. A method of treating a disease related to the nervous system comprising administering the compound of claim 1, or a tautomer, an enantiomer, a diastereomer, a racemate, or a mixture thereof, or a pharmaceutically acceptable salt thereof to a subject in need thereof.

10. The method of claim 9, wherein the diseases related to the nervous system is depression.

11. A method for preparing a compound of claim 1, or a tautomer, an enantiomer, a diastereomer, a racemate or a mixture thereof, or a pharmaceutically acceptable salt thereof, wherein,
  (1) the method comprises the steps:

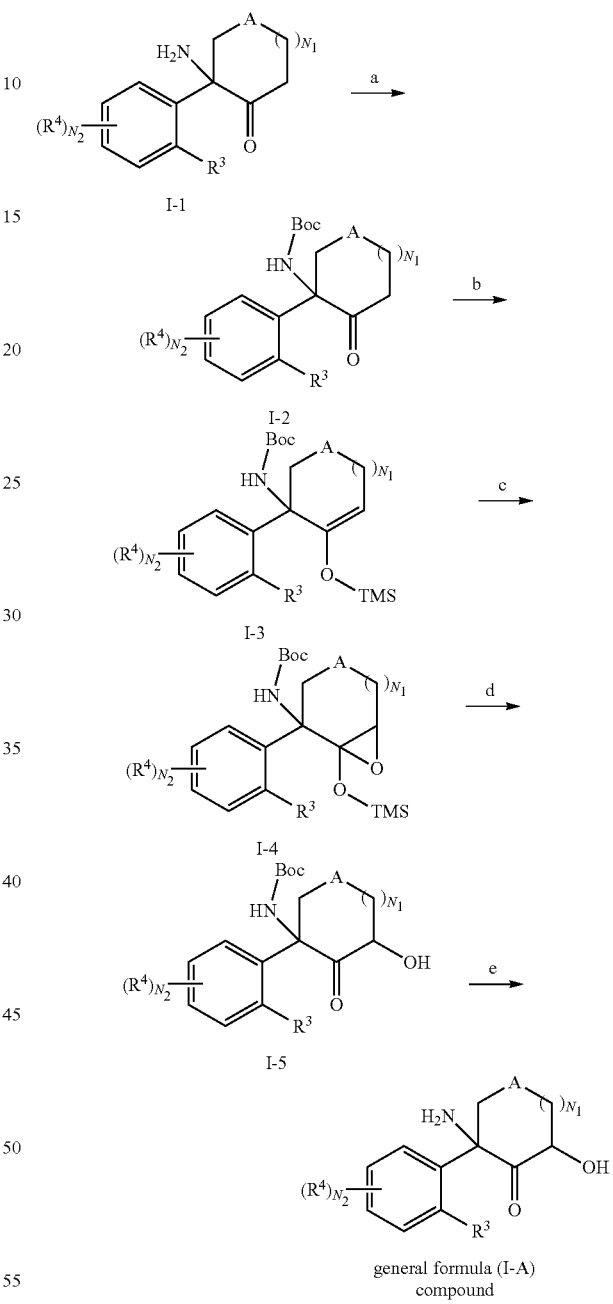

wherein, A, $N_1$, $N_2$, $R^3$ and $R^4$ are as defined in claim 1;
a. compound I-1 is reacted with di-tert-butyl dicarbonate in a protic solvent or an aprotic solvent or a mixed solvent thereof to form compound I-2;
b. in an aprotic solvent, compound I-2 is reacted with trimethylchlorosilane to form compound I-3;
c. in an aprotic solvent, compound I-3 is oxidized by an oxidizing agent to form compound I-4;
d. in an aprotic solvent, a trimethylsilyl protecting group is removed from compound I-4 to form compound I-5;

e. in a polar aprotic solvent, a tert-butoxycarbonyl protecting group is removed from compound I-5 to form compound I-A;
or
(2) the method comprises the steps:

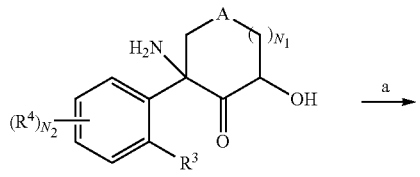

general formula (I-A) compound

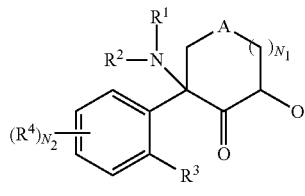

general formula (I-B) compound wherein, A, $N_1$, $N_2$, $R^3$ and $R^4$ are as defined in claims 1, $R^1$ and $R^2$ are each independently hydrogen or $C_1$-$C_6$ alkyl, and the above-mentioned alkyl can be independently substituted by 1 to 2 substituents selected from the group consisting of halogen, hydroxy, amino, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ ester, and $C_1$-$C_4$ amide;

a. in a protic or an aprotic solvent or a mixed solvent thereof and in the presence of a catalyst and a hydrogen source, the compound I-A is reacted with an aldehyde to form compound I-B.

12. The preparation method of claim 11, wherein:
the method for preparing compound I-1 comprises the steps:

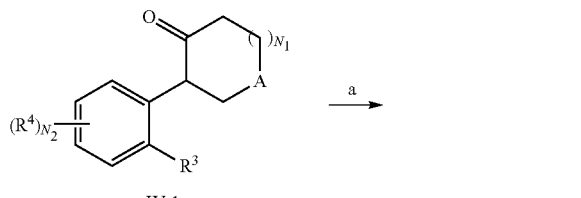

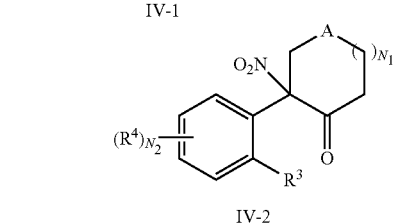

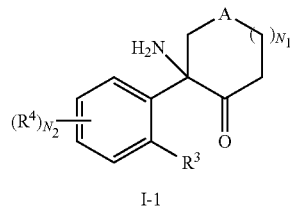

wherein, in each formula, A, $N_1$, $N_2$, $R^3$ and $R^4$ are as defined in claim 1;

a. in an aprotic solvent, compound IV-1 is reacted with a nitrating reagent under the action of a catalyst to form compound IV-2;

b. in a protic or an aprotic solvent or a mixed solvent thereof, compound IV-2 is reduced by a metal reducing agent under the action of an organic or inorganic acid to form the compound I-1;

or the method for preparing compound I-1 comprises the steps:

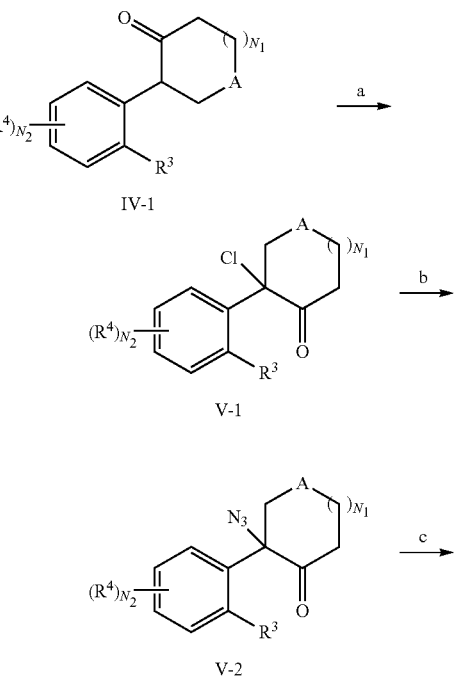

wherein, in each formula, A, $N_1$, $N_2$, $R^3$ and $R^4$ are as defined in claim 1;

a. in an aprotic solvent, compound IV-1 is reacted with a halogenated reagent to form compound V-1;

b. in an aprotic solvent, compound V-1 is reacted with an azide reagent to form compound V-2;

c. in a protic or an aprotic solvent or a mixed solvent thereof, compound V-2 is reacted in the presence of a catalyst and a hydrogen source to form compound I-1.

13. The preparation method of claim 12, wherein:
the method for preparing compound IV-1 comprises the steps:

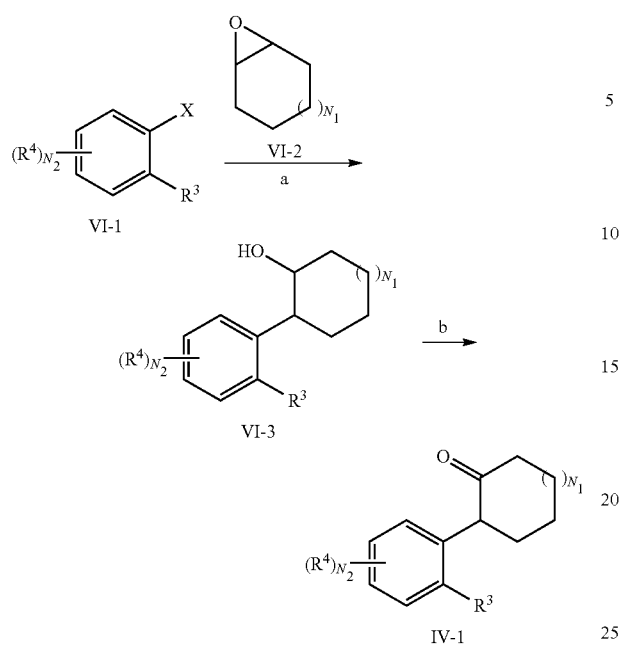

wherein, in each formula, X can be H, Br or I; N1, N2, R3 and R4 are as defined in claim 1;

a. in an aprotic solvent, compound VI-1 is reacted with an epoxy compound VI-2 to form compound VI-3;

b. in an aprotic solvent, compound VI-3 is oxidized by an oxidizing agent to form the compound IV-1;

or the method for preparing compound IV-1 comprises the steps:

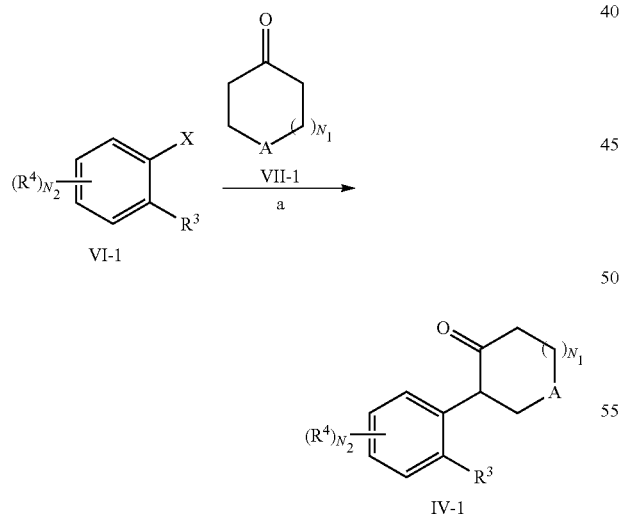

wherein, in each formula, X can be Br or I; A, N1, N2, R3 and R4 are as defined in claim 1;

a. in an aprotic solvent, compound VI-1 is reacted with a cyclic ketone compound VII-1 under catalysis of a metal-containing catalyst and a phosphine-containing ligand to form compound IV-1.

14. A compound selected from the group consisting of:

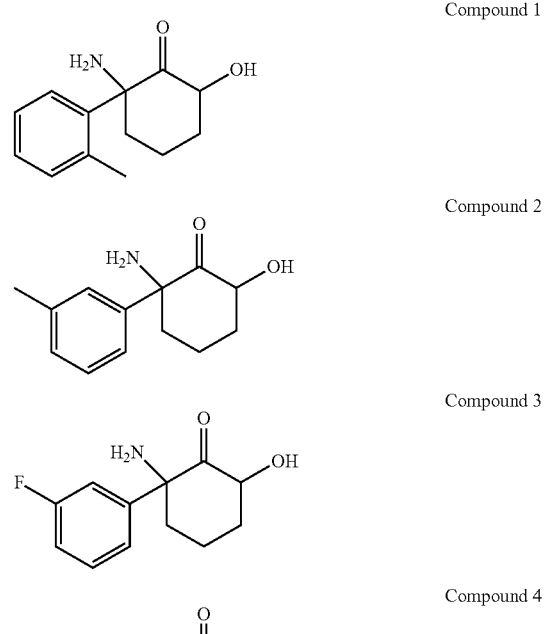

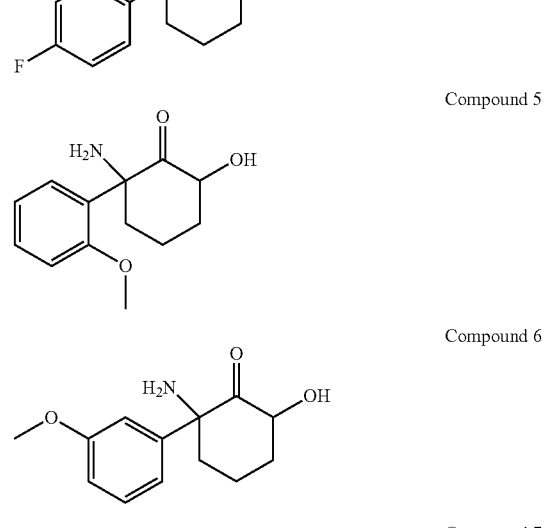

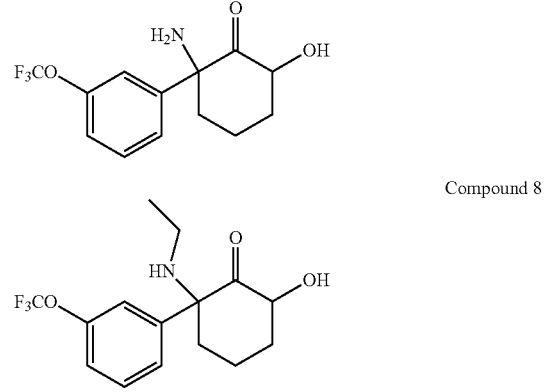

-continued
Compound 10
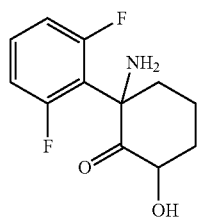
Compound 11
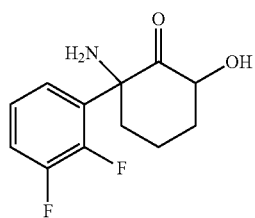
Compound 12
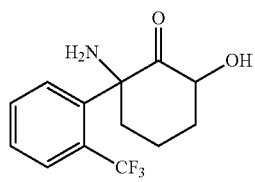
Compound 13
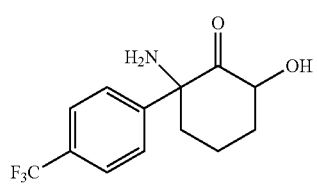
Compound 14
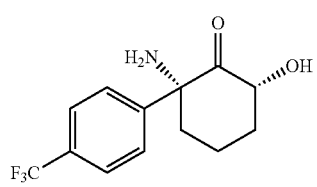
Compound 15
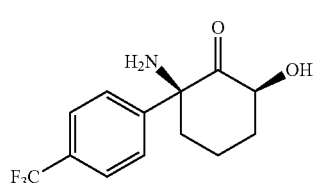
Compound 16
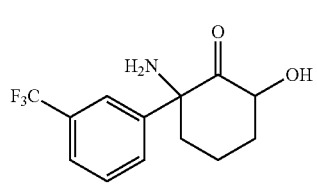
Compound 17
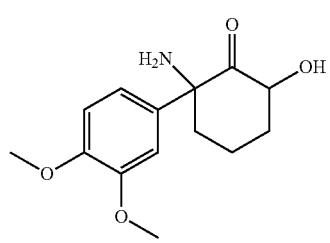
-continued
Compound 18
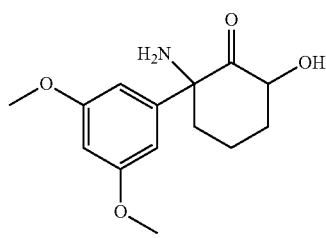
Compound 19
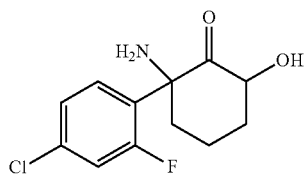
Compound 20
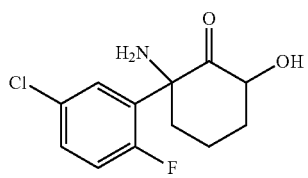
Compound 21
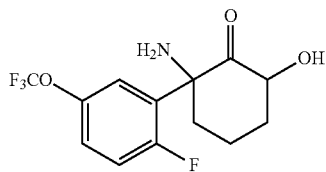
Compound 22
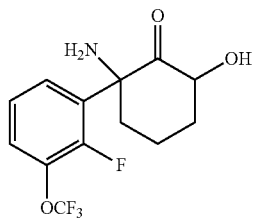
Compound 23
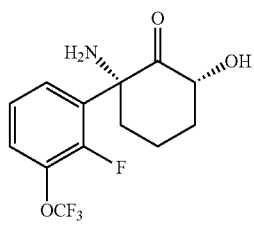
Compound 24
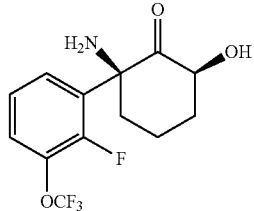

-continued
Compound 25
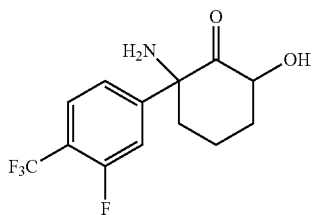
Compound 26
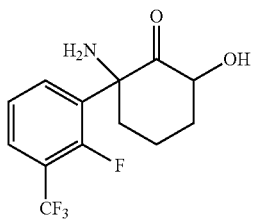
Compound 27
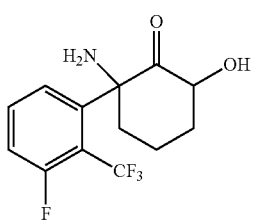
Compound 28
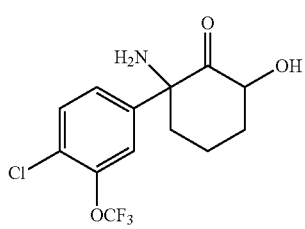
Compound 29
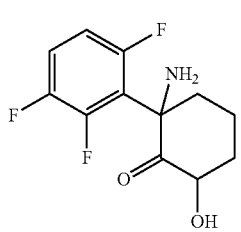
Compound 30
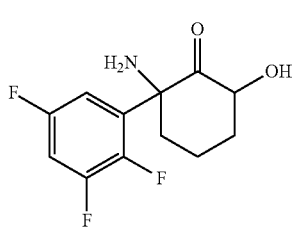
Compound 31
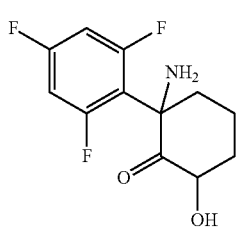
-continued
Compound 32
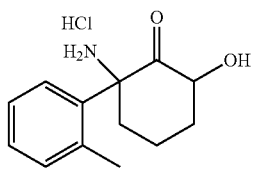
Compound 33
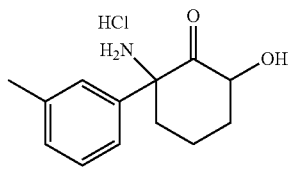
Compound 36
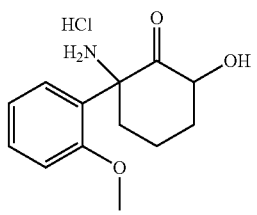
Compound 37
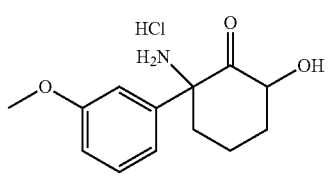
Compound 38
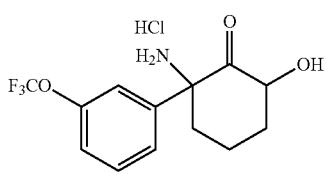
Compound 39
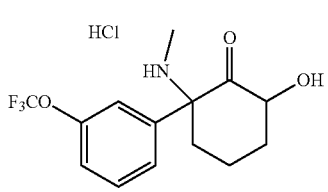
Compound 40
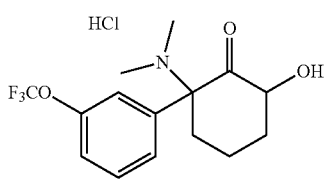
Compound 41
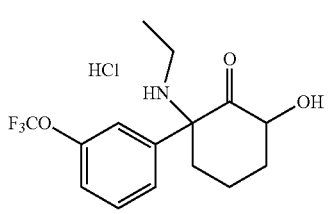

-continued
Compound 42
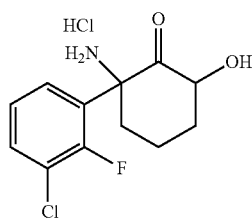
Compound 43
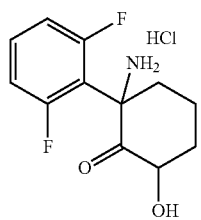
Compound 44
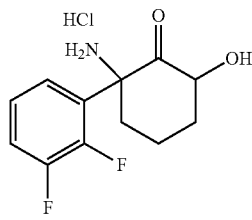
Compound 45
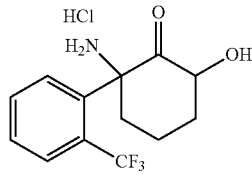
Compound 46
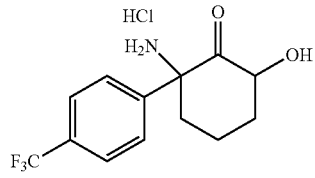
Compound 47
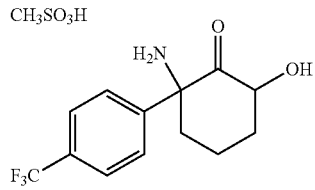
Compound 48
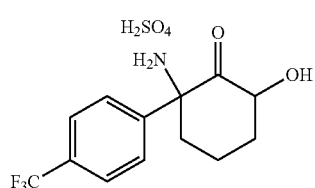
Compound 49
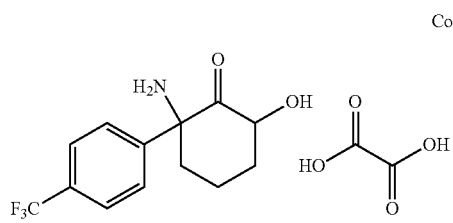
-continued
Compound 50
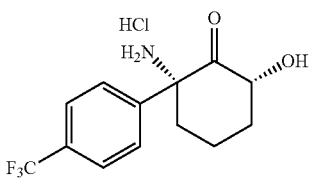
Compound 51
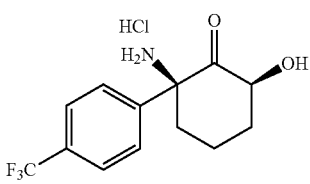
Compound 52
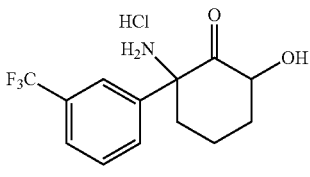
Compound 53
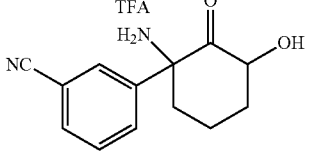
Compound 54
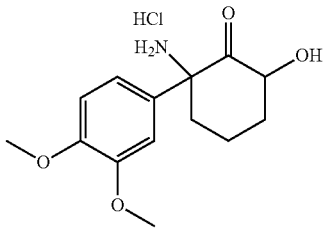
Compound 55
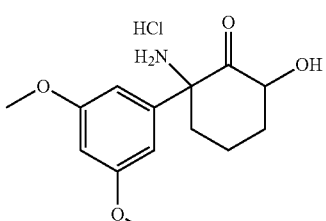
Compound 56
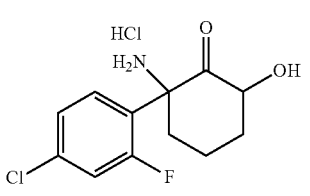
Compound 57
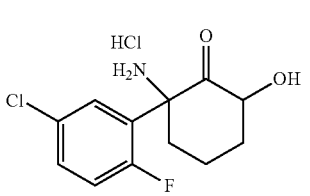

-continued
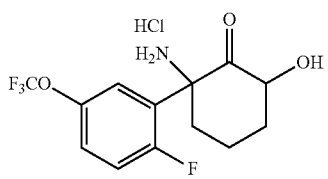
Compound 58
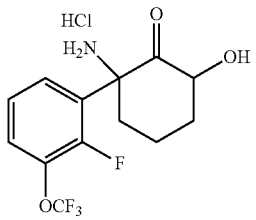
Compound 59
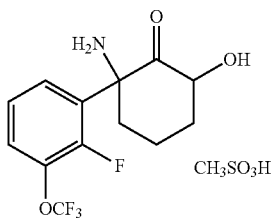
Compound 60
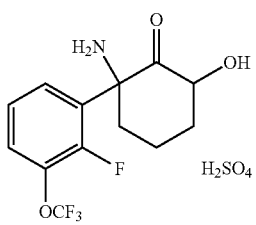
Compound 61
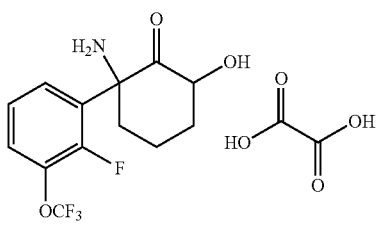
Compound 62
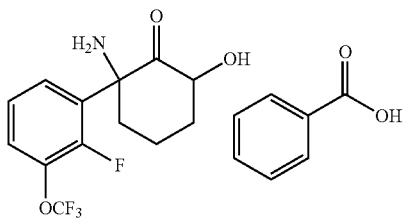
Compound 63
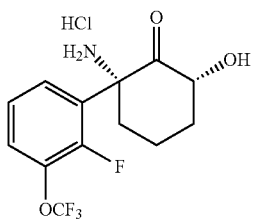
Compound 64
-continued
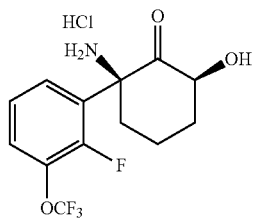
Compound 65
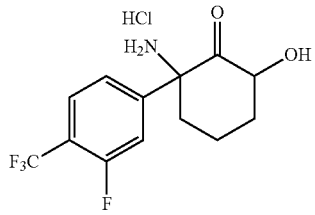
Compound 66
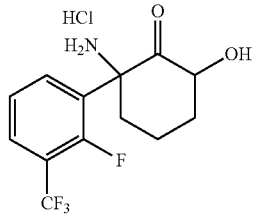
Compound 67
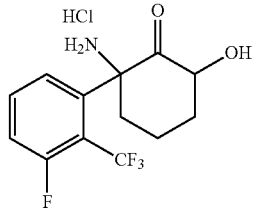
Compound 68
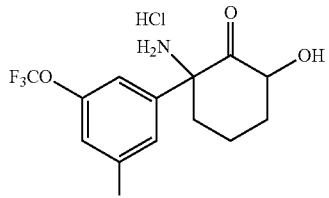
Compound 69
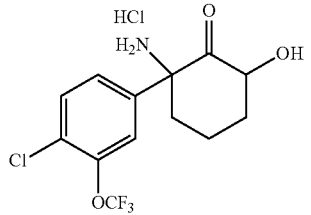
Compound 70
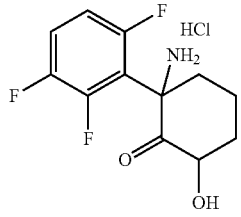
Compound 71

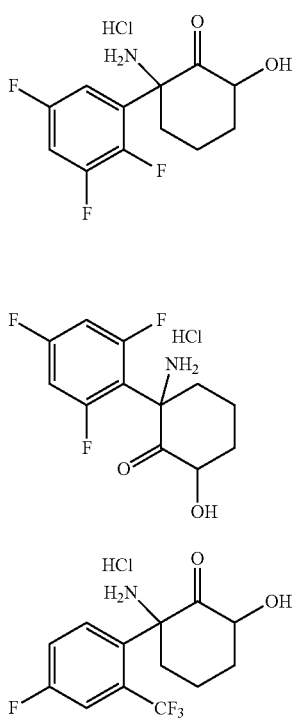
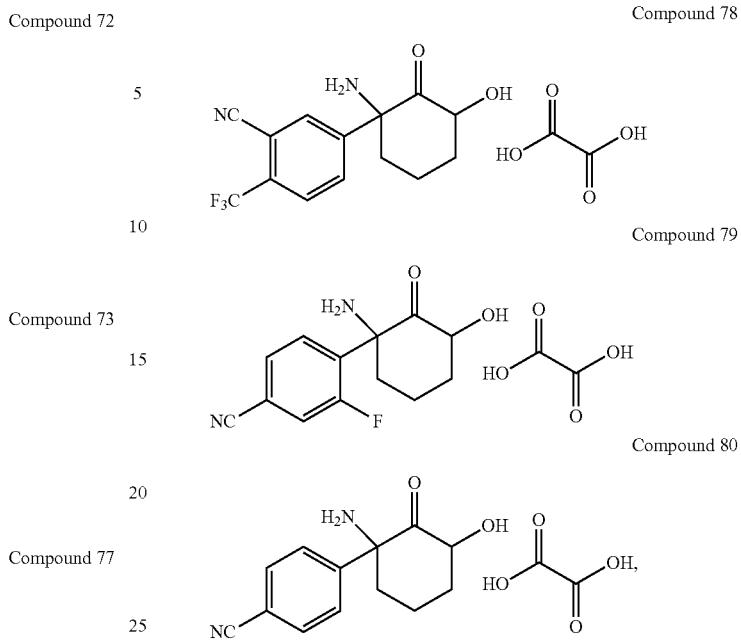
or a tautomer, an enantiomer, a diastereomer, a racemate, or a mixture thereof, or a pharmaceutically acceptable salt thereof.
* * * * *